US006211338B1

(12) United States Patent
Malcolm et al.

(10) Patent No.: US 6,211,338 B1
(45) Date of Patent: Apr. 3, 2001

(54) SINGLE-CHAIN RECOMBINANT COMPLEXES OF HEPATITIS C VIRUS NS3 PROTEASE AND NS4A COFACTOR PEPTIDE

(75) Inventors: Bruce A. Malcolm, Westfield; S. Shane Taremi, Upper Montclair, both of NJ (US); Patricia C. Weber, Yardley, PA (US); Nanhua Yao, Irvine, CA (US)

(73) Assignee: Schering Corporation, Kenilworth, NJ (US)

( * ) Notice: Subject to any disclaimer, the term of this patent is extended or adjusted under 35 U.S.C. 154(b) by 0 days.

(21) Appl. No.: 09/198,723

(22) Filed: Nov. 24, 1998

Related U.S. Application Data

(60) Provisional application No. 60/094,331, filed on Jul. 28, 1998, and provisional application No. 60/067,315, filed on Nov. 28, 1997.

(51) Int. Cl.[7] .................................................. C07K 14/02
(52) U.S. Cl. .............................. 530/350; 435/5; 435/69.7; 435/219
(58) Field of Search ................................ 435/69.1, 320.1, 435/252.3, 219, 69.7; 530/350; 536/23.2, 23.72

(56) References Cited

U.S. PATENT DOCUMENTS 5,843,752 * 12/1998 Dasmahapatra et al. ............. 435/219

FOREIGN PATENT DOCUMENTS

| WO 9636702 | 11/1996 | (WO) . |
| WO 9708304 | 3/1997 | (WO) . |

OTHER PUBLICATIONS

Urbani, A. et al. J.B.C. (1997), v. 272, 14, pp. 9204–9209.
Steinkuhler C., et al., J. Virology (1996) v. 70, 10, pp. 6694–6700.
Landro, J. et al., Biochemistry (1997) v. 36, pp. 9340–9348.
Zhang, R. et al. J. Virology (1997), v. 71, No. 8, pp. 6208–6213.
Kim, J. L. et al., "Crystal Structure of the Hepatitis C Virus NS3 Protease Domain Complexed With A Synthetic NS4A Cofactor Peptide," Cell vol. 87, No. 4, Oct. 18, 1996 pp. 343–355.

Yan, Y. et al. "Complex of NS3 Protease and NS4 Peptide of BK Strain Hepatitis C Virus," Protein Science, vol. 7, No. 4, Apr. 1998, pp. 837–847.

Bartenschlager, R. et al., "Complex Formation Between The NS3 Serine–Type Proteinase of the Hepatitis C Virus and NS4A And Its Importance For Polyprotein Maturation," Journal of Virology, vol. 69, No. 12, Dec. 1, 1995 pp. 7519–7528.

Lin, C. et al., "Hepatitis C Virus NS3 Serine Proteinase: Trans–Cleavage Requirements and Processing Kinetics," Journal of Virology, vol. 68, No. 12, Dec. 1, 1994, pp. 8147–8157.

Kim, D. W. et al., "C–Terminal Domain of the Hepatitis C Virus NS3 Protein Contains An RNA Helicase Activity," Biochemical and Biophysical Research Communications, vol. 215, No. 1,4 Oct. 1995 pp. 160–166.

Taremi, S. S. et al. "Construction, expression, and characterization of a novel fully activated recombinant single–chain hepatitis C virus protease," Protein Science, (1998 Oct.) 7 (10) 2143–9, Journal Code: BNW, ISSN,: 0961–8368.

Dimasi, N. et al., "Engineering, characterization and phage display of hepatitis C virus NS3 protease and NS4A cofactor peptide as a single–chain protein," Protein Engineering, (1998 Dec.) 11 (12) 1257–65. Journal Code: PR1, ISSN: 0269–2139.

Wilkinson et al., 1997, *Biochemical Society Transactions*, 25:S624.

* cited by examiner

*Primary Examiner*—Donna C. Wortman
*Assistant Examiner*—Robert A. Zeman
(74) *Attorney, Agent, or Firm*—Jaye P. McLaughlin; Christine F. Martin

(57) ABSTRACT

Covalent HCV NS4A-NS3 complexes comprising the central hydrophobic domain of native HCV NS4A peptide, a linker, and the HCV NS3 serine protease domain, wherein the hydrophobic domain of native HCV NS4A peptide is tethered by the linker to the amino terminus of the HCV NS3 protease domain.

11 Claims, 7 Drawing Sheets

SINGLE-CHAIN RECOMBINANT COMPLEXES OF HEPATITIS C VIRUS NS3 PROTEASE AND NS4A COFACTOR PEPTIDE

This filing is a conversion of Provisional U.S. Patent Applications U.S. Ser. No. 60/067,315, filed Nov. 28, 1997 and U.S. Ser. No. 60/094,331, filed Jul. 28, 1998, each of which is incorporated herein by reference, to a U.S. Utility Patent Application.

BACKGROUND OF THE INVENTION

Hepatitis C virus (HCV) is considered to be the major etiological agent of non-A non-B (NANB) hepatitis, chronic liver disease, and hepatocellular carcinoma (HCC) around the world, with an estimated human seroprevalence of 1% globally. [Alter et al., 1994, *Gastroenterol. Clin. North Am.* 23:437–455; Behrens et al., 1996, *EMBO J.* 15:12–22]. Four million individuals may be infected in the United States. The viral infection accounts for greater than 90% of transfusion-associated hepatitis in the U.S. and it is the predominant form of hepatitis in adults over 40 years of age. Almost all of the infections result in chronic hepatitis and nearly 20% of those infected develop liver cirrhosis.

The virus particle has not been identified due to the lack of an efficient ex vivo replication system and the extremely low amount of HCV particles in infected liver tissues or blood. However, molecular cloning of the viral genome has been accomplished by isolating the messenger RNA (mRNA) from the serum of infected chimpanzees and preparing cDNA using recombinant methodologies. [Grakoui A. et al., 1993, *J. Virol.* 67: 1385–1395]. It is now known that HCV contains a positive strand RNA genome comprising approximately 9400 nucleotides, organization of which is similar to that of flaviviruses and pestiviruses. The genome of HCV, a (+)-stranded RNA molecule of ~9.4 kb, encodes a single large polyprotein of about 3000 amino acids which undergoes proteolysis to form mature viral proteins in infected cells.

Cell-free translation of the viral polyprotein and cell culture expression studies have established that the HCV polyprotein is processed by cellular and viral proteases to produce the putative structural and nonstructural (NS) proteins. At least ten mature viral proteins are produced from the polyprotein by specific proteolysis. The order and nomenclature of the cleavage products are as follows: $NH_2$—C-E1-E2-p7-NS2-NS4A-NS3-NS4B-NS5A-NS5B-COOH (FIG. 1) [Grakoui et al., 1993, *J. Virol.* 67:1385–95; Hijikata et al., 1991, *PNAS* 88:5547–51; Lin et al., 1994, *J. Virol.* 68:5063–73]. The three amino-terminal putative structural proteins, C (capsid), E1, and E2 (two envelope glycoproteins), are believed to be cleaved by a host signal peptidase of the endoplasmic reticulum (ER). The host enzyme is also responsible for generating the amino terminus of NS2. The proteolytic processing of the nonstructural proteins are carried out by the viral proteases: NS2-3 and NS3, contained within the viral polyprotein. The NS2-3 protease catalyzes the cleavage between NS2 and NS3. It is a metalloprotease and requires both NS2 and the protease domain of NS3.

The NS3 protease catalyzes the rest of the cleavages in the nonstructural part of the polyprotein. The NS3 protein contains 631 amino acid residues and is comprised of two enzymatic activities: the protease domain contained within amino acid residues 1–181 and a helicase ATPase domain contained within the rest of the protein Kim et al., 1995, *Biochem Biophys Res. Comm.*, 215:160–166. It is not known if the 70 kD NS3 protein is cleaved further in infected cells to separate the protease domain from the helicase domain, although no cleavage has been observed in cell culture expression studies.

The NS3 protease is a member of the serine class of enzymes. It uses a His, Asp, Ser catalytic triad. Mutation of the Ser residue abolishes cleavage of NS3/4A, NS4A/4B, NS4B/5A, and NS5A/5B substrates. The cleavage between NS3 and NS4A is intramolecular, whereas the cleavages at the NS 4A/4B, 4B/5A, 5A/5B sites occur in trans.

Experiments using transient expression of various forms of HCV NS polyproteins in mammalian cells have established that the NS3 serine protease is necessary but not sufficient for efficient processing of all of these cleavages. Like the flaviviruses, the HCV NS3 protease also requires a cofactor to catalyze some of these cleavage reactions. Efficient proteolytic processing at NS3/4A, NS4A/4B, NS4B/5A, and NS5A/5B sites within the non-structural domain of hepatitis C virus requires a heterodimeric complex of the NS3 serine protease and the NS4A protein. [Bartenschlager et al. 1995, *J. Virol.* 67:3835–3844; Failla et al., 1994, *J. Virol.* 68:3753–3760]. A 13-amino acid synthetic NS4A peptide, corresponding to the central hydrophobic domain of NS4A protein, spanning residues 21–33 has been shown to be sufficient for activation of NS3 protease [Butkiewicz et al., 1996, Virology, 225: 328–338]. A smaller domain (amino acid residues 22–30) of NS4A has been shown to be sufficient for activation of the protease [Lin et al., 1995, J. Virol 69:4377–80].

The recently published three dimensional structure of the NS3 protease [Kim et al, 1996, *Cell* 87:343–355; Love et al, 1996, *Cell* 87:331–342] revealed that the N-terminal 37 residues of NS3 adopt a β (residues 6–9)-α (residues 14–22)-β (residues 33–37) structure upon binding of a synthetic peptide corresponding to the central hydrophobic domain spanning residues 21–32 of NS4A protein.

Production of an active $NS3_{1-181}$-NS4A peptide complex at present involves two steps. First, the NS3 catalytic domain (amino acid residues 1–181) is produced as a recombinant protein in *E. coli*. Next, a 13–19 residue NS4A peptide spanning the central hydrophobic domain of the full-length NS4A protein is added to form a non-covalent complex [Kim et al., 1996, *Cell* 87:343–355]. This complex, although more active than the protease alone, is approximately 8–10 fold less active than the full-length $NS3_{1-631}$-$NS4A_{1-54}$ form of the protease as judged by its proteolytic activity toward a synthetic substrate based on the native NS5A-NS5B amino acid sequence. [Urbani et al., 1997, *J. Biol. Chem.*, 272(14):9204–09; Steinkuhler et al., 1996, *J. Virol.* 70(10):6694–6700]. Moreover, NS4A peptide has been shown to have a very low affinity (10 $\mu$M) for NS3 in solution [Bianchi et al,. 1997, *Biochemistry* 36: 7890–7897], requiring addition of NS4A peptide in the high micromolar range to insure a 1:1 stoichiometric complex with NS3 protease. The limited solubility of this peptide in aqueous buffer due to its hydrophobic nature makes working with this peptide at these concentrations difficult.

Because the HCV NS3 protease cleaves the non-structural HCV proteins necessary for HCV replication, the NS3 protease can be a target for the development of therapeutic agents against the HCV virus. The gene encoding the HCV NS3 protein has been cloned as disclosed in U.S. Pat. No. 5,371,017. To date, however, the protease has not been produced in a covalent complex with the NS4A cofactor in a soluble, active and stable form. Such a complex would be useful as a target in a high throughput screen to discover therapeutic agents. A stable, active HCV protease is also required for determination of modes of binding of inhibitors by NMR, for structural determination by NMR spectroscopy, for crystallography, and for virtually all biophysical and biochemical studies interested in the activated form of the enzyme.

SUMMARY OF THE INVENTION

The present invention provides NS4A tethered forms of the HCV NS3 protease comprising single-chain recombinant covalent complexes of Hepatitis C virus NS3 protease and an NS4A cofactor peptide which require no subsequent addition of NS4A peptide for activation and which are as active as the full-length $NS3_{1-631}$ $NS4A_{1-54}$. The covalent NS4A-NS3 complexes of the invention are more soluble, stable and active than the non-covalent protease-peptide complexes previously available.

The NS4A tethered forms of the HCV NS3 protease of the invention consist of covalent NS4A-NS3 complexes comprising a central hydrophobic domain of the NS4A peptide tethered by linker of at least about 4 amino acid residues to the amino terminus of the serine protease domain of NS3. The amino acid sequences of 20 such embodiments are defined in the Sequence Listing by SEQ ID NOs: 1–20. Corresponding nucleotide sequences are provided in SEQ ID NOs: 92–111.

Preferred embodiments of the invention also provide NS4A tethered forms of the full length NS3 protease. The amino acid sequences of 8 such embodiments are defined in SEQ ID NOs: 11–18.

Other preferred embodiments of the invention further provide mutant forms of the covalent NS4A-NS3 complexes in which point mutations introduced at positions 17 and/or 18 of the NS3 domain change a hydrophobic amino acid residue to a hydrophilic residue. This further improves the solubility of the complexes and provides the protein in a monodispersed form. The amino acid sequences of 13 such embodiments are defined in the Sequence Listing by SEQ ID NOs: 2–4, 6–8, 10, 12–14, and 16–18.

The invention still further provides mutant forms of the covalent NS4A-NS3 complexes in which a mutation introduced at position 139 of the NS3 domain changes a serine residue to an alanine residue. The amino acid sequences of 9 such embodiments are defined in SEQ ID NOs: 5–8,15–18 and 20.

The invention further provides covalent HCV NS4A-NS3 complexes having an easily removable histidine tag comprising three or more histidine residues fused to the complex. This enables rapid purification of the protease with easy removal of the tag following purification.

The present invention further provides for isolated nucleic acids and vectors which encode the covalent NS4A-NS3 complexes of the present invention, and host cells transformed or transfected by said nucleic acids or vectors. The invention still further provides methods for making the covalent NS4A-NS3 complexes comprising culturing the transformed or transfected host cell under conditions in which the nucleic acid or vector is expressed.

The invention also provides methods for identifying inhibitors of HCV NS3. Methods are provided for detecting inhibitors of the protease activity, the helicase activity and the ATPase activity of NS3 using the disclosed covalent complexes.

BRIEF DESCRIPTION OF THE FIGURES

FIG. 5A illustrates the outcome expected in the absence of an uninhibited HCV protease, while 5B illustrates the outcome expected in the presence of an active, uninhibited HCV protease.

DETAILED DESCRIPTION OF THE INVENTION

Figure 1:
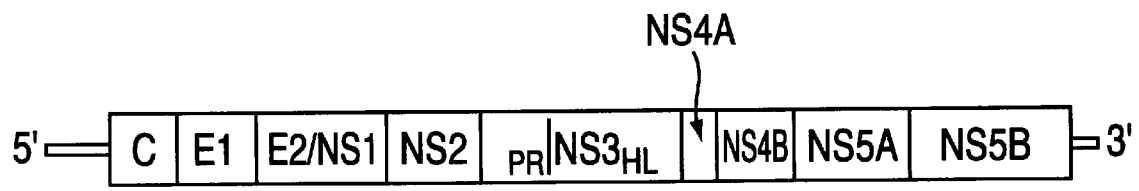
FIG. 1 schematically depicts the HCV genome.
Figure 2:
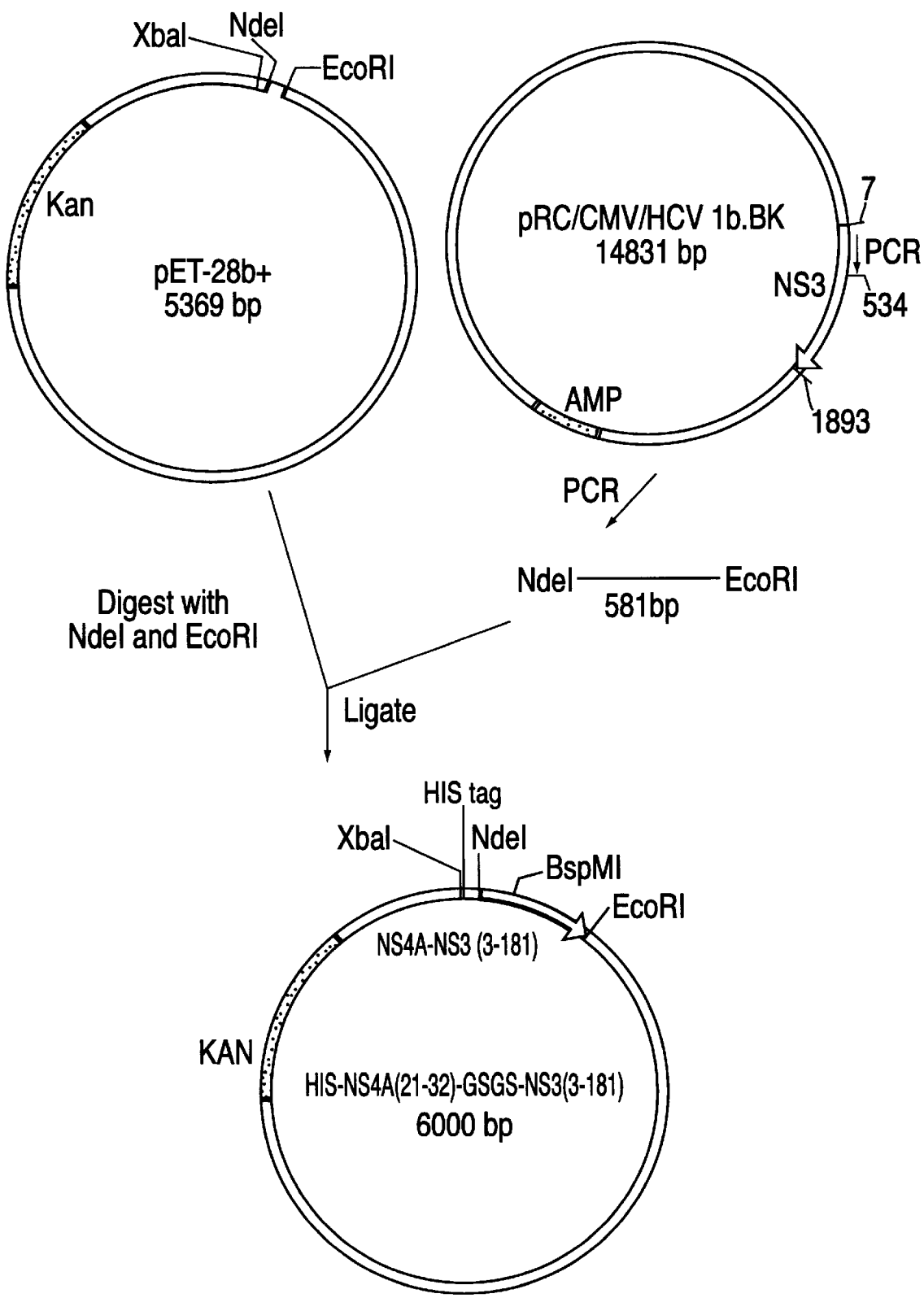
FIG. 2 depicts the recombinant synthesis of plasmid pHIS-NS4A$_{21-32}$-GSGS-NS3$_{3-181}$.
Figure 3:
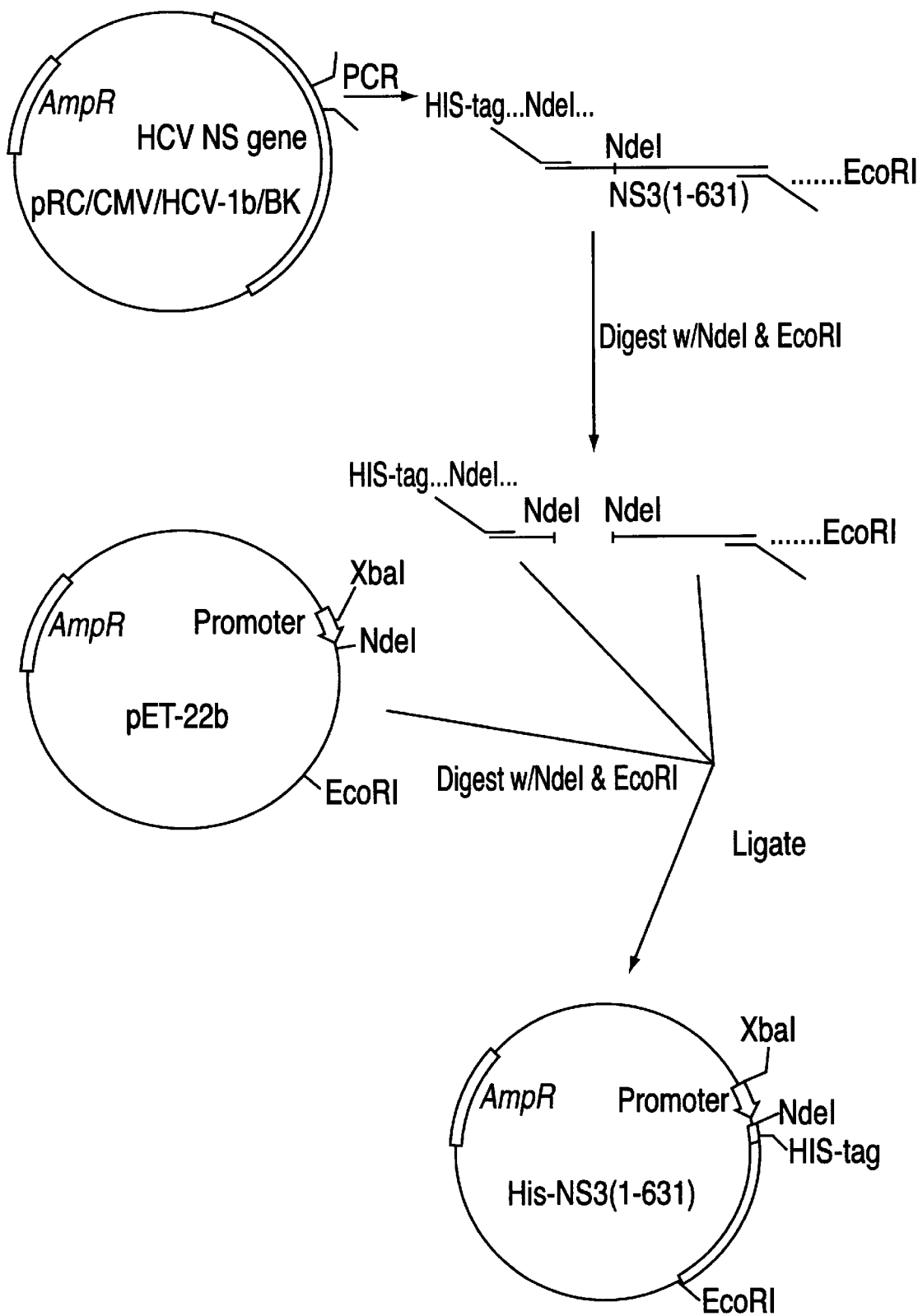
FIG. 3 depicts the recombinant synthesis of plasmid pHIS-NS3$_{1-631}$.
Figure 4:
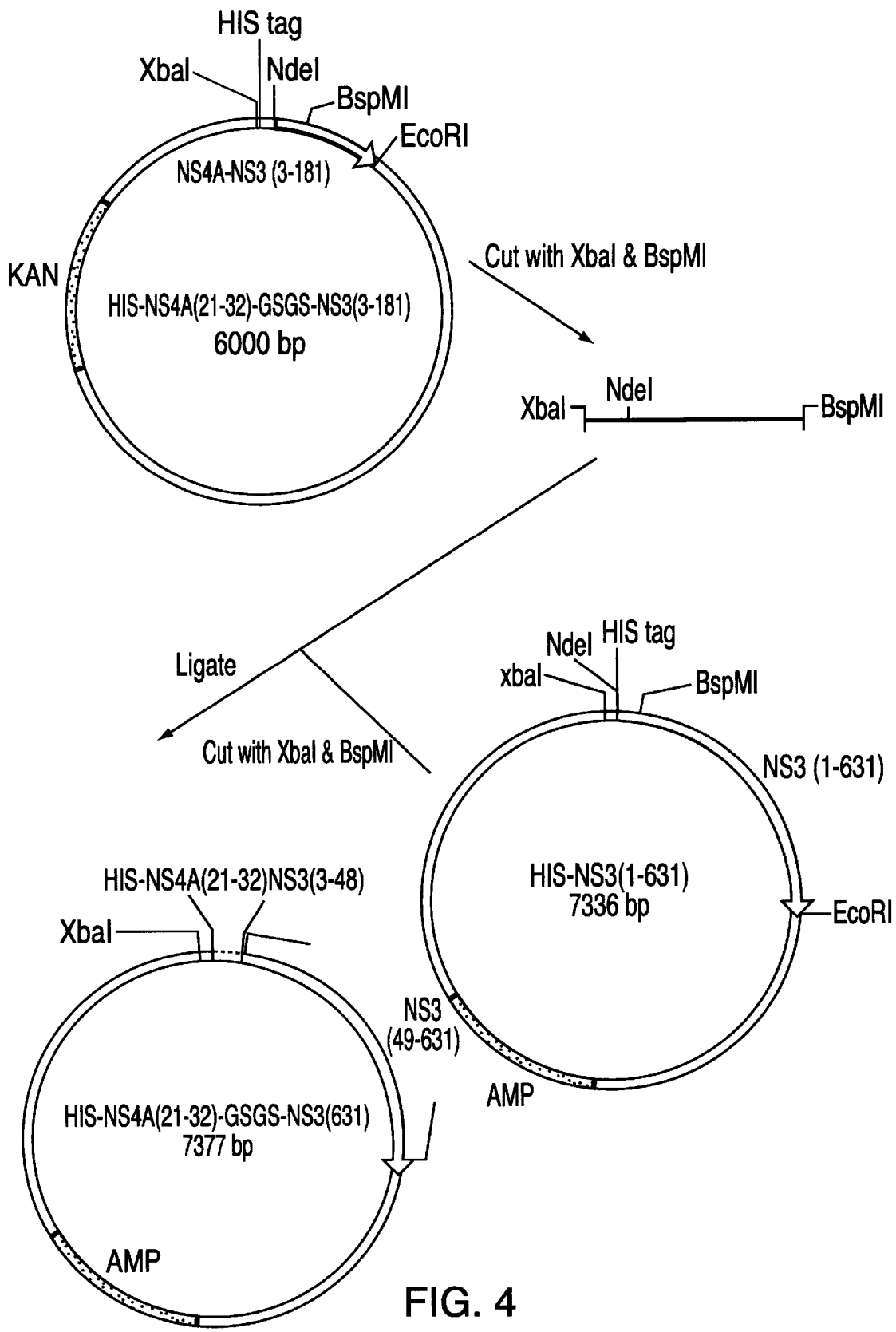
FIG. 4 depicts the recombinant synthesis of plasmid pHIS-NS4A$_{21-32}$-GSGS-NS3$_{3-631}$.

The teachings of all references cited are incorporated herein in their entirety by reference.

The covalent NS4A-NS3 complexes of the present invention are useful for structural determination and determination of mode of binding of HCV inhibitors by NMR spectroscopy. Moreover, they provide a more soluble and stable form of HCV NS3 protease than the presently available non-covalent NS3$_{1-181}$-NS4A peptide complexes for crystallography studies, high throughput screening assays and other conventional biophysical and biochemical investigations.

Several representative embodiments of the covalent NS4A-NS3 complexes of the invention are disclosed in the examples below. In one such embodiment, NS4A residues 21–32 were tethered to the amino terminus of residues 3–181 of mature NS3 protease by a 4-residue linker, GSGS (SEQ ID NO: 21). The complex was overexpressed as a soluble protein in E. coli and purified to homogeneity by a combination of metal chelate and size-exclusion chromatography. The tethered complex, HIS-NS4A$_{21-32}$-GSGS-NS3$_{3-181}$ (SEQ ID NO: 1) cleaved a NS5A/5B synthetic substrate with a catalytic efficiency identical to that of the non-covalent full-length protease, NS3$_{1-631}$-NS4A$_{1-54}$.

In other embodiments of the invention, the NS4A hydrophobic domain and the NS3 serine protease domain are covalently tethered using different amino acid linkers. The preferred amino acid linkers of the invention comprise at least about four amino acid residues. More preferably, the linkers consist of from four to six amino acid residues. More preferably, four-residue linkers are used. Most preferably, amino acid linkers having the sequence defined by SEQ ID NO: 21 or 22 are used to tether the NS4A hydrophobic domain and the NS3 serine protease domain.

Routine procedures in the art would allow one to construct covalent NS4A-NS3 complexes of the invention having linkers of various sizes. It will be understood by one skilled in the art, for example, that if smaller or larger portions of the NS3 or NS4A domains are used to construct the covalent complexes of the invention, longer or shorter amino acid linkers can be used.

Other embodiments of the present invention contain smaller or larger portions of the NS4A cofactor peptide. In preferred embodiments, the complexes contain an NS4A hydrophobic domain comprising at least amino acid residues 22–30 of the full length NS4A cofactor peptide. More preferably, the complexes contain from 12–19 amino acid residues spanning the central hydrophobic domain of the full length NS4A peptide. Most preferably, the complexes contain amino acid residues 21–32 of full length NS4A peptide.

Still further embodiments of the present invention contain smaller or larger portions of the NS3 protease. In preferred embodiments, the complexes contain an NS3 serine protease domain comprising at least amino acid residues 3–181 of the full length NS3 protease. More preferably, the complexes contain amino acid residues 1–181 of full length NS3 protease. Most preferably, the complexes contain amino acid residues 3–181 of full length NS3 protease.

The present invention thus also includes covalent NS4A-NS3 complexes comprising the central hydrophobic domain of the NS4A peptide tethered to the amino terminus of full-length mature NS3 protease (amino acids 1–631) by an amino acid linker. The amino acid sequences of preferred embodiments comprising NS4A tethered to full-length mature NS3 protease are set forth in SEQ ID NOs: 11–18.

Surprisingly, it has also been found that the introduction of point mutations at position 17 and/or 18 of the NS3 domain of the NS4A-NS3 constructs of the present invention which change a hydrophobic amino acid residue to a hydrophilic amino acid residue produces a more soluble and mono-dispersed form of the tethered complex. Thirteen representative embodiments of such mutant NS4A-NS3 complexes are disclosed in the Examples below. In some embodiments, the isoleucine at position 17 is mutated to lysine. One such mutant form is referred to as His-NS4A$_{21-32}$-GSGS-NS3$_{3-181}$/I17K (SEQ ID NO: 2). In other embodiments, the same mutation is made at position 18. One such mutant form is referred to as His-NS4A$_{21-32}$-GSGS-NS3$_{3-181}$/I18K (SEQ ID NO: 3). In yet other embodiments, the mutations are introduced at both positions. One such mutant is referred to as His-NS4A$_{21-32}$-GSGS-NS3$_{3-181}$/I17K,I18K (SEQ ID NO: 4). Each of the purified mutants results in a monodispersed (as judged by size exclusion chromatography) and more soluble (as judged by achieving higher concentration of the complex 17–20 mg/ml) form of the complex, which remains monodispersed for a period of about one week at 4° C., while still exhibiting kinetic properties identical to those of the wild type.

It will be understood that although the foregoing embodiments are presently preferred, other modifications to the hydrophobic residues at positions 17 and 18 can be made to produce other soluble complexes. Preferably, neutral amino acid residues will be substituted for charged residues. These modifications can be used in a number of combinations to produce the final modified protein chain.

Also provided are NS4A-tethered forms of NS3 full-length domain. In contrast to the NS4A-tethered forms of the catalytic domain, a considerable amount of autocleavage in the helicase domain of the NS3 protein is detected during the purification of their native full-length counterpart, HIS-NS4A$_{21-32}$-NS3$_{3-631}$. To prevent autocleavage of the full-length covalent complexes, the catalytic serine residue at position 139 is mutated to alanine. The amino acid sequence of one such embodiment is defined by SEQ ID NO: 15. The mutation of the full length constructs at position 139 can also be made in the NS4A-tethered forms of the NS3 catalytic domain, and can be made in combination with any of the aforementioned mutations to increase solubility and stability while preventing autocleavage. Representative embodiments are set forth in SEQ ID NOs: 5–8, 15–18 and 20.

As used herein, the terms "native NS3" and "full-length NS3" are used interchangeably and are defined as a protein which (a) has an amino acid sequence substantially identical to the sequence defined by SEQ ID NO: 23 and (b) has biological activity that is common to native NS3. This includes natural allelic variants and other variants having one or more conservative amino acid substitutions [Grantham, 1974, Science 185:862] that do not substantially impair biological activity. Such conservative substitutions involve groups of synonymous amino acids, e.g., as described in U.S. Pat. No. 5,017,691 to Lee et al.

The "serine protease domain" of NS3 or the "catalytic domain" of NS3 refers to amino acids 1–181 of mature NS3, which have been shown to contain the active catalytic triad His, Asp and Ser.

The term "native NS4A peptide" as used herein is defined as a peptide which (a) has an amino acid sequence substantially identical to the sequence defined by SEQ ID NO: 24; and (b) has biological activity that is common to native NS4A. This includes natural allelic variants and other variants having one or more conservative amino acid substitution [Grantham, 1974, Science 185:862] that do not substantially impair biological activity. Such conservative substitutions involve groups of synonymous amino acids, e.g., as described in U.S. Pat. No. 5,017,691 to Lee et al.

As used herein, the "central hydrophobic domain of NS4A peptide" refers to that portion of the native NS4A peptide (approximately amino acid residues 22–30) which is sufficient for activation of NS3 protease. Size and sequence variants of this domain which also activate the NS3 protease in the claimed complexes also fall within this term.

A "soluble" covalent complex as referred to herein is defined as a protein which will remain in solution after a high spin centrifugation step at 300,000×g in a standard ultracentrifuge in a buffer containing 25 mM HEPES, pH 7.6, 10% glycerol, 0.3 M NaCl, 10 mM βME.

An "active" covalent complex as referred to herein is defined as a complex which will cleave synthetic substrates corresponding to NS5A-NS5B cleavage site (for example, DTEDVVCC SMYTWTGK) (SEQ ID NO: 25)) between P1 residue, cysteine and P1' residue, serine in a buffer containing 25 mM Tris, pH 7.5, 150 mM NaCl, 10% glycerol, and 0.05% lauryl maltoside.

Nucleic acids encoding the covalent NS4A-NS3 complexes are also a part of this invention. DNA encoding the covalent NS4A-NS3 complexes of this invention can be prepared by chemical synthesis using the known nucleic acid sequence [Ratner et al., 1985, Nucleic Acids Res. 13:5007] and standard methods such as the phosphoramidite solid support method of Matteucci et al., 1981, J. Am. Chem. Soc. 103:3185 or the method of Yoo et al., 1989, J. Biol. Chem. 764:17078. See also Glick, Bernard R. and Pasternak, Molecular Biotechnology, pages 55–63, (ASM Press, Washington, D.C. 1994). The genes encoding the desired regions of the HCV protein can also be obtained using the plasmid disclosed in Grakoui, et al., 1993, J. Virol. 67:1385–1395 or that disclosed in Takamizawa et al., 1991, J. Virology 65(3):1105–1113. Also, the nucleic acid encoding HCV NS3 and NS4A can be isolated, amplified and cloned from patients infected with the HCV virus. Furthermore, the HCV genome has been disclosed in PCT WO 89/04669 and is available from the American Type Culture Collection (ATCC), 12301 Parklawn Drive, Rockville, Md. under ATCC accession no. 40394.

Of course, because of the degeneracy of the genetic code, there are many functionally equivalent nucleic acid sequences that can encode the NS3 and NS4A domains of the covalent NS4A-NS3 complexes as defined herein. Such functionally equivalent sequences, which can readily be prepared using known methods such as chemical synthesis, PCR employing modified primers and site-directed mutagenesis, are within the scope of this invention.

Various vectors can be used to express DNA encoding the covalent NS4A-NS3 complexes. Conventional vectors used for expression of recombinant proteins in prokaryotic or eukaryotic cells may be used. Preferred vectors include the pET vectors described by Studier et al, 1990, *Methods of Enzymology* 185: 60–89, and the pcD vectors described by Okayama et al., 1983, *Mol. Cell. Bio.* 3: 280–289; and Takebe et al., 1988, *Mol. Cell. Biol.* 8: 466–472. Other SV40-based mammalian expression vectors include those disclosed in Kaufman et al., 1982, *Mol. Cell. Biol.* 2:1304–1319 and U.S. Pat. No. 4,675,285. These SV40-based vectors are particularly useful in COS7 monkey cells (ATCC No. CRL 1651), as well as in other mammalian cells such as mouse L cells and CHO cells.

Standard transfection methods can be used to produce eukaryotic cell lines which express large quantities of polypeptides. Eukaryotic cell lines include mammalian, yeast and insect cell lines. Exemplary mammalian cell lines include COS-7 cells, mouse L cells and Chinese Hamster Ovary (CHO) cells. See Sambrook et al., supra and Ausubel et al., supra.

As used herein, the term "transformed bacteria" means bacteria that have been genetically engineered to produce a viral or mammalian protein. Such genetic engineering usually entails the introduction of an expression vector into a bacterium. The expression vector is capable of autonomous replication and protein expression relative to genes in the bacterial genome. Construction of bacterial expression vectors is well known in the art, provided the nucleotide sequence encoding a desired protein is known or otherwise ascertainable. For example, DeBoer in U.S. Pat. No. 4,551,433 discloses promoters for use in bacterial expression vectors; Goeddel et al. in U.S. Pat. No. 4,601,980 and Riggs, in U.S. Pat. No. 4,431,739 disclose the production of mammalian proteins by *E. coli* expression systems; and Riggs supra, Ferretti et al., 1986, *Proc. Natl. Acad. Sci.* 83:599, Sproat et al., 1985, *Nucleic Acid Research* 13:2959 and Mullenbach et al., 1986, *J. Biol. Chem* 261:719 disclose how to construct synthetic genes for expression in bacteria. Many bacterial expression vectors are available commercially and through the American Type Culture Collection (ATCC), Rockville, Md.

Insertion of DNA encoding the covalent NS4A-NS3 complexes into a vector is easily accomplished when the termini of both the DNA and the vector comprise the same restriction site. If this is not the case, it may be necessary to modify the termini of the DNA and/or vector by digesting back single-stranded DNA overhangs generated by restriction endonuclease cleavage to produce blunt ends, or to achieve the same result by filling in the single-stranded termini with an appropriate DNA polymerase.

Alternatively, any site desired may be produced by ligating nucleotide sequences (linkers) onto the termini. Such linkers may comprise specific oligonucleotide sequences that define desired restriction sites. The cleaved vector and the DNA fragments may also be modified if required by homopolymeric tailing.

Many *E. coli*-compatible expression vectors can be used to produce soluble covalent NS4A-NS3 complexes of the present invention, including but not limited to vectors containing bacterial or bacteriophage promoters such as the Tac, Lac, Trp, LacUV5, $\lambda$ $P_r$ and $\lambda$ $P_L$ promoters. Preferably, a vector selected will have expression control sequences that permit regulation of the rate of expression. Then, production of covalent NS4A-NS3 complexes can be regulated to avoid overproduction that could prove toxic to the host cells. Most preferred is a vector comprising, from 5' to 3' (upstream to downstream), a Tac promoter, a lac Iq repressor gene and DNA encoding mature human HCV protease. The vectors chosen for use in this invention may also encode secretory leaders such as the ompA or protein A leader, as long as such leaders are cleaved during post-translational processing to produce covalent NS4A-NS3 complexes or if the leaders are not cleaved, the leaders do not interfere with the enzymatic activity of the protease.

The covalent complexes of the invention, or portions thereof, can also be synthesized by a suitable method such as by exclusive solid phase synthesis, partial solid phase methods, fragment condensation or classical solution synthesis. The polypeptides are preferably prepared by solid phase peptide synthesis as described by Merrifield, 1963, *J. Am. Chem. Soc.* 85:2149. The synthesis is carried out with amino acids that are protected at the alpha-amino terminus. Trifunctional amino acids with labile side-chains are also protected with suitable groups to prevent undesired chemical reactions from occurring during the assembly of the polypeptides. The alpha-amino protecting group is selectively removed to allow subsequent reaction to take place at the amino-terminus. The conditions for the removal of the alpha-amino protecting group do not remove the side-chain protecting groups.

The alpha-amino protecting groups are those known to be useful in the art of stepwise polypeptide synthesis. Included are acyl type protecting groups (e.g., formyl, trifluoroacetyl, acetyl), aryl type protecting groups (e.g., biotinyl), aromatic urethane type protecting groups [e.g., benzyloxycarbonyl (Cbz), substituted benzyloxycarbonyl and 9-fluorenylmethyloxy-carbonyl (Fmoc)], aliphatic urethane protecting groups [e.g., t-butyloxycarbonyl (tBoc), isopropyloxycarbonyl, cyclohexyloxycarbonyl] and alkyl type protecting groups (e.g., benzyl, triphenylmethyl). The preferred protecting groups are tBoc and Fmoc, thus the peptides are said to be synthesized by tBoc and Fmoc chemistry, respectively.

The side-chain protecting groups selected must remain intact during coupling and not be removed during the deprotection of the amino-terminus protecting group or during coupling conditions. The side-chain protecting groups must also be removable upon the completion of synthesis, using reaction conditions that will not alter the finished polypeptide. In tBoc chemistry, the side-chain protecting groups for trifunctional amino acids are mostly benzyl based. In Fmoc chemistry, they are mostly tert.-butyl or trityl based.

In tBoc chemistry, the preferred side-chain protecting groups are tosyl for Arg, cyclohexyl for Asp, 4-methylbenzyl (and acetamidomethyl) for Cys, benzyl for Glu, Ser and Thr, benzyloxymethyl (and dinitrophenyl) for His, 2-Cl-benzyloxycarbonyl for Lys, formyl for Trp and 2-bromobenzyl for Tyr. In Fmoc chemistry, the preferred side-chain protecting groups are 2,2,5,7,8-pentamethylchroman-6-sulfonyl (Pmc) or 2,2,4,6,7-pentamethyldihydrobenzofuran-5-sulfonyl (Pbf for Arg, trityl for Asn, Cys, Gln and His, tert butyl for Asp, Glu, Ser, Thr and Tyr, tBoc for Lys and Trp.

For the synthesis of phosphopeptides, either direct or post-assembly incorporation of the phosphate group is used.

In the direct incorporation strategy, the phosphate group on Ser, Thr or Tyr may be protected by methyl, benzyl or tert.butyl in Fmoc chemistry or by methyl, benzyl or phenyl in tBoc chemistry. Direct incorporation of phosphotyrosine without phosphate protection can also be used in Fmoc chemistry. In the post-assembly incorporation strategy, the unprotected hydroxyl group of Ser, Thr or Tyr is derivatized on solid phase with di-tert.butyl-, dibenzyl- or dimethyl-N, N'-diisopropylphosphoramidite and then oxidized by tert-.butylhydroperoxide.

Solid phase synthesis is usually carried out from the carboxyl-terminus by coupling the alpha-amino protected (side-chain protected) amino acid to a suitable solid support. An ester linkage is formed when the attachment is made to a chloromethyl, chlortrityl or hydroxymethyl resin, and the resulting polypeptide will have a free carboxyl group at the C-terminus. Alternatively, when an amide resin such as benzhydrylamine or p-methylbenzhydrylamine resin (for tBoc chemistry) and Rink amide or PAL resin (for Fmoc chemistry) is used, an amide bond is formed and the resulting polypeptide will have a carboxamide group at the C-terminus. These resins, whether polystyrene- or polyamide-based or polyethyleneglycol-grafted, with or without a handle or linker, with or without the first amino acid attached, are commercially available, and their preparations have been described by Stewart et al (1984)., "Solid Phase Peptide Synthesis" (2nd Edition), Pierce Chemical Co., Rockford, Ill.; and Bayer & Rapp (1986) Chem. Pept. Prot. 3, 3; and Atherton, et al. (1989) Solid Phase Peptide Synthesis: A Practical Approach, IRL Press, Oxford.

The C-terminal amino acid, protected at the side-chain if necessary and at the alpha-amino group, is attached to a hydroxylmethyl resin using various activating agents including dicyclohexylcarbodiimide (DCC'), N,N'-diisopropylcarbodiimide DIPCDI) and carbonyldiimidazole (CDI). It can be attached to chloromethyl or chlorotrityl resin directly in its cesium tetramethylammonium salt form or in the presence of triethylamine (TEA) or diisopropyl-ethylamine (DIEA). First amino acid attachment to an amide resin is the same as amide bond formation during coupling reactions.

Following the attachment to the resin support, the alpha-amino protecting group is removed using various reagents depending on the protecting chemistry (e.g., tBoc, Fmoc). The extent of Fmoc removal can be monitored at 300–320 nm or by a conductivity cell. After removal of the alpha-amino protecting group, the remaining protected amino acids are coupled stepwise in the required order to obtain the desired sequence.

Various activating agents can be used for the coupling reactions including DCC, DIPCDI, 2-chloro-1,3-dimethylimidium hexafluorophosphate (CIP), benzotriazol-1-yl-oxy-tris-(dimethylamino)-phosphonium hexafluoro-phosphate (BOP) and its pyrrolidine analog (PyBOP), bromo-tris-pyrrolidino-phosphonium hexafluorophosphate (PyBroP), O-(benzotriazol-1-yl)-1,1,3,3-tetramethyluronium hexafluorophosphate (HBTU) and its tetrafluoroborate analog (TBTU) or its pyrrolidine analog (HBPyU), O-(7-azabenzotriazol-1-yl)-1,1,3,3-tetramethyluronium hexafluorophosphate (HATU) and its tetrafluoroborate analog (TATU) or pyrrolidine analog (HAPyU). The most common catalytic additives used in coupling reactions include 4-dimethylaminopyridine (DMAP), 3-hydroxy-3,4-dihydro-4-oxo-1,2,3-benzotriazine (HODhbt), N-hydroxybenzotriazole (HOBt) and 1-hydroxy-7-azabenzotriazole (HOAt). Each protected amino acid is used in excess (>2.0 equivalents), and the couplings are usually carried out in N-methylpyrrolidone (NMP) or in DMF, $CH_2Cl_2$ or mixtures thereof. The extent of completion of the coupling reaction can be monitored at each stage, e.g., by the ninhydrin reaction as described by Kaiser et al., Anal. Biochem. 34:595 (1970). In cases where incomplete coupling is found, the coupling reaction is extended and repeated and may have chaotropic salts added. The coupling reactions can be performed automatically with commercially available instruments such as ABI model 430A, 431A and 433A peptide synthesizers.

After the entire assembly of the desired polypeptide, the polypeptide-resin is cleaved with a reagent with proper scavengers. The Fmoc peptides are usually cleaved and deprotected by TFA with scavengers (e.g., $H_2O$, ethanedithiol, phenol and thioanisole). The tBoc peptides are usually cleaved and deprotected with liquid HF for 1–2 hours at −5 to 0° C., which cleaves the polypeptide from the resin and removes most of the side-chain protecting groups. Scavengers such as anisole, dimethylsulfide and p-thiocresol are usually used with the liquid HF to prevent cations formed during the cleavage from alkylating and acylating the amino acid residues present in the polypeptide. The formyl group of Trp and dinitrophenyl group of His need to be removed, respectively, by piperidine and thiophenol in DMF prior to the HF cleavage. The acetamidomethyl group of Cys can be removed by mercury (II) acetate and alternatively by iodine, thallium (III) trifluoroacetate or silver tetrafluoroborate which simultaneously oxidize cysteine to cystine. Other strong acids used for tBoc peptide cleavage and deprotection include trifluoromethanesulfonic acid (TFMSA) and trimethylsilyltrifluoroacetate (TMSOTf).

Recombinant DNA methodology can also be used to prepare the polypeptides. The known genetic code, tailored if desired with known preferred codons for more efficient expression in a given host organism, can be used to synthesize oligonucleotides encoding the desired amino acid sequences. The phosphoramidite solid support method of Matteucci et al., J. Am. Chem. Soc. 103:3185 (1981) or other known methods can be used for such syntheses. The resulting oligonucleotides can be inserted into an appropriate vector and expressed in a compatible host organism.

The polypeptides of the invention can be purified using HPLC, gel filtration, ion exchange and partition chromatography, countercurrent distribution or other well known methods. In a preferred embodiment of the present invention the covalent NS4A-NS3 complexes also contain a histidine tag which facilitates purification using a $Ni^+$ column as is illustrated below.

One can use the covalent NS4A-NS3 complexes of the invention, along with known synthetic substrates, to develop high throughput assays. These can be used to screen for compounds which inhibit proteolytic activity of the protease. This is carried out by developing techniques for determining whether or not a compound will inhibit the covalent NS4A-NS3 complexes of the invention from cleaving the viral substrates. Examples of such synthetic substrates are set forth in SEQ ID NOs 25 and 93. If the substrates are not cleaved, the virus cannot replicate. One example of such a high throughput assay is the scintillation proximity assay (SPA). SPA technology involves the use of beads coated with scintillant. Bound to the beads are acceptor molecules such as antibodies, receptors or enzyme substrates which interact with ligands or enzymes in a reversible manner.

For a typical protease assay the substrate peptide is biotinylated at one end and the other end is radiolabelled with low energy emitters such as $^{125}$I or $^3$H. The labeled substrate is then incubated with the enzyme. Avidin coated SPA beads are then added which bind to the biotin. When the substrate peptide is cleaved by the protease, the radioactive emitter is no longer in proximity to the scintillant bead and no light emission takes place. Inhibitors of the protease will leave the substrate intact and can be identified by the resulting light emission which takes place in their presence.

Another type of protease assay, utilizes the phenomenon of surface plasmon resonance (SPR). A novel, high throughput enzymatic assay utilizing surface plasmon resonance technology has been successfully developed. Using this assay, and a dedicated BIAcore™ instrument, at least 1000 samples per week can be screened for either their enzymatic activity or their inhibitory effects toward the enzymatic activity, in a 96 well plate format. This methodology is readily adaptable to any enzyme-substrate reaction. The advantage of this assay over the SPA assay is that it does not require a radiolabeled peptide substrate.

EXAMPLES

Several covalent NS4A-NS3 complexes have been constructed, purified, characterized and assayed for activity based on a cDNA clone containing an HCV Japanese (1b/BK) strain whose sequence is published in Takamizawa et al., 1991, *J. Virology* 65:1105–1113. DNA sequencing of the clone (BK 138-1) revealed four amino acid differences with the published sequence, at positions 66 (A->G), 86 (P->Q), 87 (K->A) and 147 (F->S) of the NS3 protein.

The present invention can be illustrated by the following non-limiting examples.

Reagents and General Methods

Plasmid pHCV-1b/BK can be derived from DNA fragments containing the entire DNA sequence of HCV BK cDNA as reported by Takamizawa et al., 1991, *J. Virology* 65:1105–1113, with the above-mentioned changes. Plasmid pMD-34-2 is derived from that portion of the disclosed DNA sequence which encodes NS3 residues 1–631 from HCV BK cDNA.

Restriction Enzymes, Vent Polymerase and ThermoPol buffer were obtained from New England Biolabs (Beverly, Mass.). The QuickChange mutagenesis kit and dNTP's were obtained from Stratagene (LaJolla, Calif.). Ready-to-Go T4 DNA Ligase was obtained from Pharmacia Biotech (Piscataway, N.J.). Oligonucleotide primers were synthesized by Genosys Biotechnologies (Woodland, Tex.). DNA sequencing was performed according to the Sanger-Dideoxy method by Bioserve Biotechnologies (Laurel, Md.). pET vectors and BL21(DE3) cells were obtained from Novagen (Madison, Wis.). PCR reactions were carried out in a Perkin Elmer Cetus, model 480 DNA thermocycler. DH5α cells and TAE buffer were purchased from Gibco, BRL. GTG agarose was purchased from FMC corporation. The Qiaquick gel extraction kit and Qiaquick PCR purification kit were purchased from Qiagen Inc. (Chatsworth, Calif.).

Standard DNA recombinant DNA methods were carried out essentially as described by Sambrook et. al. in "Molecular Cloning: A Laboratory Manual," $2^{nd}$ edition, 1989, Cold Springs Harbor Press, Plainview, N.Y.

Preparation of NS4A-Tethered Forms of HCV NS3 Protease

Native, NS4A-tethered forms of NS3 catalytic domain

Various NS4A-tethered forms of the NS3 catalytic domain were constructed by joining the NS4A peptide GSVVIVGRIILS (NS4A amino acids 21–32) to the amino terminus of NS3 amino acids 3–181 via various three or four residue linkers, and were cloned into the pET-28b+vector.

Single stranded oligonucleotide primers were designed to generate a 616 base pair PCR fragment containing an NdeI site followed by the NS4A peptide, a linker, and amino acids 3–181 of the NS3 catalytic domain at the 5' terminus and a stop codon flanked by an EcoRI site at the 3' terminus. The template used was the sequence disclosed in Takamizawa, et al, 1991, *J. Virology* 65(3):1105–1113, which contains the entire HCV genome from the 1b/BK strain, except for the four differences described above. Other sources for HCV DNA can be used in the disclosed methods, including plasmid pBRTM/HCV 1-3011 (Grakoui et al., 1993), which contains the entire genome from the 1a strain.

Vent DNA polymerase was utilized to amplify the DNA by PCR. Primers were diluted in $dH_2O$ to give a final concentration of 50 µg/ml. The template was diluted in $dH_2O$ to give a final concentration of 10 ng/µl; The dNTP's (GTP, ATP, CTP, GGT) were diluted to a concentration of 10 mM (2.5 mM each) in $dH_2O$.

100 µl reactions were prepared for PCR in a 500 µl Eppendorf tube by addition of the following reagents: 74 µl of dH20, 10 µl of the 10×Thermopol buffer (final 1×buffer: 10 mM KCL, 20 mMTris-HCL (pH 8.8), 2 mM $MgSO_4$ and 0.1% Triton X), 10 µl of template (100 µg), 2 µl of the 5' primer (100 µg); 1 µl of the 3' primer (50 µg), 2 µl of the dNTP mixture (200 µM) and 1 µl of Vent polymerase enzyme (1 unit). The mixture was then overlayed with 20 ul of immersion oil and placed in the thermocycler for amplification. The PCR conditions were as follows: 95° C. for 45 seconds (1 cycle); 95° C. for 30 seconds, 55° C. for 1 minute, 72° C. for 2 minutes (25 cycles).

The amplified 616 base pair fragment was purified in preparation for restriction digestion using a Qiaquick PCR purification kit according to the manufacturer's protocol without modification. Briefly, the aqueous layer was removed and placed in a 1.5 ml Eppendorf tube with a regent that aids the DNA to bind to a column matrix. The DNA was washed while bound to the column and then eluted with 43 µl of H20. The DNA was then double digested with EcoRI and NdeI in a 50 µl volume for 1 hour at 37° C. The reaction took place in a 1.5 ml polypropylene Eppendorf tube with 5 µl of 10×EcoRI buffer (final concentration of 50 mM NaCl, 100 mM Tris-HCL, 10 mM $MgCl_2$, 0.25% Triton X-100, pH 7.5) and µl 1 of EcoRI and NdeI (20 units). The pET-28b+ vector (3 µg) was also digested using the same conditions. The digests were further purified by resolving them on a 1.0% agarose electrophoresis gel for 45 minutes under 100 volts. They were rendered visible with 0.5 µg/ml of ethidium bromide, excised with a scalpel under short-wave UV, solubilized and purified using the QIAquick gel extraction kit according to manufacturer's protocol without modifications. The fragments were quantitated by visually comparing a 5 ul aliquot of the purified fragment versus Lambda Hind/III DNA standards on a 1% agarose gel. Approximately 200 ng of vector and 50 ng of PCR fragment were ligated together in a 20 ul volume for 18 hours at 16 degrees. They were combined together in a T4 ligase (Ready-to-Go) reaction tube according to standard protocol without modifications.

2 µl of this mixture was then used to transform 50 µl of DH5α cells for plasmid propagation according to manufacturer's protocol. Briefly, a 1.5 ml Eppendorf tube was placed on ice and 50 ul of DH5α cells (previously stored at −80° C. and then thawed on ice immediately prior to use) were added to the tube along with the 2 ul of ligation mixture and allowed to incubate for 30 minutes. They were then heat shocked for 1 minute at 42° C., returned to the ice for 2 minutes and then regenerated with 500 μl of SOC medium and incubated at 37° C. for 1 hour at 300 rpm.

200 μl of these cells were then plated out on LB/20-10-5 agar (per liter: tryptone 50 grams, yeast extract 25 grams, NaCl 12.5 gram) with kanamycin (25 μg/ml), spread for single colony isolation and incubated at 37° C. overnight. Three single colonies were selected for plasmid preparations. They were inoculated into 100 mls of LB/20-10-5 broth with kanamycin (25 μg/ml) in a 250 ml baffled flask and grown overnight for 18 hours at 37 degrees at 300 RPM in a shaker. The next day, the cultures were spun down in 500 ml Nalgene centrifuge bottles (8000 RPM, 10 minutes, 4° C.) and the pellet was harvested for plasmid isolation. The Qiagen midi-prep kit was used according to manufacturer's protocol. The DNA was quantitated using a UV/VIS spectrophotometer (Perkin-Elmers) at 260 nm. The purified, plasmid-DNA isolates were sequenced on an Applied Biosystems 373A DNA sequencer at Bioserve Biotechnologies, Inc. To confirm the sequence, both top and bottom strands were sequenced via primers that were synthesized by Bioserve Biotechnologies.

Native, NS4A-tethered forms of NS3 full-length domain

Both parental plasmids, HIS-NS4A$_{21-32}$-GSGS-NS3$_{3-63}$, and HIS-NS4A$_{21-32}$-GSGS-NS3$_{3-631}$/S139A parental plasmids were created via a cut and paste method. Briefly, 5 μl of plasmid PMD34-2 (1 μg), plasmid HIS-NS4A$_{21-32}$-GSGS-NS3$_{3-181}$ (5 μg) and plasmid HIS-NS3$_{1-631}$/S139A (1μg) were each digested separately in a 1.5 ml Eppendorf tube with 5 μl of NEB buffer #2 (at final concentration of 10 mM Tris-HCL, 10 mM MgCl$_2$, 50 mM NaCl, 1 mM DTT, pH 7.9), 0.5 μl of acetylated BSA (final concentration 100 μg/ml), 1 μl of XbaI (2 Units) and 38.5 μl of ddH$_2$O.

These digests were incubated at 37° C. for one hour at which time 2.5 μl of 2M NaCl (final concentration of 150 mM) 45 μl of ddH$_2$O and 2.5 μl of BspMI (2 Units) were added to the digests and incubated for 2 more hours at 37° C. The double digests were then resolved on 0.8% agarose gels and the size and quantity of the fragments were determined. The agarose gels were electorphoresed in BioRad apparatus and the fragments were excised using a scalpel. The excised backbone fragments which were derived from PMD34-2 and HIS-NS3$_{1-631}$/S139A were each 7.1 KB and the insert from HIS-NS4A$_{21-32}$-GSGS-NS3$_{3-181}$ was 275 base pairs. Approximately 2 μl of 7.1 KB backbone (200 ng) and 1 μl of 225 bp insert (50 ng) were ligated together in a 20 μl volume for 18 hours at 16° C. They were combined together in a T4 ligase (Ready-to-Go) reaction tube according to standard protocol without modifications. 2 μl of this mixture was then used to transform 50 μl of DH5α cells for plasmid propagation according to manufacturer's protocol.

Three single colonies of each construct were selected for miniprep plasmid isolations using a Qiagen miniprep kit. They were inoculated into 5 mls of LB/20-10-5 broth with ampicillin (100 μg/ml) in a 15 ml tubes and grown overnight for 18 hours at 37° C. at 300 RPM in a shaker. The next day, the cultures were spun down 3000 RPM, 10 minutes, 4° C. and the pellet was harvested for plasmid isolation. The clones were then assessed for recombination by digesting with BspMI and Xba1 according to the conditions described above. The digests were resolved on a 1% agarose gel and only those constructs yielding a 225 bp and 7.1 KB bp fragment were chosen as positives. Cultures from the positive clones were inoculated into 100 mls of LB/20-10-5 broth with ampicillin (100 ug/ml) in a 250 ml baffled flask and grown overnight for 18 hours at 37° C. at 300 RPM in a shaker. The next day, the cultures were spun down in 500 ml Nalgene centrifuge bottles (8000 RPM, 10 minutes, 4° C.) and the pellet was harvested for plasmid isolation. The Qiagen midi-prep kit was used according to manufacturer's protocol. The DNA was quantitated using a UV/VIS spectrophotometer (Perkin-Elmers) at 260 nm. The purified plasmid-DNA isolates were sequenced at the restriction site junctions on an Applied Biosystems 373A DNA sequencer at Bioserve Biotechnologies, Inc.

Site-directed Mutants.

All site-directed mutations created in either NS4A-tethered forms of catalytic or full-length domain of NS3 protease were carried out using the quikchange site-directed mutagenesis kit (Stratagene) according to the manufacturer's protocol. For each mutation, two oligonucleotide primers (10 picomoles each) containing the desired mutation were used to amplify the entire plasmid encompassing the NS4A-tethered NS3 protease gene (50 or 100 ng/reaction) using pfu DNA polymerase (2.5 units/reaction) in a final reaction volume of 50 μl. The PCR conditions were as follows: 95° C. for 45 seconds (1 cycle); 95° C. for 30 seconds, 55° C. for 1 minute, 68° C. for 15 minutes (16 cycles). After amplification, the reaction mixture was treated with 1 ul of DpnI (1 Unit) for 1 hour at 37° C. in order to digest the parental DNA.

One microliter of this digest was used to transform 50 μl of XLI Blue cells to repair nicks and propagate the mutated plasmid. Plasmid-DNA were purified and transformed into BL21 (DE3) cells for expression studies.

EXAMPLE 1

NS3 Catalytic Domain Constructs i. HIS-NS4A$_{21-32}$-GSGS-NS3$_{3-181}$ (SEQ ID NO: 1)

HIS-NS4A$_{21-32}$-GSGS-NS3$_{3-181}$ was constructed by joining amino acids 21–32 of the NS4A peptide to the N-terminal domain of NS3 protease (NS3 amino acids 3–181) via the linker GSGS (SEQ ID NO: 21), and was cloned into the pET-28b+ vector as described above. The 5' primer reads as follows:

5' GATATACATATGGGTTCTGTTGTTAT-TGTTGGTAGAATTATTTTATCT GGTAGTGGTAG-TATCACGGCCTACTCCCAA 3' (SEQ ID NO:26).

The 3' primer reads as follows:

5° CTCAGCGAATTCTCAAGACCGCATAG-TAGTTTCCAT 3' (SEQ ID NO:27).

ii. HIS-NS4A$_{21-32}$-GSGS-NS3$_{3-181}$/I17K (SEQ ID NO: 2)

A single amino acid mutant of HIS-NS4A$_{21-32}$-GSGS-NS3$_{3-181}$ was constructed by creating a point mutation at position 17 of the NS3 domain of HIS-NS4A$_{21-32}$-GSGS-NS3$_{3-181}$ construct as described above. Two oligonucleotide primers, each complementary to opposite strands of the template were generated which contain the point mutation which alters amino acid number 17 (isoleucine) to a lysine. The top strand primer was as follows:

5' CGGGGCCTACTTGGTFGCAAGATCAC-TAGCCTTACAGGC 3' (SEQ ID NO:28).

The bottom strand read as follows:

5' GCCTGTAAGGCTAGTGATCTTGCAAC-CAAGTAGGCCCCG 3' (SEQ ID NO: 29).

The template, HIS-NS4A$_{21-32}$-GSGS-NS3$_{3-181}$ along with these two primers, were utilized in a PCR reaction to generate the point mutation.

(iii) HIS-NS4A$_{21-32}$-GSGS-NS3$_{3-181}$/I18K (SEQ ID NO: 3)

A single amino acid mutant of HIS-NS4A$_{21-32}$-GSGS-NS3$_{3-181}$ was constructed by creating a point mutation at position 18 of the NS3 domain of HIS-NS4A$_{21-32}$-GSGS- NS3$_{3-181}$ construct as described above. Two oligonucleotide primers, each complementary to opposite strands of the template, were generated which contain the point mutation which alters amino acid number 18 (isoleucine) to a lysine. The top strand primer was as follows:

5° CGGGGCCTACTFGGTTGCATCAAGAC-TAGCCTTACAGGC 3' (SEQ ID NO: 30).

The bottom strand reads as follows:

5' GCCTGTAAGGCTAGTCTTGATGCAAC-CAAGTAGGCCCCG 3' (SEQ ID NO: 31).

The template, HIS-NS4A$_{21-32}$-GSGS-NS3$_{3-181}$, along with these two primers was utilized in a PCR reaction to generate the point mutation.

(iv) HIS-NS4A$_{21-32}$-GSGS-NS3$_{3-181}$/I17K, I18K (SEQ ID NO: 4)

A single amino acid mutant of HIS-NS4A$_{21-32}$-GSGS-NS3$_{3-181}$/I18K was constructed by creating a point mutation at position 17 of the NS3 domain of HIS-NS4A$_{21-32}$-GSGS-NS3$_{3-181}$/I18K construct as described above. Two oligonucleotide primers, each complementary to opposite strands of the template, were generated which contain the point mutation which alters amino acid number 18 (isoleucine) to a lysine. The top strand primer was as follows:

5' CGGGGCCTACTTGGTTGCAAGAAGAC-TAGCCTTACAGGC 3' (SEQ ID NO:32).

The bottom strand read as follows:

5'GCCTGTAAGGCTAGTCTTCTTGCAAC-CAAGTAGGCCCCG 3'. (SEQ ID NO:33).

The template HIS-NS4A$_{21-32}$-GSGS-NS3$_{3-181}$/I18K, along with these two primers, was utilized in a PCR reaction to generate the point mutation.

v. HIS-NS4A$_{21-32}$-GSGS-NS3$_{3-181}$/S139A (SEQ ID NO: 5)

A single amino acid mutant of HIS-NS4A$_{21-32}$-GSGS-NS3$_{3-181}$ was constructed by creating a point mutation at position 139 of the NS3 domain of HIS-NS4A$_{21-32}$-GSGS-NS3$_{3-181}$ construct as described above. Two oligonucleotide primers, each complementary to opposite strands of the template, were generated which contain the point mutation which alters amino acid number 139 (catalytic serine) to an alanine. The top strand primer was as follows:

5' CTCCTACTTGAAGGGCTCTGCTGGTG-GTCCACTGCTCTGC 3' (SEQ ID NO:34).

The bottom strand reads as follows:

5'GCAGAGCAGTGGACCACCAGCAGAGC-CCTTCAAGTAGGAG 3' (SEQ ID NO:35).

The template HIS-NS4A$_{21-32}$-GSGS-NS3$_{3-181}$, along with these two primers, was utilized in a PCR reaction to generate the point mutation.

vi. HIS-NS4A$_{21-32}$-GSGS-NS3$_{3-181}$/S139A, I17K (SEQ ID NO: 6)

A single amino acid mutant of HIS-NS4A$_{21-32}$-GSGS-NS3$_{3-181}$/S139A was constructed by creating a point mutation at position 17 of the NS3 domain of HIS-NS4A$_{21-32}$-GSGS-NS3$_{3-181}$/S139A construct as described above. Two oligonucleotide primers, each complementary to opposite strands of the template, were generated which contain the point mutation which alters amino acid number 17 (isoleucine) to a lysine. The top strand primer was as follows:

5' CGGGGCCTACTTGGTTGCAAGATCAC-TAGCCTTACAGGC 3' (SEQ ID NO:36).

The bottom strand reads as follows:

5'GCCTGTAAGGCTAGTGATCTTGCAAC-CAAGTAGGCCCCG 3' (SEQ ID NO:37).

The template, HIS-NS4A$_{21-32}$-GSGS-NS3$_{3-181}$/S139A, along with these two primers, was utilized in a PCR reaction to generate this point mutation.

vii. HIS-NS4A$_{21-32}$-GSGS-NS3$_{3-181}$/S139A, I18K (SEQ ID NO: 7)

A single amino acid mutant of HIS-NS4A$_{21-32}$-GSGS-NS3$_{3-181}$/S139A was constructed by creating a point mutation at position 18 of the NS3 domain of HIS-NS4A$_{21-32}$-GSGS-NS3$_{3-181}$/S139A construct as described above. Two oligonucleotide primers, each complementary to opposite strands of the template, were generated which contain the point mutation which alters amino acid number 18 (isoleucine) to a lysine. The top strand primer was as follows:

5' CGGGGCCTACTTGGTTGCATCAAGAC-TAGCCTTACAGGC 3' (SEQ ID NO:38).

The bottom strand reads as follows:

5'GCCTGTAAGGCTAGTCTTGATGCAAC-CAAGTAGGCCCCG 3' (SEQ ID NO:39).

The template, HIS-NS4A$_{21-32}$-GSGS-NS3$_{3-181}$/S139A along with these two primers was utilized in a PCR reaction to generate this point mutation.

viii. HIS-NS4A$_{21-32}$-GSGS-NS3$_{3-181}$/S139A, I17K, I18K (SEQ ID NO.8)

A single amino acid mutant of HIS-NS4A$_{21-32}$-GSGS-NS3$_{3-181}$/S139A, I17K was constructed by creating a point mutation at position 18 of the NS3 domain of HIS-NS4A$_{21-32}$-GSGS-NS3$_{3-181}$/S139A,I17K construct as described above. Two oligonucleotide primers, each complementary to opposite strands of the template were generated which contain the point mutation which alters amino acid number 18 (isoleucine) to a lysine. The top strand primer was as follows:

5' CGGGGCCTACTTGGTTGCAAGAAGAC-TAGCCTTACAGGC 3' (SEQ ID NO: 40).

The bottom strand reads as follows:

5'GCCTGTAAGGCTAGTCTTGATGCAAC-CAAGTAGGCCCCG 3' (SEQ ID NO: 41).

The template, HIS-NS4A$_{21-32}$-GSGS-NS3$_{3-181}$/S139A, I17K, along with these two primers, was utilized in a PCR reaction to generate this point mutation.

ix. HIS-NS4A$_{21-32}$-PAGG-NS3$_{3-181}$ (SEQ ID NO: 9)

An NS4A-tethered form of the NS3 catalytic domain, HIS-NS4A$_{21-32}$-PAGG-NS3$_{3-181}$, was constructed by joining the NS4A peptide GSVVIVGRIILS (NS4A amino acids 21–32) to the N-terminal domain of NS3 protease (NS3 amino acids 3–181) via the linker PAGG (SEQ ID NO: 22), and was cloned into the pET-28b+ vector as described above. Primers were designed to generate a 616 base pair PCR fragment containing an NdeI site followed by the NS4A peptide, the PAGG linker, and amino acids 3–181 of the NS3 catalytic domain at the 5' terminus and a stop codon flanked by an EcoRI site at the 3' terminus. The 5' primer reads as follows:

5'GATATACATATGGGTTCTGTTGTTAT-TGTTGGTAGAATTATTTT ATCTCCTGCTGGTGG-TATCACGGCCTACTCCCAA 3' (SEQ ID NO: 42).

The 3' primer reads as follows:

5' CTCAGCGAATTCTCAAGACCGCATAG-TAGTTTCCAT 3' (SEQ ID NO: 43).

Plasmid-DNA (PMD-34-2), comprised of pET-22b+ vector encompassing the gene insert encoding HIS-NS3 (1–631) from 1/BK strain was used as the template for PCR.

x. HIS-NS4A$_{21-32}$-PAGG-NS3$_{3-181}$/I17K (SEQ ID NO: 10)

A single amino acid mutant of HIS-NS4A$_{21-32}$-PAGG-NS3$_{3-181}$ was constructed by creating a point mutation at position 17 of the NS3 domain of the HIS-NS4A$_{21-32}$-PAGG-NS3$_{3-181}$ construct as described above. Two oligonucleotide primers, each complementary to opposite strands of the template, were generated which contain the point mutation which alters amino acid number 17 (isoleucine) to a lysine. The top strand primer was as follows:

5' CGGGGCCTACTTGGTTGCAAGATCAC-TAGCCTTACAGGC 3' (SEQ ID NO: 44).

The bottom strand reads as follows:

5' GCCTGTAAGGCTAGTGATCTTGCAAC-CAAGTAGGCCCCG 3' (SEQ ID NO: 45).

The template, HIS-NS4A$_{21-32}$-PAGG-NS3$_{3-181}$, along with these two primers was utilized in a PCR reaction to generate this point mutation.

xi. HIS-NS4A$_{21-32}$-PAG-NS3$_{3-181}$ (SEQ ID NO: 46)

A NS4A-tethered form of the NS3 catalytic domain, HIS-NS4A$_{21-32}$-PAG-NS3$_{3-181}$, was constructed by joining the NS4A peptide GSVVIVGRIILS (NS4A amino acids 21–32) to the N-terminal domain of NS3 protease (NS3 amino acids 3–181) via the linker PAG (SEQ ID NO: 47), and was cloned into the pET-28b+ vector as described above. Primers were designed to generate a 613 base pair PCR fragment containing an NdeI site followed by the NS4A peptide, the PAG linker, and amino acids 3–181 of the NS3 catalytic domain at the 5' terminus and a stop codon flanked by an EcoRI site at the 3' terminus. The 5' primer reads as follows:

5' GATATACATATGGGTTCTGTTGTTAT-TGTTGGTAGAATTATTTT ATCTCCTGCTGGTAT-CACGGCCTACTCCCAA 3' (SEQ ID NO: 48).

The 3' primer reads as follows:

5' CTCAGCGAATTCTCAAGACCGCATAG-TAGTTTCCAT 3' (SEQ ID NO: 49).

Plasmid-DNA (PMD-34-2), comprised of pET-22b+ vector encompassing the gene insert encoding HIS-NS3 (1–631) from 1b/BK strain was used as the template for PCR.

xii. HIS-NS4A$_{21-32}$-PAG-NS3$_{3-181}$/I17K (SEQ ID NO: 50)

A single amino acid mutant of HIS-NS4A$_{21-32}$-PAG-NS3$_{3-181}$ was constructed by creating a point mutation at position 17 of the NS3 domain of HIS-NS4A$_{21-32}$-PAG-NS3$_{3-181}$ construct as described above. Two oligonucleotide primers, each complementary to opposite strands of the template were generated which contains the point mutation which alters amino acid residue number 17 (isoleucine) to a lysine. The top strand primer was as follows:

5' CGGGGCCTACTTGGTTGCAAGATCAC-TAGCCTTACAGGC 3' (SEQ ID NO: 51).

The bottom strand reads as follows:

5' GCCTGTAAGGCTAGTGATCTTGCAAC-CAAGTAGGCCCCG 3' (SEQ ID NO: 52).

The template, HIS-NS4A$_{21-32}$-PAG-NS3$_{3-118}$ along with these two primers were utilized in a PCR reaction to generate this point mutation.

xiii. HIS-NS4A$_{21-32}$-GGS-NS3$_{3-181}$ (SEQ ID NO: 53)

An NS4A-tethered form of NS3 catalytic domain, HIS-NS4A$_{21-32}$-GGS-NS3$_{3-181}$ was constructed by joining the NS4A peptide GSVVIVGRIILS (NS4A amino acids 21–32) to the N-terminal domain of NS3 protease (NS3 amino acids 3–181) via the linker GGS (SEQ ID NO: 54), and was cloned into the pET-28b+ vector as described above. Primers were designed to generate a 613 base pair PCR fragment containing an NdeI site followed by the NS4A peptide, the GGS linker, and amino acids 3–181 of the NS3 catalytic domain at the 5' terminus and a stop codon flanked by an EcoRI site at the 3' terminus. The 5' primer reads as follows:

5' GATATACATATGGGTTCTGTTGTTAT-TGTTGGTAGAATTATTTT ATCTGGTGGTTCTAT-CACGGCCTACTCCCAA 3' (SEQ ID NO: 55).

The 3' primer reads as follows:

5' CTCAGCGAATTCTCAAGACCGCATAG-TAGTTTCCAT 3' (SEQ ID NO: 56).

Plasmid-DNA (PMD-34-2), comprised of pET-22b+ vector encompassing the gene insert encoding HIS-NS3 (1–631) from 1/BK strain was used as the template for PCR.

xiv. HIS-NS4A$_{21-32}$-GGS-NS3$_{3-181}$/I17K (SEQ ID NO: 57)

A single amino acid mutant of HIS-NS4A$_{21-32}$-GGS-NS3$_{3-181}$ was constructed by creating a point mutation at position 17 of the NS3 domain of HIS-NS4A$_{21-32}$-GGS-NS3$_{3-181}$ construct as described above. Two oligonucleotide primers, each complementary to opposite strands of the template, were generated which contain the point mutation which alters amino acid number 17 (isoleucine) to a lysine. The top strand primer was as follows:

5' CGGGGCCTACTTGGTTGCAAGATCAC-TAGCCTTACAGGC 3' (SEQ ID NO: 58).

The bottom strand reads as follows:

5' GCCTGTAAGGCTAGTGATCTTGCAAC-CAAGTAGGCCCCG 3' (SEQ ID NO: 59).

The template, HIS-NS4A$_{21-32}$-GGS-NS3$_{3-181}$, along with these two primers, was utilized in a PCR reaction to generate this point mutation.

EXAMPLE 2

NS3 Full-Length Constructs i. HIS-NS3$_{1-631}$/I17K (SEQ ID NO: 60)

A single amino acid mutant of HIS-NS31–631 was formed by creating a point mutation at position 17 of NS3 protease using the Plasmid-DNA (PMD-34-2), comprised of pET-22b+ vector encompassing the gene insert, encoding HIS-NS3$_{1-631}$ from 1b/BK strain as described above. Two oligonucleotide internal primers, each complementary to opposite strands of the template, were generated which contain the point mutation which alters amino acid number 17 (isoleucine) to a lysine. The top strand primer was as follows:

5' CGGGGCCTACTTGGTFGCAAGATCAC-TAGCCTTACAGGC 3' (SEQ ID NO: 61).

The bottom strand reads as follows:

5' GCCTGTAAGGCTAGTGATCTTGCAAC-CAAGTAGGCCCCG 3' (SEQ ID NO: 62).

The template, plasmid-DNA (PMD-34-2), comprised of pET-22b+ vector encompassing the gene insert, encoding HIS-NS3$_{1-631}$ from 1b/BK strain, along with these two primers was utilized in a PCR reaction to generate this point mutation.

ii. HIS-NS3$_{1-631}$/I18K (SEQ ID NO: 63)

A single amino acid mutant of HIS-NS3$_{1-631}$ was formed by creating a point mutation at position 18 of NS3 protease using the Plasmid-DNA (PMD-34-2), comprised of pET-22b+ vector encompassing the gene insert, encoding HIS-NS3$_1$-631 from 1/BK strain as described above. Two oligo-nucleotide internal primers, each complementary to opposite strands of the template, were generated which contain the point mutation which alters amino acid number 18 (isoleucine) to a lysine. The top strand primer was as follows:

5' CGGGGCCTACTTGGTTGCATCAAGAC-TAGCCTTACAGGC 3' (SEQ ID NO: 64).

The bottom strand reads as follows:

5' GCCTGTAAGGCTAGTCTTGATGCAAC-CAAGTAGGCCCCG 3' (SEQ ID NO: 65).

The template, plasmid-DNA (PMD-34-2), comprised of pET-22b+ vector encompassing the gene insert, encoding HIS-NS3,–631 from 1b/BK strain along with these two primers was utilized in a PCR reaction to generate this point mutation.

iii. HIS-NS3$_{1-631}$/S139A (SEQ ID NO: 66)

A single amino acid mutant of HIS-NS3$_{1-631}$ was formed by creating a point mutation at position 139 of the NS3 protease using the Plasmid-DNA (PMD-34-2), comprised of pET-22b+ vector encompassing the gene insert, encoding HIS-NS3$_1$631 from 1b/BK strain as described above. Two oligonucleotide internal primers, each complementary to opposite strands of the template, were generated which contain the point mutation which altered amino acid number 139 (catalytic serine) to an alanine. The top strand primer was as follows:

5' CTCCTACTTGAAGGGCTCTGCTGGTG-GTCCACTGCTCTGC 3' (SEQ ID NO: 67).

The bottom strand reads as follows:

5'GCAGAGCAGTGGACCACCAGCAGAGC-CCTTCAAGTAGGAG 3' (SEQ ID NO: 68).

The template, plasmid-DNA (PMD-34-2), comprised of pET-22b+ vector encompassing the gene insert, encoding HIS-NS3$_{1-631}$ from 1b/BKstrain along with these two primers was utilized in a PCR reaction to generate this point mutation.

iv. HIS-NS3$_{1-631}$/I403S (SEQ ID NO: 69)

A single amino acid mutant of HIS-NS31-631 was formed by creating a point mutation at position 403 of the NS3 protease using the Plasmid-DNA (PMD-34-2), comprised of pET-22b+ vector encompassing the gene insert, encoding HIS-NS3$_{1-631}$ from 1b/BKstrain as described above. Two oligonucleotide internal primers, each complementary to opposite strands of the template, were generated which contain the point mutation which alters amino acid number 403 (isoleucine) to a serine. The top strand primer was as follows:

5'GTCCGTCATACCAACTTCCG-GAGACGTCGTTGTCG 3' (SEQ ID NO: 70).

The bottom strand reads as follows:

5' CGACAACGACGTCTCCGGAAGTTGGTAT-GACGGAC 3' (SEQ ID NO: 71).

The template, plasmid-DNA (PMD-34-2), comprised of pET-22b+ vector encompassing the gene insert, encoding HIS-NS3$_{1-631}$ from 1b/BKstrain along with these two primers was utilized in a PCR reaction to generate this point mutation.

v. HIS-NS3$_{1-631}$/NdeI (SEQ ID NO. 72)

A silent mutant of HIS-NS3$_{1-631}$ was formed to eliminate the internal NdeI restriction site within NS3 protease using the Plasmid-DNA (PMD-34-2), comprised of pET-22b+ vector encompassing the gene insert, encoding HIS-NS3$_{1-631}$ from 1b/BKstrain as described above. Two oligonucleotide internal primers, each complementary to opposite strands of the template, were generated which contain point mutations which alters the codons on the reading strand of alanine 217 from GCA to GCC and tyrosine 218 from TAT to TAC. The top strand primer was as follows:

5'ACTAAAGTGCCGGCTGCCTACGCAGC-CCAAGGG 3' (SEQ ID NO: 73).

The bottom strand reads as follows:

5' CCCTTGGGCTGCGTAGGCAGCCG-GCACTTTAGT 3' (SEQ ID NO: 74).

The template, plasmid-DNA (PMD-34-2), comprised of pET-22b+ vector encompassing the gene insert encoding HIS-NS3,–631 from 1b/BKstrain, along with these two primers, was utilized in a PCR reaction to generate this point mutation.

vi. HIS-NS4A$_{21-32}$-GSGS-NS3$_{3-631}$ (SEQ ID NO: 11)

An NS4A-tethered form of the NS3 full-length domain, HIS-NS4A$_{21-32}$-GSGS-NS3$_{3-631}$, was constructed via a cut and paste strategy as described above. Briefly, a 270 bp fragment was generated by restricting HIS-NS4A$_{21-32}$-GSGS-NS3$_{3-181}$ with XbaI/BspMI; This fragment encompassed sequences encoding a histidine tag followed by a thrombin site, the NS4A peptide, GSVVIVGRIILS (NS4A amino acids 21–32), the linker GSGS (SEQ ID NO: 21) and NS3 amino acids 3–48. A second 7111 fragment (7111 bp) was generated by restricting Plasmid-DNA (PMD-34-2), comprised of pET-22b+ vector encompassing the gene insert, encoding HIS-NS3 (1–631) from 1b/BKstrain with XbaI/Bspml resulting in a fragment encompassing the pET 22b+ vector backbone in addition to amino acids 49–631. These two fragments were then ligated together with T4 DNA ligase to form HIS-NS4A$_{21-32}$-GSGS-NS3$_{3-631}$.

vii. HIS-NS4A$_{21-32}$-GSGS-NS3$_{3-631}$/I17K (SEQ ID NO: 12)

A single amino acid mutant of HIS-NS4A$_{21-32}$-GSGS-NS3$_{3-631}$ was constructed by creating a point mutation at position 17 of the NS3 domain of HIS-NS4A$_{21-32}$-GSGS-NS3$_{3-631}$ construct as described above. Two oligonucleotide primers, each complementary to opposite strands of the template, were generated which contain the point mutation which alters amino acid number 17 (isoleucine) to a lysine. The top strand primer was as follows:

5' CGGGGCCTACTTGGTTGCAAGATCAC-TAGCCTTACAGGC 3' (SEQ ID NO: 75).

The bottom strand read as follows:

5'GCCTGTAAGGCTAGTGATCTTGCAAC-CAAGTAGGCCCCG 3' (SEQ ID NO: 76).

The template, HIS-NS4A$_{21-32}$-GSGS-NS3$_{3-631}$ along with these two primers was utilized in a PCR reaction to generate this point mutation.

viii. HIS-NS4A$_{21-32}$-GSGS-NS3$_{3-631}$/I18K (SEQ ID NO: 13)

A single amino acid mutant of HIS-NS4A$_{21-32}$-GSGS-NS3$_{3-631}$ was constructed by creating a point mutation at position 18 of the NS3 domain of HIS-NS4A$_{21-32}$-GSGS-NS3$_{3-631}$ construct as described above. Two oligonucleotide primers, each complementary to opposite strands of the template were generated which contained the point mutation which alters amino acid number 18 (isoleucine) to a lysine. The top strand primer was as follows:

5' CGGGGCCTACTTGGTTGCATCAAGAC-TAGCCTTACAGGC 3' (SEQ ID NO: 77).

The bottom strand reads as follows:

5' GCCTGTAAGGCTAGTCTTGATGCAAC-CAAGTAGGCCCCG 3' (SEQ ID NO: 78).

The template, HIS-NS4A$_{21-32}$-GSGS-NS3$_{3-631}$, along with these two primers was utilized in a PCR reaction to generate this point mutation.

ix. HIS-NS4A$_{21-32}$-GSGS-NS3$_{3-631}$/I17K, I18K (SEQ ID: 14)

A double amino acid mutant of HIS-NS4A$_{21-32}$-GSGS-NS3$_{3-631}$ was constructed by creating 2 point mutations at positions 17 and 18 of the NS3 domain of the HIS-NS4A$_{21-32}$-GSGS-NS3$_{3-631}$ construct simultaneously as described above. Two oligonucleotide primers, each complementary to opposite strands of the template, were generated which contain the point mutations which alter amino acid numbers 17 (isoleucine) and 18 (isoleucine) to lysines. The top strand primer was as follows:

5' CGGGGCCTACTTGGTTGCAAGAAGAC-TAGCCTTACAGGC 3' (SEQ ID NO: 79).

The bottom strand read as follows:

5' GCCTGTAAGGCTAGTCTTCTTGCAAC-CAAGTAGGCCCCG 3' (SEQ ID NO: 80).

The template, HIS-NS4A$_{21-32}$-GSGS-NS3$_{3-631}$, along with these two primers, was utilized in a PCR reaction to generate this point mutation.

x. HIS-NS4A$_{21-32}$-GSGS-NS3$_{3-631}$/S139A (SEQ ID NO: 15)

An NS4A-tethered form of NS3 full-length domain, HIS-NS4A$_{21-32}$-GSGS-NS3$_{3-631}$/S139A, was constructed via a cut and paste strategy as described above. Briefly, a 290 bp fragment was generated by restricting HIS-NS4A$_{21-32}$-GSGS-NS3$_{3-181}$ with XbaI/BspMI; this fragment encompass sequence encoding a histidine tag, a thrombin site, amino acids 21–32 of the the NS4A peptide, the linker GSGS (SEQ ID NO. 21) and NS3 amino acids 3–48. A second 7111 fragment (7111 bp) was generated by restricting HIS-NS3$_{1-631}$/S139A construct with XbaI/BspmI resulting in a fragment encompassing the pET 22b+ vector backbone in addition to amino acids 49–631. These two fragments were then ligated together with T4 DNA ligase to form HIS-NS4A$_{21-32}$-GSGS-NS3$_{3-631}$/S139A.

xi. HIS-NS4A$_{21-32}$-GSGS-NS3$_{3-631}$/S139A, I17K (SEQ ID NO: 16)

A single amino acid mutant of HIS-NS4A$_{21-32}$-GSGS-NS3$_{3-631}$/S139A was constructed by creating a point mutation at position 17 of the NS3 domain of the HIS-NS4A$_2$1-32-GSGS-NS3$_{3-631}$/S139A construct as described above. Two oligonucleotide primers, each complementary to opposite strands of the template, were generated which contain the point mutation which alters amino acid number 17 (isoleucine) to a lysine. The top strand primer was as follows:

5' CGGGGCCTACTTGGTTGCAAGATCAC-TAGCCTTACAGGC 3' (SEQ ID NO: 81).

The bottom strand is as follows:

5'GCCTGTAAGGCTAGTGATCTTGCAAC-CAAGTAGGCCCCG 3' (SEQ ID NO: 82).

The template HIS-NS4A$_{21-32}$-GSGS-NS3$_{3-631}$/S139A, along with these two primers, was utilized in a PCR reaction to generate this point mutation.

xii. HIS-NS4A$_{21-32}$-GSGS-NS3$_{3-631}$S139A, I18K (SEQ ID NO: 17)

A single amino acid mutant of HIS-NS4A$_{21-32}$-GSGS-NS3$_{3-631}$/S139A was constructed by creating a point mutation at position 18 of the NS3 domain of the HIS-NS4A$_{21-32}$-GSGS-NS3$_{3-631}$/S139A construct as described above. Two oligonucleotide primers, each complementary to opposite strands of the template, were generated which contain the point mutation which alters amino acid number 18 (isoleucine) to a lysine. The top strand primer was as follows:

5' CGGGGCCTACTTGGTTGCATCAAGAC-TAGCCTTACAGGC 3' (SEQ ID NO: 83).

The bottom strand read as follows:

5'GCCTGTAAGGCTAGTCTTGATGCAAC-CAAGTAGGCCCCG 3' (SEQ ID NO: 84).

The template HIS-NS4A$_{21-32}$-GSGS-NS3$_3$-631/S139A, along with these two primers, was utilized in a PCR reaction to generate this point mutation.

xiii. HIS-NS4A$_{21-32}$-GSGS-NS3$_{3-631}$/S139A, I17K, I18K (SEQ ID NO: 18)

A single amino acid mutant of HIS-NS4A$_{21-32}$-GSGS-NS3$_{3-631}$/S139A, I17K was constructed by creating a point mutation at position 18 of the NS3 domain of the HIS-NS4A$_{21-32}$-GSGS-NS3$_{3-631}$/S139A, I17K construct as described above. Two oligonucleotide primers, each complementary to opposite strands of the template, were generated which contain the point mutation which alters amino acid number 18 (isoleucine) to an lysine. The top strand primer was as follows:

5' CGGGGCCTACTTGGTTGCAAGAAGAC-TAGCCTTACAGGC 3' (SEQ ID NO: 85).

The bottom strand reads as follows:

5' GCCTGTAAGGCTAGTCTTCTTGCAAC-CAAGTAGGCCCCG 3' (SEQ ID NO: 86).

The template HIS-NS4A$_{21-32}$-GSGS-NS3$_{3-631}$/S139A, I17K, along with these two primers was utilized in a PCR reaction to generate this point mutation.

xiv. HIS-NS4A$_{15-32}$-GSGS-NS3$_{3-631}$ (SEQ ID NO: 19)

A NS4A-tethered form of NS3 full-length domain, HIS-NS4A$_{21-32}$-GSGS-NS3$_{3-631}$ was constructed by joining the amino acids 15-32 of NS4A peptide to the N-terminal end of the NS3 protease (NS3 amino acids 3–631) via the linker GSGS, and was cloned into the pET-28b+ vector as described above with the following modification. Primers were designed to generate a PCR fragment containing an NdeI site followed by the NS4A peptide, the GSGS linker (SEQ ID NO: 21), and amino acids 3–631 of the NS3 catalytic domain at the 5' terminus and a stop codon flanked by an EcoRI site at the 3' terminus. The 5' primer sequence was as follows:

5'GATATACATATGGCTTACTCTCTGAC-TACGGGTFCTGTTGTTATT GTTGGTAGAAT-TATTTTATCTGGTAGTGGTAGTATCACG-GCCTACTCCCAA 3' (SEQ ID NO: 87).

The 3' primer sequence was as follows:

5'GTGGTGGTGCTCGAGGCTGCCGCGCGGCA CCAGCGTAACGACCTCCAGGTC 3' (SEQ ID NO: 88).

The template used was HIS-NS4A$_{21-32}$-GSGS-NS3$_{3-631}$. The resulting PCR fragment was 1974 bases. Vent DNA polymerase was employed and a final concentration of 200 µM dNTPS was used. The PCR conditions were as follows: 95° C. for 45 seconds (1 cycle); 95° C. for 30 seconds, 55° C. for 1 minute, 72° C. for 2 minutes (25 cycles). The product was purified with QIAquick PCR kit (Qiagen). This PCR product, along with the 6.6 kb vector backbone (HIS-NS4A$_{21}$-32-GSGS-NS3$_{3-631}$), were double digested with NdeI and BamHI. The digested fragments of 1.43 and 6.6 Kbp respectively were run on agarose gel, excised, and column purified with QIAquick gel extraction kit (Qiagen). They were quantitated and then ligated together with T4 DNA ligase.

xv. HIS-NS4A$_{15-32}$-GSGS-NS3$_{3-631}$/S139A (SEQ ID NO: 20)

An NS4A-tethered form of NS3 full-length domain, HIS-NS4A$_{21-32}$-GSGS-NS3$_{3-631}$/S139A was constructed by joining amino acids 15–32 of the NS4A peptide to the N-terminal end of the NS3 protease (NS3 amino acids 3–631) via the linker GSGS (SEQ ID NO: 21), and was cloned into the pET-28b+ vector as described above with the following modification. Primers were designed to generate a PCR fragment containing an NdeI site followed by the NS4A peptide, the GSGS linker (SEQ ID NO: 21), and amino acids 3–631 of the NS3 catalytic domain at the 5' terminus and a stop codon flanked by an EcoRI site at the 3' terminus. The 5' primer sequence was as follows:

5'GATATACATATGGCTTACTCTCTGAC-TACGGGTTCTGTTGTTATT GTTGGTAGAAT-TATTTIATCTGGTAGTGGTAGTATCACG-GCCTACTCCCAA 3' (SEQ ID NO: 89).

The 3' primer reads as follows:

5= TGGTGGTGCTCGAGGCTGCCGCGCG-GCACCAGCGTAACGACCT CCAGGTC 3' (SEQ ID NO: 90).

The template used was HIS-NS4A$_{21-32}$-GSGS-NS3$_{3-631}$/S139A. The resulting PCR fragment was 1974 bases. Vent DNA polymerase was employed and a final concentration of 200 μM dNTPS was used. The PCR conditions were as follows: 95° C. for 45 seconds (1 cycle); 95° C. for 30 seconds, 55° C. for 1 minute, 72° C. for 2 minutes (25 cycles). The product was purified with QIAquick PCR kit (Qiagen). This PCR product along with the 6.6 kb vector backbone (HIS-NS4A$_{21-32}$-GSGS-NS3$_{3-631}$) were double digested with NdeI and BamHI. The digested fragments of 1.43 and 6.6 Kbp respectively were run on agarose gel, excised, and column purified with QIAquick gel extraction kit (Qiagen). They were quantitated and then ligated together with T4 DNA ligase.

EXAMPLE 3

Expression and Purification of HCV NS4A-NS3 Complexes

A. Small Scale Expression Studies

All constructed plasmids were transformed into DH5α cells for production of large amount of plasmid-DNA. The purified plasmid-DNA was transformed into BL21(DE3) cells for expression studies. The cells were grown in Terrific Broth in baffled flasks at 37° C. to an OD of 1.0 and the temperature was lowered to 23° C. The cultures were induced with 0.4 mM IPTG and were harvested 3 hours after induction. Cells were sonicated for 1 min in 50 mM HEPES, pH 7.5, 20% glycerol, 0.1% βOG, 0.3 M NaCl, 10 mM βME and spun at 13,000 rpm for 10 min. The supernatants were analyzed on 10% Novex SDS-PAGE.

B. Large-Scale Expression And Purification Of NS4A-Tethered Forms Of HCV NS3$_{3-181}$ Protease E. coli, BL21(DE3) cells harboring either plasmid pET-22b or pET-28b encoding various native, single, or multiple mutants of NS4A-tethered forms of NS3$_{1-181}$ were grown at 37° C. in Terrific Broth supplemented with either 100 ug/ml of ampicillin (for pET-22b) or 25 ug/ml kanamycin (for pET28-b) in 10-liter fermentor. When the cell density reaches an OD of 2–3, the temperature was lowered to 23° C. within 5 minutes and cells were induced with 0.4 mM IPTG. Cells were harvested 3 hours after induction and frozen at –20° C. prior to purification.

Cell pellets were resuspended in 600 ml of lysis buffer containing 50 mM HEPES, pH 7.4, 10% glycerol, 0.3 M NaCl, 0.1% βOG, 2 mM βME (buffer A), homogenized using a cell homogenizer (Omni Mixer ES) for 2 min and the cells were disrupted by two passes through a Microfluidizer (Microfluidics Model #M-110F) at 10,000 p.s.i. The lysate was centrifuged at 85,000×g for 45 min. The supernatant was filtered through 0.8 micron filter units (Nalgene) and applied at 40 ml/min to a 11-ml Ni-imidodiacetate (POROS 20 MC resin) column in the presence of 20 mM immidazole on BIOCAD (Perseptive Biosystems). The column was washed with 10 column volumes of buffer A, followed by 15 column volume of buffer A containing 1.0 M NaCl and 20 mM imidazole (buffer B). The bound protease was eluted with the elution buffer (buffer B containing 250 mM imidazole). The eluted fractions containing the protease were pooled and dialyzed versus 16 liters of 50 mM HEPES, pH 7.4, 10% glycerol, 1 M NaCl, 10 mM βME in order to remove the imidazole and the detergent.

When the removal of the N-terminal histidine tag was required, human thrombin (Enzyme Research) was added to the eluted, pooled fractions at a thrombin:protease ratio of 8 units per mg of protease and thrombin cleavage was allowed to proceed during the dialysis step for 18 hours. The dialyzed, thrombin-cleaved protease was applied to 3 sephacryl-100 sizing column (26×60 cm, Pharmacia) in series, equilibrated in of 50 mM HEPES, pH 7.4, 10% glycerol, 1 M NaCl, 10 mM bME at 0.5 ml/min. Fractions containing purified protease at above >95% homogeneity as judged by SDS-PAGE were pooled and flash-frozen at –80° C.

C. Large-Scale Expression And Purification Of NS4A-Tethered Forms Of HCV NS3$_{3-631}$ Protease E. coli, BL21(DE3) cells harboring either plasmid pET-22b or pET-28b encoding various native, single, or multiple mutants of NS4A-tethered forms of NS31–181 were grown at 37° C. in Terrific Broth supplemented with either 100 μg/ml of ampicillin (for pET-22b) or 25 μg/ml kanamycin (for pET28-b) in 10-liter fermentor. When the cell density reaches an OD of 2–3, the temperature was lowered to 23° C. within 5 minutes and cells were induced with 0.4 mM IPTG. Cells were harvested 3 hours after induction and frozen at –20° C. prior to purification.

Cell pellets were resuspended in 600 ml of lysis buffer containing 50 mM HEPES, pH 7.4, 10% glycerol, 0.3 M NaCl, 0.1% βOG, 2 mM βME (buffer A), homogenized using a cell homogenizer (Omni Mixer ES) for 2 min and the cells were disrupted by two passes through a Microfluidizer (Microfluidics Model #M-110F) at 10,000 p.s.i. The lysate was centrifuged at 85,000×g for 45 min. The supernatant was filtered through 0.8 micron filter units (Nalgene) and applied at 40 ml/min to a 11-ml Ni-imidodiacetate (POROS 20 MC resin) column in the presence of 20 mM immidazole on BIOCAD (Perseptive Biosystems). The column was washed with 10 column volumes of buffer A, followed by 15 column volume of buffer A containing 1.0 M NaCl and 20 mM imidazole (buffer B). The bound protease was eluted with the elution buffer (buffer B containing 250 mM imidazole). The eluted fractions containing the protease were pooled and dialyzed versus 16 liters of 50 mM HEPES, pH 7.4, 10% glycerol, 1 M NaCl, 10 mM βME in order to remove the imidazole and the detergent.

When the removal of the N-terminal histidine tag was required, human thrombin (Enzyme Research) was added to the eluted, pooled fractions at a thrombin:protease ratio of 8 units per mg of protease and thrombin cleavage was allowed to proceed during the dialysis step for 18 hours. The dialyzed, thrombin-cleaved protease was applied to 3 sephacryl-100 sizing column (26×60 cm, Pharmacia) in series, equilibrated in of 50 mM HEPES, pH 7.4, 10% glycerol, 1 M NaCl, 10 mM βME at 0.5 ml/min. Fractions containing purified protease at above >95% homogeneity as judged by SDS-PAGE were pooled and flash-frozen at –80° C.

EXAMPLE 4

Molecular Weight Determination of Various NS3 Protease Forms by Size Exclusion Chromatography Two hundred μl of various purified proteins were applied to a calibrated Superdex-75 HR (1 cm×30 cm) FPLC column equilibrated with 25 mM HEPES, pH 7.4, 1M NaCl and 10% glycerol and 10 mM βME at 0.5 ml/min. The column was precalibrated using Pharmacia standard calibration proteins (BSA: 67 KDa; Ovalbumin: 43 KDa; Chymotrypsinogen A: 31 KDa; Ribonuclease A: 13.7 KDa). Protein elution was monitored at 280 nm.

The following covalent NS4A-NS3 complexes described above were characterized by the above method:

HIS-NS4A$_{21-32}$-GSGS-NS3$_{3-181}$
HIS-NS4A$_{21-32}$-GSGS-NS3$_{3-181}$/I17K
HIS-NS4A$_{21-32}$-GSGS-NS3$_{3-181}$/I18K
HIS-NS4A$_{21-32}$-GSGS-NS3$_{3-181}$/S139A
HIS-NS4A$_{21-32}$-GSGS-NS3$_{3-181}$/S139A, I17K
HIS-NS4A$_{21-32}$-GSGS-NS3$_{3-181}$/S139A, I18K
HIS-NS4A$_{21-32}$-PAGG-NS3$_{3-181}$
HIS-NS4A$_{21-32}$-PAGG-NS3$_{3-181}$/I17K
HIS-NS4A$_{21-32}$-PAG-NS3$_{3-181}$/I17K
HIS-NS4A$_{21-32}$-GSGS-NS3$_{3-631}$.
HIS-NS4A$_{21-32}$-GSGS-NS3$_{3-631}$/I17K
HIS-NS4A$_{21-32}$-GSGS-NS3$_{3-631}$/I18K
HIS-NS4A$_{21-32}$-GSGS-NS3$_{3-631}$/S139A
HIS-NS4A$_{21-32}$-GSGS-NS3$_{3-631}$/S139A, I17K
HIS-NS4A$_{21-32}$-GSGS-NS3$_{3-631}$/S139A, I18K

Of those constructs characterized, all covalent NS4A-NS3 complexes containing a three amino acid linker resulted in aggregated forms, as judged by size exclusion chromatography. NS4A-tethered forms in which a point mutation at position 17 or 18 had not been introduced also resulted in aggregated forms, although they exhibited activity identical to that of the monodispersed forms of the protease.

Covalent NS4A-NS3 complexes which contained a four amino acid linker and a point mutation at position 17 and/or 18 resulted in active, monodispersed proteins with apparent molecular weights smaller than predicted as determined by size exclusion chromatography.

EXAMPLE 5

Determination of Proteolytic Activity

Following expression and purification, newly engineered recombinant species were assayed for proteolytic activity utilizing a 1D-HPLC (reverse-phase chromatography) technique. Assays were conducted using the 5A/5B (P8P8') substrate DTEDVVCC*SMSYTWTG-K (SEQ ID NO: 25) in 25 mM Tris-HCl pH 7.5, 150 mM NaCl, 0.5 mM EDTA, 10 mM DTT, 10% glycerol, and 0.05% lauryl maltoside. Concentration of all proteins were determined by BIORAD dye method). The catalytic domain His-NS3$_1$ 8, (batch # 51072-92E) was preincubated at a concentration of 250 nM in the presence of 20 $\mu$M 4A peptide (KKGSVVIVGRIVLSGKPAIIPKK) for 15 minutes at 4° C. This mixture was then diluted into the reaction volume at a final concentration of 8 $\mu$M 4A peptide and 100 nM catalytic domain. Reactions were incubated at room temperature for 60 minutes and were quenched with an equal volume of 10% phosphoric acid. Following injection, cleavage products were monitored under a linear 0–80% acetonitrile gradient in 0.1% TFA. The product P1'P8'K peak areas were automatically converted to product quantity in nanomoles by a standard curve.

The various covalent NS4A-NS3 complexes whose proteolytic efficiency has been determined according to the above method, and the results of each determination, are shown in Table 1.

TABLE 1

Catalytic Efficiency Of Various Forms Of NS3 Protease

| Construct | $k_{cat}$ (min$^{-1}$) | $K_m$ ($\mu$M) | $k_{cat}/K_m$ (M$^{-1}$ s$^{-1}$) |
|---|---|---|---|
| NS3$_{1-631}$-NS4A$_{1-54}$ | 10 ± 2 | 20 ± 2 | (8 ± 2) × 10$^3$ |
| His-NS3$_{1-181}$ + NS4A Peptide[a] | 3 ± 1 | 80 ± 20 | (0.5 ± 0.2) × 10$^3$ |
| His-NS4A$_{21-32}$-GSGS-NS3$_{3-181}$ | 9 ± 2 | 19 ± 3 | (8 ± 2) × 10$^3$ |
| His-NS4A$_{21-32}$-GSGS-NS3$_{3-181}$/I17K | 16 ± 3 | 20 ± 2 | (14 ± 2) × 10$^3$ |
| His-NS4A$_{21-32}$-GSGS-NS3$_{3-181}$/I18K | 10 ± 2 | 22 ± 2 | (8 ± 2) × 10$^3$ |

[a][E] = 0.25 $\mu$M, [NS4A Peptide] = 10 $\mu$M

As can be seen from the forgoing results, all covalent NS4A-NS3 complexes were shown to have an equivalent catalytic efficiency to that of full-length NS3$_{1-631}$-NS4A$_{1-54}$. In contrast, the non-covalent complex of NS3$_{1-181}$ with the NS4A peptide (0.1:8 EM), KK-(NS4A$_{21-39}$)-KK, had an catalytic activity which is 8 fold lower than the full-length NS3$_{1-631}$-NS4A$_{1-54}$.

EXAMPLE 6

High Throughput Screening Assays Using Covalent NS4A-NS3 Complexes

The claimed covalent NS4A-NS3 complexes are useful in screening methods for identifying NS3 protease inhibitors. One such method in which the claimed covalent complexes can be used is illustrated below.

Surface Plasmon Resonance Assay

Figure 5A:
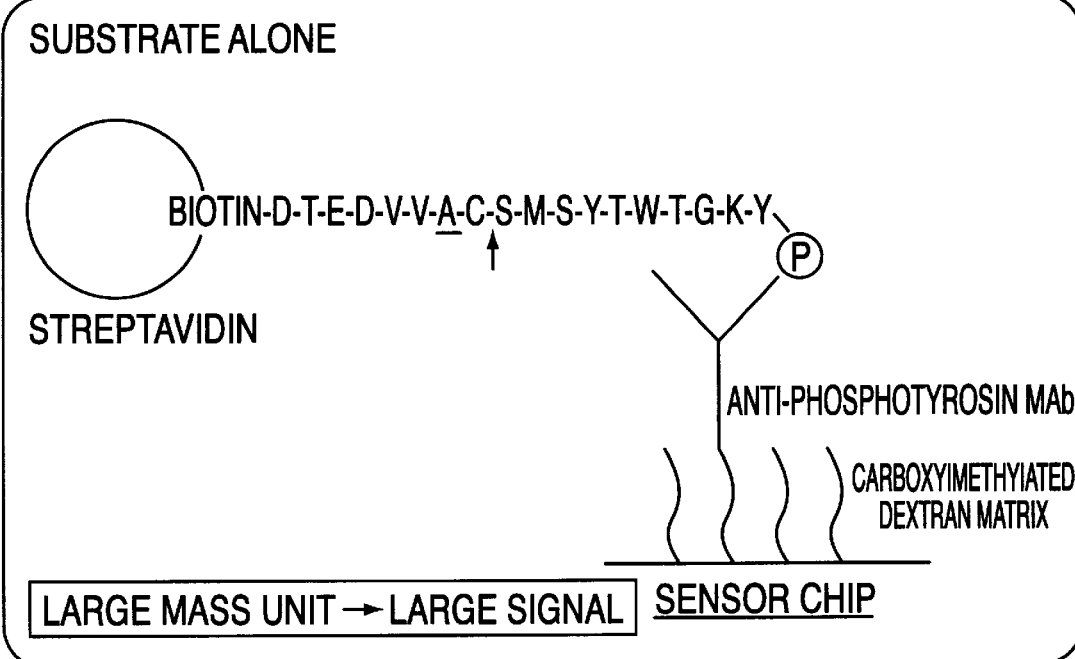
FIGS. 5A and 5B schematically depict a high throughput assay for discovering HCV protease inhibitors using surface plasmon resonance technology.
Figure 5B:
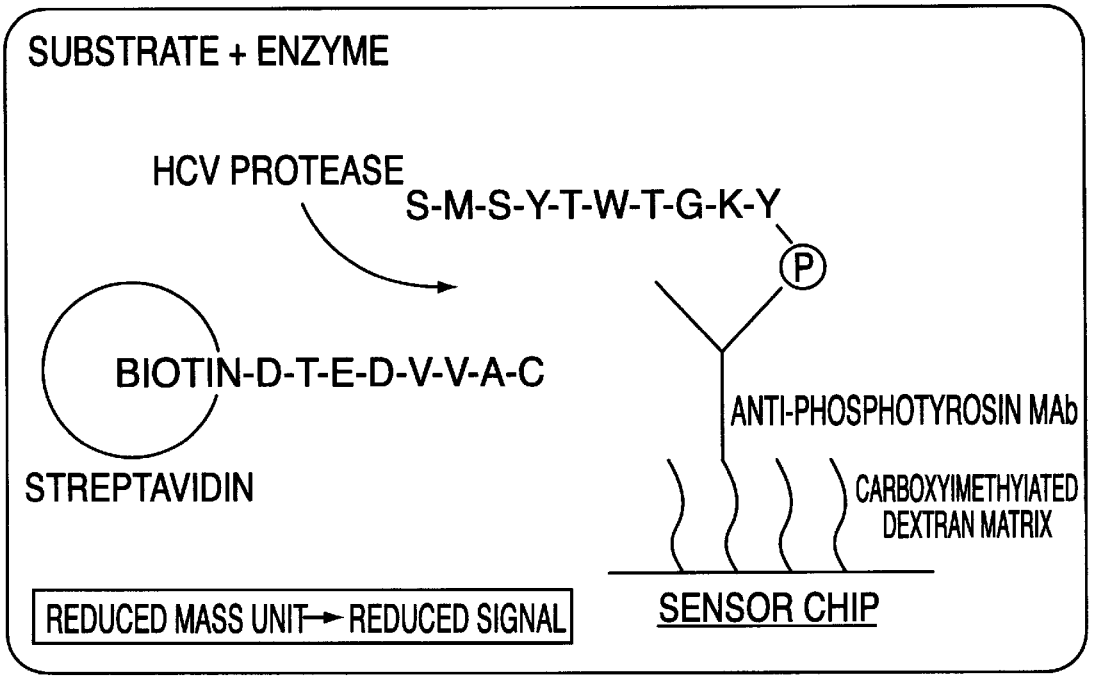

The present example illustrates a method for determining if a compound can be useful as an HCV protease inhibitor using the surface plasmon resonance assay. FIGS. 5A and 5B schematically depict the technique.

BIAcore™ is a processing unit for Biospecific Interaction Analysis. The processing unit integrates an optical detection system with an autosampler and a microfluidic system. BIAcore™ uses the optical phenomena of surface plasmon resonance to monitor interaction between biomolecules.

SPR is a resonance phenomenon between incoming photons and electrons on the surface of thin metal film. Resonance occurs at a sharply defined angle of incident light. At this angle, called the resonance angle, energy is transferred to the electrons in the metal film, resulting in a decreased intensity of the reflected light. SPR response depends on a change in refractive index in the close vicinity of the sensor chip surface, and is proportional to the mass of analyte bound to the surface. The BIAcore™ continuously measures the resonance angle by a relative scale of resonance units (RU) and displays it as an SPR signal in a sensorgram, where RU are plotted as a function of time.

BIAcore™ uses continuous flow technology. One interactant is immobilized irreversibly on the sensor chip, comprising a non-crosslinked carboxymethylated dextran providing a hydrophilic environment for bimolecular interaction. Solution containing the other interactant flows continuously over the sensor chip surface. As molecules from the solution bind to the immobilized ligand, the resonance angle changes resulting in a signal registered by the instrument.

In this methodology, the enzymatic reactions are carried out outside of the BIAcore™, in reaction tubes or 96-well tissue culture plates, as it is conventionally done for any of the other available high throughput assays. The SPR is only used as a detection means for determination of the amount of an intact substrate remaining in a solution after the reaction is quenched.

In order to measure the amount of the intact substrate prior to the addition of enzyme, a means of capturing the substrate onto the sensor chip had to be established. In addition, to satisfy the requirement for a high throughput assay on the BIAcore™, the substrate needed to be removed from the surface after completion of analysis, so that the same surface can be used for subsequent reactions. To accomplish these two requirements, a phosphotyrosine is synthetically attached to one end of the substrate. The phosphotyrosine was chosen due to the commercial availability of an anti-phosphotyrosine monoclonal antibody. The antibody is covalently attached to the sensor chip by standard amine coupling chemistry. The anti-phosphotyrosine antibody, bound permanently to the chip, is used to capture the phosphotyrosine in a reversible manner. The antibody-phosphotyrosine interaction is ultimately used to capture and release the attached peptide substrate. After completion of analysis, the surface can be regenerated using various reagents such as 2 M $MgCl_2$.

When an intact peptide substrate is introduced onto the antibody surface, a large mass is detected by the instrument. To follow the extent of peptide cleavage, a mixture of peptide substrate and enzyme is incubated for the desired time and then quenched. Introduction of this mixture, containing both cleaved peptide and intact peptide, to a regenerated antibody surface results in detection by the instrument of a lower mass than that detected for the sample containing only intact peptide. The difference in the two values is then used to calculate the exact amount of intact peptide remaining after cleavage by the enzyme.

Although the reduction in mass can be directly followed with many large substrates, due to the small mass of a typical synthetic peptide substrate (10–20 amino acids, 1–3 Daltons), the mass difference, and thus the signal difference between the intact and cleaved peptide, is very small within the signal to noise ratio of the instrument. To circumvent this low sensitivity, a biotin can be attached at the N-terminus of the peptide. Streptavidin can then be added, thus tagging the peptide. When the tagged peptide is introduced onto the antibody surface of the chip, the signal will be higher. The signal resulting from introduction of a cleaved peptide which lacks the N-terminal half, (and thus the streptavidin), will be much lower.

To carry out this method, an HCV protease 5A-5B peptide substrate, (such as 5A/5B substrate DTEDVVACSMSYTWYG-K (SEQ ID NO: 91)) is synthesized with an additional phosphotyrosine at the C-terminus and a biotin at the N-terminus. The biotin is then tagged with streptavidin. An anti-phosphotyrosine monoclonal antibody, 4G10 (Upstate Biotechnology Inc., Lake Placid, N.Y.) is coupled to the sensor chip. In the absence of an active, uninhibited HCV protease, introduction of the intact phosphotyrosine peptide results in a large signal (large mass unit/large signal) through its interaction with the anti-phosphotyrosine monoclonal antibody (Mab).

The protease-catalyzed hydrolysis of the phosphotyrosine-biotinylated peptide is carried out in a 96 well plate. The reaction is stopped with an equal volume of mercuribenzoate. The cleaved peptide which lacks the tagged streptavidin (less mass) results in the loss of response units (lower signal).

Using this method, numerous compounds can be tested for their inhibitory activity since the antibody surface can be regenerated repetitively with 2 M $MgCl_2$.

Procedure for Coupling Anti-phosphotyrosine Mab to the Sensor Chip

The anti-phosphotyrosine Mab is coupled to the carboxymethylated dextran surface of a sensor chip in the following manner. The flow rate used throughout the coupling procedure is 5 $\mu$l/min. The surface is first activated with a 35 $\mu$l injection of NHS/EDC (N-hydroxysuccinimide/N-dimethyllaminopropyl-N'-ethylcarbodiimide-HCl). This is followed by a 40 ml injection of Mab 4G10 at 50 $\mu$g/ml in 10 mM sodium acetate buffer, pH=4.0. Any remaining activated esters are then blocked by the injection of 35 $\mu$l of 1 M ethanolamine. These conditions result in the immobilization of approximately 7,500 response units (420 $\mu$M) of antibody.

Binding of Peptide and Regeneration of Mab 4G10 Surface

The flow rate used throughout the BIAcore analysis run is 5 $\mu$l/min. A 4 $\mu$l injection containing streptavidin-tagged peptide (peptide concentration at 2 $\mu$M, streptavidin binding sites concentration at 9 $\mu$M) is carried out. The amount of streptavidin-tagged peptide bound to the antibody surface (in response units) is measured 30 seconds after the injection is complete.

Regeneration of Sensor Chip Surface

Regeneration of the Mab 4G10 surface is achieved using a 4 $\mu$l pulse of 2 M $MgCl_2$ after each peptide injection. Surfaces regenerated up to 500 times still showed 100% binding of tagged peptide.

Determination of the Optimal Concentration of Peptide and Streptavidin

To determine the optimal peptide concentration, a standard curve was generated using various amounts of peptide (0–10 $\mu$M) in the presence of excess streptavidin. A value in the linear range, 2 $\mu$M, was chosen for standard assay conditions.

The amount of streptavidin required to completely tag the peptide is determined using a peptide concentration of 2.5 $\mu$M and titrating the amount of streptavidin ($\mu$M of binding sites). All the peptides were shown to be completely tagged when streptavidin concentrations greater than 3 $\mu$M (approximately equimolar to the peptide concentration) were used. A streptavidin concentration of 9 $\mu$M (a 4.5 fold excess) was chosen for standard assay conditions.

Application of Described Methodology to Covalent HCV NS4A-NS3 Complexes

The HCV protease 5A/5B peptide substrate, (such as 5A/5B substrate DTEDVVACSMSYTWYG-K (SEQ ID NO: 91)), with a phophotyrosine synthetically attached to the C-terminus and a biotin attached at the N-terminus, is synthesized. Anti-phosphotyrosine monoclonal antibody, 4G10 is coupled to the sensor chip.

In the absence of active, uninhibited covalent HCV NS4A-NS3 complex, the introduction of the intact streptavidin-tagged biotinylated phosphotyrosine peptide to the sensor chip results in a large signal (large mass unit/large response units) through its interaction with the anti-phosphotyrosine monoclonal antibody.

The protease-catalyzed hydrolysis of the phosphotyrosine-biotinylated peptide is carried out with and without a suspected inhibitor in a 96 well plate. The reaction is stopped with an equal volume of the quenching buffer containing mercuribenzoate. Streptavidin is then added to tag the peptide. The cleaved peptide, which lacks the streptavidin (less mass), results in the loss of response units.

Using this assay, numerous compounds can be tested for their inhibitory activity since the antibody surface can be regenerated repetitively with 2 M $MgCl_2$.

Standard Operating Procedure for BIAcore-based HCV Assay

Reactions are prepared in a 96-well tissue culture plate using the Reaction Buffer (50 mM HEPES, pH 7.4, 20% glycerol, 150 mM NaCl, 1 mM EDTA, 0.1% Tween-20,1 mM DTT ) as diluent. The final reaction volume is 100 μl. Sample with the peptide alone (Biotin-DTEDVVAC SMSYTWTGKpY) is prepared by addition of 10 μl of peptide stock at 100 μM (prepared in the reaction buffer) to 90 μl of reaction buffer, so that the final concentration of peptide is 10 μM. Samples comprised of peptide and the covalent NS4A-NS3 complexes are prepared by addition of 10 μl of peptide stock at 100 μM and 10 μl of covalent NS4A-NS3 stock at 0.17 mg/ml (both prepared in the reaction buffer) to 80 μl of reaction buffer, so that the final concentration of peptide and the enzyme is 10 and 0.1 μM respectively. The reaction is held at 30° C. for the specified time and then quenched. Quenching is achieved by transferring a 20-μl aliquot of the reaction mixture to a new tissue culture plate containing an equal volume of PMB Quenching Buffer (50 mM HEPES, pH 7.8,150 mM NaCl, 5 mM P-Hydroxymercuribenzoic Acid, and 13 mM EDTA).

To prepare the quenched reaction mixture for injection onto the sensor surface, 30 μl PMB BIAcore Buffer (50 mM HEPES, pH 7.4, 1 M NaCl) and 30 μl of streptavidin at 0.5 mg/ml in water is added to the 40 μl of the quenched reaction mixture to a final volume of 100 μl. In this step, all the peptides are tagged with streptavidin prior to the injection of samples. Finally, 4 μl of this sample is injected over the antiphosphotyrosine surface for determination of the intact versus cleaved peptide. The final concentration of peptide and the streptavidin in the BIAcore sample is 2 and 9 μM, respectively.

Experimental Conditions

Substrate:
   Biotin-DTEDVVAC SMSYTWTGK-pY (SEQ ID NO: 91) in Reaction buffer without DTT
Concentration:
   170 μM (Crude peptide, based on weight)
Enzyme:
   10 μl of concentrated His-NS4A$_{21-32}$-GSGS-NS3$_{3-181}$ at 0.17 mg/ml
Reaction volume:
   100 μl
Reaction buffer:
   50 mM HEPES, pH 7.8
   20% glycerol
   150 mM NaCl
   1 mM EDTA
   1 mM DTT
   0.1% Tween-20
Temp:
   30° C.
Quench with:
   p-hydroxymercuribenzoate

EXAMPLE 7

Determination of Nucleic Acid Unwinding Activity

The newly engineered single-chain recombinant His-NS4A$_{21-32}$-GSGS-NS3$_{3-631}$ (SEQ ID NO: 4) was assayed for nucleic acid unwinding activity using a scintillation proximity assay (SPA, Amersham Life Science Inc., Arlington Height, Ill.). The unwinding activity present in this covalent His-NS4A$_{21-32}$-GSGS-NS3$_{3-631}$ complex was compared with that of the full length His-NS3$_{1-631}$-NS4A$_{1-54}$ complex under their corresponding optimal buffer conditions. The double stranded RNA substrate (Oligos, Etc., Inc. Wilsonville, Oreg.) used in the assay contained a template 5'-GCU CGC CCG GGG AUC CUC UAG GAA UAC ACG UUC GAU-3' (SEQ ID NO: 121) annealed to a primer 5'-CUA GAG GAU CCC CGG GCG AGC CCU AUA GUG AGU CGU-3' (complementary sequences of the template and the primer are underlined). This substrate is end-labeled with $^{33}$P using T4 polynucleotide kinase.

The assay conditions for the covalent His-NS4A$_{21-32}$-GSGS-NS3$_{3-631}$ complex were 100 mM MOPS [pH 7.0], 0.5 mM $MgCl_2$, 2 mM ATP, 0.5 mM DTT, 100 mg/ml BSA, 2% dimethylsulfoxide (DMSO) and 1 U RNase inhibitor (5 prime->3 prime, Inc., Boulder, Colo.). For the full length His-NS3$_{1-631}$/NS4A$_{1-54}$ complex, the assay conditions were 100 mM PIPES [pH 6.0], 1 mM $MgCl_2$, 2 mM ATP, 0.6 mM DTT, 100 mg/ml BSA and 1 U RNase inhibitor. In both reactions, 0.5 nM double stranded RNA substrate in a final volume of 50 ml was used. The reaction was carried out at 37 ∞C for 1 h and terminated by an addition of 10 ml of 0.5 M EDTA. The released primer was captured using 60 ml of 100 nM biotinylated capture oligomer (5'-biotin-GCT-CGC-CCG-GGG-ATC-CTC-TAG-3') (Gibco/BRL, Grand Island, N.Y.) (SEQ ID NO: 123) in 2X hybridization buffer (40 mM HEPES [pH 7.3], 2M NaCl, 2 mg/ml BSA) at 37 ∞C for 1 h. The primer-oligomer complex was retained by Streptavidin coated SPA beads (SPA, Amersham Life Science Inc., Arlington Height, Ill.), filtered and washed thoroughly with wash buffer (20 mM HEPES [pH 7.3], 15 mM NaCl, 1.5 mM sodium citrate and 0.05% SDS). The amount of the released labeled primer was quantified using a TopCount reader (Packard A991200, Meriden, Conn.).

Figure 6:
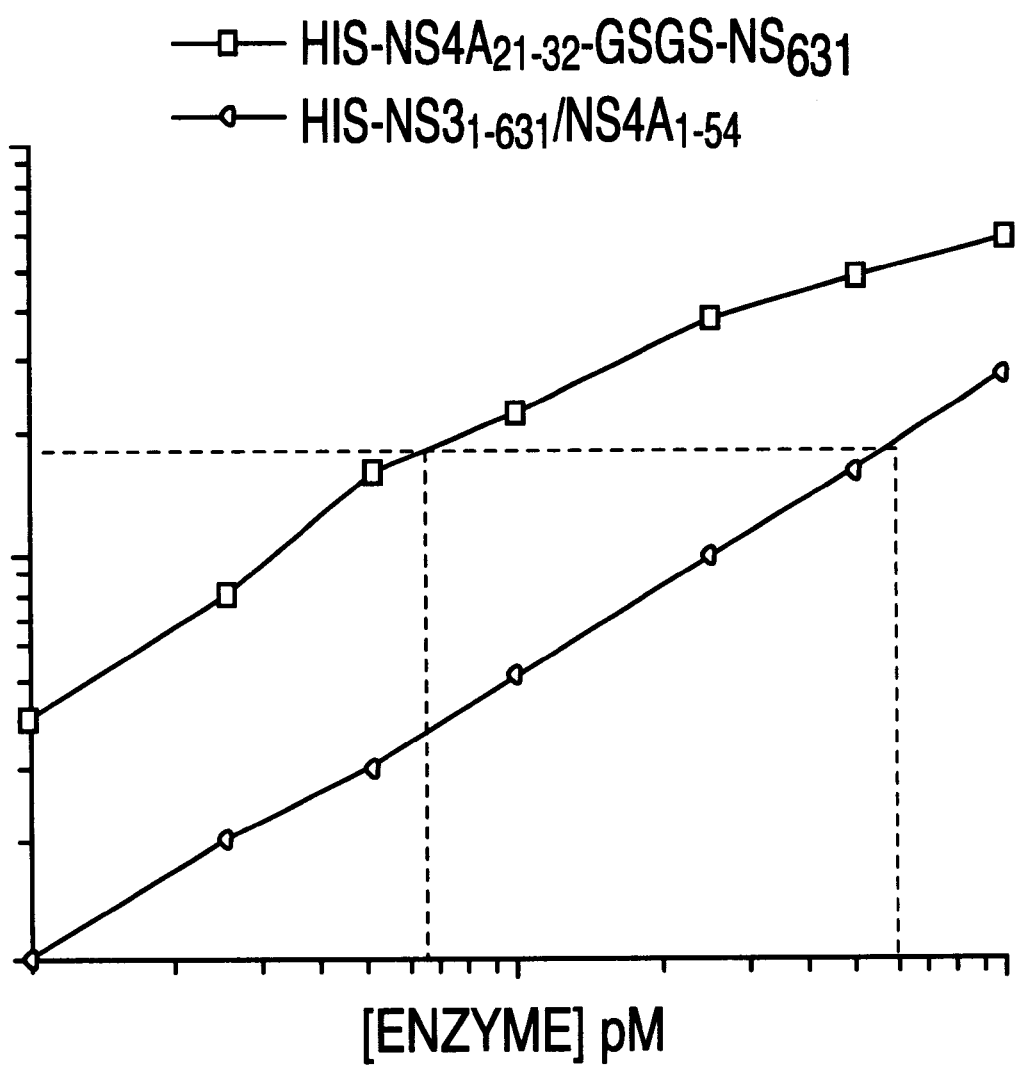
FIG. 6 shows the nucleic acid unwinding activity of the covalent His-NS4A$_{21-32}$-GSGS-NS$_{3-631}$ as compared to that of the His NS3$_{1-631}$/NS4A$_{1-54}$.

As shown in FIG. 6, the covalent His-NS4A$_{21-32}$-GSGS-NS3$_{3-631}$ displayed nucleic acid unwinding activity which was proportional to the concentration of enzyme. In the linear range of the assay for both enzymes (1–10 pM), about 5–6 fold more product was released by the His-NS4A$_{21-32}$-GSGS-NS3$_{3-631}$ than that from an equivalent concentration of full length His-NS3$_{1-631}$/NS4A$_{1-54}$ complex. In addition, 10 fold less covalent His-NS4A$_{21-32}$-GSGS-NS3$_{3-631}$ complex was required to yield a similar percentage of unwound products compared with the full length His-NS3$_{1-631}$/NS4A -54 complex in the corresponding reactions.

The nucleic acid unwinding activity associated with the recombinant covalent His-NS4A$_{21-32}$-GSGS-NS3$_{3-631}$ complex is useful for screening inhibitors of this function. For antiviral screening, compounds were tested at concentrations of less than 40 mM in the assay conditions as described above except that 0.3 nM of the double stranded RNA substrate and 20 pM of the covalent His-NS4A$_{21-32}$-GSGS-NS3$_{3-631}$ complex were used in a reaction which was carried out at room temperature for 30 minutes. The inhibition of the enzyme was monitored by a decrease in the level of released labeled primer as reflected in fewer counts in the capture assay. IC$_{50}$ of the inhibitory compounds was determined as the concentration of the compounds required to inhibit 50% of the unwinding activity.

EXAMPLE 8

Determination of ATPase Activity

ATPase activity of the covalent His-NS4A$_{21-32}$-GSGS-NS3$_{3-631}$ complex (SEQ ID NO: 11) was monitored by direct measurement of [a-$^{32}$P]ATP hydrolysis using thin layer chromatography. The enzyme was incubated with 1 mM ATP mixed with [a-$^{32}$P]ATP (3000 Ci/mmol, approximately 0.5 mCi per reaction) in a reaction buffer containing 50 mM HEPES [pH 7.3], 10 mM KCl, 0.5 mM DTT, 100 mg/ml bovine serum albumin, fraction V (BSA), 1 mM MgCl$_2$ in the presence or absence of 1 mM polyuridylic acid (poly U) (Pharmacia, Piscataway, N.J.) in a final volume of 10 ml. The reaction was carried out at 37 ∞C for 1 h and terminated by an addition of 1 ml of 0.5 M EDTA. Half a microliter of the reaction mix was spotted onto a polyethyleneimine-cellulose sheet (SA Scientific Adsorbents Inc., Atlanta, Ga.) and developed by ascending chromatography in 0.375 M potassium phosphate buffer [pH 3.5]. The cellulose sheet was dried and quantified with a Storm 860 PhosphoImager (Molecular Dynamics, Sunnyvale, Calif.).

Figure 7:
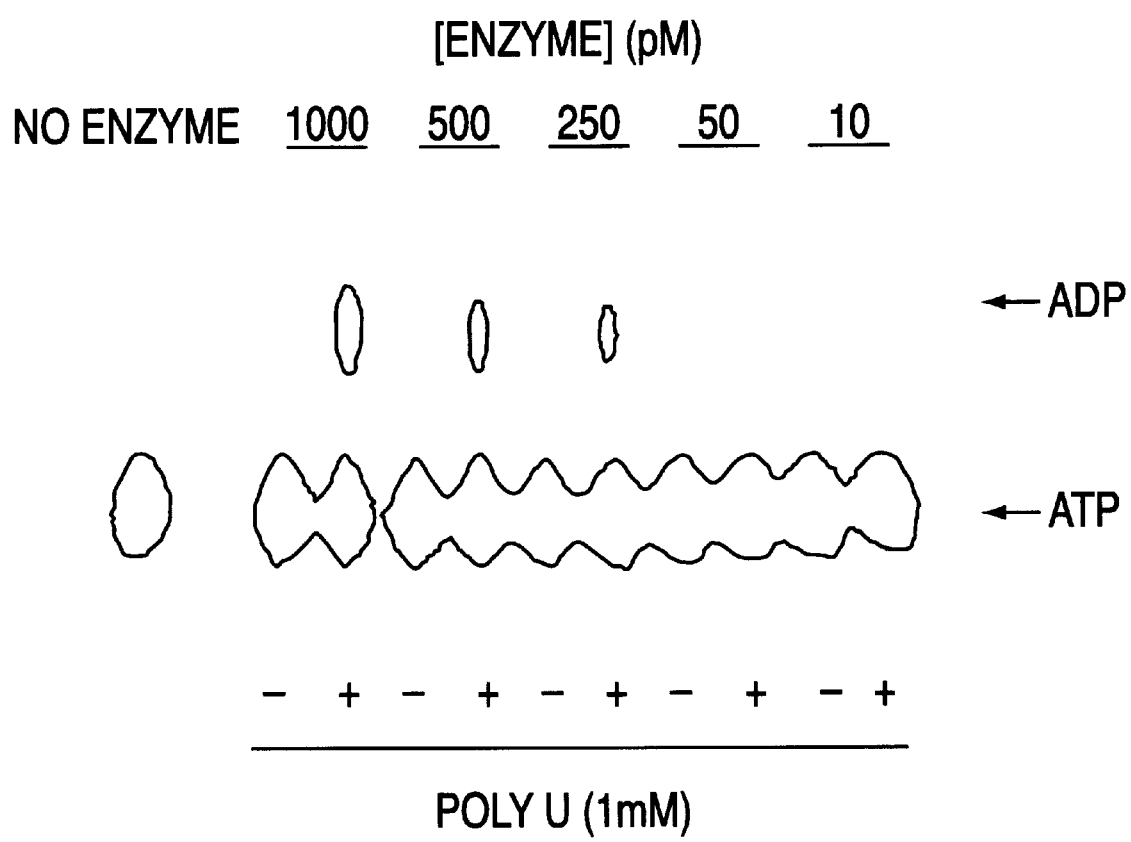
FIG. 7 shows the ATPase activity of the covalent His-NS4A$_{2-32}$-GSGS-NS$_{33-631}$ complex as monitored by thin layer chromatography.

The covalent His-NS4A$_{21-32}$-GSGS-NS3$_{3-631}$ complex exhibited poly U dependent ATPase activity which was proportional to the concentration of the enzyme. The ATP hydrolysis (8–13 fold increase) was enhanced in the presence of poly U at all enzyme concentrations examined (see FIG. 7). Only minimal ATP hydrolysis was observed in the absence of poly U.

The presence of ATPase activity in this covalent His-NS4A$_{21-32}$-GSGS-NS3$_{3-631}$ complex makes it suitable for screening inhibitors against HCV helicase.

---

We claim:

1. A covalent HCV NS4A-NS3 complex comprising a central hydrophobic domain of native HCV NS4A peptide wherein the central hydrophobic domain comprises at least amino acid residues 22–30 of the native HCV NS4A peptide, a linker, and the HCV NS3 serine protease domain, wherein the hydrophobic domain of native HCV NS4A peptide is tethered by the linker to the amino terminus of the HCV NS3 protease domain.

2. The covalent HCV NS4A-NS3 complex of claim 1, wherein the linker comprises at least 4 amino acid residues.

3. The covalent HCV NS4A-NS3 complex of claim 2, wherein the linker consists of 4–6 amino acid residues.

4. The covalent HCV NS4A-NS3 complex of claim 3, wherein the linker consists of about 4 amino acid residues.

5. The covalent HCV NS4A-NS3 complex of claim 4, wherein the linker has a sequence defined by SEQ ID NO: 21 or SEQ ID NO: 22.

6. The covalent HCV NS4A-NS3 complex of claim 5, having an amino acid sequence selected from the group consisting of SEQ ID NOs: 1–20.

7. The covalent HCV NS4A-NS3 complex of claim 1 which is modified by replacement of one or more hydrophobic amino acid residues at position 17 or 18 of the HCV NS3 serine protease domain with a hydrophilic amino acid residue.

8. The covalent HCV NS4A-NS3 complex of claim 7 in which one or more isoleucine residues at position 17 or 18 of the HCV NS3 serine protease domain is replaced by a lysine residue.

9. The covalent HCV NS4A-NS3 complex of claim 8, having an amino acid sequence selected from the group consisting of SEQ ID NOs: 2–4, 6–8, 10, 12–14 and 16–18.

10. The covalent HCV NS4A-NS3 complex of claim 1 which is modified by replacement of a serine residue at position 139 of the HCV NS3 serine protease domain with an alanine residue.

11. The covalent HCV NS4A-NS3 complex of claim 10, having an amino acid sequence selected from the group consisting of SEQ ID NOs: 5–8, 15–18 and 20.

* * * * *

SEQUENCE LISTING (1) GENERAL INFORMATION:

(iii) NUMBER OF SEQUENCES: 123

(2) INFORMATION FOR SEQ ID NO:1:

(i) SEQUENCE CHARACTERISTICS:
      (A) LENGTH: 216 amino acids
      (B) TYPE: amino acid
      (D) TOPOLOGY: linear (ii) MOLECULE TYPE: protein (xi) SEQUENCE DESCRIPTION: SEQ ID NO:1:

```
Met Gly Ser Ser His His His His His His Ser Ser Gly Leu Val Pro
 1               5                  10                  15

Arg Gly Ser His Met Gly Ser Val Val Ile Val Gly Arg Ile Ile Leu
                20                  25                  30

Ser Gly Ser Gly Ser Ile Thr Ala Tyr Ser Gln Gln Thr Arg Gly Leu
            35                  40                  45

Leu Gly Cys Ile Ile Thr Ser Leu Thr Gly Arg Asp Lys Asn Gln Val
    50                  55                  60

Glu Gly Glu Val Gln Val Val Ser Thr Ala Thr Gln Ser Phe Leu Ala
65                  70                  75                  80

Thr Cys Val Asn Gly Val Cys Trp Thr Val Tyr His Gly Ala Gly Ser
                85                  90                  95

Lys Thr Leu Ala Gly Pro Lys Gly Pro Ile Thr Gln Met Tyr Thr Asn
               100                 105                 110

Val Asp Gln Asp Leu Val Gly Trp Gln Ala Pro Pro Gly Ala Arg Ser
            115                 120                 125

Leu Thr Pro Cys Thr Cys Gly Ser Ser Asp Leu Tyr Leu Val Thr Arg
    130                 135                 140

His Ala Asp Val Ile Pro Val Arg Arg Arg Gly Asp Ser Arg Gly Ser
145                 150                 155                 160

Leu Leu Ser Pro Arg Pro Val Ser Tyr Leu Lys Gly Ser Ser Gly Gly
                165                 170                 175
```

```
Pro Leu Leu Cys Pro Ser Gly His Ala Val Gly Ile Phe Arg Ala Ala
            180                 185                 190

Val Cys Thr Arg Gly Val Ala Lys Ala Val Asp Phe Val Pro Val Glu
        195                 200                 205

Ser Met Glu Thr Thr Met Arg Ser
    210                 215
```

(2) INFORMATION FOR SEQ ID NO:2:

(i) SEQUENCE CHARACTERISTICS:
        (A) LENGTH: 216 amino acids
        (B) TYPE: amino acid
        (D) TOPOLOGY: linear (ii) MOLECULE TYPE: protein (xi) SEQUENCE DESCRIPTION: SEQ ID NO:2:

```
Met Gly Ser Ser His His His His His His Ser Ser Gly Leu Val Pro
 1               5                  10                  15

Arg Gly Ser His Met Gly Ser Val Val Ile Val Gly Arg Ile Ile Leu
            20                  25                  30

Ser Gly Ser Gly Ser Ile Thr Ala Tyr Ser Gln Gln Thr Arg Gly Leu
        35                  40                  45

Leu Gly Cys Lys Ile Thr Ser Leu Thr Gly Arg Asp Lys Asn Gln Val
 50                  55                  60

Glu Gly Glu Val Gln Val Val Ser Thr Ala Thr Gln Ser Phe Leu Ala
 65                  70                  75                  80

Thr Cys Val Asn Gly Val Cys Trp Thr Val Tyr His Gly Ala Gly Ser
            85                  90                  95

Lys Thr Leu Ala Gly Pro Lys Gly Pro Ile Thr Gln Met Tyr Thr Asn
            100                 105                 110

Val Asp Gln Asp Leu Val Gly Trp Gln Ala Pro Pro Gly Ala Arg Ser
            115                 120                 125

Leu Thr Pro Cys Thr Cys Gly Ser Ser Asp Leu Tyr Leu Val Thr Arg
130                 135                 140

His Ala Asp Val Ile Pro Val Arg Arg Arg Gly Asp Ser Arg Gly Ser
145                 150                 155                 160

Leu Leu Ser Pro Arg Pro Val Ser Tyr Leu Lys Gly Ser Ser Gly Gly
            165                 170                 175

Pro Leu Leu Cys Pro Ser Gly His Ala Val Gly Ile Phe Arg Ala Ala
            180                 185                 190

Val Cys Thr Arg Gly Val Ala Lys Ala Val Asp Phe Val Pro Val Glu
        195                 200                 205

Ser Met Glu Thr Thr Met Arg Ser
    210                 215
```

(2) INFORMATION FOR SEQ ID NO:3:

(i) SEQUENCE CHARACTERISTICS:
        (A) LENGTH: 216 amino acids
        (B) TYPE: amino acid
       (D) TOPOLOGY: linear (ii) MOLECULE TYPE: protein (xi) SEQUENCE DESCRIPTION: SEQ ID NO:3:

```
Met Gly Ser Ser His His His His His His Ser Ser Gly Leu Val Pro
 1               5                  10                  15
```

-continued

```
Arg Gly Ser His Met Gly Ser Val Val Ile Val Gly Arg Ile Ile Leu
             20                  25                  30

Ser Gly Ser Gly Ser Ile Thr Ala Tyr Ser Gln Gln Thr Arg Gly Leu
         35                  40                  45

Leu Gly Cys Ile Lys Thr Ser Leu Thr Gly Arg Asp Lys Asn Gln Val
     50                  55                  60

Glu Gly Glu Val Gln Val Val Ser Thr Ala Thr Gln Ser Phe Leu Ala
 65                  70                  75                  80

Thr Cys Val Asn Gly Val Cys Trp Thr Val Tyr His Gly Ala Gly Ser
             85                  90                  95

Lys Thr Leu Ala Gly Pro Lys Gly Pro Ile Thr Gln Met Tyr Thr Asn
            100                 105                 110

Val Asp Gln Asp Leu Val Gly Trp Gln Ala Pro Pro Gly Ala Arg Ser
        115                 120                 125

Leu Thr Pro Cys Thr Cys Gly Ser Ser Asp Leu Tyr Leu Val Thr Arg
    130                 135                 140

His Ala Asp Val Ile Pro Val Arg Arg Arg Gly Asp Ser Arg Gly Ser
145                 150                 155                 160

Leu Leu Ser Pro Arg Pro Val Ser Tyr Leu Lys Gly Ser Ser Gly Gly
                165                 170                 175

Pro Leu Leu Cys Pro Ser Gly His Ala Val Gly Ile Phe Arg Ala Ala
            180                 185                 190

Val Cys Thr Arg Gly Val Ala Lys Ala Val Asp Phe Val Pro Val Glu
        195                 200                 205

Ser Met Glu Thr Thr Met Arg Ser
    210                 215

(2) INFORMATION FOR SEQ ID NO:4:

(i) SEQUENCE CHARACTERISTICS:
        (A) LENGTH: 216 amino acids
        (B) TYPE: amino acid
        (D) TOPOLOGY: linear (ii) MOLECULE TYPE: protein (xi) SEQUENCE DESCRIPTION: SEQ ID NO:4:

Met Gly Ser Ser His His His His His His Ser Ser Gly Leu Val Pro
  1               5                  10                  15

Arg Gly Ser His Met Gly Ser Val Val Ile Val Gly Arg Ile Ile Leu
             20                  25                  30

Ser Gly Ser Gly Ser Ile Thr Ala Tyr Ser Gln Gln Thr Arg Gly Leu
         35                  40                  45

Leu Gly Cys Lys Lys Thr Ser Leu Thr Gly Arg Asp Lys Asn Gln Val
     50                  55                  60

Glu Gly Glu Val Gln Val Val Ser Thr Ala Thr Gln Ser Phe Leu Ala
 65                  70                  75                  80

Thr Cys Val Asn Gly Val Cys Trp Thr Val Tyr His Gly Ala Gly Ser
             85                  90                  95

Lys Thr Leu Ala Gly Pro Lys Gly Pro Ile Thr Gln Met Tyr Thr Asn
            100                 105                 110

Val Asp Gln Asp Leu Val Gly Trp Gln Ala Pro Pro Gly Ala Arg Ser
        115                 120                 125

Leu Thr Pro Cys Thr Cys Gly Ser Ser Asp Leu Tyr Leu Val Thr Arg
    130                 135                 140
```

His Ala Asp Val Ile Pro Val Arg Arg Arg Gly Asp Ser Arg Gly Ser
145                 150                 155                 160

Leu Leu Ser Pro Arg Pro Val Ser Tyr Leu Lys Gly Ser Ser Gly Gly
            165                 170                 175

Pro Leu Leu Cys Pro Ser Gly His Ala Val Gly Ile Phe Arg Ala Ala
            180                 185                 190

Val Cys Thr Arg Gly Val Ala Lys Ala Val Asp Phe Val Pro Val Glu
            195                 200                 205

Ser Met Glu Thr Thr Met Arg Ser
    210                 215

(2) INFORMATION FOR SEQ ID NO:5:

(i) SEQUENCE CHARACTERISTICS:
        (A) LENGTH: 216 amino acids
        (B) TYPE: amino acid
        (D) TOPOLOGY: linear (ii) MOLECULE TYPE: protein (xi) SEQUENCE DESCRIPTION: SEQ ID NO:5:

Met Gly Ser Ser His His His His His His Ser Ser Gly Leu Val Pro
1               5                   10                  15

Arg Gly Ser His Met Gly Ser Val Val Ile Val Gly Arg Ile Ile Leu
            20                  25                  30

Ser Gly Ser Gly Ser Ile Thr Ala Tyr Ser Gln Gln Thr Arg Gly Leu
            35                  40                  45

Leu Gly Cys Ile Ile Thr Ser Leu Thr Gly Arg Asp Lys Asn Gln Val
    50                  55                  60

Glu Gly Glu Val Gln Val Val Ser Thr Ala Thr Gln Ser Phe Leu Ala
65                  70                  75                  80

Thr Cys Val Asn Gly Val Cys Trp Thr Val Tyr His Gly Ala Gly Ser
            85                  90                  95

Lys Thr Leu Ala Gly Pro Lys Gly Pro Ile Thr Gln Met Tyr Thr Asn
            100                 105                 110

Val Asp Gln Asp Leu Val Gly Trp Gln Ala Pro Pro Gly Ala Arg Ser
            115                 120                 125

Leu Thr Pro Cys Thr Cys Gly Ser Ser Asp Leu Tyr Leu Val Thr Arg
    130                 135                 140

His Ala Asp Val Ile Pro Val Arg Arg Arg Gly Asp Ser Arg Gly Ser
145                 150                 155                 160

Leu Leu Ser Pro Arg Pro Val Ser Tyr Leu Lys Gly Ser Ala Gly Gly
            165                 170                 175

Pro Leu Leu Cys Pro Ser Gly His Ala Val Gly Ile Phe Arg Ala Ala
            180                 185                 190

Val Cys Thr Arg Gly Val Ala Lys Ala Val Asp Phe Val Pro Val Glu
            195                 200                 205

Ser Met Glu Thr Thr Met Arg Ser
    210                 215

(2) INFORMATION FOR SEQ ID NO:6:

(i) SEQUENCE CHARACTERISTICS:
        (A) LENGTH: 216 amino acids
        (B) TYPE: amino acid
        (D) TOPOLOGY: linear (ii) MOLECULE TYPE: protein (xi) SEQUENCE DESCRIPTION: SEQ ID NO:6:

Met Gly Ser Ser His His His His His Ser Ser Gly Leu Val Pro
 1               5                   10                  15

Arg Gly Ser His Met Gly Ser Val Val Ile Val Gly Arg Ile Ile Leu
                20                  25                  30

Ser Gly Ser Gly Ser Ile Thr Ala Tyr Ser Gln Gln Thr Arg Gly Leu
            35                  40                  45

Leu Gly Cys Lys Ile Thr Ser Leu Thr Gly Arg Asp Lys Asn Gln Val
        50                  55                  60

Glu Gly Glu Val Gln Val Val Ser Thr Ala Thr Gln Ser Phe Leu Ala
 65                 70                  75                  80

Thr Cys Val Asn Gly Val Cys Trp Thr Val Tyr His Gly Ala Gly Ser
                85                  90                  95

Lys Thr Leu Ala Gly Pro Lys Gly Pro Ile Thr Gln Met Tyr Thr Asn
                100                 105                 110

Val Asp Gln Asp Leu Val Gly Trp Gln Ala Pro Pro Gly Ala Arg Ser
            115                 120                 125

Leu Thr Pro Cys Thr Cys Gly Ser Ser Asp Leu Tyr Leu Val Thr Arg
    130                 135                 140

His Ala Asp Val Ile Pro Val Arg Arg Arg Gly Asp Ser Arg Gly Ser
145                 150                 155                 160

Leu Leu Ser Pro Arg Pro Val Ser Tyr Leu Lys Gly Ser Ala Gly Gly
                165                 170                 175

Pro Leu Leu Cys Pro Ser Gly His Ala Val Gly Ile Phe Arg Ala Ala
                180                 185                 190

Val Cys Thr Arg Gly Val Ala Lys Ala Val Asp Phe Val Pro Val Glu
        195                 200                 205

Ser Met Glu Thr Thr Met Arg Ser
    210                 215

(2) INFORMATION FOR SEQ ID NO:7:

(i) SEQUENCE CHARACTERISTICS:
        (A) LENGTH: 216 amino acids
        (B) TYPE: amino acid
        (D) TOPOLOGY: linear (ii) MOLECULE TYPE: protein (xi) SEQUENCE DESCRIPTION: SEQ ID NO:7:

Met Gly Ser Ser His His His His His Ser Ser Gly Leu Val Pro
 1               5                   10                  15

Arg Gly Ser His Met Gly Ser Val Val Ile Val Gly Arg Ile Ile Leu
                20                  25                  30

Ser Gly Ser Gly Ser Ile Thr Ala Tyr Ser Gln Gln Thr Arg Gly Leu
            35                  40                  45

Leu Gly Cys Ile Lys Thr Ser Leu Thr Gly Arg Asp Lys Asn Gln Val
        50                  55                  60

Glu Gly Glu Val Gln Val Val Ser Thr Ala Thr Gln Ser Phe Leu Ala
 65                 70                  75                  80

Thr Cys Val Asn Gly Val Cys Trp Thr Val Tyr His Gly Ala Gly Ser
                85                  90                  95

Lys Thr Leu Ala Gly Pro Lys Gly Pro Ile Thr Gln Met Tyr Thr Asn
                100                 105                 110

Val Asp Gln Asp Leu Val Gly Trp Gln Ala Pro Pro Gly Ala Arg Ser
            115                 120                 125

```
Leu Thr Pro Cys Thr Cys Gly Ser Ser Asp Leu Tyr Leu Val Thr Arg
        130                 135                 140

His Ala Asp Val Ile Pro Val Arg Arg Arg Gly Asp Ser Arg Gly Ser
145                 150                 155                 160

Leu Leu Ser Pro Arg Pro Val Ser Tyr Leu Lys Gly Ser Ala Gly Gly
                165                 170                 175

Pro Leu Leu Cys Pro Ser Gly His Ala Val Gly Ile Phe Arg Ala Ala
                180                 185                 190

Val Cys Thr Arg Gly Val Ala Lys Ala Val Asp Phe Val Pro Val Glu
            195                 200                 205

Ser Met Glu Thr Thr Met Arg Ser
210                 215
```

(2) INFORMATION FOR SEQ ID NO:8:

(i) SEQUENCE CHARACTERISTICS:
        (A) LENGTH: 216 amino acids
        (B) TYPE: amino acid
        (D) TOPOLOGY: linear (ii) MOLECULE TYPE: protein (xi) SEQUENCE DESCRIPTION: SEQ ID NO:8:

```
Met Gly Ser Ser His His His His His His Ser Ser Gly Leu Val Pro
1               5                   10                  15

Arg Gly Ser His Met Gly Ser Val Val Ile Val Gly Arg Ile Ile Leu
                20                  25                  30

Ser Gly Ser Gly Ser Ile Thr Ala Tyr Ser Gln Gln Thr Arg Gly Leu
            35                  40                  45

Leu Gly Cys Lys Lys Thr Ser Leu Thr Gly Arg Asp Lys Asn Gln Val
    50                  55                  60

Glu Gly Glu Val Gln Val Val Ser Thr Ala Thr Gln Ser Phe Leu Ala
65                  70                  75                  80

Thr Cys Val Asn Gly Val Cys Trp Thr Val Tyr His Gly Ala Gly Ser
                85                  90                  95

Lys Thr Leu Ala Gly Pro Lys Gly Pro Ile Thr Gln Met Tyr Thr Asn
                100                 105                 110

Val Asp Gln Asp Leu Val Gly Trp Gln Ala Pro Pro Gly Ala Arg Ser
            115                 120                 125

Leu Thr Pro Cys Thr Cys Gly Ser Ser Asp Leu Tyr Leu Val Thr Arg
        130                 135                 140

His Ala Asp Val Ile Pro Val Arg Arg Arg Gly Asp Ser Arg Gly Ser
145                 150                 155                 160

Leu Leu Ser Pro Arg Pro Val Ser Tyr Leu Lys Gly Ser Ala Gly Gly
                165                 170                 175

Pro Leu Leu Cys Pro Ser Gly His Ala Val Gly Ile Phe Arg Ala Ala
                180                 185                 190

Val Cys Thr Arg Gly Val Ala Lys Ala Val Asp Phe Val Pro Val Glu
            195                 200                 205

Ser Met Glu Thr Thr Met Arg Ser
210                 215
```

(2) INFORMATION FOR SEQ ID NO:9:

(i) SEQUENCE CHARACTERISTICS:
        (A) LENGTH: 216 amino acids
        (B) TYPE: amino acid
        (D) TOPOLOGY: linear (ii) MOLECULE TYPE: protein (xi) SEQUENCE DESCRIPTION: SEQ ID NO:9:

```
Met Gly Ser Ser His His His His His Ser Ser Gly Leu Val Pro
 1               5                  10                  15

Arg Gly Ser His Met Gly Ser Val Val Ile Val Gly Arg Ile Ile Leu
                20                  25                  30

Ser Pro Ala Gly Gly Ile Thr Ala Tyr Ser Gln Gln Thr Arg Gly Leu
            35                  40                  45

Leu Gly Cys Ile Ile Thr Ser Leu Thr Gly Arg Asp Lys Asn Gln Val
        50                  55                  60

Glu Gly Glu Val Gln Val Val Ser Thr Ala Thr Gln Ser Phe Leu Ala
 65                 70                  75                  80

Thr Cys Val Asn Gly Val Cys Trp Thr Val Tyr His Gly Ala Gly Ser
                85                  90                  95

Lys Thr Leu Ala Gly Pro Lys Gly Pro Ile Thr Gln Met Tyr Thr Asn
            100                 105                 110

Val Asp Gln Asp Leu Val Gly Trp Gln Ala Pro Pro Gly Ala Arg Ser
        115                 120                 125

Leu Thr Pro Cys Thr Cys Gly Ser Ser Asp Leu Tyr Leu Val Thr Arg
130                 135                 140

His Ala Asp Val Ile Pro Val Arg Arg Arg Gly Asp Ser Arg Gly Ser
145                 150                 155                 160

Leu Leu Ser Pro Arg Pro Val Ser Tyr Leu Lys Gly Ser Ser Gly Gly
                165                 170                 175

Pro Leu Leu Cys Pro Ser Gly His Ala Val Gly Ile Phe Arg Ala Ala
            180                 185                 190

Val Cys Thr Arg Gly Val Ala Lys Ala Val Asp Phe Val Pro Val Glu
        195                 200                 205

Ser Met Glu Thr Thr Met Arg Ser
210                 215
```

(2) INFORMATION FOR SEQ ID NO:10:

(i) SEQUENCE CHARACTERISTICS:
        (A) LENGTH: 216 amino acids
        (B) TYPE: amino acid
        (D) TOPOLOGY: linear (ii) MOLECULE TYPE: protein (xi) SEQUENCE DESCRIPTION: SEQ ID NO:10:

```
Met Gly Ser Ser His His His His His Ser Ser Gly Leu Val Pro
 1               5                  10                  15

Arg Gly Ser His Met Gly Ser Val Val Ile Val Gly Arg Ile Ile Leu
                20                  25                  30

Ser Pro Ala Gly Gly Ile Thr Ala Tyr Ser Gln Gln Thr Arg Gly Leu
            35                  40                  45

Leu Gly Cys Lys Ile Thr Ser Leu Thr Gly Arg Asp Lys Asn Gln Val
        50                  55                  60

Glu Gly Glu Val Gln Val Val Ser Thr Ala Thr Gln Ser Phe Leu Ala
 65                 70                  75                  80

Thr Cys Val Asn Gly Val Cys Trp Thr Val Tyr His Gly Ala Gly Ser
                85                  90                  95

Lys Thr Leu Ala Gly Pro Lys Gly Pro Ile Thr Gln Met Tyr Thr Asn
            100                 105                 110
```

```
Val Asp Gln Asp Leu Val Gly Trp Gln Ala Pro Pro Gly Ala Arg Ser
        115                 120                 125

Leu Thr Pro Cys Thr Cys Gly Ser Ser Asp Leu Tyr Leu Val Thr Arg
    130                 135                 140

His Ala Asp Val Ile Pro Val Arg Arg Arg Gly Asp Ser Arg Gly Ser
145                 150                 155                 160

Leu Leu Ser Pro Arg Pro Val Ser Tyr Leu Lys Gly Ser Ser Gly Gly
                165                 170                 175

Pro Leu Leu Cys Pro Ser Gly His Ala Val Gly Ile Phe Arg Ala Ala
                180                 185                 190

Val Cys Thr Arg Gly Val Ala Lys Ala Val Asp Phe Val Pro Val Glu
            195                 200                 205

Ser Met Glu Thr Thr Met Arg Ser
    210                 215
```

(2) INFORMATION FOR SEQ ID NO:11:

(i) SEQUENCE CHARACTERISTICS:
        (A) LENGTH: 666 amino acids
        (B) TYPE: amino acid
        (D) TOPOLOGY: linear (ii) MOLECULE TYPE: protein (xi) SEQUENCE DESCRIPTION: SEQ ID NO:11:

```
Met Gly Ser Ser His His His His His His Ser Ser Gly Leu Val Pro
  1               5                  10                  15

Arg Gly Ser His Met Gly Ser Val Val Ile Val Gly Arg Ile Ile Leu
                 20                  25                  30

Ser Gly Ser Gly Ser Ile Thr Ala Tyr Ser Gln Gln Thr Arg Gly Leu
            35                  40                  45

Leu Gly Cys Ile Ile Thr Ser Leu Thr Gly Arg Asp Lys Asn Gln Val
        50                  55                  60

Glu Gly Glu Val Gln Val Val Ser Thr Ala Thr Gln Ser Phe Leu Ala
 65                  70                  75                  80

Thr Cys Val Asn Gly Val Cys Trp Thr Val Tyr His Gly Ala Gly Ser
                85                  90                  95

Lys Thr Leu Ala Gly Pro Lys Gly Pro Ile Thr Gln Met Tyr Thr Asn
            100                 105                 110

Val Asp Gln Asp Leu Val Gly Trp Gln Ala Pro Pro Gly Ala Arg Ser
        115                 120                 125

Leu Thr Pro Cys Thr Cys Gly Ser Ser Asp Leu Tyr Leu Val Thr Arg
    130                 135                 140

His Ala Asp Val Ile Pro Val Arg Arg Arg Gly Asp Ser Arg Gly Ser
145                 150                 155                 160

Leu Leu Ser Pro Arg Pro Val Ser Tyr Leu Lys Gly Ser Ser Gly Gly
                165                 170                 175

Pro Leu Leu Cys Pro Ser Gly His Ala Val Gly Ile Phe Arg Ala Ala
                180                 185                 190

Val Cys Thr Arg Gly Val Ala Lys Ala Val Asp Phe Val Pro Val Glu
            195                 200                 205

Ser Met Glu Thr Thr Met Arg Ser Pro Val Phe Thr Asp Asn Ser Ser
    210                 215                 220

Pro Pro Ala Val Pro Gln Ser Phe Gln Val Ala His Leu His Ala Pro
225                 230                 235                 240
```

-continued

```
Thr Gly Ser Gly Lys Ser Thr Lys Val Pro Ala Ala Tyr Ala Ala Gln
                245                 250                 255

Gly Tyr Lys Val Leu Val Leu Asn Pro Ser Val Ala Ala Thr Leu Gly
            260                 265                 270

Phe Gly Ala Tyr Met Ser Lys Ala His Gly Ile Asp Pro Asn Ile Arg
            275                 280                 285

Thr Gly Val Arg Thr Ile Thr Thr Gly Ala Pro Val Thr Tyr Ser Thr
        290                 295                 300

Tyr Gly Lys Phe Leu Ala Asp Gly Gly Cys Ser Gly Gly Ala Tyr Asp
305                 310                 315                 320

Ile Ile Ile Cys Asp Glu Cys His Ser Thr Asp Ser Thr Thr Ile Leu
                325                 330                 335

Gly Ile Gly Thr Val Leu Asp Gln Ala Glu Thr Ala Gly Ala Arg Leu
            340                 345                 350

Val Val Leu Ala Thr Ala Thr Pro Pro Gly Ser Val Thr Val Pro His
        355                 360                 365

Pro Asn Ile Glu Glu Val Ala Leu Ser Asn Thr Gly Glu Ile Pro Phe
    370                 375                 380

Tyr Gly Lys Ala Ile Pro Ile Glu Ala Ile Arg Gly Gly Arg His Leu
385                 390                 395                 400

Ile Phe Cys His Ser Lys Lys Lys Cys Asp Glu Leu Ala Ala Lys Leu
                405                 410                 415

Ser Gly Leu Gly Ile Asn Ala Val Ala Tyr Tyr Arg Gly Leu Asp Val
            420                 425                 430

Ser Val Ile Pro Thr Ile Gly Asp Val Val Val Val Ala Thr Asp Ala
        435                 440                 445

Leu Met Thr Gly Tyr Thr Gly Asp Phe Asp Ser Val Ile Asp Cys Asn
    450                 455                 460

Thr Cys Val Thr Gln Thr Val Asp Phe Ser Leu Asp Pro Thr Phe Thr
465                 470                 475                 480

Ile Glu Thr Thr Thr Val Pro Gln Asp Ala Val Ser Arg Ser Gln Arg
                485                 490                 495

Arg Gly Arg Thr Gly Arg Gly Arg Gly Ile Tyr Arg Phe Val Thr
            500                 505                 510

Pro Gly Glu Arg Pro Ser Gly Met Phe Asp Ser Ser Val Leu Cys Glu
        515                 520                 525

Cys Tyr Asp Ala Gly Cys Ala Trp Tyr Glu Leu Thr Pro Ala Glu Thr
    530                 535                 540

Ser Val Arg Leu Arg Ala Tyr Leu Asn Thr Pro Gly Leu Pro Val Cys
545                 550                 555                 560

Gln Asp His Leu Glu Phe Trp Glu Ser Val Phe Thr Gly Leu Thr His
                565                 570                 575

Ile Asp Ala His Phe Leu Ser Gln Thr Lys Gln Ala Gly Asp Asn Phe
            580                 585                 590

Pro Tyr Leu Val Ala Tyr Gln Ala Thr Val Cys Ala Arg Ala Gln Ala
        595                 600                 605

Pro Pro Pro Ser Trp Asp Gln Met Trp Lys Cys Leu Ile Arg Leu Lys
    610                 615                 620

Pro Thr Leu His Gly Pro Thr Pro Leu Leu Tyr Arg Leu Gly Ala Val
625                 630                 635                 640
```

```
Gln Asn Glu Val Thr Leu Thr His Pro Ile Thr Lys Tyr Ile Met Ala
                645                 650                 655
Cys Met Ser Ala Asp Leu Glu Val Val Thr
                660                 665

(2) INFORMATION FOR SEQ ID NO:12:

(i) SEQUENCE CHARACTERISTICS:
        (A) LENGTH: 666 amino acids
        (B) TYPE: amino acid
        (D) TOPOLOGY: linear (ii) MOLECULE TYPE: protein (xi) SEQUENCE DESCRIPTION: SEQ ID NO:12:

Met Gly Ser Ser His His His His His His Ser Ser Gly Leu Val Pro
  1               5                  10                  15
Arg Gly Ser His Met Gly Ser Val Val Ile Val Gly Arg Ile Ile Leu
                 20                  25                  30
Ser Gly Ser Gly Ser Ile Thr Ala Tyr Ser Gln Gln Thr Arg Gly Leu
             35                  40                  45
Leu Gly Cys Lys Ile Thr Ser Leu Thr Gly Arg Asp Lys Asn Gln Val
 50                  55                  60
Glu Gly Glu Val Gln Val Val Ser Thr Ala Thr Gln Ser Phe Leu Ala
 65                  70                  75                  80
Thr Cys Val Asn Gly Val Cys Trp Thr Val Tyr His Gly Ala Gly Ser
                 85                  90                  95
Lys Thr Leu Ala Gly Pro Lys Gly Pro Ile Thr Gln Met Tyr Thr Asn
                100                 105                 110
Val Asp Gln Asp Leu Val Gly Trp Gln Ala Pro Pro Gly Ala Arg Ser
            115                 120                 125
Leu Thr Pro Cys Thr Cys Gly Ser Ser Asp Leu Tyr Leu Val Thr Arg
130                 135                 140
His Ala Asp Val Ile Pro Val Arg Arg Arg Gly Asp Ser Arg Gly Ser
145                 150                 155                 160
Leu Leu Ser Pro Arg Pro Val Ser Tyr Leu Lys Gly Ser Ser Gly Gly
                165                 170                 175
Pro Leu Leu Cys Pro Ser Gly His Ala Val Gly Ile Phe Arg Ala Ala
                180                 185                 190
Val Cys Thr Arg Gly Val Ala Lys Ala Val Asp Phe Val Pro Val Glu
            195                 200                 205
Ser Met Glu Thr Thr Met Arg Ser Pro Val Phe Thr Asp Asn Ser Ser
    210                 215                 220
Pro Pro Ala Val Pro Gln Ser Phe Gln Val Ala His Leu His Ala Pro
225                 230                 235                 240
Thr Gly Ser Gly Lys Ser Thr Lys Val Pro Ala Ala Tyr Ala Ala Gln
                245                 250                 255
Gly Tyr Lys Val Leu Val Leu Asn Pro Ser Val Ala Ala Thr Leu Gly
            260                 265                 270
Phe Gly Ala Tyr Met Ser Lys Ala His Gly Ile Asp Pro Asn Ile Arg
            275                 280                 285
Thr Gly Val Arg Thr Ile Thr Thr Gly Ala Pro Val Thr Tyr Ser Thr
            290                 295                 300
Tyr Gly Lys Phe Leu Ala Asp Gly Gly Cys Ser Gly Gly Ala Tyr Asp
305                 310                 315                 320
```

-continued

```
Ile Ile Ile Cys Asp Glu Cys His Ser Thr Asp Ser Thr Thr Ile Leu
            325                 330                 335
Gly Ile Gly Thr Val Leu Asp Gln Ala Glu Thr Ala Gly Ala Arg Leu
            340                 345                 350
Val Val Leu Ala Thr Ala Thr Pro Pro Gly Ser Val Thr Val Pro His
            355                 360                 365
Pro Asn Ile Glu Glu Val Ala Leu Ser Asn Thr Gly Glu Ile Pro Phe
370                 375                 380
Tyr Gly Lys Ala Ile Pro Ile Glu Ala Ile Arg Gly Gly Arg His Leu
385                 390                 395                 400
Ile Phe Cys His Ser Lys Lys Cys Asp Glu Leu Ala Ala Lys Leu
            405                 410                 415
Ser Gly Leu Gly Ile Asn Ala Val Ala Tyr Tyr Arg Gly Leu Asp Val
            420                 425                 430
Ser Val Ile Pro Thr Ile Gly Asp Val Val Val Ala Thr Asp Ala
            435                 440                 445
Leu Met Thr Gly Tyr Thr Gly Asp Phe Asp Ser Val Ile Asp Cys Asn
    450                 455                 460
Thr Cys Val Thr Gln Thr Val Asp Phe Ser Leu Asp Pro Thr Phe Thr
465                 470                 475                 480
Ile Glu Thr Thr Thr Val Pro Gln Asp Ala Val Ser Arg Ser Gln Arg
                485                 490                 495
Arg Gly Arg Thr Gly Arg Gly Arg Arg Gly Ile Tyr Arg Phe Val Thr
            500                 505                 510
Pro Gly Glu Arg Pro Ser Gly Met Phe Asp Ser Ser Val Leu Cys Glu
            515                 520                 525
Cys Tyr Asp Ala Gly Cys Ala Trp Tyr Glu Leu Thr Pro Ala Glu Thr
    530                 535                 540
Ser Val Arg Leu Arg Ala Tyr Leu Asn Thr Pro Gly Leu Pro Val Cys
545                 550                 555                 560
Gln Asp His Leu Glu Phe Trp Glu Ser Val Phe Thr Gly Leu Thr His
                565                 570                 575
Ile Asp Ala His Phe Leu Ser Gln Thr Lys Gln Ala Gly Asp Asn Phe
            580                 585                 590
Pro Tyr Leu Val Ala Tyr Gln Ala Thr Val Cys Ala Arg Ala Gln Ala
            595                 600                 605
Pro Pro Pro Ser Trp Asp Gln Met Trp Lys Cys Leu Ile Arg Leu Lys
610                 615                 620
Pro Thr Leu His Gly Pro Thr Pro Leu Leu Tyr Arg Leu Gly Ala Val
625                 630                 635                 640
Gln Asn Glu Val Thr Leu Thr His Pro Ile Thr Lys Tyr Ile Met Ala
                645                 650                 655
Cys Met Ser Ala Asp Leu Glu Val Val Thr
                660                 665
```

(2) INFORMATION FOR SEQ ID NO:13:

(i) SEQUENCE CHARACTERISTICS:
       (A) LENGTH: 666 amino acids
       (B) TYPE: amino acid
       (D) TOPOLOGY: linear (ii) MOLECULE TYPE: protein (xi) SEQUENCE DESCRIPTION: SEQ ID NO:13:

```
Met Gly Ser Ser His His His His His His Ser Ser Gly Leu Val Pro
  1               5                  10                  15

Arg Gly Ser His Met Gly Ser Val Val Ile Val Gly Arg Ile Ile Leu
             20                  25                  30

Ser Gly Ser Gly Ser Ile Thr Ala Tyr Ser Gln Gln Thr Arg Gly Leu
         35                  40                  45

Leu Gly Cys Ile Lys Thr Ser Leu Thr Gly Arg Asp Lys Asn Gln Val
     50                  55                  60

Glu Gly Glu Val Gln Val Ser Thr Ala Thr Gln Ser Phe Leu Ala
 65                  70                  75                  80

Thr Cys Val Asn Gly Val Cys Trp Thr Val Tyr His Gly Ala Gly Ser
                 85                  90                  95

Lys Thr Leu Ala Gly Pro Lys Gly Pro Ile Thr Gln Met Tyr Thr Asn
             100                 105                 110

Val Asp Gln Asp Leu Val Gly Trp Gln Ala Pro Gly Ala Arg Ser
             115                 120                 125

Leu Thr Pro Cys Thr Cys Gly Ser Ser Asp Leu Tyr Leu Val Thr Arg
    130                 135                 140

His Ala Asp Val Ile Pro Val Arg Arg Arg Gly Asp Ser Arg Gly Ser
145                 150                 155                 160

Leu Leu Ser Pro Arg Pro Val Ser Tyr Leu Lys Gly Ser Ser Gly Gly
                165                 170                 175

Pro Leu Leu Cys Pro Ser Gly His Ala Val Gly Ile Phe Arg Ala Ala
                180                 185                 190

Val Cys Thr Arg Gly Val Ala Lys Ala Val Asp Phe Val Pro Val Glu
        195                 200                 205

Ser Met Glu Thr Thr Met Arg Ser Pro Val Phe Thr Asp Asn Ser Ser
    210                 215                 220

Pro Pro Ala Val Pro Gln Ser Phe Gln Val Ala His Leu His Ala Pro
225                 230                 235                 240

Thr Gly Ser Gly Lys Ser Thr Lys Val Pro Ala Ala Tyr Ala Ala Gln
                245                 250                 255

Gly Tyr Lys Val Leu Val Leu Asn Pro Ser Val Ala Ala Thr Leu Gly
            260                 265                 270

Phe Gly Ala Tyr Met Ser Lys Ala His Gly Ile Asp Pro Asn Ile Arg
    275                 280                 285

Thr Gly Val Arg Thr Ile Thr Thr Gly Ala Pro Val Thr Tyr Ser Thr
    290                 295                 300

Tyr Gly Lys Phe Leu Ala Asp Gly Gly Cys Ser Gly Gly Ala Tyr Asp
305                 310                 315                 320

Ile Ile Ile Cys Asp Glu Cys His Ser Thr Asp Ser Thr Thr Ile Leu
                325                 330                 335

Gly Ile Gly Thr Val Leu Asp Gln Ala Glu Thr Ala Gly Ala Arg Leu
            340                 345                 350

Val Val Leu Ala Thr Ala Thr Pro Pro Gly Ser Val Thr Val Pro His
        355                 360                 365

Pro Asn Ile Glu Glu Val Ala Leu Ser Asn Thr Gly Glu Ile Pro Phe
    370                 375                 380

Tyr Gly Lys Ala Ile Pro Ile Glu Ala Ile Arg Gly Gly Arg His Leu
385                 390                 395                 400

Ile Phe Cys His Ser Lys Lys Cys Asp Glu Leu Ala Ala Lys Leu
                405                 410                 415
```

-continued

```
Ser Gly Leu Gly Ile Asn Ala Val Ala Tyr Tyr Arg Gly Leu Asp Val
                420                 425                 430

Ser Val Ile Pro Thr Ile Gly Asp Val Val Val Ala Thr Asp Ala
            435                 440                 445

Leu Met Thr Gly Tyr Thr Gly Asp Phe Asp Ser Val Ile Asp Cys Asn
        450                 455                 460

Thr Cys Val Thr Gln Thr Val Asp Phe Ser Leu Asp Pro Thr Phe Thr
465                 470                 475                 480

Ile Glu Thr Thr Thr Val Pro Gln Asp Ala Val Ser Arg Ser Gln Arg
                485                 490                 495

Arg Gly Arg Thr Gly Arg Gly Arg Gly Ile Tyr Arg Phe Val Thr
            500                 505                 510

Pro Gly Glu Arg Pro Ser Gly Met Phe Asp Ser Ser Val Leu Cys Glu
        515                 520                 525

Cys Tyr Asp Ala Gly Cys Ala Trp Tyr Glu Leu Thr Pro Ala Glu Thr
        530                 535                 540

Ser Val Arg Leu Arg Ala Tyr Leu Asn Thr Pro Gly Leu Pro Val Cys
545                 550                 555                 560

Gln Asp His Leu Glu Phe Trp Glu Ser Val Phe Thr Gly Leu Thr His
                565                 570                 575

Ile Asp Ala His Phe Leu Ser Gln Thr Lys Gln Ala Gly Asp Asn Phe
            580                 585                 590

Pro Tyr Leu Val Ala Tyr Gln Ala Thr Val Cys Ala Arg Ala Gln Ala
        595                 600                 605

Pro Pro Pro Ser Trp Asp Gln Met Trp Lys Cys Leu Ile Arg Leu Lys
        610                 615                 620

Pro Thr Leu His Gly Pro Thr Pro Leu Leu Tyr Arg Leu Gly Ala Val
625                 630                 635                 640

Gln Asn Glu Val Thr Leu Thr His Pro Ile Thr Lys Tyr Ile Met Ala
                645                 650                 655

Cys Met Ser Ala Asp Leu Glu Val Val Thr
            660                 665
```

(2) INFORMATION FOR SEQ ID NO:14:

(i) SEQUENCE CHARACTERISTICS:
        (A) LENGTH: 666 amino acids
        (B) TYPE: amino acid
        (D) TOPOLOGY: linear (ii) MOLECULE TYPE: protein (xi) SEQUENCE DESCRIPTION: SEQ ID NO:14:

```
Met Gly Ser Ser His His His His His His Ser Ser Gly Leu Val Pro
1               5                   10                  15

Arg Gly Ser His Met Gly Ser Val Val Ile Val Gly Arg Ile Ile Leu
            20                  25                  30

Ser Gly Ser Gly Ser Ile Thr Ala Tyr Ser Gln Gln Thr Arg Gly Leu
        35                  40                  45

Leu Gly Cys Lys Lys Thr Ser Leu Thr Gly Arg Asp Lys Asn Gln Val
        50                  55                  60

Glu Gly Glu Val Gln Val Val Ser Thr Ala Thr Gln Ser Phe Leu Ala
65                  70                  75                  80

Thr Cys Val Asn Gly Val Cys Trp Thr Val Tyr His Gly Ala Gly Ser
                85                  90                  95
```

-continued

```
Lys Thr Leu Ala Gly Pro Lys Gly Pro Ile Thr Gln Met Tyr Thr Asn
            100                 105                 110

Val Asp Gln Asp Leu Val Gly Trp Gln Ala Pro Pro Gly Ala Arg Ser
            115                 120                 125

Leu Thr Pro Cys Thr Cys Gly Ser Ser Asp Leu Tyr Leu Val Thr Arg
            130                 135                 140

His Ala Asp Val Ile Pro Val Arg Arg Gly Asp Ser Arg Gly Ser
145                 150                 155                 160

Leu Leu Ser Pro Arg Pro Val Ser Tyr Leu Lys Gly Ser Ser Gly Gly
            165                 170                 175

Pro Leu Leu Cys Pro Ser Gly His Ala Val Gly Ile Phe Arg Ala Ala
            180                 185                 190

Val Cys Thr Arg Gly Val Ala Lys Ala Val Asp Phe Val Pro Val Glu
            195                 200                 205

Ser Met Glu Thr Thr Met Arg Ser Pro Val Phe Thr Asp Asn Ser Ser
210                 215                 220

Pro Pro Ala Val Pro Gln Ser Phe Gln Val Ala His Leu His Ala Pro
225                 230                 235                 240

Thr Gly Ser Gly Lys Ser Thr Lys Val Pro Ala Ala Tyr Ala Ala Gln
            245                 250                 255

Gly Tyr Lys Val Leu Val Leu Asn Pro Ser Val Ala Ala Thr Leu Gly
            260                 265                 270

Phe Gly Ala Tyr Met Ser Lys Ala His Gly Ile Asp Pro Asn Ile Arg
            275                 280                 285

Thr Gly Val Arg Thr Ile Thr Thr Gly Ala Pro Val Thr Tyr Ser Thr
            290                 295                 300

Tyr Gly Lys Phe Leu Ala Asp Gly Gly Cys Ser Gly Gly Ala Tyr Asp
305                 310                 315                 320

Ile Ile Ile Cys Asp Glu Cys His Ser Thr Asp Ser Thr Thr Ile Leu
            325                 330                 335

Gly Ile Gly Thr Val Leu Asp Gln Ala Glu Thr Ala Gly Ala Arg Leu
            340                 345                 350

Val Val Leu Ala Thr Ala Thr Pro Pro Gly Ser Val Thr Val Pro His
            355                 360                 365

Pro Asn Ile Glu Glu Val Ala Leu Ser Asn Thr Gly Glu Ile Pro Phe
370                 375                 380

Tyr Gly Lys Ala Ile Pro Ile Glu Ala Ile Arg Gly Gly Arg His Leu
385                 390                 395                 400

Ile Phe Cys His Ser Lys Lys Lys Cys Asp Glu Leu Ala Ala Lys Leu
            405                 410                 415

Ser Gly Leu Gly Ile Asn Ala Val Ala Tyr Tyr Arg Gly Leu Asp Val
            420                 425                 430

Ser Val Ile Pro Thr Ile Gly Asp Val Val Val Ala Thr Asp Ala
            435                 440                 445

Leu Met Thr Gly Tyr Thr Gly Asp Phe Asp Ser Val Ile Asp Cys Asn
450                 455                 460

Thr Cys Val Thr Gln Thr Val Asp Phe Ser Leu Asp Pro Thr Phe Thr
465                 470                 475                 480

Ile Glu Thr Thr Thr Val Pro Gln Asp Ala Val Ser Arg Ser Gln Arg
            485                 490                 495

Arg Gly Arg Thr Gly Arg Gly Arg Arg Gly Ile Tyr Arg Phe Val Thr
            500                 505                 510
```

```
Pro Gly Glu Arg Pro Ser Gly Met Phe Asp Ser Ser Val Leu Cys Glu
            515                 520                 525

Cys Tyr Asp Ala Gly Cys Ala Trp Tyr Glu Leu Thr Pro Ala Glu Thr
        530                 535                 540

Ser Val Arg Leu Arg Ala Tyr Leu Asn Thr Pro Gly Leu Pro Val Cys
545                 550                 555                 560

Gln Asp His Leu Glu Phe Trp Glu Ser Val Phe Thr Gly Leu Thr His
            565                 570                 575

Ile Asp Ala His Phe Leu Ser Gln Thr Lys Gln Ala Gly Asp Asn Phe
        580                 585                 590

Pro Tyr Leu Val Ala Tyr Gln Ala Thr Val Cys Ala Arg Ala Gln Ala
            595                 600                 605

Pro Pro Pro Ser Trp Asp Gln Met Trp Lys Cys Leu Ile Arg Leu Lys
        610                 615                 620

Pro Thr Leu His Gly Pro Thr Pro Leu Leu Tyr Arg Leu Gly Ala Val
625                 630                 635                 640

Gln Asn Glu Val Thr Leu Thr His Pro Ile Thr Lys Tyr Ile Met Ala
            645                 650                 655

Cys Met Ser Ala Asp Leu Glu Val Val Thr
        660                 665

(2) INFORMATION FOR SEQ ID NO:15:

(i) SEQUENCE CHARACTERISTICS:
        (A) LENGTH: 666 amino acids
        (B) TYPE: amino acid
        (D) TOPOLOGY: linear (ii) MOLECULE TYPE: protein (xi) SEQUENCE DESCRIPTION: SEQ ID NO:15:

Met Gly Ser Ser His His His His His His Ser Ser Gly Leu Val Pro
  1               5                  10                  15

Arg Gly Ser His Met Gly Ser Val Val Ile Val Gly Arg Ile Ile Leu
             20                  25                  30

Ser Gly Ser Gly Ser Ile Thr Ala Tyr Ser Gln Gln Thr Arg Gly Leu
         35                  40                  45

Leu Gly Cys Ile Ile Thr Ser Leu Thr Gly Arg Asp Lys Asn Gln Val
     50                  55                  60

Glu Gly Glu Val Gln Val Val Ser Thr Ala Thr Gln Ser Phe Leu Ala
 65                  70                  75                  80

Thr Cys Val Asn Gly Val Cys Trp Thr Val Tyr His Gly Ala Gly Ser
             85                  90                  95

Lys Thr Leu Ala Gly Pro Lys Gly Pro Ile Thr Gln Met Tyr Thr Asn
            100                 105                 110

Val Asp Gln Asp Leu Val Gly Trp Gln Ala Pro Pro Gly Ala Arg Ser
            115                 120                 125

Leu Thr Pro Cys Thr Cys Gly Ser Ser Asp Leu Tyr Leu Val Thr Arg
        130                 135                 140

His Ala Asp Val Ile Pro Val Arg Arg Arg Gly Asp Ser Arg Gly Ser
145                 150                 155                 160

Leu Leu Ser Pro Arg Pro Val Ser Tyr Leu Lys Gly Ser Ala Gly Gly
            165                 170                 175

Pro Leu Leu Cys Pro Ser Gly His Ala Val Gly Ile Phe Arg Ala Ala
            180                 185                 190
```

-continued

```
Val Cys Thr Arg Gly Val Ala Lys Ala Val Asp Phe Val Pro Val Glu
            195                 200                 205
Ser Met Glu Thr Thr Met Arg Ser Pro Val Phe Thr Asp Asn Ser Ser
        210                 215                 220
Pro Pro Ala Val Pro Gln Ser Phe Gln Val Ala His Leu His Ala Pro
225                 230                 235                 240
Thr Gly Ser Gly Lys Ser Thr Lys Val Pro Ala Ala Tyr Ala Ala Gln
                245                 250                 255
Gly Tyr Lys Val Leu Val Leu Asn Pro Ser Val Ala Ala Thr Leu Gly
            260                 265                 270
Phe Gly Ala Tyr Met Ser Lys Ala His Gly Ile Asp Pro Asn Ile Arg
        275                 280                 285
Thr Gly Val Arg Thr Ile Thr Thr Gly Ala Pro Val Thr Tyr Ser Thr
    290                 295                 300
Tyr Gly Lys Phe Leu Ala Asp Gly Gly Cys Ser Gly Gly Ala Tyr Asp
305                 310                 315                 320
Ile Ile Ile Cys Asp Glu Cys His Ser Thr Asp Ser Thr Thr Ile Leu
                325                 330                 335
Gly Ile Gly Thr Val Leu Asp Gln Ala Glu Thr Ala Gly Ala Arg Leu
            340                 345                 350
Val Val Leu Ala Thr Ala Thr Pro Pro Gly Ser Val Thr Val Pro His
        355                 360                 365
Pro Asn Ile Glu Glu Val Ala Leu Ser Asn Thr Gly Glu Ile Pro Phe
    370                 375                 380
Tyr Gly Lys Ala Ile Pro Ile Glu Ala Ile Arg Gly Gly Arg His Leu
385                 390                 395                 400
Ile Phe Cys His Ser Lys Lys Cys Asp Glu Leu Ala Ala Lys Leu
                405                 410                 415
Ser Gly Leu Gly Ile Asn Ala Val Ala Tyr Tyr Arg Gly Leu Asp Val
            420                 425                 430
Ser Val Ile Pro Thr Ile Gly Asp Val Val Val Ala Thr Asp Ala
        435                 440                 445
Leu Met Thr Gly Tyr Thr Gly Asp Phe Asp Ser Val Ile Asp Cys Asn
    450                 455                 460
Thr Cys Val Thr Gln Thr Val Asp Phe Ser Leu Asp Pro Thr Phe Thr
465                 470                 475                 480
Ile Glu Thr Thr Thr Val Pro Gln Asp Ala Val Ser Arg Ser Gln Arg
                485                 490                 495
Arg Gly Arg Thr Gly Arg Gly Arg Gly Ile Tyr Arg Phe Val Thr
            500                 505                 510
Pro Gly Glu Arg Pro Ser Gly Met Phe Asp Ser Ser Val Leu Cys Glu
        515                 520                 525
Cys Tyr Asp Ala Gly Cys Ala Trp Tyr Glu Leu Thr Pro Ala Glu Thr
    530                 535                 540
Ser Val Arg Leu Arg Ala Tyr Leu Asn Thr Pro Gly Leu Pro Val Cys
545                 550                 555                 560
Gln Asp His Leu Glu Phe Trp Glu Ser Val Phe Thr Gly Leu Thr His
                565                 570                 575
Ile Asp Ala His Phe Leu Ser Gln Thr Lys Gln Ala Gly Asp Asn Phe
            580                 585                 590
Pro Tyr Leu Val Ala Tyr Gln Ala Thr Val Cys Ala Arg Ala Gln Ala
        595                 600                 605
```

```
Pro Pro Pro Ser Trp Asp Gln Met Trp Lys Cys Leu Ile Arg Leu Lys
    610             615                 620

Pro Thr Leu His Gly Pro Thr Pro Leu Leu Tyr Arg Leu Gly Ala Val
625             630                 635                 640

Gln Asn Glu Val Thr Leu Thr His Pro Ile Thr Lys Tyr Ile Met Ala
                645                 650                 655

Cys Met Ser Ala Asp Leu Glu Val Val Thr
            660                 665
```

(2) INFORMATION FOR SEQ ID NO:16:

(i) SEQUENCE CHARACTERISTICS:
        (A) LENGTH: 666 amino acids
        (B) TYPE: amino acid
        (D) TOPOLOGY: linear (ii) MOLECULE TYPE: protein (xi) SEQUENCE DESCRIPTION: SEQ ID NO:16:

```
Met Gly Ser Ser His His His His His His Ser Ser Gly Leu Val Pro
1               5                   10                  15

Arg Gly Ser His Met Gly Ser Val Val Ile Val Gly Arg Ile Ile Leu
                20                  25                  30

Ser Gly Ser Gly Ser Ile Thr Ala Tyr Ser Gln Gln Thr Arg Gly Leu
            35                  40                  45

Leu Gly Cys Lys Ile Thr Ser Leu Thr Gly Arg Asp Lys Asn Gln Val
        50                  55                  60

Glu Gly Glu Val Gln Val Val Ser Thr Ala Thr Gln Ser Phe Leu Ala
65                  70                  75                  80

Thr Cys Val Asn Gly Val Cys Trp Thr Val Tyr His Gly Ala Gly Ser
                85                  90                  95

Lys Thr Leu Ala Gly Pro Lys Gly Pro Ile Thr Gln Met Tyr Thr Asn
            100                 105                 110

Val Asp Gln Asp Leu Val Gly Trp Gln Ala Pro Pro Gly Ala Arg Ser
        115                 120                 125

Leu Thr Pro Cys Thr Cys Gly Ser Ser Asp Leu Tyr Leu Val Thr Arg
    130                 135                 140

His Ala Asp Val Ile Pro Val Arg Arg Arg Gly Asp Ser Arg Gly Ser
145                 150                 155                 160

Leu Leu Ser Pro Arg Pro Val Ser Tyr Leu Lys Gly Ser Ala Gly Gly
                165                 170                 175

Pro Leu Leu Cys Pro Ser Gly His Ala Val Gly Ile Phe Arg Ala Ala
            180                 185                 190

Val Cys Thr Arg Gly Val Ala Lys Ala Val Asp Phe Val Pro Val Glu
        195                 200                 205

Ser Met Glu Thr Thr Met Arg Ser Pro Val Phe Thr Asp Asn Ser Ser
    210                 215                 220

Pro Pro Ala Val Pro Gln Ser Phe Gln Val Ala His Leu His Ala Pro
225                 230                 235                 240

Thr Gly Ser Gly Lys Ser Thr Lys Val Pro Ala Ala Tyr Ala Ala Gln
                245                 250                 255

Gly Tyr Lys Val Leu Val Leu Asn Pro Ser Val Ala Ala Thr Leu Gly
            260                 265                 270

Phe Gly Ala Tyr Met Ser Lys Ala His Gly Ile Asp Pro Asn Ile Arg
        275                 280                 285
```

```
Thr Gly Val Arg Thr Ile Thr Thr Gly Ala Pro Val Thr Tyr Ser Thr
    290                 295                 300

Tyr Gly Lys Phe Leu Ala Asp Gly Gly Cys Ser Gly Gly Ala Tyr Asp
305                 310                 315                 320

Ile Ile Ile Cys Asp Glu Cys His Ser Thr Asp Ser Thr Thr Ile Leu
                325                 330                 335

Gly Ile Gly Thr Val Leu Asp Gln Ala Glu Thr Ala Gly Ala Arg Leu
            340                 345                 350

Val Val Leu Ala Thr Ala Thr Pro Pro Gly Ser Val Thr Val Pro His
        355                 360                 365

Pro Asn Ile Glu Glu Val Ala Leu Ser Asn Thr Gly Glu Ile Pro Phe
    370                 375                 380

Tyr Gly Lys Ala Ile Pro Ile Glu Ala Ile Arg Gly Gly Arg His Leu
385                 390                 395                 400

Ile Phe Cys His Ser Lys Lys Cys Asp Glu Leu Ala Ala Lys Leu
                405                 410                 415

Ser Gly Leu Gly Ile Asn Ala Val Ala Tyr Tyr Arg Gly Leu Asp Val
            420                 425                 430

Ser Val Ile Pro Thr Ile Gly Asp Val Val Val Ala Thr Asp Ala
        435                 440                 445

Leu Met Thr Gly Tyr Thr Gly Asp Phe Asp Ser Val Ile Asp Cys Asn
    450                 455                 460

Thr Cys Val Thr Gln Thr Val Asp Phe Ser Leu Asp Pro Thr Phe Thr
465                 470                 475                 480

Ile Glu Thr Thr Thr Val Pro Gln Asp Ala Val Ser Arg Ser Gln Arg
                485                 490                 495

Arg Gly Arg Thr Gly Arg Gly Arg Gly Ile Tyr Arg Phe Val Thr
            500                 505                 510

Pro Gly Glu Arg Pro Ser Gly Met Phe Asp Ser Ser Val Leu Cys Glu
        515                 520                 525

Cys Tyr Asp Ala Gly Cys Ala Trp Tyr Glu Leu Thr Pro Ala Glu Thr
    530                 535                 540

Ser Val Arg Leu Arg Ala Tyr Leu Asn Thr Pro Gly Leu Pro Val Cys
545                 550                 555                 560

Gln Asp His Leu Glu Phe Trp Glu Ser Val Phe Thr Gly Leu Thr His
                565                 570                 575

Ile Asp Ala His Phe Leu Ser Gln Thr Lys Gln Ala Gly Asp Asn Phe
            580                 585                 590

Pro Tyr Leu Val Ala Tyr Gln Ala Thr Val Cys Ala Arg Ala Gln Ala
        595                 600                 605

Pro Pro Pro Ser Trp Asp Gln Met Trp Lys Cys Leu Ile Arg Leu Lys
    610                 615                 620

Pro Thr Leu His Gly Pro Thr Pro Leu Leu Tyr Arg Leu Gly Ala Val
625                 630                 635                 640

Gln Asn Glu Val Thr Leu Thr His Pro Ile Thr Lys Tyr Ile Met Ala
                645                 650                 655

Cys Met Ser Ala Asp Leu Glu Val Val Thr
            660                 665
```

(2) INFORMATION FOR SEQ ID NO:17:

(i) SEQUENCE CHARACTERISTICS:
        (A) LENGTH: 666 amino acids
        (B) TYPE: amino acid
        (D) TOPOLOGY: linear (ii) MOLECULE TYPE: protein (xi) SEQUENCE DESCRIPTION: SEQ ID NO:17:

```
Met Gly Ser Ser His His His His Ser Ser Gly Leu Val Pro
 1               5                  10                  15

Arg Gly Ser His Met Gly Ser Val Val Ile Val Gly Arg Ile Ile Leu
                20                  25                  30

Ser Gly Ser Gly Ser Ile Thr Ala Tyr Ser Gln Gln Thr Arg Gly Leu
            35                  40                  45

Leu Gly Cys Ile Lys Thr Ser Leu Thr Gly Arg Asp Lys Asn Gln Val
        50                  55                  60

Glu Gly Glu Val Gln Val Val Ser Thr Ala Thr Gln Ser Phe Leu Ala
 65                  70                  75                  80

Thr Cys Val Asn Gly Val Cys Trp Thr Val Tyr His Gly Ala Gly Ser
                85                  90                  95

Lys Thr Leu Ala Gly Pro Lys Gly Pro Ile Thr Gln Met Tyr Thr Asn
                100                 105                 110

Val Asp Gln Asp Leu Val Gly Trp Gln Ala Pro Pro Gly Ala Arg Ser
            115                 120                 125

Leu Thr Pro Cys Thr Cys Gly Ser Ser Asp Leu Tyr Leu Val Thr Arg
        130                 135                 140

His Ala Asp Val Ile Pro Val Arg Arg Arg Gly Asp Ser Arg Gly Ser
145                 150                 155                 160

Leu Leu Ser Pro Arg Pro Val Ser Tyr Leu Lys Gly Ser Ala Gly Gly
                165                 170                 175

Pro Leu Leu Cys Pro Ser Gly His Ala Val Gly Ile Phe Arg Ala Ala
                180                 185                 190

Val Cys Thr Arg Gly Val Ala Lys Ala Val Asp Phe Val Pro Val Glu
            195                 200                 205

Ser Met Glu Thr Thr Met Arg Ser Pro Val Phe Thr Asp Asn Ser Ser
        210                 215                 220

Pro Pro Ala Val Pro Gln Ser Phe Gln Val Ala His Leu His Ala Pro
225                 230                 235                 240

Thr Gly Ser Gly Lys Ser Thr Lys Val Pro Ala Ala Tyr Ala Ala Gln
                245                 250                 255

Gly Tyr Lys Val Leu Val Leu Asn Pro Ser Val Ala Ala Thr Leu Gly
                260                 265                 270

Phe Gly Ala Tyr Met Ser Lys Ala His Gly Ile Asp Pro Asn Ile Arg
            275                 280                 285

Thr Gly Val Arg Thr Ile Thr Thr Gly Ala Pro Val Thr Tyr Ser Thr
        290                 295                 300

Tyr Gly Lys Phe Leu Ala Asp Gly Gly Cys Ser Gly Gly Ala Tyr Asp
305                 310                 315                 320

Ile Ile Ile Cys Asp Glu Cys His Ser Thr Asp Ser Thr Thr Ile Leu
                325                 330                 335

Gly Ile Gly Thr Val Leu Asp Gln Ala Glu Thr Ala Gly Ala Arg Leu
            340                 345                 350

Val Val Leu Ala Thr Ala Thr Pro Pro Gly Ser Val Thr Val Pro His
        355                 360                 365

Pro Asn Ile Glu Glu Val Ala Leu Ser Asn Thr Gly Glu Ile Pro Phe
370                 375                 380

Tyr Gly Lys Ala Ile Pro Ile Glu Ala Ile Arg Gly Gly Arg His Leu
385                 390                 395                 400
```

```
Ile Phe Cys His Ser Lys Lys Cys Asp Glu Leu Ala Ala Lys Leu
                405                 410                 415

Ser Gly Leu Gly Ile Asn Ala Val Ala Tyr Tyr Arg Gly Leu Asp Val
                420                 425                 430

Ser Val Ile Pro Thr Ile Gly Asp Val Val Val Ala Thr Asp Ala
                435                 440                 445

Leu Met Thr Gly Tyr Thr Gly Asp Phe Asp Ser Val Ile Asp Cys Asn
    450                 455                 460

Thr Cys Val Thr Gln Thr Val Asp Phe Ser Leu Asp Pro Thr Phe Thr
465                 470                 475                 480

Ile Glu Thr Thr Thr Val Pro Gln Asp Ala Val Ser Arg Ser Gln Arg
                485                 490                 495

Arg Gly Arg Thr Gly Arg Gly Arg Gly Ile Tyr Arg Phe Val Thr
                500                 505                 510

Pro Gly Glu Arg Pro Ser Gly Met Phe Asp Ser Ser Val Leu Cys Glu
                515                 520                 525

Cys Tyr Asp Ala Gly Cys Ala Trp Tyr Glu Leu Thr Pro Ala Glu Thr
                530                 535                 540

Ser Val Arg Leu Arg Ala Tyr Leu Asn Thr Pro Gly Leu Pro Val Cys
545                 550                 555                 560

Gln Asp His Leu Glu Phe Trp Glu Ser Val Phe Thr Gly Leu Thr His
                565                 570                 575

Ile Asp Ala His Phe Leu Ser Gln Thr Lys Gln Ala Gly Asp Asn Phe
                580                 585                 590

Pro Tyr Leu Val Ala Tyr Gln Ala Thr Val Cys Ala Arg Ala Gln Ala
                595                 600                 605

Pro Pro Pro Ser Trp Asp Gln Met Trp Lys Cys Leu Ile Arg Leu Lys
                610                 615                 620

Pro Thr Leu His Gly Pro Thr Pro Leu Leu Tyr Arg Leu Gly Ala Val
625                 630                 635                 640

Gln Asn Glu Val Thr Leu Thr His Pro Ile Thr Lys Tyr Ile Met Ala
                645                 650                 655

Cys Met Ser Ala Asp Leu Glu Val Val Thr
                660                 665

(2) INFORMATION FOR SEQ ID NO:18:

(i) SEQUENCE CHARACTERISTICS:
        (A) LENGTH: 666 amino acids
        (B) TYPE: amino acid
        (D) TOPOLOGY: linear (ii) MOLECULE TYPE: protein (xi) SEQUENCE DESCRIPTION: SEQ ID NO:18:

Met Gly Ser Ser His His His His His His Ser Ser Gly Leu Val Pro
1               5                   10                  15

Arg Gly Ser His Met Gly Ser Val Val Ile Val Gly Arg Ile Ile Leu
                20                  25                  30

Ser Gly Ser Gly Ser Ile Thr Ala Tyr Ser Gln Gln Thr Arg Gly Leu
                35                  40                  45

Leu Gly Cys Lys Lys Thr Ser Leu Thr Gly Arg Asp Lys Asn Gln Val
    50                  55                  60

Glu Gly Glu Val Gln Val Val Ser Thr Ala Thr Gln Ser Phe Leu Ala
65                  70                  75                  80
```

-continued

```
Thr Cys Val Asn Gly Val Cys Trp Thr Val Tyr His Gly Ala Gly Ser
                85                  90                  95
Lys Thr Leu Ala Gly Pro Lys Gly Pro Ile Thr Gln Met Tyr Thr Asn
            100                 105                 110
Val Asp Gln Asp Leu Val Gly Trp Gln Ala Pro Gly Ala Arg Ser
        115                 120                 125
Leu Thr Pro Cys Thr Cys Gly Ser Ser Asp Leu Tyr Leu Val Thr Arg
    130                 135                 140
His Ala Asp Val Ile Pro Val Arg Arg Gly Asp Ser Arg Gly Ser
145                 150                 155                 160
Leu Leu Ser Pro Arg Pro Val Ser Tyr Leu Lys Gly Ser Ala Gly Gly
                165                 170                 175
Pro Leu Leu Cys Pro Ser Gly His Ala Val Gly Ile Phe Arg Ala Ala
            180                 185                 190
Val Cys Thr Arg Gly Val Ala Lys Ala Val Asp Phe Val Pro Val Glu
        195                 200                 205
Ser Met Glu Thr Thr Met Arg Ser Pro Val Phe Thr Asp Asn Ser Ser
    210                 215                 220
Pro Pro Ala Val Pro Gln Ser Phe Gln Val Ala His Leu His Ala Pro
225                 230                 235                 240
Thr Gly Ser Gly Lys Ser Thr Lys Val Pro Ala Ala Tyr Ala Ala Gln
                245                 250                 255
Gly Tyr Lys Val Leu Val Leu Asn Pro Ser Val Ala Ala Thr Leu Gly
            260                 265                 270
Phe Gly Ala Tyr Met Ser Lys Ala His Gly Ile Asp Pro Asn Ile Arg
        275                 280                 285
Thr Gly Val Arg Thr Ile Thr Thr Gly Ala Pro Val Thr Tyr Ser Thr
    290                 295                 300
Tyr Gly Lys Phe Leu Ala Asp Gly Gly Cys Ser Gly Gly Ala Tyr Asp
305                 310                 315                 320
Ile Ile Ile Cys Asp Glu Cys His Ser Thr Asp Ser Thr Thr Ile Leu
                325                 330                 335
Gly Ile Gly Thr Val Leu Asp Gln Ala Glu Thr Ala Gly Ala Arg Leu
            340                 345                 350
Val Val Leu Ala Thr Ala Thr Pro Pro Gly Ser Val Thr Val Pro His
        355                 360                 365
Pro Asn Ile Glu Glu Val Ala Leu Ser Asn Thr Gly Glu Ile Pro Phe
    370                 375                 380
Tyr Gly Lys Ala Ile Pro Ile Glu Ala Ile Arg Gly Gly Arg His Leu
385                 390                 395                 400
Ile Phe Cys His Ser Lys Lys Cys Asp Glu Leu Ala Ala Lys Leu
                405                 410                 415
Ser Gly Leu Gly Ile Asn Ala Val Ala Tyr Tyr Arg Gly Leu Asp Val
            420                 425                 430
Ser Val Ile Pro Thr Ile Gly Asp Val Val Val Ala Thr Asp Ala
        435                 440                 445
Leu Met Thr Gly Tyr Thr Gly Asp Phe Asp Ser Val Ile Asp Cys Asn
    450                 455                 460
Thr Cys Val Thr Gln Thr Val Asp Phe Ser Leu Asp Pro Thr Phe Thr
465                 470                 475                 480
Ile Glu Thr Thr Thr Val Pro Gln Asp Ala Val Ser Arg Ser Gln Arg
                485                 490                 495
```

```
Arg Gly Arg Thr Gly Arg Gly Arg Arg Gly Ile Tyr Arg Phe Val Thr
            500                 505                 510

Pro Gly Glu Arg Pro Ser Gly Met Phe Asp Ser Ser Val Leu Cys Glu
            515                 520                 525

Cys Tyr Asp Ala Gly Cys Ala Trp Tyr Glu Leu Thr Pro Ala Glu Thr
            530                 535                 540

Ser Val Arg Leu Arg Ala Tyr Leu Asn Thr Pro Gly Leu Pro Val Cys
545                 550                 555                 560

Gln Asp His Leu Glu Phe Trp Glu Ser Val Phe Thr Gly Leu Thr His
                565                 570                 575

Ile Asp Ala His Phe Leu Ser Gln Thr Lys Gln Ala Gly Asp Asn Phe
            580                 585                 590

Pro Tyr Leu Val Ala Tyr Gln Ala Thr Val Cys Ala Arg Ala Gln Ala
            595                 600                 605

Pro Pro Pro Ser Trp Asp Gln Met Trp Lys Cys Leu Ile Arg Leu Lys
            610                 615                 620

Pro Thr Leu His Gly Pro Thr Pro Leu Leu Tyr Arg Leu Gly Ala Val
625                 630                 635                 640

Gln Asn Glu Val Thr Leu Thr His Pro Ile Thr Lys Tyr Ile Met Ala
                645                 650                 655

Cys Met Ser Ala Asp Leu Glu Val Val Thr
            660                 665

(2) INFORMATION FOR SEQ ID NO:19:

(i) SEQUENCE CHARACTERISTICS:
        (A) LENGTH: 672 amino acids
        (B) TYPE: amino acid
        (D) TOPOLOGY: linear (ii) MOLECULE TYPE: protein (xi) SEQUENCE DESCRIPTION: SEQ ID NO:19:

Met Gly Ser Ser His His His His His His Ser Ser Gly Leu Val Pro
1               5                   10                  15

Arg Gly Ser His Met Ala Tyr Ser Leu Thr Thr Gly Ser Val Val Ile
            20                  25                  30

Val Gly Arg Ile Ile Leu Ser Gly Ser Gly Ser Ile Thr Ala Tyr Ser
            35                  40                  45

Gln Gln Thr Arg Gly Leu Leu Gly Cys Ile Ile Thr Ser Leu Thr Gly
        50                  55                  60

Arg Asp Lys Asn Gln Val Glu Gly Glu Val Gln Val Val Ser Thr Ala
65                  70                  75                  80

Thr Gln Ser Phe Leu Ala Thr Cys Val Asn Gly Val Cys Trp Thr Val
                85                  90                  95

Tyr His Gly Ala Gly Ser Lys Thr Leu Ala Gly Pro Lys Gly Pro Ile
            100                 105                 110

Thr Gln Met Tyr Thr Asn Val Asp Gln Asp Leu Val Gly Trp Gln Ala
            115                 120                 125

Pro Pro Gly Ala Arg Ser Leu Thr Pro Cys Thr Cys Gly Ser Ser Asp
            130                 135                 140

Leu Tyr Leu Val Thr Arg His Ala Asp Val Ile Pro Val Arg Arg Arg
145                 150                 155                 160

Gly Asp Ser Arg Gly Ser Leu Leu Ser Pro Arg Pro Val Ser Tyr Leu
                165                 170                 175
```

-continued

```
Lys Gly Ser Ser Gly Gly Pro Leu Leu Cys Pro Ser Gly His Ala Val
            180                 185                 190
Gly Ile Phe Arg Ala Ala Val Cys Thr Arg Gly Val Ala Lys Ala Val
            195                 200                 205
Asp Phe Val Pro Val Glu Ser Met Glu Thr Thr Met Arg Ser Pro Val
            210                 215                 220
Phe Thr Asp Asn Ser Ser Pro Ala Val Pro Gln Ser Phe Gln Val
225                 230                 235                 240
Ala His Leu His Ala Pro Thr Gly Ser Gly Lys Ser Thr Lys Val Pro
                    245                 250                 255
Ala Ala Tyr Ala Ala Gln Gly Tyr Lys Val Leu Val Leu Asn Pro Ser
            260                 265                 270
Val Ala Ala Thr Leu Gly Phe Gly Ala Tyr Met Ser Lys Ala His Gly
            275                 280                 285
Ile Asp Pro Asn Ile Arg Thr Gly Val Arg Thr Ile Thr Thr Gly Ala
            290                 295                 300
Pro Val Thr Tyr Ser Thr Tyr Gly Lys Phe Leu Ala Asp Gly Gly Cys
305                 310                 315                 320
Ser Gly Gly Ala Tyr Asp Ile Ile Cys Asp Glu Cys His Ser Thr
                    325                 330                 335
Asp Ser Thr Thr Ile Leu Gly Ile Gly Thr Val Leu Asp Gln Ala Glu
            340                 345                 350
Thr Ala Gly Ala Arg Leu Val Val Leu Ala Thr Ala Thr Pro Pro Gly
            355                 360                 365
Ser Val Thr Val Pro His Pro Asn Ile Glu Glu Val Ala Leu Ser Asn
    370                 375                 380
Thr Gly Glu Ile Pro Phe Tyr Gly Lys Ala Ile Pro Ile Glu Ala Ile
385                 390                 395                 400
Arg Gly Gly Arg His Leu Ile Phe Cys His Ser Lys Lys Lys Cys Asp
                    405                 410                 415
Glu Leu Ala Ala Lys Leu Ser Gly Leu Gly Ile Asn Ala Val Ala Tyr
            420                 425                 430
Tyr Arg Gly Leu Asp Val Ser Val Ile Pro Thr Ile Gly Asp Val Val
            435                 440                 445
Val Val Ala Thr Asp Ala Leu Met Thr Gly Tyr Thr Gly Asp Phe Asp
            450                 455                 460
Ser Val Ile Asp Cys Asn Thr Cys Val Thr Gln Thr Val Asp Phe Ser
465                 470                 475                 480
Leu Asp Pro Thr Phe Thr Ile Glu Thr Thr Val Pro Gln Asp Ala
                    485                 490                 495
Val Ser Arg Ser Gln Arg Arg Gly Arg Thr Gly Arg Gly Arg Arg Gly
            500                 505                 510
Ile Tyr Arg Phe Val Thr Pro Gly Glu Arg Pro Ser Gly Met Phe Asp
            515                 520                 525
Ser Ser Val Leu Cys Glu Cys Tyr Asp Ala Gly Cys Ala Trp Tyr Glu
            530                 535                 540
Leu Thr Pro Ala Glu Thr Ser Val Arg Leu Arg Ala Tyr Leu Asn Thr
545                 550                 555                 560
Pro Gly Leu Pro Val Cys Gln Asp His Leu Glu Phe Trp Glu Ser Val
                    565                 570                 575
Phe Thr Gly Leu Thr His Ile Asp Ala His Phe Leu Ser Gln Thr Lys
            580                 585                 590
```

-continued

```
Gln Ala Gly Asp Asn Phe Pro Tyr Leu Val Ala Tyr Gln Ala Thr Val
            595                 600                 605

Cys Ala Arg Ala Gln Ala Pro Pro Ser Trp Asp Gln Met Trp Lys
            610                 615                 620

Cys Leu Ile Arg Leu Lys Pro Thr Leu His Gly Pro Thr Pro Leu Leu
625                 630                 635                 640

Tyr Arg Leu Gly Ala Val Gln Asn Glu Val Thr Leu Thr His Pro Ile
            645                 650                 655

Thr Lys Tyr Ile Met Ala Cys Met Ser Ala Asp Leu Glu Val Val Thr
            660                 665                 670

(2) INFORMATION FOR SEQ ID NO:20:

(i) SEQUENCE CHARACTERISTICS:
        (A) LENGTH: 672 amino acids
        (B) TYPE: amino acid
        (D) TOPOLOGY: linear (ii) MOLECULE TYPE: protein (xi) SEQUENCE DESCRIPTION: SEQ ID NO:20:

Met Gly Ser Ser His His His His His His Ser Ser Gly Leu Val Pro
  1               5                  10                  15

Arg Gly Ser His Met Ala Tyr Ser Leu Thr Thr Gly Ser Val Val Ile
             20                  25                  30

Val Gly Arg Ile Ile Leu Ser Gly Ser Gly Ser Ile Thr Ala Tyr Ser
         35                  40                  45

Gln Gln Thr Arg Gly Leu Leu Gly Cys Ile Ile Thr Ser Leu Thr Gly
     50                  55                  60

Arg Asp Lys Asn Gln Val Glu Gly Glu Val Gln Val Val Ser Thr Ala
65                  70                  75                  80

Thr Gln Ser Phe Leu Ala Thr Cys Val Asn Gly Val Cys Trp Thr Val
             85                  90                  95

Tyr His Gly Ala Gly Ser Lys Thr Leu Ala Gly Pro Lys Gly Pro Ile
            100                 105                 110

Thr Gln Met Tyr Thr Asn Val Asp Gln Asp Leu Val Gly Trp Gln Ala
            115                 120                 125

Pro Pro Gly Ala Arg Ser Leu Thr Pro Cys Thr Cys Gly Ser Ser Asp
130                 135                 140

Leu Tyr Leu Val Thr Arg His Ala Asp Val Ile Pro Val Arg Arg Arg
145                 150                 155                 160

Gly Asp Ser Arg Gly Ser Leu Leu Ser Pro Arg Pro Val Ser Tyr Leu
            165                 170                 175

Lys Gly Ser Ala Gly Gly Pro Leu Leu Cys Pro Ser Gly His Ala Val
            180                 185                 190

Gly Ile Phe Arg Ala Ala Val Cys Thr Arg Gly Val Ala Lys Ala Val
            195                 200                 205

Asp Phe Val Pro Val Glu Ser Met Glu Thr Thr Met Arg Ser Pro Val
            210                 215                 220

Phe Thr Asp Asn Ser Ser Pro Pro Ala Val Pro Gln Ser Phe Gln Val
225                 230                 235                 240

Ala His Leu His Ala Pro Thr Gly Ser Gly Lys Ser Thr Lys Val Pro
            245                 250                 255

Ala Ala Tyr Ala Ala Gln Gly Tyr Lys Val Leu Val Leu Asn Pro Ser
            260                 265                 270
```

-continued

```
Val Ala Ala Thr Leu Gly Phe Gly Ala Tyr Met Ser Lys Ala His Gly
            275                 280                 285

Ile Asp Pro Asn Ile Arg Thr Gly Val Arg Thr Ile Thr Thr Gly Ala
            290                 295                 300

Pro Val Thr Tyr Ser Thr Tyr Gly Lys Phe Leu Ala Asp Gly Gly Cys
305                 310                 315                 320

Ser Gly Gly Ala Tyr Asp Ile Ile Cys Asp Glu Cys His Ser Thr
                325                 330                 335

Asp Ser Thr Thr Ile Leu Gly Ile Gly Thr Val Leu Asp Gln Ala Glu
                340                 345                 350

Thr Ala Gly Ala Arg Leu Val Val Leu Ala Thr Ala Thr Pro Pro Gly
                355                 360                 365

Ser Val Thr Val Pro His Pro Asn Ile Glu Glu Val Ala Leu Ser Asn
            370                 375                 380

Thr Gly Glu Ile Pro Phe Tyr Gly Lys Ala Ile Pro Ile Glu Ala Ile
385                 390                 395                 400

Arg Gly Gly Arg His Leu Ile Phe Cys His Ser Lys Lys Cys Asp
                        405                 410                 415

Glu Leu Ala Ala Lys Leu Ser Gly Leu Gly Ile Asn Ala Val Ala Tyr
                420                 425                 430

Tyr Arg Gly Leu Asp Val Ser Val Ile Pro Thr Ile Gly Asp Val Val
            435                 440                 445

Val Val Ala Thr Asp Ala Leu Met Thr Gly Tyr Thr Gly Asp Phe Asp
            450                 455                 460

Ser Val Ile Asp Cys Asn Thr Cys Val Thr Gln Thr Val Asp Phe Ser
465                 470                 475                 480

Leu Asp Pro Thr Phe Thr Ile Glu Thr Thr Val Pro Gln Asp Ala
                    485                 490                 495

Val Ser Arg Ser Gln Arg Arg Gly Arg Thr Gly Arg Gly Arg Arg Gly
                500                 505                 510

Ile Tyr Arg Phe Val Thr Pro Gly Glu Arg Pro Ser Gly Met Phe Asp
            515                 520                 525

Ser Ser Val Leu Cys Glu Cys Tyr Asp Ala Gly Cys Ala Trp Tyr Glu
530                 535                 540

Leu Thr Pro Ala Glu Thr Ser Val Arg Leu Arg Ala Tyr Leu Asn Thr
545                 550                 555                 560

Pro Gly Leu Pro Val Cys Gln Asp His Leu Glu Phe Trp Glu Ser Val
                565                 570                 575

Phe Thr Gly Leu Thr His Ile Asp Ala His Phe Leu Ser Gln Thr Lys
                580                 585                 590

Gln Ala Gly Asp Asn Phe Pro Tyr Leu Val Ala Tyr Gln Ala Thr Val
            595                 600                 605

Cys Ala Arg Ala Gln Ala Pro Pro Ser Trp Asp Gln Met Trp Lys
610                 615                 620

Cys Leu Ile Arg Leu Lys Pro Thr Leu His Gly Pro Thr Pro Leu Leu
625                 630                 635                 640

Tyr Arg Leu Gly Ala Val Gln Asn Glu Val Thr Leu Thr His Pro Ile
                645                 650                 655

Thr Lys Tyr Ile Met Ala Cys Met Ser Ala Asp Leu Glu Val Val Thr
                660                 665                 670
```

-continued (2) INFORMATION FOR SEQ ID NO:21:

(i) SEQUENCE CHARACTERISTICS:
        (A) LENGTH: 4 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:21:

```
Gly Ser Gly Ser
1
```

(2) INFORMATION FOR SEQ ID NO:22:

(i) SEQUENCE CHARACTERISTICS:
        (A) LENGTH: 4 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:22:

```
Pro Ala Gly Gly
1
```

(2) INFORMATION FOR SEQ ID NO:23:

(i) SEQUENCE CHARACTERISTICS:
        (A) LENGTH: 632 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:23:

```
Met Ala Pro Ile Thr Ala Tyr Ser Gln Gln Thr Arg Gly Leu Leu Gly
1               5                   10                  15

Cys Ile Ile Thr Ser Leu Thr Gly Arg Asp Lys Asn Gln Val Glu Gly
            20                  25                  30

Glu Val Gln Val Val Ser Thr Ala Thr Gln Ser Phe Leu Ala Thr Cys
        35                  40                  45

Val Asn Gly Val Cys Trp Thr Val Tyr His Gly Ala Gly Ser Lys Thr
    50                  55                  60

Leu Ala Gly Pro Lys Gly Pro Ile Thr Gln Met Tyr Thr Asn Val Asp
65                  70                  75                  80

Gln Asp Leu Val Gly Trp Gln Ala Pro Pro Gly Ala Arg Ser Leu Thr
                85                  90                  95

Pro Cys Thr Cys Gly Ser Ser Asp Leu Tyr Leu Val Thr Arg His Ala
            100                 105                 110

Asp Val Ile Pro Val Arg Arg Arg Gly Asp Ser Arg Gly Ser Leu Leu
        115                 120                 125

Ser Pro Arg Pro Val Ser Tyr Leu Lys Gly Ser Ser Gly Gly Pro Leu
    130                 135                 140

Leu Cys Pro Ser Gly His Ala Val Gly Ile Phe Arg Ala Ala Val Cys
145                 150                 155                 160

Thr Arg Gly Val Ala Lys Ala Val Asp Phe Val Pro Val Glu Ser Met
                165                 170                 175

Glu Thr Thr Met Arg Ser Pro Val Phe Thr Asp Asn Ser Ser Pro Pro
            180                 185                 190
```

-continued

```
Ala Val Pro Gln Ser Phe Gln Val Ala His Leu His Ala Pro Thr Gly
            195                 200                 205

Ser Gly Lys Ser Thr Lys Val Pro Ala Ala Tyr Ala Ala Gln Gly Tyr
        210                 215                 220

Lys Val Leu Val Leu Asn Pro Ser Val Ala Ala Thr Leu Gly Phe Gly
225                 230                 235                 240

Ala Tyr Met Ser Lys Ala His Gly Ile Asp Pro Asn Ile Arg Thr Gly
                245                 250                 255

Val Arg Thr Ile Thr Thr Gly Ala Pro Val Thr Tyr Ser Thr Tyr Gly
            260                 265                 270

Lys Phe Leu Ala Asp Gly Gly Cys Ser Gly Gly Ala Tyr Asp Ile Ile
        275                 280                 285

Ile Cys Asp Glu Cys His Ser Thr Asp Ser Thr Thr Ile Leu Gly Ile
    290                 295                 300

Gly Thr Val Leu Asp Gln Ala Glu Thr Ala Gly Ala Arg Leu Val Val
305                 310                 315                 320

Leu Ala Thr Ala Thr Pro Pro Gly Ser Val Thr Val Pro His Pro Asn
                325                 330                 335

Ile Glu Glu Val Ala Leu Ser Asn Thr Gly Glu Ile Pro Phe Tyr Gly
            340                 345                 350

Lys Ala Ile Pro Ile Glu Ala Ile Arg Gly Gly Arg His Leu Ile Phe
        355                 360                 365

Cys His Ser Lys Lys Lys Cys Asp Glu Leu Ala Ala Lys Leu Ser Gly
    370                 375                 380

Leu Gly Ile Asn Ala Val Ala Tyr Tyr Arg Gly Leu Asp Val Ser Val
385                 390                 395                 400

Ile Pro Thr Ile Gly Asp Val Val Val Ala Thr Asp Ala Leu Met
                405                 410                 415

Thr Gly Tyr Thr Gly Asp Phe Asp Ser Val Ile Asp Cys Asn Thr Cys
            420                 425                 430

Val Thr Gln Thr Val Asp Phe Ser Leu Asp Pro Thr Phe Thr Ile Glu
        435                 440                 445

Thr Thr Thr Val Pro Gln Asp Ala Val Ser Arg Ser Gln Arg Arg Gly
    450                 455                 460

Arg Thr Gly Arg Gly Arg Arg Gly Ile Tyr Arg Phe Val Thr Pro Gly
465                 470                 475                 480

Glu Arg Pro Ser Gly Met Phe Asp Ser Ser Val Leu Cys Glu Cys Tyr
                485                 490                 495

Asp Ala Gly Cys Ala Trp Tyr Glu Leu Thr Pro Ala Glu Thr Ser Val
            500                 505                 510

Arg Leu Arg Ala Tyr Leu Asn Thr Pro Gly Leu Pro Val Cys Gln Asp
        515                 520                 525

His Leu Glu Phe Trp Glu Ser Val Phe Thr Gly Leu Thr His Ile Asp
    530                 535                 540

Ala His Phe Leu Ser Gln Thr Lys Gln Ala Gly Asp Asn Phe Pro Tyr
545                 550                 555                 560

Leu Val Ala Tyr Gln Ala Thr Val Cys Ala Arg Ala Gln Ala Pro Pro
                565                 570                 575

Pro Ser Trp Asp Gln Met Trp Lys Cys Leu Ile Arg Leu Lys Pro Thr
            580                 585                 590

Leu His Gly Pro Thr Pro Leu Leu Tyr Arg Leu Gly Ala Val Gln Asn
        595                 600                 605
```

```
Glu Val Thr Leu Thr His Pro Ile Thr Lys Tyr Ile Met Ala Cys Met
    610                 615                 620

Ser Ala Asp Leu Glu Val Val Thr
625                 630

(2) INFORMATION FOR SEQ ID NO:24:

(i) SEQUENCE CHARACTERISTICS:
        (A) LENGTH: 54 amino acids
        (B) TYPE: amino acid
        (C) STRANDEDNESS: single
        (D) TOPOLOGY: linear (ii) MOLECULE TYPE: cDNA (xi) SEQUENCE DESCRIPTION: SEQ ID NO:24:

Ser Thr Trp Val Leu Val Gly Gly Val Leu Ala Ala Leu Ala Ala Tyr
1               5                   10                  15

Cys Leu Thr Thr Gly Ser Val Val Ile Val Gly Arg Ile Ile Leu Ser
                20                  25                  30

Gly Arg Pro Ala Ile Val Pro Asp Arg Glu Leu Leu Tyr Gln Glu Phe
            35                  40                  45

Asp Glu Met Glu Glu Cys
            50

(2) INFORMATION FOR SEQ ID NO:25:

(i) SEQUENCE CHARACTERISTICS:
        (A) LENGTH: 16 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:25:

Asp Thr Glu Asp Val Val Cys Cys Ser Met Tyr Thr Trp Thr Gly Lys
1               5                   10                  15

(2) INFORMATION FOR SEQ ID NO:26:

(i) SEQUENCE CHARACTERISTICS:
        (A) LENGTH: 78 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:26:

GATATACATA TGGGTTCTGT TGTTATTGTT GGTAGAATTA TTTTATCTGG TAGTGGTAGT      60

ATCACGGCCT ACTCCCAA                                                   78

(2) INFORMATION FOR SEQ ID NO:27:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:27:

CTCAGCGAAT TCTCAAGACC GCATAGTAGT TTCCAT                               36
```

(2) INFORMATION FOR SEQ ID NO:28:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:28:

CGGGGCCTAC TTGGTTGCAA GATCACTAGC CTTACAGGC                      39

(2) INFORMATION FOR SEQ ID NO:29:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:29:

GCCTGTAAGG CTAGTGATCT TGCAACCAAG TAGGCCCCG                      39

(2) INFORMATION FOR SEQ ID NO:30:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:30:

CGGGGCCTAC TTGGTTGCAT CAAGACTAGC CTTACAGGC                      39

(2) INFORMATION FOR SEQ ID NO:31:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:31:

GCCTGTAAGG CTAGTCTTGA TGCAACCAAG TAGGCCCCG                      39

(2) INFORMATION FOR SEQ ID NO:32:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:32:

CGGGGCCTAC TTGGTTGCAA GAAGACTAGC CTTACAGGC                      39

(2) INFORMATION FOR SEQ ID NO:33:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:33:

GCCTGTAAGG CTAGTCTTCT TGCAACCAAG TAGGCCCCG                      39

(2) INFORMATION FOR SEQ ID NO:34:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:34:

CTCCTACTTG AAGGGCTCTG CTGGTGGTCC ACTGCTCTGC                     40

(2) INFORMATION FOR SEQ ID NO:35:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:35:

GCAGAGCAGT GGACCACCAG CAGAGCCCTT CAAGTAGGAG                     40

(2) INFORMATION FOR SEQ ID NO:36:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:36:

CGGGGCCTAC TTGGTTGCAA GATCACTAGC CTTACAGGC                      39

(2) INFORMATION FOR SEQ ID NO:37:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:37:

GCCTGTAAGG CTAGTGATCT TGCAACCAAG TAGGCCCCG                      39

(2) INFORMATION FOR SEQ ID NO:38:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:38:

```
CGGGGCCTAC TTGGTTGCAT CAAGACTAGC CTTACAGGC                           39
```

(2) INFORMATION FOR SEQ ID NO:39:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:39:

```
GCCTGTAAGG CTAGTCTTGA TGCAACCAAG TAGGCCCCG                           39
```

(2) INFORMATION FOR SEQ ID NO:40:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:40:

```
CGGGGCCTAC TTGGTTGCAA GAAGACTAGC CTTACAGGC                           39
```

(2) INFORMATION FOR SEQ ID NO:41:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:41:

```
GCCTGTAAGG CTAGTCTTGA TGCAACCAAG TAGGCCCCG                           39
```

(2) INFORMATION FOR SEQ ID NO:42:

(i) SEQUENCE CHARACTERISTICS:
        (A) LENGTH: 78 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:42:

```
GATATACATA TGGGTTCTGT TGTTATTGTT GGTAGAATTA TTTTATCTCC TGCTGGTGGT    60
ATCACGGCCT ACTCCCAA                                                  78
```

(2) INFORMATION FOR SEQ ID NO:43:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:43:

CTCAGCGAAT TCTCAAGACC GCATAGTAGT TTCCAT                    36

(2) INFORMATION FOR SEQ ID NO:44:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:44:

CGGGGCCTAC TTGGTTGCAA GATCACTAGC CTTACAGGC                 39

(2) INFORMATION FOR SEQ ID NO:45:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:45:

GCCTGTAAGG CTAGTGATCT TGCAACCAAG TAGGCCCCG                 39

(2) INFORMATION FOR SEQ ID NO:46:

(i) SEQUENCE CHARACTERISTICS:
        (A) LENGTH: 215 amino acids
        (B) TYPE: amino acid
        (D) TOPOLOGY: linear (ii) MOLECULE TYPE: protein (xi) SEQUENCE DESCRIPTION: SEQ ID NO:46:

```
Met Gly Ser Ser His His His His His His Ser Ser Gly Leu Val Pro
 1               5                  10                  15

Arg Gly Ser His Met Gly Ser Val Val Ile Val Gly Arg Ile Ile Leu
            20                  25                  30

Ser Pro Ala Gly Ile Thr Ala Tyr Ser Gln Gln Thr Arg Gly Leu Leu
        35                  40                  45

Gly Cys Ile Ile Thr Ser Leu Thr Gly Arg Asp Lys Asn Gln Val Glu
    50                  55                  60

Gly Glu Val Gln Val Val Ser Thr Ala Thr Gln Ser Phe Leu Ala Thr
65                  70                  75                  80

Cys Val Asn Gly Val Cys Trp Thr Val Tyr His Gly Ala Gly Ser Lys
                85                  90                  95

Thr Leu Ala Gly Pro Lys Gly Pro Ile Thr Gln Met Tyr Thr Asn Val
            100                 105                 110

Asp Gln Asp Leu Val Gly Trp Gln Ala Pro Pro Gly Ala Arg Ser Leu
        115                 120                 125
```

```
Thr Pro Cys Thr Cys Gly Ser Ser Asp Leu Tyr Leu Val Thr Arg His
    130                 135                 140
Ala Asp Val Ile Pro Val Arg Arg Gly Asp Ser Arg Gly Ser Leu
145                 150                 155                 160
Leu Ser Pro Arg Pro Val Ser Tyr Leu Lys Gly Ser Ser Gly Gly Pro
                165                 170                 175
Leu Leu Cys Pro Ser Gly His Ala Val Gly Ile Phe Arg Ala Ala Val
            180                 185                 190
Cys Thr Arg Gly Val Ala Lys Ala Val Asp Phe Val Pro Val Glu Ser
            195                 200                 205
Met Glu Thr Thr Met Arg Ser
    210                 215
```

(2) INFORMATION FOR SEQ ID NO:47:

(i) SEQUENCE CHARACTERISTICS:
        (A) LENGTH: 3 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:47:

```
Pro Ala Gly
1
```

(2) INFORMATION FOR SEQ ID NO:48:

(i) SEQUENCE CHARACTERISTICS:
        (A) LENGTH: 75 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:48:

```
GATATACATA TGGGTTCTGT TGTTATTGTT GGTAGAATTA TTTTATCTCC TGCTGGTATC    60

ACGGCCTACT CCCAA                                                    75
```

(2) INFORMATION FOR SEQ ID NO:49:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:49:

```
CTCAGCGAAT TCTCAAGACC GCATAGTAGT TTCCAT                             36
```

(2) INFORMATION FOR SEQ ID NO:50:

(i) SEQUENCE CHARACTERISTICS:
        (A) LENGTH: 215 amino acids
        (B) TYPE: amino acid
        (D) TOPOLOGY: linear (ii) MOLECULE TYPE: protein (xi) SEQUENCE DESCRIPTION: SEQ ID NO:50:

Met Gly Ser Ser His His His His His His Ser Gly Leu Val Pro
 1               5                   10                  15

Arg Gly Ser His Met Gly Ser Val Val Ile Val Gly Arg Ile Ile Leu
                20                  25                  30

Ser Pro Ala Gly Ile Thr Ala Tyr Ser Gln Gln Thr Arg Gly Leu Leu
            35                  40                  45

Gly Cys Lys Ile Thr Ser Leu Thr Gly Arg Asp Lys Asn Gln Val Glu
        50                  55                  60

Gly Glu Val Gln Val Val Ser Thr Ala Thr Gln Ser Phe Leu Ala Thr
65                  70                  75                  80

Cys Val Asn Gly Val Cys Trp Thr Val Tyr His Gly Ala Gly Ser Lys
                85                  90                  95

Thr Leu Ala Gly Pro Lys Gly Pro Ile Thr Gln Met Tyr Thr Asn Val
                100                 105                 110

Asp Gln Asp Leu Val Gly Trp Gln Ala Pro Gly Ala Arg Ser Leu
            115                 120                 125

Thr Pro Cys Thr Cys Gly Ser Ser Asp Leu Tyr Leu Val Thr Arg His
    130                 135                 140

Ala Asp Val Ile Pro Val Arg Arg Arg Gly Asp Ser Arg Gly Ser Leu
145                 150                 155                 160

Leu Ser Pro Arg Pro Val Ser Tyr Leu Lys Gly Ser Ser Gly Gly Pro
                165                 170                 175

Leu Leu Cys Pro Ser Gly His Ala Val Gly Ile Phe Arg Ala Ala Val
                180                 185                 190

Cys Thr Arg Gly Val Ala Lys Ala Val Asp Phe Val Pro Val Glu Ser
                195                 200                 205

Met Glu Thr Thr Met Arg Ser
            210             215

(2) INFORMATION FOR SEQ ID NO:51:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:51:

CGGGGCCTAC TTGGTTGCAA GATCACTAGC CTTACAGGC                                   39

(2) INFORMATION FOR SEQ ID NO:52:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:52:

GCCTGTAAGG CTAGTGATCT TGCAACCAAG TAGGCCCCG                                   39

(2) INFORMATION FOR SEQ ID NO:53:

(i) SEQUENCE CHARACTERISTICS:
       (A) LENGTH: 215 amino acids
       (B) TYPE: amino acid
       (D) TOPOLOGY: linear (ii) MOLECULE TYPE: protein (xi) SEQUENCE DESCRIPTION: SEQ ID NO:53:

```
Met Gly Ser Ser His His His His His Ser Ser Gly Leu Val Pro
 1               5                  10                  15

Arg Gly Ser His Met Gly Ser Val Val Ile Val Gly Arg Ile Ile Leu
            20                  25                  30

Ser Gly Gly Ser Ile Thr Ala Tyr Ser Gln Gln Thr Arg Gly Leu Leu
        35                  40                  45

Gly Cys Ile Ile Thr Ser Leu Thr Gly Arg Asp Lys Asn Gln Val Glu
    50                  55                  60

Gly Glu Val Gln Val Val Ser Thr Ala Thr Gln Ser Phe Leu Ala Thr
65                  70                  75                  80

Cys Val Asn Gly Val Cys Trp Thr Val Tyr His Gly Ala Gly Ser Lys
                85                  90                  95

Thr Leu Ala Gly Pro Lys Gly Pro Ile Thr Gln Met Tyr Thr Asn Val
            100                 105                 110

Asp Gln Asp Leu Val Gly Trp Gln Ala Pro Pro Gly Ala Arg Ser Leu
        115                 120                 125

Thr Pro Cys Thr Cys Gly Ser Ser Asp Leu Tyr Leu Val Thr Arg His
    130                 135                 140

Ala Asp Val Ile Pro Val Arg Arg Arg Gly Asp Ser Arg Gly Ser Leu
145                 150                 155                 160

Leu Ser Pro Arg Pro Val Ser Tyr Leu Lys Gly Ser Ser Gly Gly Pro
                165                 170                 175

Leu Leu Cys Pro Ser Gly His Ala Val Gly Ile Phe Arg Ala Ala Val
            180                 185                 190

Cys Thr Arg Gly Val Ala Lys Ala Val Asp Phe Val Pro Val Glu Ser
        195                 200                 205

Met Glu Thr Thr Met Arg Ser
    210                 215
```

(2) INFORMATION FOR SEQ ID NO:54:

(i) SEQUENCE CHARACTERISTICS:
       (A) LENGTH: 3 amino acids
       (B) TYPE: amino acid
       (C) STRANDEDNESS: single
       (D) TOPOLOGY: linear (ii) MOLECULE TYPE: peptide (xi) SEQUENCE DESCRIPTION: SEQ ID NO:54:

Gly Gly Ser
 1

(2) INFORMATION FOR SEQ ID NO:55:

(i) SEQUENCE CHARACTERISTICS:
       (A) LENGTH: 75 base pairs
       (B) TYPE: nucleic acid
       (C) STRANDEDNESS: single
       (D) TOPOLOGY: linear (ii) MOLECULE TYPE: cDNA -continued (xi) SEQUENCE DESCRIPTION: SEQ ID NO:55:

GATATACATA TGGGTTCTGT TGTTATTGTT GGTAGAATTA TTTTATCTGG TGGTTCTATC    60

ACGGCCTACT CCCAA    75

(2) INFORMATION FOR SEQ ID NO:56:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:56:

CTCAGCGAAT TCTCAAGACC GCATAGTAGT TTCCAT    36

(2) INFORMATION FOR SEQ ID NO:57:

(i) SEQUENCE CHARACTERISTICS:
        (A) LENGTH: 215 amino acids
        (B) TYPE: amino acid
        (D) TOPOLOGY: linear (ii) MOLECULE TYPE: protein (xi) SEQUENCE DESCRIPTION: SEQ ID NO:57:

```
Met Gly Ser Ser His His His His His His Ser Ser Gly Leu Val Pro
 1               5                  10                  15

Arg Gly Ser His Met Gly Ser Val Val Ile Val Gly Arg Ile Ile Leu
            20                  25                  30

Ser Gly Gly Ser Ile Thr Ala Tyr Ser Gln Gln Thr Arg Gly Leu Leu
        35                  40                  45

Gly Cys Lys Ile Thr Ser Leu Thr Gly Arg Asp Lys Asn Gln Val Glu
    50                  55                  60

Gly Glu Val Gln Val Val Ser Thr Ala Thr Gln Ser Phe Leu Ala Thr
65                  70                  75                  80

Cys Val Asn Gly Val Cys Trp Thr Val Tyr His Gly Ala Gly Ser Lys
                85                  90                  95

Thr Leu Ala Gly Pro Lys Gly Pro Ile Thr Gln Met Tyr Thr Asn Val
            100                 105                 110

Asp Gln Asp Leu Val Gly Trp Gln Ala Pro Pro Gly Ala Arg Ser Leu
        115                 120                 125

Thr Pro Cys Thr Cys Gly Ser Ser Asp Leu Tyr Leu Val Thr Arg His
    130                 135                 140

Ala Asp Val Ile Pro Val Arg Arg Arg Gly Asp Ser Arg Gly Ser Leu
145                 150                 155                 160

Leu Ser Pro Arg Pro Val Ser Tyr Leu Lys Gly Ser Ser Gly Gly Pro
                165                 170                 175

Leu Leu Cys Pro Ser Gly His Ala Val Gly Ile Phe Arg Ala Ala Val
            180                 185                 190

Cys Thr Arg Gly Val Ala Lys Ala Val Asp Phe Val Pro Val Glu Ser
        195                 200                 205

Met Glu Thr Thr Met Arg Ser
    210                 215
```

(2) INFORMATION FOR SEQ ID NO:58:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:58:

CGGGGCCTAC TTGGTTGCAA GATCACTAGC CTTACAGGC                                    39

(2) INFORMATION FOR SEQ ID NO:59:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:59:

GCCTGTAAGG CTAGTGATCT TGCAACCAAG TAGGCCCCG                                    39

(2) INFORMATION FOR SEQ ID NO:60:

(i) SEQUENCE CHARACTERISTICS:
        (A) LENGTH: 646 amino acids
        (B) TYPE: amino acid
        (D) TOPOLOGY: linear (ii) MOLECULE TYPE: protein (xi) SEQUENCE DESCRIPTION: SEQ ID NO:60:

```
Met His Met His His His His His His Leu Val Pro Arg Gly Ser Ala
  1               5                  10                  15

Pro Ile Thr Ala Tyr Ser Gln Gln Thr Arg Gly Leu Leu Gly Cys Lys
             20                  25                  30

Ile Thr Ser Leu Thr Gly Arg Asp Lys Asn Gln Val Glu Gly Glu Val
         35                  40                  45

Gln Val Val Ser Thr Ala Thr Gln Ser Phe Leu Ala Thr Cys Val Asn
 50                  55                  60

Gly Val Cys Trp Thr Val Tyr His Gly Ala Gly Ser Lys Thr Leu Ala
 65                  70                  75                  80

Gly Pro Lys Gly Pro Ile Thr Gln Met Tyr Thr Asn Val Asp Gln Asp
                 85                  90                  95

Leu Val Gly Trp Gln Ala Pro Pro Gly Ala Arg Ser Leu Thr Pro Cys
            100                 105                 110

Thr Cys Gly Ser Ser Asp Leu Tyr Leu Val Thr Arg His Ala Asp Val
        115                 120                 125

Ile Pro Val Arg Arg Arg Gly Asp Ser Arg Gly Ser Leu Leu Ser Pro
    130                 135                 140

Arg Pro Val Ser Tyr Leu Lys Gly Ser Ser Gly Gly Pro Leu Leu Cys
145                 150                 155                 160

Pro Ser Gly His Ala Val Gly Ile Phe Arg Ala Ala Val Cys Thr Arg
                165                 170                 175

Gly Val Ala Lys Ala Val Asp Phe Val Pro Val Glu Ser Met Glu Thr
            180                 185                 190

Thr Met Arg Ser Pro Val Phe Thr Asp Asn Ser Ser Pro Pro Ala Val
        195                 200                 205
```

-continued

```
Pro Gln Ser Phe Gln Val Ala His Leu His Ala Pro Thr Gly Ser Gly
    210                 215                 220
Lys Ser Thr Lys Val Pro Ala Ala Tyr Ala Ala Gln Gly Tyr Lys Val
225                 230                 235                 240
Leu Val Leu Asn Pro Ser Val Ala Ala Thr Leu Gly Phe Gly Ala Tyr
                245                 250                 255
Met Ser Lys Ala His Gly Ile Asp Pro Asn Ile Arg Thr Gly Val Arg
            260                 265                 270
Thr Ile Thr Thr Gly Ala Pro Val Thr Tyr Ser Thr Tyr Gly Lys Phe
        275                 280                 285
Leu Ala Asp Gly Gly Cys Ser Gly Gly Ala Tyr Asp Ile Ile Ile Cys
    290                 295                 300
Asp Glu Cys His Ser Thr Asp Ser Thr Thr Ile Leu Gly Ile Gly Thr
305                 310                 315                 320
Val Leu Asp Gln Ala Glu Thr Ala Gly Ala Arg Leu Val Val Leu Ala
                325                 330                 335
Thr Ala Thr Pro Pro Gly Ser Val Thr Val Pro His Pro Asn Ile Glu
            340                 345                 350
Glu Val Ala Leu Ser Asn Thr Gly Glu Ile Pro Phe Tyr Gly Lys Ala
        355                 360                 365
Ile Pro Ile Glu Ala Ile Arg Gly Gly Arg His Leu Ile Phe Cys His
    370                 375                 380
Ser Lys Lys Lys Cys Asp Glu Leu Ala Ala Lys Leu Ser Gly Leu Gly
385                 390                 395                 400
Ile Asn Ala Val Ala Tyr Tyr Arg Gly Leu Asp Val Ser Val Ile Pro
                405                 410                 415
Thr Ile Gly Asp Val Val Val Ala Thr Asp Ala Leu Met Thr Gly
            420                 425                 430
Tyr Thr Gly Asp Phe Asp Ser Val Ile Asp Cys Asn Thr Cys Val Thr
        435                 440                 445
Gln Thr Val Asp Phe Ser Leu Asp Pro Thr Phe Thr Ile Glu Thr Thr
    450                 455                 460
Thr Val Pro Gln Asp Ala Val Ser Arg Ser Gln Arg Arg Gly Arg Thr
465                 470                 475                 480
Gly Arg Gly Arg Arg Gly Ile Tyr Arg Phe Val Thr Pro Gly Glu Arg
                485                 490                 495
Pro Ser Gly Met Phe Asp Ser Ser Val Leu Cys Glu Cys Tyr Asp Ala
            500                 505                 510
Gly Cys Ala Trp Tyr Glu Leu Thr Pro Ala Glu Thr Ser Val Arg Leu
        515                 520                 525
Arg Ala Tyr Leu Asn Thr Pro Gly Leu Pro Val Cys Gln Asp His Leu
    530                 535                 540
Glu Phe Trp Glu Ser Val Phe Thr Gly Leu Thr His Ile Asp Ala His
545                 550                 555                 560
Phe Leu Ser Gln Thr Lys Gln Ala Gly Asp Asn Phe Pro Tyr Leu Val
                565                 570                 575
Ala Tyr Gln Ala Thr Val Cys Ala Arg Ala Gln Ala Pro Pro Pro Ser
            580                 585                 590
Trp Asp Gln Met Trp Lys Cys Leu Ile Arg Leu Lys Pro Thr Leu His
        595                 600                 605
Gly Pro Thr Pro Leu Leu Tyr Arg Leu Gly Ala Val Gln Asn Glu Val
    610                 615                 620
```

```
Thr Leu Thr His Pro Ile Thr Lys Tyr Ile Met Ala Cys Met Ser Ala
625                 630                 635                 640

Asp Leu Glu Val Val Thr
            645
```

(2) INFORMATION FOR SEQ ID NO:61:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:61:

```
CGGGGCCTAC TTGGTTGCAA GATCACTAGC CTTACAGGC                    39
```

(2) INFORMATION FOR SEQ ID NO:62:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:62:

```
GCCTGTAAGG CTAGTGATCT TGCAACCAAG TAGGCCCCG                    39
```

(2) INFORMATION FOR SEQ ID NO:63:

(i) SEQUENCE CHARACTERISTICS:
        (A) LENGTH: 646 amino acids
        (B) TYPE: amino acid
        (D) TOPOLOGY: linear (ii) MOLECULE TYPE: protein (xi) SEQUENCE DESCRIPTION: SEQ ID NO:63:

```
Met His Met His His His His His Leu Val Pro Arg Gly Ser Ala
 1               5                  10                  15

Pro Ile Thr Ala Tyr Ser Gln Gln Thr Arg Gly Leu Leu Gly Cys Ile
                20                  25                  30

Lys Thr Ser Leu Thr Gly Arg Asp Lys Asn Gln Val Glu Gly Glu Val
            35                  40                  45

Gln Val Val Ser Thr Ala Thr Gln Ser Phe Leu Ala Thr Cys Val Asn
        50                  55                  60

Gly Val Cys Trp Thr Val Tyr His Gly Ala Gly Ser Lys Thr Leu Ala
65                  70                  75                  80

Gly Pro Lys Gly Pro Ile Thr Gln Met Tyr Thr Asn Val Asp Gln Asp
                85                  90                  95

Leu Val Gly Trp Gln Ala Pro Pro Gly Ala Arg Ser Leu Thr Pro Cys
            100                 105                 110

Thr Cys Gly Ser Ser Asp Leu Tyr Leu Val Thr Arg His Ala Asp Val
        115                 120                 125

Ile Pro Val Arg Arg Arg Gly Asp Ser Arg Gly Ser Leu Leu Ser Pro
    130                 135                 140

Arg Pro Val Ser Tyr Leu Lys Gly Ser Ser Gly Gly Pro Leu Leu Cys
145                 150                 155                 160
```

-continued

```
Pro Ser Gly His Ala Val Gly Ile Phe Arg Ala Ala Val Cys Thr Arg
            165                 170                 175

Gly Val Ala Lys Ala Val Asp Phe Val Pro Val Glu Ser Met Glu Thr
        180                 185                 190

Thr Met Arg Ser Pro Val Phe Thr Asp Asn Ser Ser Pro Pro Ala Val
    195                 200                 205

Pro Gln Ser Phe Gln Val Ala His Leu His Ala Pro Thr Gly Ser Gly
210                 215                 220

Lys Ser Thr Lys Val Pro Ala Ala Tyr Ala Ala Gln Gly Tyr Lys Val
225                 230                 235                 240

Leu Val Leu Asn Pro Ser Val Ala Ala Thr Leu Gly Phe Gly Ala Tyr
                245                 250                 255

Met Ser Lys Ala His Gly Ile Asp Pro Asn Ile Arg Thr Gly Val Arg
            260                 265                 270

Thr Ile Thr Thr Gly Ala Pro Val Thr Tyr Ser Thr Tyr Gly Lys Phe
        275                 280                 285

Leu Ala Asp Gly Gly Cys Ser Gly Gly Ala Tyr Asp Ile Ile Ile Cys
290                 295                 300

Asp Glu Cys His Ser Thr Asp Ser Thr Thr Ile Leu Gly Ile Gly Thr
305                 310                 315                 320

Val Leu Asp Gln Ala Glu Thr Ala Gly Ala Arg Leu Val Val Leu Ala
                325                 330                 335

Thr Ala Thr Pro Pro Gly Ser Val Thr Val Pro His Pro Asn Ile Glu
            340                 345                 350

Glu Val Ala Leu Ser Asn Thr Gly Glu Ile Pro Phe Tyr Gly Lys Ala
        355                 360                 365

Ile Pro Ile Glu Ala Ile Arg Gly Gly Arg His Leu Ile Phe Cys His
    370                 375                 380

Ser Lys Lys Lys Cys Asp Glu Leu Ala Ala Lys Leu Ser Gly Leu Gly
385                 390                 395                 400

Ile Asn Ala Val Ala Tyr Tyr Arg Gly Leu Asp Val Ser Val Ile Pro
                405                 410                 415

Thr Ile Gly Asp Val Val Val Ala Thr Asp Ala Leu Met Thr Gly
            420                 425                 430

Tyr Thr Gly Asp Phe Asp Ser Val Ile Asp Cys Asn Thr Cys Val Thr
        435                 440                 445

Gln Thr Val Asp Phe Ser Leu Asp Pro Thr Phe Thr Ile Glu Thr Thr
    450                 455                 460

Thr Val Pro Gln Asp Ala Val Ser Arg Ser Gln Arg Arg Gly Arg Thr
465                 470                 475                 480

Gly Arg Gly Arg Arg Gly Ile Tyr Arg Phe Val Thr Pro Gly Glu Arg
                485                 490                 495

Pro Ser Gly Met Phe Asp Ser Ser Val Leu Cys Glu Cys Tyr Asp Ala
            500                 505                 510

Gly Cys Ala Trp Tyr Glu Leu Thr Pro Ala Glu Thr Ser Val Arg Leu
        515                 520                 525

Arg Ala Tyr Leu Asn Thr Pro Gly Leu Pro Val Cys Gln Asp His Leu
    530                 535                 540

Glu Phe Trp Glu Ser Val Phe Thr Gly Leu Thr His Ile Asp Ala His
545                 550                 555                 560

Phe Leu Ser Gln Thr Lys Gln Ala Gly Asp Asn Phe Pro Tyr Leu Val
                565                 570                 575
```

```
Ala Tyr Gln Ala Thr Val Cys Ala Arg Ala Gln Ala Pro Pro Pro Ser
        580                 585                 590

Trp Asp Gln Met Trp Lys Cys Leu Ile Arg Leu Lys Pro Thr Leu His
        595                 600                 605

Gly Pro Thr Pro Leu Leu Tyr Arg Leu Gly Ala Val Gln Asn Glu Val
        610                 615                 620

Thr Leu Thr His Pro Ile Thr Lys Tyr Ile Met Ala Cys Met Ser Ala
625                 630                 635                 640

Asp Leu Glu Val Val Thr
                645
```

(2) INFORMATION FOR SEQ ID NO:64:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:64:

CGGGGCCTAC TTGGTTGCAT CAAGACTAGC CTTACAGGC          39

(2) INFORMATION FOR SEQ ID NO:65:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:65:

GCCTGTAAGG CTAGTCTTGA TGCAACCAAG TAGGCCCCG          39

(2) INFORMATION FOR SEQ ID NO:66:

(i) SEQUENCE CHARACTERISTICS:
        (A) LENGTH: 646 amino acids
        (B) TYPE: amino acid
        (D) TOPOLOGY: linear (ii) MOLECULE TYPE: protein (xi) SEQUENCE DESCRIPTION: SEQ ID NO:66:

```
Met His Met His His His His His Leu Val Pro Arg Gly Ser Ala
1               5                   10                  15

Pro Ile Thr Ala Tyr Ser Gln Gln Thr Arg Gly Leu Leu Gly Cys Ile
                20                  25                  30

Ile Thr Ser Leu Thr Gly Arg Asp Lys Asn Gln Val Glu Gly Glu Val
            35                  40                  45

Gln Val Val Ser Thr Ala Thr Gln Ser Phe Leu Ala Thr Cys Val Asn
        50                  55                  60

Gly Val Cys Trp Thr Val Tyr His Gly Ala Gly Ser Lys Thr Leu Ala
65                  70                  75                  80

Gly Pro Lys Gly Pro Ile Thr Gln Met Tyr Thr Asn Val Asp Gln Asp
                85                  90                  95

Leu Val Gly Trp Gln Ala Pro Pro Gly Ala Arg Ser Leu Thr Pro Cys
            100                 105                 110
```

-continued

```
Thr Cys Gly Ser Ser Asp Leu Tyr Leu Val Thr Arg His Ala Asp Val
        115                 120                 125

Ile Pro Val Arg Arg Gly Asp Ser Arg Gly Ser Leu Leu Ser Pro
130                 135                 140

Arg Pro Val Ser Tyr Leu Lys Gly Ser Ala Gly Pro Leu Leu Cys
145                 150                 155                 160

Pro Ser Gly His Ala Val Gly Ile Phe Arg Ala Val Cys Thr Arg
                165                 170                 175

Gly Val Ala Lys Ala Val Asp Phe Val Pro Val Glu Ser Met Glu Thr
            180                 185                 190

Thr Met Arg Ser Pro Val Phe Thr Asp Asn Ser Ser Pro Ala Val
        195                 200                 205

Pro Gln Ser Phe Gln Val Ala His Leu His Ala Pro Thr Gly Ser Gly
    210                 215                 220

Lys Ser Thr Lys Val Pro Ala Ala Tyr Ala Ala Gln Gly Tyr Lys Val
225                 230                 235                 240

Leu Val Leu Asn Pro Ser Val Ala Ala Thr Leu Gly Phe Gly Ala Tyr
                245                 250                 255

Met Ser Lys Ala His Gly Ile Asp Pro Asn Ile Arg Thr Gly Val Arg
        260                 265                 270

Thr Ile Thr Thr Gly Ala Pro Val Thr Tyr Ser Thr Tyr Gly Lys Phe
        275                 280                 285

Leu Ala Asp Gly Gly Cys Ser Gly Gly Ala Tyr Asp Ile Ile Ile Cys
        290                 295                 300

Asp Glu Cys His Ser Thr Asp Ser Thr Thr Ile Leu Gly Ile Gly Thr
305                 310                 315                 320

Val Leu Asp Gln Ala Glu Thr Ala Gly Ala Arg Leu Val Val Leu Ala
            325                 330                 335

Thr Ala Thr Pro Pro Gly Ser Val Thr Val Pro His Pro Asn Ile Glu
                340                 345                 350

Glu Val Ala Leu Ser Asn Thr Gly Glu Ile Pro Phe Tyr Gly Lys Ala
        355                 360                 365

Ile Pro Ile Glu Ala Ile Arg Gly Gly Arg His Leu Ile Phe Cys His
370                 375                 380

Ser Lys Lys Lys Cys Asp Glu Leu Ala Ala Lys Leu Ser Gly Leu Gly
385                 390                 395                 400

Ile Asn Ala Val Ala Tyr Tyr Arg Gly Leu Asp Val Ser Val Ile Pro
                405                 410                 415

Thr Ile Gly Asp Val Val Val Ala Thr Asp Ala Leu Met Thr Gly
            420                 425                 430

Tyr Thr Gly Asp Phe Asp Ser Val Ile Asp Cys Asn Thr Cys Val Thr
        435                 440                 445

Gln Thr Val Asp Phe Ser Leu Asp Pro Thr Phe Thr Ile Glu Thr Thr
    450                 455                 460

Thr Val Pro Gln Asp Ala Val Ser Arg Ser Gln Arg Arg Gly Arg Thr
465                 470                 475                 480

Gly Arg Gly Arg Arg Gly Ile Tyr Arg Phe Val Thr Pro Gly Glu Arg
                485                 490                 495

Pro Ser Gly Met Phe Asp Ser Ser Val Leu Cys Glu Cys Tyr Asp Ala
            500                 505                 510

Gly Cys Ala Trp Tyr Glu Leu Thr Pro Ala Glu Thr Ser Val Arg Leu
        515                 520                 525
```

```
Arg Ala Tyr Leu Asn Thr Pro Gly Leu Pro Val Cys Gln Asp His Leu
    530                 535                 540

Glu Phe Trp Glu Ser Val Phe Thr Gly Leu Thr His Ile Asp Ala His
545                 550                 555                 560

Phe Leu Ser Gln Thr Lys Gln Ala Gly Asp Asn Phe Pro Tyr Leu Val
                565                 570                 575

Ala Tyr Gln Ala Thr Val Cys Ala Arg Ala Gln Ala Pro Pro Pro Ser
            580                 585                 590

Trp Asp Gln Met Trp Lys Cys Leu Ile Arg Leu Lys Pro Thr Leu His
            595                 600                 605

Gly Pro Thr Pro Leu Leu Tyr Arg Leu Gly Ala Val Gln Asn Glu Val
        610                 615                 620

Thr Leu Thr His Pro Ile Thr Lys Tyr Ile Met Ala Cys Met Ser Ala
625                 630                 635                 640

Asp Leu Glu Val Val Thr
                645
```

(2) INFORMATION FOR SEQ ID NO:67:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:67:

CTCCTACTTG AAGGGCTCTG CTGGTGGTCC ACTGCTCTGC    40

(2) INFORMATION FOR SEQ ID NO:68:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:68:

GCAGAGCAGT GGACCACCAG CAGAGCCCTT CAAGTAGGAG    40

(2) INFORMATION FOR SEQ ID NO:69:

(i) SEQUENCE CHARACTERISTICS:
        (A) LENGTH: 646 amino acids
        (B) TYPE: amino acid
        (D) TOPOLOGY: linear (ii) MOLECULE TYPE: protein (xi) SEQUENCE DESCRIPTION: SEQ ID NO:69:

```
Met His Met His His His His His Leu Val Pro Arg Gly Ser Ala
1               5                   10                  15

Pro Ile Thr Ala Tyr Ser Gln Gln Thr Arg Gly Leu Leu Gly Cys Ile
            20                  25                  30

Ile Thr Ser Leu Thr Gly Arg Asp Lys Asn Gln Val Glu Gly Glu Val
        35                  40                  45

Gln Val Val Ser Thr Ala Thr Gln Ser Phe Leu Ala Thr Cys Val Asn
    50                  55                  60
```

-continued

```
Gly Val Cys Trp Thr Val Tyr His Gly Ala Gly Ser Lys Thr Leu Ala
 65                  70                  75                  80

Gly Pro Lys Gly Pro Ile Thr Gln Met Tyr Thr Asn Val Asp Gln Asp
                 85                  90                  95

Leu Val Gly Trp Gln Ala Pro Pro Gly Ala Arg Ser Leu Thr Pro Cys
            100                 105                 110

Thr Cys Gly Ser Ser Asp Leu Tyr Leu Val Thr Arg His Ala Asp Val
            115                 120                 125

Ile Pro Val Arg Arg Gly Asp Ser Arg Gly Ser Leu Leu Ser Pro
130                 135                 140

Arg Pro Val Ser Tyr Leu Lys Gly Ser Gly Gly Pro Leu Leu Cys
145                 150                 155                 160

Pro Ser Gly His Ala Val Gly Ile Phe Arg Ala Val Cys Thr Arg
                165                 170                 175

Gly Val Ala Lys Ala Val Asp Phe Val Pro Val Glu Ser Met Glu Thr
                180                 185                 190

Thr Met Arg Ser Pro Val Phe Thr Asp Asn Ser Ser Pro Pro Ala Val
            195                 200                 205

Pro Gln Ser Phe Gln Val Ala His Leu His Ala Pro Thr Gly Ser Gly
            210                 215                 220

Lys Ser Thr Lys Val Pro Ala Ala Tyr Ala Ala Gln Gly Tyr Lys Val
225                 230                 235                 240

Leu Val Leu Asn Pro Ser Val Ala Ala Thr Leu Gly Phe Gly Ala Tyr
                245                 250                 255

Met Ser Lys Ala His Gly Ile Asp Pro Asn Ile Arg Thr Gly Val Arg
            260                 265                 270

Thr Ile Thr Thr Gly Ala Pro Val Thr Tyr Ser Thr Tyr Gly Lys Phe
            275                 280                 285

Leu Ala Asp Gly Gly Cys Ser Gly Gly Ala Tyr Asp Ile Ile Ile Cys
            290                 295                 300

Asp Glu Cys His Ser Thr Asp Ser Thr Thr Ile Leu Gly Ile Gly Thr
305                 310                 315                 320

Val Leu Asp Gln Ala Glu Thr Ala Gly Ala Arg Leu Val Val Leu Ala
                325                 330                 335

Thr Ala Thr Pro Pro Gly Ser Val Thr Val Pro His Pro Asn Ile Glu
            340                 345                 350

Glu Val Ala Leu Ser Asn Thr Gly Glu Ile Pro Phe Tyr Gly Lys Ala
            355                 360                 365

Ile Pro Ile Glu Ala Ile Arg Gly Gly Arg His Leu Ile Phe Cys His
370                 375                 380

Ser Lys Lys Lys Cys Asp Glu Leu Ala Ala Lys Leu Ser Gly Leu Gly
385                 390                 395                 400

Ile Asn Ala Val Ala Tyr Tyr Arg Gly Leu Asp Val Ser Val Ile Pro
                405                 410                 415

Thr Ser Gly Asp Val Val Val Ala Thr Asp Ala Leu Met Thr Gly
            420                 425                 430

Tyr Thr Gly Asp Phe Asp Ser Val Ile Asp Cys Asn Thr Cys Val Thr
            435                 440                 445

Gln Thr Val Asp Phe Ser Leu Asp Pro Thr Phe Thr Ile Glu Thr Thr
            450                 455                 460

Thr Val Pro Gln Asp Ala Val Ser Arg Ser Gln Arg Arg Gly Arg Thr
465                 470                 475                 480
```

-continued

```
Gly Arg Gly Arg Gly Ile Tyr Arg Phe Val Thr Pro Gly Glu Arg
                485                 490                 495

Pro Ser Gly Met Phe Asp Ser Ser Val Leu Cys Glu Cys Tyr Asp Ala
            500                 505                 510

Gly Cys Ala Trp Tyr Glu Leu Thr Pro Ala Glu Thr Ser Val Arg Leu
        515                 520                 525

Arg Ala Tyr Leu Asn Thr Pro Gly Leu Pro Val Cys Gln Asp His Leu
    530                 535                 540

Glu Phe Trp Glu Ser Val Phe Thr Gly Leu Thr His Ile Asp Ala His
545                 550                 555                 560

Phe Leu Ser Gln Thr Lys Gln Ala Gly Asp Asn Phe Pro Tyr Leu Val
                565                 570                 575

Ala Tyr Gln Ala Thr Val Cys Ala Arg Ala Gln Ala Pro Pro Pro Ser
            580                 585                 590

Trp Asp Gln Met Trp Lys Cys Leu Ile Arg Leu Lys Pro Thr Leu His
        595                 600                 605

Gly Pro Thr Pro Leu Leu Tyr Arg Leu Gly Ala Val Gln Asn Glu Val
    610                 615                 620

Thr Leu Thr His Pro Ile Thr Lys Tyr Ile Met Ala Cys Met Ser Ala
625                 630                 635                 640

Asp Leu Glu Val Val Thr
                645
```

(2) INFORMATION FOR SEQ ID NO:70:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:70:

GTCCGTCATA CCAACTTCCG GAGACGTCGT TGTCG                      35

(2) INFORMATION FOR SEQ ID NO:71:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:71:

CGACAACGAC GTCTCCGGAA GTTGGTATGA CGGAC                      35

(2) INFORMATION FOR SEQ ID NO:72:

(i) SEQUENCE CHARACTERISTICS:
        (A) LENGTH: 646 amino acids
        (B) TYPE: amino acid
        (D) TOPOLOGY: linear (ii) MOLECULE TYPE: protein (xi) SEQUENCE DESCRIPTION: SEQ ID NO:72:

```
Met His Met His His His His His Leu Val Pro Arg Gly Ser Ala
  1               5                  10                  15
```

```
Pro Ile Thr Ala Tyr Ser Gln Gln Thr Arg Gly Leu Leu Gly Cys Ile
            20                  25                  30

Ile Thr Ser Leu Thr Gly Arg Asp Lys Asn Gln Val Glu Gly Glu Val
            35                  40                  45

Gln Val Val Ser Thr Ala Thr Gln Ser Phe Leu Ala Thr Cys Val Asn
        50                  55                  60

Gly Val Cys Trp Thr Val Tyr His Gly Ala Gly Ser Lys Thr Leu Ala
65                  70                  75                  80

Gly Pro Lys Gly Pro Ile Thr Gln Met Tyr Thr Asn Val Asp Gln Asp
                85                  90                  95

Leu Val Gly Trp Gln Ala Pro Gly Ala Arg Ser Leu Thr Pro Cys
                100                 105                 110

Thr Cys Gly Ser Ser Asp Leu Tyr Leu Val Thr Arg His Ala Asp Val
            115                 120                 125

Ile Pro Val Arg Arg Arg Gly Asp Ser Arg Gly Ser Leu Leu Ser Pro
            130                 135                 140

Arg Pro Val Ser Tyr Leu Lys Gly Ser Ser Gly Gly Pro Leu Leu Cys
145                 150                 155                 160

Pro Ser Gly His Ala Val Gly Ile Phe Arg Ala Ala Val Cys Thr Arg
                165                 170                 175

Gly Val Ala Lys Ala Val Asp Phe Val Pro Val Glu Ser Met Glu Thr
            180                 185                 190

Thr Met Arg Ser Pro Val Phe Thr Asp Asn Ser Ser Pro Pro Ala Val
            195                 200                 205

Pro Gln Ser Phe Gln Val Ala His Leu His Ala Pro Thr Gly Ser Gly
        210                 215                 220

Lys Ser Thr Lys Val Pro Ala Ala Tyr Ala Ala Gln Gly Tyr Lys Val
225                 230                 235                 240

Leu Val Leu Asn Pro Ser Val Ala Ala Thr Leu Gly Phe Gly Ala Tyr
                245                 250                 255

Met Ser Lys Ala His Gly Ile Asp Pro Asn Ile Arg Thr Gly Val Arg
            260                 265                 270

Thr Ile Thr Thr Gly Ala Pro Val Thr Tyr Ser Thr Tyr Gly Lys Phe
            275                 280                 285

Leu Ala Asp Gly Gly Cys Ser Gly Gly Ala Tyr Asp Ile Ile Ile Cys
            290                 295                 300

Asp Glu Cys His Ser Thr Asp Ser Thr Thr Ile Leu Gly Ile Gly Thr
305                 310                 315                 320

Val Leu Asp Gln Ala Glu Thr Ala Gly Ala Arg Leu Val Val Leu Ala
                325                 330                 335

Thr Ala Thr Pro Pro Gly Ser Val Thr Val Pro His Pro Asn Ile Glu
            340                 345                 350

Glu Val Ala Leu Ser Asn Thr Gly Glu Ile Pro Phe Tyr Gly Lys Ala
            355                 360                 365

Ile Pro Ile Glu Ala Ile Arg Gly Gly Arg His Leu Ile Phe Cys His
            370                 375                 380

Ser Lys Lys Lys Cys Asp Glu Leu Ala Ala Lys Leu Ser Gly Leu Gly
385                 390                 395                 400

Ile Asn Ala Val Ala Tyr Tyr Arg Gly Leu Asp Val Ser Val Ile Pro
                405                 410                 415

Thr Ile Gly Asp Val Val Val Ala Thr Asp Ala Leu Met Thr Gly
            420                 425                 430
```

```
Tyr Thr Gly Asp Phe Asp Ser Val Ile Asp Cys Asn Thr Cys Val Thr
            435                 440                 445

Gln Thr Val Asp Phe Ser Leu Asp Pro Thr Phe Thr Ile Glu Thr Thr
        450                 455                 460

Thr Val Pro Gln Asp Ala Val Ser Arg Ser Gln Arg Arg Gly Arg Thr
465                 470                 475                 480

Gly Arg Gly Arg Gly Ile Tyr Arg Phe Val Thr Pro Gly Glu Arg
                485                 490                 495

Pro Ser Gly Met Phe Asp Ser Ser Val Leu Cys Glu Cys Tyr Asp Ala
                500                 505                 510

Gly Cys Ala Trp Tyr Glu Leu Thr Pro Ala Glu Thr Ser Val Arg Leu
            515                 520                 525

Arg Ala Tyr Leu Asn Thr Pro Gly Leu Pro Val Cys Gln Asp His Leu
            530                 535                 540

Glu Phe Trp Glu Ser Val Phe Thr Gly Leu Thr His Ile Asp Ala His
545                 550                 555                 560

Phe Leu Ser Gln Thr Lys Gln Ala Gly Asp Asn Phe Pro Tyr Leu Val
                565                 570                 575

Ala Tyr Gln Ala Thr Val Cys Ala Arg Ala Gln Ala Pro Pro Pro Ser
                580                 585                 590

Trp Asp Gln Met Trp Lys Cys Leu Ile Arg Leu Lys Pro Thr Leu His
            595                 600                 605

Gly Pro Thr Pro Leu Leu Tyr Arg Leu Gly Ala Val Gln Asn Glu Val
        610                 615                 620

Thr Leu Thr His Pro Ile Thr Lys Tyr Ile Met Ala Cys Met Ser Ala
625                 630                 635                 640

Asp Leu Glu Val Val Thr
                645

(2) INFORMATION FOR SEQ ID NO:73:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:73:

ACTAAAGTGC CGGCTGCCTA CGCAGCCCAA GGG                              33

(2) INFORMATION FOR SEQ ID NO:74:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:74:

CCCTTGGGCT GCGTAGGCAG CCGGCACTTT AGT                              33

(2) INFORMATION FOR SEQ ID NO:75:

(i) SEQUENCE CHARACTERISTICS:
        (A) LENGTH: 39 base pairs
        (B) TYPE: nucleic acid
```

```
        (C) STRANDEDNESS: single
        (D) TOPOLOGY: linear (ii) MOLECULE TYPE: cDNA (xi) SEQUENCE DESCRIPTION: SEQ ID NO:75:

CGGGGCCTAC TTGGTTGCAA GATCACTAGC CTTACAGGC                              39

(2) INFORMATION FOR SEQ ID NO:76:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:76:

GCCTGTAAGG CTAGTGATCT TGCAACCAAG TAGGCCCCG                              39

(2) INFORMATION FOR SEQ ID NO:77:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:77:

CGGGGCCTAC TTGGTTGCAT CAAGACTAGC CTTACAGGC                              39

(2) INFORMATION FOR SEQ ID NO:78:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:78:

GCCTGTAAGG CTAGTCTTGA TGCAACCAAG TAGGCCCCG                              39

(2) INFORMATION FOR SEQ ID NO:79:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:79:

CGGGGCCTAC TTGGTTGCAA GAAGACTAGC CTTACAGG                               38

(2) INFORMATION FOR SEQ ID NO:80:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: cDNA
```

(xi) SEQUENCE DESCRIPTION: SEQ ID NO:80:

GCCTGTAAGG CTAGTCTTCT TGCAACCAAG TAGGCCCCG                                    39

(2) INFORMATION FOR SEQ ID NO:81:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:81:

CGGGGCCTAC TTGGTTGCAA GATCACTAGC CTTACAGGC                                    39

(2) INFORMATION FOR SEQ ID NO:82:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:82:

GCCTGTAAGG CTAGTGATCT TGCAACCAAG TAGGCCCCG                                    39

(2) INFORMATION FOR SEQ ID NO:83:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:83:

CGGGGCCTAC TTGGTTGCAT CAAGACTAGC CTTACAGGC                                    39

(2) INFORMATION FOR SEQ ID NO:84:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:84:

GCCTGTAAGG CTAGTCTTGA TGCAACCAAG TAGGCCCCG                                    39

(2) INFORMATION FOR SEQ ID NO:85:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:85:

CGGGGCCTAC TTGGTTGCAA GAAGACTAGC CTTACAGGC                                    39

(2) INFORMATION FOR SEQ ID NO:86:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:86:

```
GCCTGTAAGG CTAGTCTTCT TGCAACCAAG TAGGCCCCG                           39
```

(2) INFORMATION FOR SEQ ID NO:87:

(i) SEQUENCE CHARACTERISTICS:
        (A) LENGTH: 96 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:87:

```
GATATACATA TGGCTTACTC TCTGACTACG GGTTCTGTTG TTATTGTTGG TAGAATTATT    60

TTATCTGGTA GTGGTAGTAT CACGGCCTAC TCCCAA                              96
```

(2) INFORMATION FOR SEQ ID NO:88:

(i) SEQUENCE CHARACTERISTICS:
        (A) LENGTH: 51 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:88:

```
GTGGTGGTGC TCGAGGCTGC CGCGCGGCAC CAGCGTAACG ACCTCCAGGT C             51
```

(2) INFORMATION FOR SEQ ID NO:89:

(i) SEQUENCE CHARACTERISTICS:
        (A) LENGTH: 96 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:89:

```
GATATACATA TGGCTTACTC TCTGACTACG GGTTCTGTTG TTATTGTTGG TAGAATTATT    60

TTATCTGGTA GTGGTAGTAT CACGGCCTAC TCCCAA                              96
```

(2) INFORMATION FOR SEQ ID NO:90:

(i) SEQUENCE CHARACTERISTICS:
        (A) LENGTH: 50 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:90:

```
TGGTGGTGCT CGAGGCTGCC GCGCGGCACC AGCGTAACGA CCTCCAGGTC               50
```

(2) INFORMATION FOR SEQ ID NO:91:

(i) SEQUENCE CHARACTERISTICS:
        (A) LENGTH: 17 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:91:

```
Asp Thr Glu Asp Val Val Ala Cys Ser Met Ser Tyr Thr Trp Tyr Gly
1               5                   10                  15

Lys
```

(2) INFORMATION FOR SEQ ID NO:92:

(i) SEQUENCE CHARACTERISTICS:
        (A) LENGTH: 651 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..651

(xi) SEQUENCE DESCRIPTION: SEQ ID NO:92:

```
ATG GGC AGC AGC CAT CAT CAT CAT CAT CAC AGC AGC GGC CTG GTG CCG      48
Met Gly Ser Ser His His His His His His Ser Ser Gly Leu Val Pro
1               5                   10                  15

CGC GGC AGC CAT ATG GGT TCT GTT GTT ATT GTT GGT AGA ATT ATT TTA      96
Arg Gly Ser His Met Gly Ser Val Val Ile Val Gly Arg Ile Ile Leu
            20                  25                  30

TCT GGT AGT GGT AGT ATC ACG GCC TAC TCC CAA CAG ACG CGG GGC CTA     144
Ser Gly Ser Gly Ser Ile Thr Ala Tyr Ser Gln Gln Thr Arg Gly Leu
        35                  40                  45

CTT GGT TGC ATC ATC ACT AGC CTT ACA GGC CGG GAC AAG AAC CAG GTC     192
Leu Gly Cys Ile Ile Thr Ser Leu Thr Gly Arg Asp Lys Asn Gln Val
    50                  55                  60

GAG GGA GAG GTT CAG GTG GTT TCC ACC GCA ACA CAA TCC TTC CTG GCG     240
Glu Gly Glu Val Gln Val Val Ser Thr Ala Thr Gln Ser Phe Leu Ala
65                  70                  75                  80

ACC TGC GTC AAC GGC GTG TGT TGG ACC GTT TAC CAT GGT GCT GGC TCA     288
Thr Cys Val Asn Gly Val Cys Trp Thr Val Tyr His Gly Ala Gly Ser
                85                  90                  95

AAG ACC TTA GCC GGC CCA AAG GGG CCA ATC ACC CAG ATG TAC ACT AAT     336
Lys Thr Leu Ala Gly Pro Lys Gly Pro Ile Thr Gln Met Tyr Thr Asn
            100                 105                 110

GTG GAC CAG GAC CTC GTC GGC TGG CAG GCG CCC CCC GGG GCG CGT TCC     384
Val Asp Gln Asp Leu Val Gly Trp Gln Ala Pro Pro Gly Ala Arg Ser
        115                 120                 125

TTG ACA CCA TGC ACC TGT GGC AGC TCA GAC CTT TAC TTG GTC ACG AGA     432
Leu Thr Pro Cys Thr Cys Gly Ser Ser Asp Leu Tyr Leu Val Thr Arg
    130                 135                 140

CAT GCT GAC GTC ATT CCG GTG CGC CGG CGG GGC GAC AGT AGG GGG AGC     480
His Ala Asp Val Ile Pro Val Arg Arg Arg Gly Asp Ser Arg Gly Ser
145                 150                 155                 160

CTG CTC TCC CCC AGG CCT GTC TCC TAC TTG AAG GGC TCT TCG GGT GGT     528
Leu Leu Ser Pro Arg Pro Val Ser Tyr Leu Lys Gly Ser Ser Gly Gly
                165                 170                 175
```

```
CCA CTG CTC TGC CCT TCG GGG CAC GCT GTG GGC ATC TTC CGG GCT GCC         576
Pro Leu Leu Cys Pro Ser Gly His Ala Val Gly Ile Phe Arg Ala Ala
        180                 185                 190

GTA TGC ACC CGG GGG GTT GCG AAG GCG GTG GAC TTT GTG CCC GTA GAG         624
Val Cys Thr Arg Gly Val Ala Lys Ala Val Asp Phe Val Pro Val Glu
            195                 200                 205

TCC ATG GAA ACT ACT ATG CGG TCT TGA                                     651
Ser Met Glu Thr Thr Met Arg Ser
        210                 215

(2) INFORMATION FOR SEQ ID NO:93:

(i) SEQUENCE CHARACTERISTICS:
        (A) LENGTH: 651 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 1..651

(xi) SEQUENCE DESCRIPTION: SEQ ID NO:93:

ATG GGC AGC AGC CAT CAT CAT CAT CAT CAC AGC AGC GGC CTG GTG CCG          48
Met Gly Ser Ser His His His His His His Ser Ser Gly Leu Val Pro
  1               5                  10                  15

CGC GGC AGC CAT ATG GGT TCT GTT GTT ATT GTT GGT AGA ATT ATT TTA          96
Arg Gly Ser His Met Gly Ser Val Val Ile Val Gly Arg Ile Ile Leu
                 20                  25                  30

TCT GGT AGT GGT AGT ATC ACG GCC TAC TCC CAA CAG ACG CGG GGC CTA         144
Ser Gly Ser Gly Ser Ile Thr Ala Tyr Ser Gln Gln Thr Arg Gly Leu
            35                  40                  45

CTT GGT TGC AAG ATC ACT AGC CTT ACA GGC CGG GAC AAG AAC CAG GTC         192
Leu Gly Cys Lys Ile Thr Ser Leu Thr Gly Arg Asp Lys Asn Gln Val
        50                  55                  60

GAG GGA GAG GTT CAG GTG GTT TCC ACC GCA ACA CAA TCC TTC CTG GCG         240
Glu Gly Glu Val Gln Val Val Ser Thr Ala Thr Gln Ser Phe Leu Ala
 65                  70                  75                  80

ACC TGC GTC AAC GGC GTG TGT TGG ACC GTT TAC CAT GGT GCT GGC TCA         288
Thr Cys Val Asn Gly Val Cys Trp Thr Val Tyr His Gly Ala Gly Ser
                 85                  90                  95

AAG ACC TTA GCC GGC CCA AAG GGG CCA ATC ACC CAG ATG TAC ACT AAT         336
Lys Thr Leu Ala Gly Pro Lys Gly Pro Ile Thr Gln Met Tyr Thr Asn
            100                 105                 110

GTG GAC CAG GAC CTC GTC GGC TGG CAG GCG CCC CCC GGG GCG CGT TCC         384
Val Asp Gln Asp Leu Val Gly Trp Gln Ala Pro Pro Gly Ala Arg Ser
        115                 120                 125

TTG ACA CCA TGC ACC TGT GGC AGC TCA GAC CTT TAC TTG GTC ACG AGA         432
Leu Thr Pro Cys Thr Cys Gly Ser Ser Asp Leu Tyr Leu Val Thr Arg
    130                 135                 140

CAT GCT GAC GTC ATT CCG GTG CGC CGG CGG GGC GAC AGT AGG GGG AGC         480
His Ala Asp Val Ile Pro Val Arg Arg Arg Gly Asp Ser Arg Gly Ser
145                 150                 155                 160

CTG CTC TCC CCC AGG CCT GTC TCC TAC TTG AAG GGC TCT TCG GGT GGT         528
Leu Leu Ser Pro Arg Pro Val Ser Tyr Leu Lys Gly Ser Ser Gly Gly
                165                 170                 175

CCA CTG CTC TGC CCT TCG GGG CAC GCT GTG GGC ATC TTC CGG GCT GCC         576
Pro Leu Leu Cys Pro Ser Gly His Ala Val Gly Ile Phe Arg Ala Ala
        180                 185                 190
```

```
GTA TGC ACC CGG GGG GTT GCG AAG GCG GTG GAC TTT GTG CCC GTA GAG      624
Val Cys Thr Arg Gly Val Ala Lys Ala Val Asp Phe Val Pro Val Glu
    195                 200                 205

TCC ATG GAA ACT ACT ATG CGG TCT TGA                                  651
Ser Met Glu Thr Thr Met Arg Ser
    210                 215
```

(2) INFORMATION FOR SEQ ID NO:94:

(i) SEQUENCE CHARACTERISTICS:
        (A) LENGTH: 651 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 1..651

(xi) SEQUENCE DESCRIPTION: SEQ ID NO:94:

```
ATG GGC AGC AGC CAT CAT CAT CAT CAT CAC AGC AGC GGC CTG GTG CCG       48
Met Gly Ser Ser His His His His His His Ser Ser Gly Leu Val Pro
  1               5                  10                  15

CGC GGC AGC CAT ATG GGT TCT GTT GTT ATT GTT GGT AGA ATT ATT TTA       96
Arg Gly Ser His Met Gly Ser Val Val Ile Val Gly Arg Ile Ile Leu
             20                  25                  30

TCT GGT AGT GGT AGT ATC ACG GCC TAC TCC CAA CAG ACG CGG GGC CTA      144
Ser Gly Ser Gly Ser Ile Thr Ala Tyr Ser Gln Gln Thr Arg Gly Leu
         35                  40                  45

CTT GGT TGC ATC AAG ACT AGC CTT ACA GGC CGG GAC AAG AAC CAG GTC      192
Leu Gly Cys Ile Lys Thr Ser Leu Thr Gly Arg Asp Lys Asn Gln Val
     50                  55                  60

GAG GGA GAG GTT CAG GTG GTT TCC ACC GCA ACA CAA TCC TTC CTG GCG      240
Glu Gly Glu Val Gln Val Val Ser Thr Ala Thr Gln Ser Phe Leu Ala
 65                  70                  75                  80

ACC TGC GTC AAC GGC GTG TGT TGG ACC GTT TAC CAT GGT GCT GGC TCA      288
Thr Cys Val Asn Gly Val Cys Trp Thr Val Tyr His Gly Ala Gly Ser
                 85                  90                  95

AAG ACC TTA GCC GGC CCA AAG GGG CCA ATC ACC CAG ATG TAC ACT AAT      336
Lys Thr Leu Ala Gly Pro Lys Gly Pro Ile Thr Gln Met Tyr Thr Asn
            100                 105                 110

GTG GAC CAG GAC CTC GTC GGC TGG CAG GCG CCC CCC GGG GCG CGT TCC      384
Val Asp Gln Asp Leu Val Gly Trp Gln Ala Pro Pro Gly Ala Arg Ser
        115                 120                 125

TTG ACA CCA TGC ACC TGT GGC AGC TCA GAC CTT TAC TTG GTC ACG AGA      432
Leu Thr Pro Cys Thr Cys Gly Ser Ser Asp Leu Tyr Leu Val Thr Arg
    130                 135                 140

CAT GCT GAC GTC ATT CCG GTG CGC CGG CGG GGC GAC AGT AGG GGG AGC      480
His Ala Asp Val Ile Pro Val Arg Arg Arg Gly Asp Ser Arg Gly Ser
145                 150                 155                 160

CTG CTC TCC CCC AGG CCT GTC TCC TAC TTG AAG GGC TCT TCG GGT GGT      528
Leu Leu Ser Pro Arg Pro Val Ser Tyr Leu Lys Gly Ser Ser Gly Gly
                165                 170                 175

CCA CTG CTC TGC CCT TCG GGG CAC GCT GTG GGC ATC TTC CGG GCT GCC      576
Pro Leu Leu Cys Pro Ser Gly His Ala Val Gly Ile Phe Arg Ala Ala
            180                 185                 190

GTA TGC ACC CGG GGG GTT GCG AAG GCG GTG GAC TTT GTG CCC GTA GAG      624
Val Cys Thr Arg Gly Val Ala Lys Ala Val Asp Phe Val Pro Val Glu
        195                 200                 205
```

```
TCC ATG GAA ACT ACT ATG CGG TCT TGA                                    651
Ser Met Glu Thr Thr Met Arg Ser
    210                 215
```

(2) INFORMATION FOR SEQ ID NO:95:

(i) SEQUENCE CHARACTERISTICS:
        (A) LENGTH: 651 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 1..651

(xi) SEQUENCE DESCRIPTION: SEQ ID NO:95:

```
ATG GGC AGC AGC CAT CAT CAT CAT CAT CAC AGC AGC GGC CTG GTG CCG         48
Met Gly Ser Ser His His His His His His Ser Ser Gly Leu Val Pro
  1               5                  10                  15

CGC GGC AGC CAT ATG GGT TCT GTT GTT ATT GTT GGT AGA ATT ATT TTA         96
Arg Gly Ser His Met Gly Ser Val Val Ile Val Gly Arg Ile Ile Leu
             20                  25                  30

TCT GGT AGT GGT AGT ATC ACG GCC TAC TCC CAA CAG ACG CGG GGC CTA        144
Ser Gly Ser Gly Ser Ile Thr Ala Tyr Ser Gln Gln Thr Arg Gly Leu
         35                  40                  45

CTT GGT TGC AAG AAG ACT AGC CTT ACA GGC CGG GAC AAG AAC CAG GTC        192
Leu Gly Cys Lys Lys Thr Ser Leu Thr Gly Arg Asp Lys Asn Gln Val
     50                  55                  60

GAG GGA GAG GTT CAG GTG GTT TCC ACC GCA ACA CAA TCC TTC CTG GCG        240
Glu Gly Glu Val Gln Val Val Ser Thr Ala Thr Gln Ser Phe Leu Ala
 65                  70                  75                  80

ACC TGC GTC AAC GGC GTG TGT TGG ACC GTT TAC CAT GGT GCT GGC TCA        288
Thr Cys Val Asn Gly Val Cys Trp Thr Val Tyr His Gly Ala Gly Ser
                 85                  90                  95

AAG ACC TTA GCC GGC CCA AAG GGG CCA ATC ACC CAG ATG TAC ACT AAT        336
Lys Thr Leu Ala Gly Pro Lys Gly Pro Ile Thr Gln Met Tyr Thr Asn
            100                 105                 110

GTG GAC CAG GAC CTC GTC GGC TGG CAG GCG CCC CCC GGG GCG CGT TCC        384
Val Asp Gln Asp Leu Val Gly Trp Gln Ala Pro Pro Gly Ala Arg Ser
        115                 120                 125

TTG ACA CCA TGC ACC TGT GGC AGC TCA GAC CTT TAC TTG GTC ACG AGA        432
Leu Thr Pro Cys Thr Cys Gly Ser Ser Asp Leu Tyr Leu Val Thr Arg
    130                 135                 140

CAT GCT GAC GTC ATT CCG GTG CGC CGG CGG GGC GAC AGT AGG GGG AGC        480
His Ala Asp Val Ile Pro Val Arg Arg Arg Gly Asp Ser Arg Gly Ser
145                 150                 155                 160

CTG CTC TCC CCC AGG CCT GTC TCC TAC TTG AAG GGC TCT TCG GGT GGT        528
Leu Leu Ser Pro Arg Pro Val Ser Tyr Leu Lys Gly Ser Ser Gly Gly
                165                 170                 175

CCA CTG CTC TGC CCT TCG GGG CAC GCT GTG GGC ATC TTC CGG GCT GCC        576
Pro Leu Leu Cys Pro Ser Gly His Ala Val Gly Ile Phe Arg Ala Ala
            180                 185                 190

GTA TGC ACC CGG GGG GTT GCG AAG GCG GTG GAC TTT GTG CCC GTA GAG        624
Val Cys Thr Arg Gly Val Ala Lys Ala Val Asp Phe Val Pro Val Glu
        195                 200                 205

TCC ATG GAA ACT ACT ATG CGG TCT TGA                                    651
Ser Met Glu Thr Thr Met Arg Ser
    210                 215
```

(2) INFORMATION FOR SEQ ID NO:96:

(i) SEQUENCE CHARACTERISTICS:
　　　　(A) LENGTH: 651 base pairs
　　　　(B) TYPE: nucleic acid
　　　　(C) STRANDEDNESS: single
　　　　(D) TOPOLOGY: linear (ii) MOLECULE TYPE: cDNA (ix) FEATURE:
　　　　(A) NAME/KEY: CDS
　　　　(B) LOCATION: 1..651

(xi) SEQUENCE DESCRIPTION: SEQ ID NO:96:

```
ATG GGC AGC AGC CAT CAT CAT CAT CAT CAC AGC AGC GGC CTG GTG CCG        48
Met Gly Ser Ser His His His His His His Ser Ser Gly Leu Val Pro
 1               5                  10                  15

CGC GGC AGC CAT ATG GGT TCT GTT GTT ATT GTT GGT AGA ATT ATT TTA        96
Arg Gly Ser His Met Gly Ser Val Val Ile Val Gly Arg Ile Ile Leu
             20                  25                  30

TCT GGT AGT GGT AGT ATC ACG GCC TAC TCC CAA CAG ACG CGG GGC CTA       144
Ser Gly Ser Gly Ser Ile Thr Ala Tyr Ser Gln Gln Thr Arg Gly Leu
         35                  40                  45

CTT GGT TGC ATC ATC ACT AGC CTT ACA GGC CGG GAC AAG AAC CAG GTC       192
Leu Gly Cys Ile Ile Thr Ser Leu Thr Gly Arg Asp Lys Asn Gln Val
     50                  55                  60

GAG GGA GAG GTT CAG GTG GTT TCC ACC GCA ACA CAA TCC TTC CTG GCG       240
Glu Gly Glu Val Gln Val Val Ser Thr Ala Thr Gln Ser Phe Leu Ala
 65                  70                  75                  80

ACC TGC GTC AAC GGC GTG TGT TGG ACC GTT TAC CAT GGT GCT GGC TCA       288
Thr Cys Val Asn Gly Val Cys Trp Thr Val Tyr His Gly Ala Gly Ser
                 85                  90                  95

AAG ACC TTA GCC GGC CCA AAG GGG CCA ATC ACC CAG ATG TAC ACT AAT       336
Lys Thr Leu Ala Gly Pro Lys Gly Pro Ile Thr Gln Met Tyr Thr Asn
             100                 105                 110

GTG GAC CAG GAC CTC GTC GGC TGG CAG GCG CCC CCC GGG GCG CGT TCC       384
Val Asp Gln Asp Leu Val Gly Trp Gln Ala Pro Pro Gly Ala Arg Ser
         115                 120                 125

TTG ACA CCA TGC ACC TGT GGC AGC TCA GAC CTT TAC TTG GTC ACG AGA       432
Leu Thr Pro Cys Thr Cys Gly Ser Ser Asp Leu Tyr Leu Val Thr Arg
     130                 135                 140

CAT GCT GAC GTC ATT CCG GTG CGC CGG CGG GGC GAC AGT AGG GGG AGC       480
His Ala Asp Val Ile Pro Val Arg Arg Arg Gly Asp Ser Arg Gly Ser
145                 150                 155                 160

CTG CTC TCC CCC AGG CCT GTC TCC TAC TTG AAG GGC TCT GCT GGT GGT       528
Leu Leu Ser Pro Arg Pro Val Ser Tyr Leu Lys Gly Ser Ala Gly Gly
                 165                 170                 175

CCA CTG CTC TGC CCT TCG GGG CAC GCT GTG GGC ATC TTC CGG GCT GCC       576
Pro Leu Leu Cys Pro Ser Gly His Ala Val Gly Ile Phe Arg Ala Ala
             180                 185                 190

GTA TGC ACC CGG GGG GTT GCG AAG GCG GTG GAC TTT GTG CCC GTA GAG       624
Val Cys Thr Arg Gly Val Ala Lys Ala Val Asp Phe Val Pro Val Glu
         195                 200                 205

TCC ATG GAA ACT ACT ATG CGG TCT TGA                                   651
Ser Met Glu Thr Thr Met Arg Ser
     210                 215
```

(2) INFORMATION FOR SEQ ID NO:97:

(i) SEQUENCE CHARACTERISTICS:
　　　　(A) LENGTH: 651 base pairs
　　　　(B) TYPE: nucleic acid (C) STRANDEDNESS: single
            (D) TOPOLOGY: linear (ii) MOLECULE TYPE: cDNA (ix) FEATURE:
            (A) NAME/KEY: CDS
            (B) LOCATION: 1..651

(xi) SEQUENCE DESCRIPTION: SEQ ID NO:97:

```
ATG GGC AGC AGC CAT CAT CAT CAT CAT CAC AGC AGC GGC CTG GTG CCG        48
Met Gly Ser Ser His His His His His His Ser Ser Gly Leu Val Pro
 1               5                  10                  15

CGC GGC AGC CAT ATG GGT TCT GTT GTT ATT GTT GGT AGA ATT ATT TTA        96
Arg Gly Ser His Met Gly Ser Val Val Ile Val Gly Arg Ile Ile Leu
            20                  25                  30

TCT GGT AGT GGT AGT ATC ACG GCC TAC TCC CAA CAG ACG CGG GGC CTA       144
Ser Gly Ser Gly Ser Ile Thr Ala Tyr Ser Gln Gln Thr Arg Gly Leu
        35                  40                  45

CTT GGT TGC AAG ATC ACT AGC CTT ACA GGC CGG GAC AAG AAC CAG GTC       192
Leu Gly Cys Lys Ile Thr Ser Leu Thr Gly Arg Asp Lys Asn Gln Val
50                  55                  60

GAG GGA GAG GTT CAG GTG GTT TCC ACC GCA ACA CAA TCC TTC CTG GCG       240
Glu Gly Glu Val Gln Val Val Ser Thr Ala Thr Gln Ser Phe Leu Ala
 65                  70                  75                  80

ACC TGC GTC AAC GGC GTG TGT TGG ACC GTT TAC CAT GGT GCT GGC TCA       288
Thr Cys Val Asn Gly Val Cys Trp Thr Val Tyr His Gly Ala Gly Ser
                85                  90                  95

AAG ACC TTA GCC GGC CCA AAG GGG CCA ATC ACC CAG ATG TAC ACT AAT       336
Lys Thr Leu Ala Gly Pro Lys Gly Pro Ile Thr Gln Met Tyr Thr Asn
            100                 105                 110

GTG GAC CAG GAC CTC GTC GGC TGG CAG GCG CCC CCC GGG GCG CGT TCC       384
Val Asp Gln Asp Leu Val Gly Trp Gln Ala Pro Pro Gly Ala Arg Ser
        115                 120                 125

TTG ACA CCA TGC ACC TGT GGC AGC TCA GAC CTT TAC TTG GTC ACG AGA       432
Leu Thr Pro Cys Thr Cys Gly Ser Ser Asp Leu Tyr Leu Val Thr Arg
    130                 135                 140

CAT GCT GAC GTC ATT CCG GTG CGC CGG CGG GGC GAC AGT AGG GGG AGC       480
His Ala Asp Val Ile Pro Val Arg Arg Arg Gly Asp Ser Arg Gly Ser
145                 150                 155                 160

CTG CTC TCC CCC AGG CCT GTC TCC TAC TTG AAG GGC TCT GCT GGT GGT       528
Leu Leu Ser Pro Arg Pro Val Ser Tyr Leu Lys Gly Ser Ala Gly Gly
                165                 170                 175

CCA CTG CTC TGC CCT TCG GGG CAC GCT GTG GGC ATC TTC CGG GCT GCC       576
Pro Leu Leu Cys Pro Ser Gly His Ala Val Gly Ile Phe Arg Ala Ala
            180                 185                 190

GTA TGC ACC CGG GGG GTT GCG AAG GCG GTG GAC TTT GTG CCC GTA GAG       624
Val Cys Thr Arg Gly Val Ala Lys Ala Val Asp Phe Val Pro Val Glu
        195                 200                 205

TCC ATG GAA ACT ACT ATG CGG TCT TGA                                   651
Ser Met Glu Thr Thr Met Arg Ser
    210                 215
```

(2) INFORMATION FOR SEQ ID NO:98:

(i) SEQUENCE CHARACTERISTICS:
            (A) LENGTH: 651 base pairs
            (B) TYPE: nucleic acid
            (C) STRANDEDNESS: single
            (D) TOPOLOGY: linear (ii) MOLECULE TYPE: cDNA (ix) FEATURE:
    (A) NAME/KEY: CDS
    (B) LOCATION: 1..651

(xi) SEQUENCE DESCRIPTION: SEQ ID NO:98:

| | | | | | | | | | | | | | | | | |
|---|---|---|---|---|---|---|---|---|---|---|---|---|---|---|---|---|
| ATG | GGC | AGC | AGC | CAT | CAT | CAT | CAT | CAT | CAC | AGC | AGC | GGC | CTG | GTG | CCG | 48 |
| Met | Gly | Ser | Ser | His | His | His | His | His | His | Ser | Ser | Gly | Leu | Val | Pro | |
| 1 | | | | 5 | | | | | 10 | | | | | 15 | | |
| CGC | GGC | AGC | CAT | ATG | GGT | TCT | GTT | GTT | ATT | GTT | GGT | AGA | ATT | ATT | TTA | 96 |
| Arg | Gly | Ser | His | Met | Gly | Ser | Val | Val | Ile | Val | Gly | Arg | Ile | Ile | Leu | |
| | | | | 20 | | | | | 25 | | | | | 30 | | |
| TCT | GGT | AGT | GGT | AGT | ATC | ACG | GCC | TAC | TCC | CAA | CAG | ACG | CGG | GGC | CTA | 144 |
| Ser | Gly | Ser | Gly | Ser | Ile | Thr | Ala | Tyr | Ser | Gln | Gln | Thr | Arg | Gly | Leu | |
| | | | 35 | | | | | 40 | | | | | 45 | | | |
| CTT | GGT | TGC | ATC | AAG | ACT | AGC | CTT | ACA | GGC | CGG | GAC | AAG | AAC | CAG | GTC | 192 |
| Leu | Gly | Cys | Ile | Lys | Thr | Ser | Leu | Thr | Gly | Arg | Asp | Lys | Asn | Gln | Val | |
| | | 50 | | | | | 55 | | | | | 60 | | | | |
| GAG | GGA | GAG | GTT | CAG | GTG | GTT | TCC | ACC | GCA | ACA | CAA | TCC | TTC | CTG | GCG | 240 |
| Glu | Gly | Glu | Val | Gln | Val | Val | Ser | Thr | Ala | Thr | Gln | Ser | Phe | Leu | Ala | |
| 65 | | | | | 70 | | | | | 75 | | | | | 80 | |
| ACC | TGC | GTC | AAC | GGC | GTG | TGT | TGG | ACC | GTT | TAC | CAT | GGT | GCT | GGC | TCA | 288 |
| Thr | Cys | Val | Asn | Gly | Val | Cys | Trp | Thr | Val | Tyr | His | Gly | Ala | Gly | Ser | |
| | | | | 85 | | | | | 90 | | | | | 95 | | |
| AAG | ACC | TTA | GCC | GGC | CCA | AAG | GGG | CCA | ATC | ACC | CAG | ATG | TAC | ACT | AAT | 336 |
| Lys | Thr | Leu | Ala | Gly | Pro | Lys | Gly | Pro | Ile | Thr | Gln | Met | Tyr | Thr | Asn | |
| | | | | 100 | | | | | 105 | | | | | 110 | | |
| GTG | GAC | CAG | GAC | CTC | GTC | GGC | TGG | CAG | GCG | CCC | CCC | GGG | GCG | CGT | TCC | 384 |
| Val | Asp | Gln | Asp | Leu | Val | Gly | Trp | Gln | Ala | Pro | Pro | Gly | Ala | Arg | Ser | |
| | | | 115 | | | | | 120 | | | | | 125 | | | |
| TTG | ACA | CCA | TGC | ACC | TGT | GGC | AGC | TCA | GAC | CTT | TAC | TTG | GTC | ACG | AGA | 432 |
| Leu | Thr | Pro | Cys | Thr | Cys | Gly | Ser | Ser | Asp | Leu | Tyr | Leu | Val | Thr | Arg | |
| | | 130 | | | | | 135 | | | | | 140 | | | | |
| CAT | GCT | GAC | GTC | ATT | CCG | GTG | CGC | CGG | CGG | GGC | GAC | AGT | AGG | GGG | AGC | 480 |
| His | Ala | Asp | Val | Ile | Pro | Val | Arg | Arg | Arg | Gly | Asp | Ser | Arg | Gly | Ser | |
| 145 | | | | | 150 | | | | | 155 | | | | | 160 | |
| CTG | CTC | TCC | CCC | AGG | CCT | GTC | TCC | TAC | TTG | AAG | GGC | TCT | GCT | GGT | GGT | 528 |
| Leu | Leu | Ser | Pro | Arg | Pro | Val | Ser | Tyr | Leu | Lys | Gly | Ser | Ala | Gly | Gly | |
| | | | | 165 | | | | | 170 | | | | | 175 | | |
| CCA | CTG | CTC | TGC | CCT | TCG | GGG | CAC | GCT | GTG | GGC | ATC | TTC | CGG | GCT | GCC | 576 |
| Pro | Leu | Leu | Cys | Pro | Ser | Gly | His | Ala | Val | Gly | Ile | Phe | Arg | Ala | Ala | |
| | | | 180 | | | | | 185 | | | | | 190 | | | |
| GTA | TGC | ACC | CGG | GGG | GTT | GCG | AAG | GCG | GTG | GAC | TTT | GTG | CCC | GTA | GAG | 624 |
| Val | Cys | Thr | Arg | Gly | Val | Ala | Lys | Ala | Val | Asp | Phe | Val | Pro | Val | Glu | |
| | | 195 | | | | | 200 | | | | | 205 | | | | |
| TCC | ATG | GAA | ACT | ACT | ATG | CGG | TCT | TGA | | | | | | | | 651 |
| Ser | Met | Glu | Thr | Thr | Met | Arg | Ser | | | | | | | | | |
| | 210 | | | | 215 | | | | | | | | | | | |

(2) INFORMATION FOR SEQ ID NO:99:

(i) SEQUENCE CHARACTERISTICS:
        (A) LENGTH: 651 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..651

(xi) SEQUENCE DESCRIPTION: SEQ ID NO:99:

```
ATG GGC AGC AGC CAT CAT CAT CAT CAT CAC AGC AGC GGC CTG GTG CCG      48
Met Gly Ser Ser His His His His His His Ser Ser Gly Leu Val Pro
 1               5                  10                  15

CGC GGC AGC CAT ATG GGT TCT GTT GTT ATT GTT GGT AGA ATT ATT TTA      96
Arg Gly Ser His Met Gly Ser Val Val Ile Val Gly Arg Ile Ile Leu
                 20                  25                  30

TCT GGT AGT GGT AGT ATC ACG GCC TAC TCC CAA CAG ACG CGG GGC CTA     144
Ser Gly Ser Gly Ser Ile Thr Ala Tyr Ser Gln Gln Thr Arg Gly Leu
             35                  40                  45

CTT GGT TGC AAG AAG ACT AGC CTT ACA GGC CGG GAC AAG AAC CAG GTC     192
Leu Gly Cys Lys Lys Thr Ser Leu Thr Gly Arg Asp Lys Asn Gln Val
         50                  55                  60

GAG GGA GAG GTT CAG GTG GTT TCC ACC GCA ACA CAA TCC TTC CTG GCG     240
Glu Gly Glu Val Gln Val Val Ser Thr Ala Thr Gln Ser Phe Leu Ala
 65                  70                  75                  80

ACC TGC GTC AAC GGC GTG TGT TGG ACC GTT TAC CAT GGT GCT GGC TCA     288
Thr Cys Val Asn Gly Val Cys Trp Thr Val Tyr His Gly Ala Gly Ser
                 85                  90                  95

AAG ACC TTA GCC GGC CCA AAG GGG CCA ATC ACC CAG ATG TAC ACT AAT     336
Lys Thr Leu Ala Gly Pro Lys Gly Pro Ile Thr Gln Met Tyr Thr Asn
            100                 105                 110

GTG GAC CAG GAC CTC GTC GGC TGG CAG GCG CCC CCC GGG GCG CGT TCC     384
Val Asp Gln Asp Leu Val Gly Trp Gln Ala Pro Pro Gly Ala Arg Ser
        115                 120                 125

TTG ACA CCA TGC ACC TGT GGC AGC TCA GAC CTT TAC TTG GTC ACG AGA     432
Leu Thr Pro Cys Thr Cys Gly Ser Ser Asp Leu Tyr Leu Val Thr Arg
    130                 135                 140

CAT GCT GAC GTC ATT CCG GTG CGC CGG CGG GGC GAC AGT AGG GGG AGC     480
His Ala Asp Val Ile Pro Val Arg Arg Arg Gly Asp Ser Arg Gly Ser
145                 150                 155                 160

CTG CTC TCC CCC AGG CCT GTC TCC TAC TTG AAG GGC TCT GCT GGT GGT     528
Leu Leu Ser Pro Arg Pro Val Ser Tyr Leu Lys Gly Ser Ala Gly Gly
                165                 170                 175

CCA CTG CTC TGC CCT TCG GGG CAC GCT GTG GGC ATC TTC CGG GCT GCC     576
Pro Leu Leu Cys Pro Ser Gly His Ala Val Gly Ile Phe Arg Ala Ala
            180                 185                 190

GTA TGC ACC CGG GGG GTT GCG AAG GCG GTG GAC TTT GTG CCC GTA GAG     624
Val Cys Thr Arg Gly Val Ala Lys Ala Val Asp Phe Val Pro Val Glu
        195                 200                 205

TCC ATG GAA ACT ACT ATG CGG TCT TGA                                 651
Ser Met Glu Thr Thr Met Arg Ser
    210                 215
```

(2) INFORMATION FOR SEQ ID NO:100:

(i) SEQUENCE CHARACTERISTICS:
        (A) LENGTH: 651 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..651

(xi) SEQUENCE DESCRIPTION: SEQ ID NO:100:

```
ATG GGC AGC AGC CAT CAT CAT CAT CAT CAC AGC AGC GGC CTG GTG CCG      48
Met Gly Ser Ser His His His His His His Ser Ser Gly Leu Val Pro
 1               5                  10                  15
```

```
CGC GGC AGC CAT ATG GGT TCT GTT GTT ATT GTT GGT AGA ATT ATT TTA        96
Arg Gly Ser His Met Gly Ser Val Val Ile Val Gly Arg Ile Ile Leu
             20                  25                  30

TCT CCT GCT GGT GGT ATC ACG GCC TAC TCC CAA CAG ACG CGG GGC CTA       144
Ser Pro Ala Gly Gly Ile Thr Ala Tyr Ser Gln Gln Thr Arg Gly Leu
         35                  40                  45

CTT GGT TGC ATC ATC ACT AGC CTT ACA GGC CGG GAC AAG AAC CAG GTC       192
Leu Gly Cys Ile Ile Thr Ser Leu Thr Gly Arg Asp Lys Asn Gln Val
 50                  55                  60

GAG GGA GAG GTT CAG GTG GTT TCC ACC GCA ACA CAA TCC TTC CTG GCG       240
Glu Gly Glu Val Gln Val Val Ser Thr Ala Thr Gln Ser Phe Leu Ala
 65                  70                  75                  80

ACC TGC GTC AAC GGC GTG TGT TGG ACC GTT TAC CAT GGT GCT GGC TCA       288
Thr Cys Val Asn Gly Val Cys Trp Thr Val Tyr His Gly Ala Gly Ser
             85                  90                  95

AAG ACC TTA GCC GGC CCA AAG GGG CCA ATC ACC CAG ATG TAC ACT AAT       336
Lys Thr Leu Ala Gly Pro Lys Gly Pro Ile Thr Gln Met Tyr Thr Asn
        100                 105                 110

GTG GAC CAG GAC CTC GTC GGC TGG CAG GCG CCC CCC GGG GCG CGT TCC       384
Val Asp Gln Asp Leu Val Gly Trp Gln Ala Pro Pro Gly Ala Arg Ser
        115                 120                 125

TTG ACA CCA TGC ACC TGT GGC AGC TCA GAC CTT TAC TTG GTC ACG AGA       432
Leu Thr Pro Cys Thr Cys Gly Ser Ser Asp Leu Tyr Leu Val Thr Arg
130                 135                 140

CAT GCT GAC GTC ATT CCG GTG CGC CGG CGG GGC GAC AGT AGG GGG AGC       480
His Ala Asp Val Ile Pro Val Arg Arg Arg Gly Asp Ser Arg Gly Ser
145                 150                 155                 160

CTG CTC TCC CCC AGG CCT GTC TCC TAC TTG AAG GGC TCT TCG GGT GGT       528
Leu Leu Ser Pro Arg Pro Val Ser Tyr Leu Lys Gly Ser Ser Gly Gly
                165                 170                 175

CCA CTG CTC TGC CCT TCG GGG CAC GCT GTG GGC ATC TTC CGG GCT GCC       576
Pro Leu Leu Cys Pro Ser Gly His Ala Val Gly Ile Phe Arg Ala Ala
            180                 185                 190

GTA TGC ACC CGG GGG GTT GCG AAG GCG GTG GAC TTT GTG CCC GTA GAG       624
Val Cys Thr Arg Gly Val Ala Lys Ala Val Asp Phe Val Pro Val Glu
        195                 200                 205

TCC ATG GAA ACT ACT ATG CGG TCT TGA                                    651
Ser Met Glu Thr Thr Met Arg Ser
210                 215

(2) INFORMATION FOR SEQ ID NO:101:

(i) SEQUENCE CHARACTERISTICS:
        (A) LENGTH: 651 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..651

(xi) SEQUENCE DESCRIPTION: SEQ ID NO:101:

ATG GGC AGC AGC CAT CAT CAT CAT CAT CAC AGC AGC GGC CTG GTG CCG        48
Met Gly Ser Ser His His His His His His Ser Ser Gly Leu Val Pro
 1               5                  10                  15

CGC GGC AGC CAT ATG GGT TCT GTT GTT ATT GTT GGT AGA ATT ATT TTA        96
Arg Gly Ser His Met Gly Ser Val Val Ile Val Gly Arg Ile Ile Leu
             20                  25                  30
```

```
TCT CCT GCT GGT GGT ATC ACG GCC TAC TCC CAA CAG ACG CGG GGC CTA      144
Ser Pro Ala Gly Gly Ile Thr Ala Tyr Ser Gln Gln Thr Arg Gly Leu
        35                  40                  45

CTT GGT TGC AAG ATC ACT AGC CTT ACA GGC CGG GAC AAG AAC CAG GTC      192
Leu Gly Cys Lys Ile Thr Ser Leu Thr Gly Arg Asp Lys Asn Gln Val
 50                  55                  60

GAG GGA GAG GTT CAG GTG GTT TCC ACC GCA ACA CAA TCC TTC CTG GCG      240
Glu Gly Glu Val Gln Val Val Ser Thr Ala Thr Gln Ser Phe Leu Ala
 65                  70                  75                  80

ACC TGC GTC AAC GGC GTG TGT TGG ACC GTT TAC CAT GGT GCT GGC TCA      288
Thr Cys Val Asn Gly Val Cys Trp Thr Val Tyr His Gly Ala Gly Ser
                 85                  90                  95

AAG ACC TTA GCC GGC CCA AAG GGG CCA ATC ACC CAG ATG TAC ACT AAT      336
Lys Thr Leu Ala Gly Pro Lys Gly Pro Ile Thr Gln Met Tyr Thr Asn
            100                 105                 110

GTG GAC CAG GAC CTC GTC GGC TGG CAG GCG CCC CCC GGG GCG CGT TCC      384
Val Asp Gln Asp Leu Val Gly Trp Gln Ala Pro Pro Gly Ala Arg Ser
            115                 120                 125

TTG ACA CCA TGC ACC TGT GGC AGC TCA GAC CTT TAC TTG GTC ACG AGA      432
Leu Thr Pro Cys Thr Cys Gly Ser Ser Asp Leu Tyr Leu Val Thr Arg
    130                 135                 140

CAT GCT GAC GTC ATT CCG GTG CGC CGG CGG GGC GAC AGT AGG GGG AGC      480
His Ala Asp Val Ile Pro Val Arg Arg Arg Gly Asp Ser Arg Gly Ser
145                 150                 155                 160

CTG CTC TCC CCC AGG CCT GTC TCC TAC TTG AAG GGC TCT TCG GGT GGT      528
Leu Leu Ser Pro Arg Pro Val Ser Tyr Leu Lys Gly Ser Ser Gly Gly
                165                 170                 175

CCA CTG CTC TGC CCT TCG GGG CAC GCT GTG GGC ATC TTC CGG GCT GCC      576
Pro Leu Leu Cys Pro Ser Gly His Ala Val Gly Ile Phe Arg Ala Ala
            180                 185                 190

GTA TGC ACC CGG GGG GTT GCG AAG GCG GTG GAC TTT GTG CCC GTA GAG      624
Val Cys Thr Arg Gly Val Ala Lys Ala Val Asp Phe Val Pro Val Glu
            195                 200                 205

TCC ATG GAA ACT ACT ATG CGG TCT TGA                                  651
Ser Met Glu Thr Thr Met Arg Ser
    210                 215

(2) INFORMATION FOR SEQ ID NO:102:

(i) SEQUENCE CHARACTERISTICS:
        (A) LENGTH: 1998 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..1998

(xi) SEQUENCE DESCRIPTION: SEQ ID NO:102:

ATG GGC AGC AGC CAT CAT CAT CAT CAT CAC AGC AGC GGC CTG GTG CCG       48
Met Gly Ser Ser His His His His His His Ser Ser Gly Leu Val Pro
  1               5                  10                  15

CGC GGC AGC CAT ATG GGT TCT GTT GTT ATT GTT GGT AGA ATT ATT TTA       96
Arg Gly Ser His Met Gly Ser Val Val Ile Val Gly Arg Ile Ile Leu
             20                  25                  30

TCT GGT AGT GGT AGT ATC ACG GCC TAC TCC CAA CAG ACG CGG GGC CTA      144
Ser Gly Ser Gly Ser Ile Thr Ala Tyr Ser Gln Gln Thr Arg Gly Leu
        35                  40                  45
```

-continued

```
CTT GGT TGC ATC ATC ACT AGC CTT ACA GGC CGG GAC AAG AAC CAG GTC       192
Leu Gly Cys Ile Ile Thr Ser Leu Thr Gly Arg Asp Lys Asn Gln Val
     50                  55                  60

GAG GGA GAG GTT CAG GTG GTT TCC ACC GCA ACA CAA TCC TTC CTG GCG       240
Glu Gly Glu Val Gln Val Val Ser Thr Ala Thr Gln Ser Phe Leu Ala
 65                  70                  75                  80

ACC TGC GTC AAC GGC GTG TGT TGG ACC GTT TAC CAT GGT GCT GGC TCA       288
Thr Cys Val Asn Gly Val Cys Trp Thr Val Tyr His Gly Ala Gly Ser
                     85                  90                  95

AAG ACC TTA GCC GGC CCA AAG GGG CCA ATC ACC CAG ATG TAC ACT AAT       336
Lys Thr Leu Ala Gly Pro Lys Gly Pro Ile Thr Gln Met Tyr Thr Asn
                100                 105                 110

GTG GAC CAG GAC CTC GTC GGC TGG CAG GCG CCC CCC GGG GCG CGT TCC       384
Val Asp Gln Asp Leu Val Gly Trp Gln Ala Pro Pro Gly Ala Arg Ser
            115                 120                 125

TTG ACA CCA TGC ACC TGT GGC AGC TCA GAC CTT TAC TTG GTC ACG AGA       432
Leu Thr Pro Cys Thr Cys Gly Ser Ser Asp Leu Tyr Leu Val Thr Arg
        130                 135                 140

CAT GCT GAC GTC ATT CCG GTG CGC CGG CGG GGC GAC AGT AGG GGG AGC       480
His Ala Asp Val Ile Pro Val Arg Arg Arg Gly Asp Ser Arg Gly Ser
145                 150                 155                 160

CTG CTC TCC CCC AGG CCT GTC TCC TAC TTG AAG GGC TCT TCG GGT GGT       528
Leu Leu Ser Pro Arg Pro Val Ser Tyr Leu Lys Gly Ser Ser Gly Gly
                165                 170                 175

CCA CTG CTC TGC CCT TCG GGG CAC GCT GTG GGC ATC TTC CGG GCT GCC       576
Pro Leu Leu Cys Pro Ser Gly His Ala Val Gly Ile Phe Arg Ala Ala
            180                 185                 190

GTA TGC ACC CGG GGG GTT GCG AAG GCG GTG GAC TTT GTG CCC GTA GAG       624
Val Cys Thr Arg Gly Val Ala Lys Ala Val Asp Phe Val Pro Val Glu
        195                 200                 205

TCC ATG GAA ACT ACT ATG CGG TCT CCG GTC TTC ACG GAC AAC TCA TCC       672
Ser Met Glu Thr Thr Met Arg Ser Pro Val Phe Thr Asp Asn Ser Ser
210                 215                 220

CCC CCG GCC GTA CCG CAG TCA TTT CAA GTG GCC CAC CTA CAC GCT CCC       720
Pro Pro Ala Val Pro Gln Ser Phe Gln Val Ala His Leu His Ala Pro
225                 230                 235                 240

ACT GGC AGC GGC AAG AGT ACT AAA GTG CCG GCT GCA TAT GCA GCC CAA       768
Thr Gly Ser Gly Lys Ser Thr Lys Val Pro Ala Ala Tyr Ala Ala Gln
                245                 250                 255

GGG TAC AAG GTG CTC GTC CTC AAT CCG TCC GTT GCC GCT ACC TTA GGG       816
Gly Tyr Lys Val Leu Val Leu Asn Pro Ser Val Ala Ala Thr Leu Gly
            260                 265                 270

TTT GGG GCG TAT ATG TCT AAG GCA CAC GGT ATT GAC CCC AAC ATC AGA       864
Phe Gly Ala Tyr Met Ser Lys Ala His Gly Ile Asp Pro Asn Ile Arg
        275                 280                 285

ACT GGG GTA AGG ACC ATT ACC ACA GGC GCC CCC GTC ACA TAC TCT ACC       912
Thr Gly Val Arg Thr Ile Thr Thr Gly Ala Pro Val Thr Tyr Ser Thr
    290                 295                 300

TAT GGC AAG TTT CTT GCC GAT GGT GGT TGC TCT GGG GGC GCT TAT GAC       960
Tyr Gly Lys Phe Leu Ala Asp Gly Gly Cys Ser Gly Gly Ala Tyr Asp
305                 310                 315                 320

ATC ATA ATA TGT GAT GAG TGC CAT TCA ACT GAC TCG ACT ACA ATC TTG      1008
Ile Ile Ile Cys Asp Glu Cys His Ser Thr Asp Ser Thr Thr Ile Leu
                325                 330                 335

GGC ATC GGC ACA GTC CTG GAC CAA GCG GAG ACG GCT GGA GCG CGG CTT      1056
Gly Ile Gly Thr Val Leu Asp Gln Ala Glu Thr Ala Gly Ala Arg Leu
            340                 345                 350

GTC GTG CTC GCC ACC GCT ACG CCT CCG GGA TCG GTC ACC GTG CCA CAC      1104
Val Val Leu Ala Thr Ala Thr Pro Pro Gly Ser Val Thr Val Pro His
        355                 360                 365
```

```
CCA AAC ATC GAG GAG GTG GCC CTG TCT AAT ACT GGA GAG ATC CCC TTC       1152
Pro Asn Ile Glu Glu Val Ala Leu Ser Asn Thr Gly Glu Ile Pro Phe
    370                 375                 380

TAT GGC AAA GCC ATC CCC ATT GAA GCC ATC AGG GGG GGA AGG CAT CTC       1200
Tyr Gly Lys Ala Ile Pro Ile Glu Ala Ile Arg Gly Gly Arg His Leu
385                 390                 395                 400

ATT TTC TGT CAT TCC AAG AAG AAG TGC GAC GAG CTC GCC GCA AAG CTG       1248
Ile Phe Cys His Ser Lys Lys Lys Cys Asp Glu Leu Ala Ala Lys Leu
                405                 410                 415

TCA GGC CTC GGA ATC AAC GCT GTG GCG TAT TAC CGG GGG CTC GAT GTG       1296
Ser Gly Leu Gly Ile Asn Ala Val Ala Tyr Tyr Arg Gly Leu Asp Val
            420                 425                 430

TCC GTC ATA CCA ACT ATC GGA GAC GTC GTT GTC GTG GCA ACA GAC GCT       1344
Ser Val Ile Pro Thr Ile Gly Asp Val Val Val Val Ala Thr Asp Ala
            435                 440                 445

CTG ATG ACG GGC TAT ACG GGC GAC TTT GAC TCA GTG ATC GAC TGT AAC       1392
Leu Met Thr Gly Tyr Thr Gly Asp Phe Asp Ser Val Ile Asp Cys Asn
    450                 455                 460

ACA TGT GTC ACC CAG ACA GTC GAC TTC AGC TTG GAT CCC ACC TTC ACC       1440
Thr Cys Val Thr Gln Thr Val Asp Phe Ser Leu Asp Pro Thr Phe Thr
465                 470                 475                 480

ATT GAG ACG ACG ACC GTG CCT CAA GAC GCA GTG TCG CGC TCG CAG CGG       1488
Ile Glu Thr Thr Thr Val Pro Gln Asp Ala Val Ser Arg Ser Gln Arg
                485                 490                 495

CGG GGT AGG ACT GGC AGG GGT AGG AGA GGC ATC TAC AGG TTT GTG ACT       1536
Arg Gly Arg Thr Gly Arg Gly Arg Arg Gly Ile Tyr Arg Phe Val Thr
            500                 505                 510

CCG GGA GAA CGG CCC TCG GGC ATG TTC GAT TCC TCG GTC CTG TGT GAG       1584
Pro Gly Glu Arg Pro Ser Gly Met Phe Asp Ser Ser Val Leu Cys Glu
            515                 520                 525

TGC TAT GAC GCG GGC TGT GCT TGG TAC GAG CTC ACC CCC GCC GAG ACC       1632
Cys Tyr Asp Ala Gly Cys Ala Trp Tyr Glu Leu Thr Pro Ala Glu Thr
    530                 535                 540

TCG GTT AGG TTG CGG GCC TAC CTG AAC ACA CCA GGG TTG CCC GTT TGC       1680
Ser Val Arg Leu Arg Ala Tyr Leu Asn Thr Pro Gly Leu Pro Val Cys
545                 550                 555                 560

CAG GAC CAC CTG GAG TTC TGG GAG AGT GTC TTC ACA GGC CTC ACC CAT       1728
Gln Asp His Leu Glu Phe Trp Glu Ser Val Phe Thr Gly Leu Thr His
                565                 570                 575

ATA GAT GCA CAC TTC TTG TCC CAG ACC AAG CAG GCA GGA GAC AAC TTC       1776
Ile Asp Ala His Phe Leu Ser Gln Thr Lys Gln Ala Gly Asp Asn Phe
            580                 585                 590

CCC TAC CTG GTA GCA TAC CAA GCC ACG GTG TGC GCC AGG GCT CAG GCC       1824
Pro Tyr Leu Val Ala Tyr Gln Ala Thr Val Cys Ala Arg Ala Gln Ala
            595                 600                 605

CCA CCT CCA TCA TGG GAT CAA ATG TGG AAG TGT CTC ATA CGG CTG AAA       1872
Pro Pro Pro Ser Trp Asp Gln Met Trp Lys Cys Leu Ile Arg Leu Lys
    610                 615                 620

CCT ACG CTG CAC GGG CCA ACA CCC TTG CTG TAC AGG CTG GGA GCC GTC       1920
Pro Thr Leu His Gly Pro Thr Pro Leu Leu Tyr Arg Leu Gly Ala Val
625                 630                 635                 640

CAA AAT GAG GTC ACC CTC ACC CAC CCC ATA ACC AAA TAC ATC ATG GCA       1968
Gln Asn Glu Val Thr Leu Thr His Pro Ile Thr Lys Tyr Ile Met Ala
                645                 650                 655

TGC ATG TCG GCT GAC CTG GAG GTC GTC ACT                               1998
Cys Met Ser Ala Asp Leu Glu Val Val Thr
            660                 665
```

(2) INFORMATION FOR SEQ ID NO:103:

(i) SEQUENCE CHARACTERISTICS:
        (A) LENGTH: 1998 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..1998

(xi) SEQUENCE DESCRIPTION: SEQ ID NO:103:

```
ATG GGC AGC AGC CAT CAT CAT CAT CAC AGC AGC GGC CTG GTG CCG        48
Met Gly Ser Ser His His His His His Ser Ser Gly Leu Val Pro
 1               5                  10                  15

CGC GGC AGC CAT ATG GGT TCT GTT GTT ATT GTT GGT AGA ATT ATT TTA    96
Arg Gly Ser His Met Gly Ser Val Val Ile Val Gly Arg Ile Ile Leu
             20                  25                  30

TCT GGT AGT GGT AGT ATC ACG GCC TAC TCC CAA CAG ACG CGG GGC CTA   144
Ser Gly Ser Gly Ser Ile Thr Ala Tyr Ser Gln Gln Thr Arg Gly Leu
         35                  40                  45

CTT GGT TGC AAG ATC ACT AGC CTT ACA GGC CGG GAC AAG AAC CAG GTC   192
Leu Gly Cys Lys Ile Thr Ser Leu Thr Gly Arg Asp Lys Asn Gln Val
 50                  55                  60

GAG GGA GAG GTT CAG GTG GTT TCC ACC GCA ACA CAA TCC TTC CTG GCG   240
Glu Gly Glu Val Gln Val Val Ser Thr Ala Thr Gln Ser Phe Leu Ala
 65                  70                  75                  80

ACC TGC GTC AAC GGC GTG TGT TGG ACC GTT TAC CAT GGT GCT GGC TCA   288
Thr Cys Val Asn Gly Val Cys Trp Thr Val Tyr His Gly Ala Gly Ser
                 85                  90                  95

AAG ACC TTA GCC GGC CCA AAG GGG CCA ATC ACC CAG ATG TAC ACT AAT   336
Lys Thr Leu Ala Gly Pro Lys Gly Pro Ile Thr Gln Met Tyr Thr Asn
            100                 105                 110

GTG GAC CAG GAC CTC GTC GGC TGG CAG GCG CCC CCC GGG GCG CGT TCC   384
Val Asp Gln Asp Leu Val Gly Trp Gln Ala Pro Pro Gly Ala Arg Ser
        115                 120                 125

TTG ACA CCA TGC ACC TGT GGC AGC TCA GAC CTT TAC TTG GTC ACG AGA   432
Leu Thr Pro Cys Thr Cys Gly Ser Ser Asp Leu Tyr Leu Val Thr Arg
    130                 135                 140

CAT GCT GAC GTC ATT CCG GTG CGC CGG CGG GGC GAC AGT AGG GGG AGC   480
His Ala Asp Val Ile Pro Val Arg Arg Arg Gly Asp Ser Arg Gly Ser
145                 150                 155                 160

CTG CTC TCC CCC AGG CCT GTC TCC TAC TTG AAG GGC TCT TCG GGT GGT   528
Leu Leu Ser Pro Arg Pro Val Ser Tyr Leu Lys Gly Ser Ser Gly Gly
                165                 170                 175

CCA CTG CTC TGC CCT TCG GGG CAC GCT GTG GGC ATC TTC CGG GCT GCC   576
Pro Leu Leu Cys Pro Ser Gly His Ala Val Gly Ile Phe Arg Ala Ala
            180                 185                 190

GTA TGC ACC CGG GGG GTT GCG AAG GCG GTG GAC TTT GTG CCC GTA GAG   624
Val Cys Thr Arg Gly Val Ala Lys Ala Val Asp Phe Val Pro Val Glu
        195                 200                 205

TCC ATG GAA ACT ACT ATG CGG TCT CCG GTC TTC ACG GAC AAC TCA TCC   672
Ser Met Glu Thr Thr Met Arg Ser Pro Val Phe Thr Asp Asn Ser Ser
    210                 215                 220

CCC CCG GCC GTA CCG CAG TCA TTT CAA GTG GCC CAC CTA CAC GCT CCC   720
Pro Pro Ala Val Pro Gln Ser Phe Gln Val Ala His Leu His Ala Pro
225                 230                 235                 240

ACT GGC AGC GGC AAG AGT ACT AAA GTG CCG GCT GCA TAT GCA GCC CAA   768
Thr Gly Ser Gly Lys Ser Thr Lys Val Pro Ala Ala Tyr Ala Ala Gln
                245                 250                 255
```

```
GGG TAC AAG GTG CTC GTC CTC AAT CCG TCC GTT GCC GCT ACC TTA GGG      816
Gly Tyr Lys Val Leu Val Leu Asn Pro Ser Val Ala Ala Thr Leu Gly
            260                 265                 270

TTT GGG GCG TAT ATG TCT AAG GCA CAC GGT ATT GAC CCC AAC ATC AGA      864
Phe Gly Ala Tyr Met Ser Lys Ala His Gly Ile Asp Pro Asn Ile Arg
            275                 280                 285

ACT GGG GTA AGG ACC ATT ACC ACA GGC GCC CCC GTC ACA TAC TCT ACC      912
Thr Gly Val Arg Thr Ile Thr Thr Gly Ala Pro Val Thr Tyr Ser Thr
290                 295                 300

TAT GGC AAG TTT CTT GCC GAT GGT GGT TGC TCT GGG GGC GCT TAT GAC      960
Tyr Gly Lys Phe Leu Ala Asp Gly Gly Cys Ser Gly Gly Ala Tyr Asp
305                 310                 315                 320

ATC ATA ATA TGT GAT GAG TGC CAT TCA ACT GAC TCG ACT ACA ATC TTG     1008
Ile Ile Ile Cys Asp Glu Cys His Ser Thr Asp Ser Thr Thr Ile Leu
                325                 330                 335

GGC ATC GGC ACA GTC CTG GAC CAA GCG GAG ACG GCT GGA GCG CGG CTT     1056
Gly Ile Gly Thr Val Leu Asp Gln Ala Glu Thr Ala Gly Ala Arg Leu
            340                 345                 350

GTC GTG CTC GCC ACC GCT ACG CCT CCG GGA TCG GTC ACC GTG CCA CAC     1104
Val Val Leu Ala Thr Ala Thr Pro Pro Gly Ser Val Thr Val Pro His
            355                 360                 365

CCA AAC ATC GAG GAG GTG GCC CTG TCT AAT ACT GGA GAG ATC CCC TTC     1152
Pro Asn Ile Glu Glu Val Ala Leu Ser Asn Thr Gly Glu Ile Pro Phe
370                 375                 380

TAT GGC AAA GCC ATC CCC ATT GAA GCC ATC AGG GGG GGA AGG CAT CTC     1200
Tyr Gly Lys Ala Ile Pro Ile Glu Ala Ile Arg Gly Gly Arg His Leu
385                 390                 395                 400

ATT TTC TGT CAT TCC AAG AAG AAG TGC GAC GAG CTC GCC GCA AAG CTG     1248
Ile Phe Cys His Ser Lys Lys Lys Cys Asp Glu Leu Ala Ala Lys Leu
                405                 410                 415

TCA GGC CTC GGA ATC AAC GCT GTG GCG TAT TAC CGG GGG CTC GAT GTG     1296
Ser Gly Leu Gly Ile Asn Ala Val Ala Tyr Tyr Arg Gly Leu Asp Val
            420                 425                 430

TCC GTC ATA CCA ACT ATC GGA GAC GTC GTT GTC GTG GCA ACA GAC GCT     1344
Ser Val Ile Pro Thr Ile Gly Asp Val Val Val Val Ala Thr Asp Ala
            435                 440                 445

CTG ATG ACG GGC TAT ACG GGC GAC TTT GAC TCA GTG ATC GAC TGT AAC     1392
Leu Met Thr Gly Tyr Thr Gly Asp Phe Asp Ser Val Ile Asp Cys Asn
450                 455                 460

ACA TGT GTC ACC CAG ACA GTC GAC TTC AGC TTG GAT CCC ACC TTC ACC     1440
Thr Cys Val Thr Gln Thr Val Asp Phe Ser Leu Asp Pro Thr Phe Thr
465                 470                 475                 480

ATT GAG ACG ACG ACC GTG CCT CAA GAC GCA GTG TCG CGC TCG CAG CGG     1488
Ile Glu Thr Thr Thr Val Pro Gln Asp Ala Val Ser Arg Ser Gln Arg
                485                 490                 495

CGG GGT AGG ACT GGC AGG GGT AGG AGA GGC ATC TAC AGG TTT GTG ACT     1536
Arg Gly Arg Thr Gly Arg Gly Arg Arg Gly Ile Tyr Arg Phe Val Thr
            500                 505                 510

CCG GGA GAA CGG CCC TCG GGC ATG TTC GAT TCC TCG GTC CTG TGT GAG     1584
Pro Gly Glu Arg Pro Ser Gly Met Phe Asp Ser Ser Val Leu Cys Glu
            515                 520                 525

TGC TAT GAC GCG GGC TGT GCT TGG TAC GAG CTC ACC CCC GCC GAG ACC     1632
Cys Tyr Asp Ala Gly Cys Ala Trp Tyr Glu Leu Thr Pro Ala Glu Thr
530                 535                 540

TCG GTT AGG TTG CGG GCC TAC CTG AAC ACA CCA GGG TTG CCC GTT TGC     1680
Ser Val Arg Leu Arg Ala Tyr Leu Asn Thr Pro Gly Leu Pro Val Cys
545                 550                 555                 560

CAG GAC CAC CTG GAG TTC TGG GAG AGT GTC TTC ACA GGC CTC ACC CAT     1728
Gln Asp His Leu Glu Phe Trp Glu Ser Val Phe Thr Gly Leu Thr His
                565                 570                 575
```

```
ATA GAT GCA CAC TTC TTG TCC CAG ACC AAG CAG GCA GGA GAC AAC TTC      1776
Ile Asp Ala His Phe Leu Ser Gln Thr Lys Gln Ala Gly Asp Asn Phe
        580                 585                 590

CCC TAC CTG GTA GCA TAC CAA GCC ACG GTG TGC GCC AGG GCT CAG GCC      1824
Pro Tyr Leu Val Ala Tyr Gln Ala Thr Val Cys Ala Arg Ala Gln Ala
            595                 600                 605

CCA CCT CCA TCA TGG GAT CAA ATG TGG AAG TGT CTC ATA CGG CTG AAA      1872
Pro Pro Pro Ser Trp Asp Gln Met Trp Lys Cys Leu Ile Arg Leu Lys
        610                 615                 620

CCT ACG CTG CAC GGG CCA ACA CCC TTG CTG TAC AGG CTG GGA GCC GTC      1920
Pro Thr Leu His Gly Pro Thr Pro Leu Leu Tyr Arg Leu Gly Ala Val
625                 630                 635                 640

CAA AAT GAG GTC ACC CTC ACC CAC CCC ATA ACC AAA TAC ATC ATG GCA      1968
Gln Asn Glu Val Thr Leu Thr His Pro Ile Thr Lys Tyr Ile Met Ala
            645                 650                 655

TGC ATG TCG GCT GAC CTG GAG GTC GTC ACT                              1998
Cys Met Ser Ala Asp Leu Glu Val Val Thr
        660                 665

(2) INFORMATION FOR SEQ ID NO:104:

(i) SEQUENCE CHARACTERISTICS:
        (A) LENGTH: 1998 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..1998

(xi) SEQUENCE DESCRIPTION: SEQ ID NO:104:

ATG GGC AGC AGC CAT CAT CAT CAT CAT CAC AGC AGC GGC CTG GTG CCG        48
Met Gly Ser Ser His His His His His His Ser Ser Gly Leu Val Pro
1               5                   10                  15

CGC GGC AGC CAT ATG GGT TCT GTT GTT ATT GTT GGT AGA ATT ATT TTA       96
Arg Gly Ser His Met Gly Ser Val Val Ile Val Gly Arg Ile Ile Leu
            20                  25                  30

TCT GGT AGT GGT AGT ATC ACG GCC TAC TCC CAA CAG ACG CGG GGC CTA      144
Ser Gly Ser Gly Ser Ile Thr Ala Tyr Ser Gln Gln Thr Arg Gly Leu
        35                  40                  45

CTT GGT TGC ATC AAG ACT AGC CTT ACA GGC CGG GAC AAG AAC CAG GTC      192
Leu Gly Cys Ile Lys Thr Ser Leu Thr Gly Arg Asp Lys Asn Gln Val
    50                  55                  60

GAG GGA GAG GTT CAG GTG GTT TCC ACC GCA ACA CAA TCC TTC CTG GCG      240
Glu Gly Glu Val Gln Val Val Ser Thr Ala Thr Gln Ser Phe Leu Ala
65                  70                  75                  80

ACC TGC GTC AAC GGC GTG TGT TGG ACC GTT TAC CAT GGT GCT GGC TCA      288
Thr Cys Val Asn Gly Val Cys Trp Thr Val Tyr His Gly Ala Gly Ser
            85                  90                  95

AAG ACC TTA GCC GGC CCA AAG GGG CCA ATC ACC CAG ATG TAC ACT AAT      336
Lys Thr Leu Ala Gly Pro Lys Gly Pro Ile Thr Gln Met Tyr Thr Asn
        100                 105                 110

GTG GAC CAG GAC CTC GTC GGC TGG CAG GCG CCC CCC GGG GCG CGT TCC      384
Val Asp Gln Asp Leu Val Gly Trp Gln Ala Pro Pro Gly Ala Arg Ser
            115                 120                 125

TTG ACA CCA TGC ACC TGT GGC AGC TCA GAC CTT TAC TTG GTC ACG AGA      432
Leu Thr Pro Cys Thr Cys Gly Ser Ser Asp Leu Tyr Leu Val Thr Arg
        130                 135                 140
```

```
CAT GCT GAC GTC ATT CCG GTG CGC CGG CGG GGC GAC AGT AGG GGG AGC        480
His Ala Asp Val Ile Pro Val Arg Arg Arg Gly Asp Ser Arg Gly Ser
145                 150                 155                 160

CTG CTC TCC CCC AGG CCT GTC TCC TAC TTG AAG GGC TCT TCG GGT GGT        528
Leu Leu Ser Pro Arg Pro Val Ser Tyr Leu Lys Gly Ser Ser Gly Gly
                165                 170                 175

CCA CTG CTC TGC CCT TCG GGG CAC GCT GTG GGC ATC TTC CGG GCT GCC        576
Pro Leu Leu Cys Pro Ser Gly His Ala Val Gly Ile Phe Arg Ala Ala
            180                 185                 190

GTA TGC ACC CGG GGG GTT GCG AAG GCG GTG GAC TTT GTG CCC GTA GAG        624
Val Cys Thr Arg Gly Val Ala Lys Ala Val Asp Phe Val Pro Val Glu
        195                 200                 205

TCC ATG GAA ACT ACT ATG CGG TCT CCG GTC TTC ACG GAC AAC TCA TCC        672
Ser Met Glu Thr Thr Met Arg Ser Pro Val Phe Thr Asp Asn Ser Ser
    210                 215                 220

CCC CCG GCC GTA CCG CAG TCA TTT CAA GTG GCC CAC CTA CAC GCT CCC        720
Pro Pro Ala Val Pro Gln Ser Phe Gln Val Ala His Leu His Ala Pro
225                 230                 235                 240

ACT GGC AGC GGC AAG AGT ACT AAA GTG CCG GCT GCA TAT GCA GCC CAA        768
Thr Gly Ser Gly Lys Ser Thr Lys Val Pro Ala Ala Tyr Ala Ala Gln
                245                 250                 255

GGG TAC AAG GTG CTC GTC CTC AAT CCG TCC GTT GCC GCT ACC TTA GGG        816
Gly Tyr Lys Val Leu Val Leu Asn Pro Ser Val Ala Ala Thr Leu Gly
            260                 265                 270

TTT GGG GCG TAT ATG TCT AAG GCA CAC GGT ATT GAC CCC AAC ATC AGA        864
Phe Gly Ala Tyr Met Ser Lys Ala His Gly Ile Asp Pro Asn Ile Arg
        275                 280                 285

ACT GGG GTA AGG ACC ATT ACC ACA GGC GCC CCC GTC ACA TAC TCT ACC        912
Thr Gly Val Arg Thr Ile Thr Thr Gly Ala Pro Val Thr Tyr Ser Thr
    290                 295                 300

TAT GGC AAG TTT CTT GCC GAT GGT GGT TGC TCT GGG GGC GCT TAT GAC        960
Tyr Gly Lys Phe Leu Ala Asp Gly Gly Cys Ser Gly Gly Ala Tyr Asp
305                 310                 315                 320

ATC ATA ATA TGT GAT GAG TGC CAT TCA ACT GAC TCG ACT ACA ATC TTG       1008
Ile Ile Ile Cys Asp Glu Cys His Ser Thr Asp Ser Thr Thr Ile Leu
                325                 330                 335

GGC ATC GGC ACA GTC CTG GAC CAA GCG GAG ACG GCT GGA GCG CGG CTT       1056
Gly Ile Gly Thr Val Leu Asp Gln Ala Glu Thr Ala Gly Ala Arg Leu
            340                 345                 350

GTC GTG CTC GCC ACC GCT ACG CCT CCG GGA TCG GTC ACC GTG CCA CAC       1104
Val Val Leu Ala Thr Ala Thr Pro Pro Gly Ser Val Thr Val Pro His
        355                 360                 365

CCA AAC ATC GAG GAG GTG GCC CTG TCT AAT ACT GGA GAG ATC CCC TTC       1152
Pro Asn Ile Glu Glu Val Ala Leu Ser Asn Thr Gly Glu Ile Pro Phe
    370                 375                 380

TAT GGC AAA GCC ATC CCC ATT GAA GCC ATC AGG GGG GGA AGG CAT CTC       1200
Tyr Gly Lys Ala Ile Pro Ile Glu Ala Ile Arg Gly Gly Arg His Leu
385                 390                 395                 400

ATT TTC TGT CAT TCC AAG AAG AAG TGC GAC GAG CTC GCC GCA AAG CTG       1248
Ile Phe Cys His Ser Lys Lys Lys Cys Asp Glu Leu Ala Ala Lys Leu
                405                 410                 415

TCA GGC CTC GGA ATC AAC GCT GTG GCG TAT TAC CGG GGG CTC GAT GTG       1296
Ser Gly Leu Gly Ile Asn Ala Val Ala Tyr Tyr Arg Gly Leu Asp Val
            420                 425                 430

TCC GTC ATA CCA ACT ATC GGA GAC GTC GTT GTC GTG GCA ACA GAC GCT       1344
Ser Val Ile Pro Thr Ile Gly Asp Val Val Val Val Ala Thr Asp Ala
        435                 440                 445

CTG ATG ACG GGC TAT ACG GGC GAC TTT GAC TCA GTG ATC GAC TGT AAC       1392
Leu Met Thr Gly Tyr Thr Gly Asp Phe Asp Ser Val Ile Asp Cys Asn
    450                 455                 460
```

```
ACA TGT GTC ACC CAG ACA GTC GAC TTC AGC TTG GAT CCC ACC TTC ACC    1440
Thr Cys Val Thr Gln Thr Val Asp Phe Ser Leu Asp Pro Thr Phe Thr
465             470                 475                 480

ATT GAG ACG ACG ACC GTG CCT CAA GAC GCA GTG TCG CGC TCG CAG CGG    1488
Ile Glu Thr Thr Thr Val Pro Gln Asp Ala Val Ser Arg Ser Gln Arg
                485                 490                 495

CGG GGT AGG ACT GGC AGG GGT AGG AGA GGC ATC TAC AGG TTT GTG ACT    1536
Arg Gly Arg Thr Gly Arg Gly Arg Arg Gly Ile Tyr Arg Phe Val Thr
            500                 505                 510

CCG GGA GAA CGG CCC TCG GGC ATG TTC GAT TCC TCG GTC CTG TGT GAG    1584
Pro Gly Glu Arg Pro Ser Gly Met Phe Asp Ser Ser Val Leu Cys Glu
        515                 520                 525

TGC TAT GAC GCG GGC TGT GCT TGG TAC GAG CTC ACC CCC GCC GAG ACC    1632
Cys Tyr Asp Ala Gly Cys Ala Trp Tyr Glu Leu Thr Pro Ala Glu Thr
    530                 535                 540

TCG GTT AGG TTG CGG GCC TAC CTG AAC ACA CCA GGG TTG CCC GTT TGC    1680
Ser Val Arg Leu Arg Ala Tyr Leu Asn Thr Pro Gly Leu Pro Val Cys
545                 550                 555                 560

CAG GAC CAC CTG GAG TTC TGG GAG AGT GTC TTC ACA GGC CTC ACC CAT    1728
Gln Asp His Leu Glu Phe Trp Glu Ser Val Phe Thr Gly Leu Thr His
                565                 570                 575

ATA GAT GCA CAC TTC TTG TCC CAG ACC AAG CAG GCA GGA GAC AAC TTC    1776
Ile Asp Ala His Phe Leu Ser Gln Thr Lys Gln Ala Gly Asp Asn Phe
                580                 585                 590

CCC TAC CTG GTA GCA TAC CAA GCC ACG GTG TGC GCC AGG GCT CAG GCC    1824
Pro Tyr Leu Val Ala Tyr Gln Ala Thr Val Cys Ala Arg Ala Gln Ala
            595                 600                 605

CCA CCT CCA TCA TGG GAT CAA ATG TGG AAG TGT CTC ATA CGG CTG AAA    1872
Pro Pro Pro Ser Trp Asp Gln Met Trp Lys Cys Leu Ile Arg Leu Lys
610                 615                 620

CCT ACG CTG CAC GGG CCA ACA CCC TTG CTG TAC AGG CTG GGA GCC GTC    1920
Pro Thr Leu His Gly Pro Thr Pro Leu Leu Tyr Arg Leu Gly Ala Val
625                 630                 635                 640

CAA AAT GAG GTC ACC CTC ACC CAC CCC ATA ACC AAA TAC ATC ATG GCA    1968
Gln Asn Glu Val Thr Leu Thr His Pro Ile Thr Lys Tyr Ile Met Ala
                645                 650                 655

TGC ATG TCG GCT GAC CTG GAG GTC GTC ACT                            1998
Cys Met Ser Ala Asp Leu Glu Val Val Thr
                660                 665

(2) INFORMATION FOR SEQ ID NO:105:

(i) SEQUENCE CHARACTERISTICS:
        (A) LENGTH: 1998 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..1998

(xi) SEQUENCE DESCRIPTION: SEQ ID NO:105:

ATG GGC AGC AGC CAT CAT CAT CAT CAT CAC AGC AGC GGC CTG GTG CCG     48
Met Gly Ser Ser His His His His His His Ser Ser Gly Leu Val Pro
1               5                   10                  15

CGC GGC AGC CAT ATG GGT TCT GTT GTT ATT GTT GGT AGA ATT ATT TTA     96
Arg Gly Ser His Met Gly Ser Val Val Ile Val Gly Arg Ile Ile Leu
            20                  25                  30
```

```
TCT GGT AGT GGT AGT ATC ACG GCC TAC TCC CAA CAG ACG CGG GGC CTA        144
Ser Gly Ser Gly Ser Ile Thr Ala Tyr Ser Gln Gln Thr Arg Gly Leu
        35                  40                  45

CTT GGT TGC AAG AAG ACT AGC CTT ACA GGC CGG GAC AAG AAC CAG GTC        192
Leu Gly Cys Lys Lys Thr Ser Leu Thr Gly Arg Asp Lys Asn Gln Val
    50                  55                  60

GAG GGA GAG GTT CAG GTG GTT TCC ACC GCA ACA CAA TCC TTC CTG GCG        240
Glu Gly Glu Val Gln Val Val Ser Thr Ala Thr Gln Ser Phe Leu Ala
65                  70                  75                  80

ACC TGC GTC AAC GGC GTG TGT TGG ACC GTT TAC CAT GGT GCT GGC TCA        288
Thr Cys Val Asn Gly Val Cys Trp Thr Val Tyr His Gly Ala Gly Ser
                85                  90                  95

AAG ACC TTA GCC GGC CCA AAG GGG CCA ATC ACC CAG ATG TAC ACT AAT        336
Lys Thr Leu Ala Gly Pro Lys Gly Pro Ile Thr Gln Met Tyr Thr Asn
            100                 105                 110

GTG GAC CAG GAC CTC GTC GGC TGG CAG GCG CCC CCC GGG GCG CGT TCC        384
Val Asp Gln Asp Leu Val Gly Trp Gln Ala Pro Pro Gly Ala Arg Ser
        115                 120                 125

TTG ACA CCA TGC ACC TGT GGC AGC TCA GAC CTT TAC TTG GTC ACG AGA        432
Leu Thr Pro Cys Thr Cys Gly Ser Ser Asp Leu Tyr Leu Val Thr Arg
    130                 135                 140

CAT GCT GAC GTC ATT CCG GTG CGC CGG CGG GGC GAC AGT AGG GGG AGC        480
His Ala Asp Val Ile Pro Val Arg Arg Arg Gly Asp Ser Arg Gly Ser
145                 150                 155                 160

CTG CTC TCC CCC AGG CCT GTC TCC TAC TTG AAG GGC TCT TCG GGT GGT        528
Leu Leu Ser Pro Arg Pro Val Ser Tyr Leu Lys Gly Ser Ser Gly Gly
                165                 170                 175

CCA CTG CTC TGC CCT TCG GGG CAC GCT GTG GGC ATC TTC CGG GCT GCC        576
Pro Leu Leu Cys Pro Ser Gly His Ala Val Gly Ile Phe Arg Ala Ala
            180                 185                 190

GTA TGC ACC CGG GGG GTT GCG AAG GCG GTG GAC TTT GTG CCC GTA GAG        624
Val Cys Thr Arg Gly Val Ala Lys Ala Val Asp Phe Val Pro Val Glu
        195                 200                 205

TCC ATG GAA ACT ACT ATG CGG TCT CCG GTC TTC ACG GAC AAC TCA TCC        672
Ser Met Glu Thr Thr Met Arg Ser Pro Val Phe Thr Asp Asn Ser Ser
    210                 215                 220

CCC CCG GCC GTA CCG CAG TCA TTT CAA GTG GCC CAC CTA CAC GCT CCC        720
Pro Pro Ala Val Pro Gln Ser Phe Gln Val Ala His Leu His Ala Pro
225                 230                 235                 240

ACT GGC AGC GGC AAG AGT ACT AAA GTG CCG GCT GCA TAT GCA GCC CAA        768
Thr Gly Ser Gly Lys Ser Thr Lys Val Pro Ala Ala Tyr Ala Ala Gln
                245                 250                 255

GGG TAC AAG GTG CTC GTC CTC AAT CCG TCC GTT GCC GCT ACC TTA GGG        816
Gly Tyr Lys Val Leu Val Leu Asn Pro Ser Val Ala Ala Thr Leu Gly
            260                 265                 270

TTT GGG GCG TAT ATG TCT AAG GCA CAC GGT ATT GAC CCC AAC ATC AGA        864
Phe Gly Ala Tyr Met Ser Lys Ala His Gly Ile Asp Pro Asn Ile Arg
        275                 280                 285

ACT GGG GTA AGG ACC ATT ACC ACA GGC GCC CCC GTC ACA TAC TCT ACC        912
Thr Gly Val Arg Thr Ile Thr Thr Gly Ala Pro Val Thr Tyr Ser Thr
    290                 295                 300

TAT GGC AAG TTT CTT GCC GAT GGT GGT TGC TCT GGG GGC GCT TAT GAC        960
Tyr Gly Lys Phe Leu Ala Asp Gly Gly Cys Ser Gly Gly Ala Tyr Asp
305                 310                 315                 320

ATC ATA ATA TGT GAT GAG TGC CAT TCA ACT GAC TCG ACT ACA ATC TTG       1008
Ile Ile Ile Cys Asp Glu Cys His Ser Thr Asp Ser Thr Thr Ile Leu
                325                 330                 335

GGC ATC GGC ACA GTC CTG GAC CAA GCG GAG ACG GCT GGA GCG CGG CTT       1056
Gly Ile Gly Thr Val Leu Asp Gln Ala Glu Thr Ala Gly Ala Arg Leu
            340                 345                 350
```

-continued

```
GTC GTG CTC GCC ACC GCT ACG CCT CCG GGA TCG GTC ACC GTG CCA CAC        1104
Val Val Leu Ala Thr Ala Thr Pro Pro Gly Ser Val Thr Val Pro His
        355                 360                 365

CCA AAC ATC GAG GAG GTG GCC CTG TCT AAT ACT GGA GAG ATC CCC TTC        1152
Pro Asn Ile Glu Glu Val Ala Leu Ser Asn Thr Gly Glu Ile Pro Phe
        370                 375                 380

TAT GGC AAA GCC ATC CCC ATT GAA GCC ATC AGG GGG GGA AGG CAT CTC        1200
Tyr Gly Lys Ala Ile Pro Ile Glu Ala Ile Arg Gly Gly Arg His Leu
385                 390                 395                 400

ATT TTC TGT CAT TCC AAG AAG AAG TGC GAC GAG CTC GCC GCA AAG CTG        1248
Ile Phe Cys His Ser Lys Lys Lys Cys Asp Glu Leu Ala Ala Lys Leu
                405                 410                 415

TCA GGC CTC GGA ATC AAC GCT GTG GCG TAT TAC CGG GGG CTC GAT GTG        1296
Ser Gly Leu Gly Ile Asn Ala Val Ala Tyr Tyr Arg Gly Leu Asp Val
        420                 425                 430

TCC GTC ATA CCA ACT ATC GGA GAC GTC GTT GTC GTG GCA ACA GAC GCT        1344
Ser Val Ile Pro Thr Ile Gly Asp Val Val Val Val Ala Thr Asp Ala
        435                 440                 445

CTG ATG ACG GGC TAT ACG GGC GAC TTT GAC TCA GTG ATC GAC TGT AAC        1392
Leu Met Thr Gly Tyr Thr Gly Asp Phe Asp Ser Val Ile Asp Cys Asn
        450                 455                 460

ACA TGT GTC ACC CAG ACA GTC GAC TTC AGC TTG GAT CCC ACC TTC ACC        1440
Thr Cys Val Thr Gln Thr Val Asp Phe Ser Leu Asp Pro Thr Phe Thr
465                 470                 475                 480

ATT GAG ACG ACG ACC GTG CCT CAA GAC GCA GTG TCG CGC TCG CAG CGG        1488
Ile Glu Thr Thr Thr Val Pro Gln Asp Ala Val Ser Arg Ser Gln Arg
                485                 490                 495

CGG GGT AGG ACT GGC AGG GGT AGG AGA GGC ATC TAC AGG TTT GTG ACT        1536
Arg Gly Arg Thr Gly Arg Gly Arg Arg Gly Ile Tyr Arg Phe Val Thr
                500                 505                 510

CCG GGA GAA CGG CCC TCG GGC ATG TTC GAT TCC TCG GTC CTG TGT GAG        1584
Pro Gly Glu Arg Pro Ser Gly Met Phe Asp Ser Ser Val Leu Cys Glu
        515                 520                 525

TGC TAT GAC GCG GGC TGT GCT TGG TAC GAG CTC ACC CCC GCC GAG ACC        1632
Cys Tyr Asp Ala Gly Cys Ala Trp Tyr Glu Leu Thr Pro Ala Glu Thr
530                 535                 540

TCG GTT AGG TTG CGG GCC TAC CTG AAC ACA CCA GGG TTG CCC GTT TGC        1680
Ser Val Arg Leu Arg Ala Tyr Leu Asn Thr Pro Gly Leu Pro Val Cys
545                 550                 555                 560

CAG GAC CAC CTG GAG TTC TGG GAG AGT GTC TTC ACA GGC CTC ACC CAT        1728
Gln Asp His Leu Glu Phe Trp Glu Ser Val Phe Thr Gly Leu Thr His
                565                 570                 575

ATA GAT GCA CAC TTC TTG TCC CAG ACC AAG CAG GCA GGA GAC AAC TTC        1776
Ile Asp Ala His Phe Leu Ser Gln Thr Lys Gln Ala Gly Asp Asn Phe
                580                 585                 590

CCC TAC CTG GTA GCA TAC CAA GCC ACG GTG TGC GCC AGG GCT CAG GCC        1824
Pro Tyr Leu Val Ala Tyr Gln Ala Thr Val Cys Ala Arg Ala Gln Ala
        595                 600                 605

CCA CCT CCA TCA TGG GAT CAA ATG TGG AAG TGT CTC ATA CGG CTG AAA        1872
Pro Pro Pro Ser Trp Asp Gln Met Trp Lys Cys Leu Ile Arg Leu Lys
610                 615                 620

CCT ACG CTG CAC GGG CCA ACA CCC TTG CTG TAC AGG CTG GGA GCC GTC        1920
Pro Thr Leu His Gly Pro Thr Pro Leu Leu Tyr Arg Leu Gly Ala Val
625                 630                 635                 640

CAA AAT GAG GTC ACC CTC ACC CAC CCC ATA ACC AAA TAC ATC ATG GCA        1968
Gln Asn Glu Val Thr Leu Thr His Pro Ile Thr Lys Tyr Ile Met Ala
                645                 650                 655

TGC ATG TCG GCT GAC CTG GAG GTC GTC ACT                                1998
Cys Met Ser Ala Asp Leu Glu Val Val Thr
                660                 665
```

(2) INFORMATION FOR SEQ ID NO:106:

(i) SEQUENCE CHARACTERISTICS:
        (A) LENGTH: 1998 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..1998

(xi) SEQUENCE DESCRIPTION: SEQ ID NO:106:

```
ATG GGC AGC AGC CAT CAT CAT CAT CAT CAC AGC AGC GGC CTG GTG CCG      48
Met Gly Ser Ser His His His His His His Ser Ser Gly Leu Val Pro
  1               5                  10                  15

CGC GGC AGC CAT ATG GGT TCT GTT GTT ATT GTT GGT AGA ATT ATT TTA      96
Arg Gly Ser His Met Gly Ser Val Val Ile Val Gly Arg Ile Ile Leu
             20                  25                  30

TCT GGT AGT GGT AGT ATC ACG GCC TAC TCC CAA CAG ACG CGG GGC CTA     144
Ser Gly Ser Gly Ser Ile Thr Ala Tyr Ser Gln Gln Thr Arg Gly Leu
         35                  40                  45

CTT GGT TGC ATC ATC ACT AGC CTT ACA GGC CGG GAC AAG AAC CAG GTC     192
Leu Gly Cys Ile Ile Thr Ser Leu Thr Gly Arg Asp Lys Asn Gln Val
     50                  55                  60

GAG GGA GAG GTT CAG GTG GTT TCC ACC GCA ACA CAA TCC TTC CTG GCG     240
Glu Gly Glu Val Gln Val Val Ser Thr Ala Thr Gln Ser Phe Leu Ala
 65                  70                  75                  80

ACC TGC GTC AAC GGC GTG TGT TGG ACC GTT TAC CAT GGT GCT GGC TCA     288
Thr Cys Val Asn Gly Val Cys Trp Thr Val Tyr His Gly Ala Gly Ser
                 85                  90                  95

AAG ACC TTA GCC GGC CCA AAG GGG CCA ATC ACC CAG ATG TAC ACT AAT     336
Lys Thr Leu Ala Gly Pro Lys Gly Pro Ile Thr Gln Met Tyr Thr Asn
            100                 105                 110

GTG GAC CAG GAC CTC GTC GGC TGG CAG GCG CCC CCC GGG GCG CGT TCC     384
Val Asp Gln Asp Leu Val Gly Trp Gln Ala Pro Pro Gly Ala Arg Ser
        115                 120                 125

TTG ACA CCA TGC ACC TGT GGC AGC TCA GAC CTT TAC TTG GTC ACG AGA     432
Leu Thr Pro Cys Thr Cys Gly Ser Ser Asp Leu Tyr Leu Val Thr Arg
    130                 135                 140

CAT GCT GAC GTC ATT CCG GTG CGC CGG CGG GGC GAC AGT AGG GGG AGC     480
His Ala Asp Val Ile Pro Val Arg Arg Arg Gly Asp Ser Arg Gly Ser
145                 150                 155                 160

CTG CTC TCC CCC AGG CCT GTC TCC TAC TTG AAG GGC TCT GCT GGT GGT     528
Leu Leu Ser Pro Arg Pro Val Ser Tyr Leu Lys Gly Ser Ala Gly Gly
                165                 170                 175

CCA CTG CTC TGC CCT TCG GGG CAC GCT GTG GGC ATC TTC CGG GCT GCC     576
Pro Leu Leu Cys Pro Ser Gly His Ala Val Gly Ile Phe Arg Ala Ala
            180                 185                 190

GTA TGC ACC CGG GGG GTT GCG AAG GCG GTG GAC TTT GTG CCC GTA GAG     624
Val Cys Thr Arg Gly Val Ala Lys Ala Val Asp Phe Val Pro Val Glu
        195                 200                 205

TCC ATG GAA ACT ACT ATG CGG TCT CCG GTC TTC ACG GAC AAC TCA TCC     672
Ser Met Glu Thr Thr Met Arg Ser Pro Val Phe Thr Asp Asn Ser Ser
    210                 215                 220

CCC CCG GCC GTA CCG CAG TCA TTT CAA GTG GCC CAC CTA CAC GCT CCC     720
Pro Pro Ala Val Pro Gln Ser Phe Gln Val Ala His Leu His Ala Pro
225                 230                 235                 240

ACT GGC AGC GGC AAG AGT ACT AAA GTG CCG GCT GCA TAT GCA GCC CAA     768
Thr Gly Ser Gly Lys Ser Thr Lys Val Pro Ala Ala Tyr Ala Ala Gln
                245                 250                 255
```

```
GGG TAC AAG GTG CTC GTC CTC AAT CCG TCC GTT GCC GCT ACC TTA GGG      816
Gly Tyr Lys Val Leu Val Leu Asn Pro Ser Val Ala Ala Thr Leu Gly
        260                 265                 270

TTT GGG GCG TAT ATG TCT AAG GCA CAC GGT ATT GAC CCC AAC ATC AGA      864
Phe Gly Ala Tyr Met Ser Lys Ala His Gly Ile Asp Pro Asn Ile Arg
        275                 280                 285

ACT GGG GTA AGG ACC ATT ACC ACA GGC GCC CCC GTC ACA TAC TCT ACC      912
Thr Gly Val Arg Thr Ile Thr Thr Gly Ala Pro Val Thr Tyr Ser Thr
        290                 295                 300

TAT GGC AAG TTT CTT GCC GAT GGT GGT TGC TCT GGG GGC GCT TAT GAC      960
Tyr Gly Lys Phe Leu Ala Asp Gly Gly Cys Ser Gly Gly Ala Tyr Asp
305                 310                 315                 320

ATC ATA ATA TGT GAT GAG TGC CAT TCA ACT GAC TCG ACT ACA ATC TTG     1008
Ile Ile Ile Cys Asp Glu Cys His Ser Thr Asp Ser Thr Thr Ile Leu
                325                 330                 335

GGC ATC GGC ACA GTC CTG GAC CAA GCG GAG ACG GCT GGA GCG CGG CTT     1056
Gly Ile Gly Thr Val Leu Asp Gln Ala Glu Thr Ala Gly Ala Arg Leu
                340                 345                 350

GTC GTG CTC GCC ACC GCT ACG CCT CCG GGA TCG GTC ACC GTG CCA CAC     1104
Val Val Leu Ala Thr Ala Thr Pro Pro Gly Ser Val Thr Val Pro His
                355                 360                 365

CCA AAC ATC GAG GAG GTG GCC CTG TCT AAT ACT GGA GAG ATC CCC TTC     1152
Pro Asn Ile Glu Glu Val Ala Leu Ser Asn Thr Gly Glu Ile Pro Phe
        370                 375                 380

TAT GGC AAA GCC ATC CCC ATT GAA GCC ATC AGG GGG GGA AGG CAT CTC     1200
Tyr Gly Lys Ala Ile Pro Ile Glu Ala Ile Arg Gly Gly Arg His Leu
385                 390                 395                 400

ATT TTC TGT CAT TCC AAG AAG AAG TGC GAC GAG CTC GCC GCA AAG CTG     1248
Ile Phe Cys His Ser Lys Lys Lys Cys Asp Glu Leu Ala Ala Lys Leu
                405                 410                 415

TCA GGC CTC GGA ATC AAC GCT GTG GCG TAT TAC CGG GGG CTC GAT GTG     1296
Ser Gly Leu Gly Ile Asn Ala Val Ala Tyr Tyr Arg Gly Leu Asp Val
                420                 425                 430

TCC GTC ATA CCA ACT ATC GGA GAC GTC GTT GTC GTG GCA ACA GAC GCT     1344
Ser Val Ile Pro Thr Ile Gly Asp Val Val Val Val Ala Thr Asp Ala
                435                 440                 445

CTG ATG ACG GGC TAT ACG GGC GAC TTT GAC TCA GTG ATC GAC TGT AAC     1392
Leu Met Thr Gly Tyr Thr Gly Asp Phe Asp Ser Val Ile Asp Cys Asn
450                 455                 460

ACA TGT GTC ACC CAG ACA GTC GAC TTC AGC TTG GAT CCC ACC TTC ACC     1440
Thr Cys Val Thr Gln Thr Val Asp Phe Ser Leu Asp Pro Thr Phe Thr
465                 470                 475                 480

ATT GAG ACG ACG ACC GTG CCT CAA GAC GCA GTG TCG CGC TCG CAG CGG     1488
Ile Glu Thr Thr Thr Val Pro Gln Asp Ala Val Ser Arg Ser Gln Arg
                485                 490                 495

CGG GGT AGG ACT GGC AGG GGT AGG AGA GGC ATC TAC AGG TTT GTG ACT     1536
Arg Gly Arg Thr Gly Arg Gly Arg Arg Gly Ile Tyr Arg Phe Val Thr
                500                 505                 510

CCG GGA GAA CGG CCC TCG GGC ATG TTC GAT TCC TCG GTC CTG TGT GAG     1584
Pro Gly Glu Arg Pro Ser Gly Met Phe Asp Ser Ser Val Leu Cys Glu
        515                 520                 525

TGC TAT GAC GCG GGC TGT GCT TGG TAC GAG CTC ACC CCC GCC GAG ACC     1632
Cys Tyr Asp Ala Gly Cys Ala Trp Tyr Glu Leu Thr Pro Ala Glu Thr
        530                 535                 540

TCG GTT AGG TTG CGG GCC TAC CTG AAC ACA CCA GGG TTG CCC GTT TGC     1680
Ser Val Arg Leu Arg Ala Tyr Leu Asn Thr Pro Gly Leu Pro Val Cys
545                 550                 555                 560

CAG GAC CAC CTG GAG TTC TGG GAG AGT GTC TTC ACA GGC CTC ACC CAT     1728
Gln Asp His Leu Glu Phe Trp Glu Ser Val Phe Thr Gly Leu Thr His
                565                 570                 575
```

```
ATA GAT GCA CAC TTC TTG TCC CAG ACC AAG CAG GCA GGA GAC AAC TTC        1776
Ile Asp Ala His Phe Leu Ser Gln Thr Lys Gln Ala Gly Asp Asn Phe
            580                 585                 590

CCC TAC CTG GTA GCA TAC CAA GCC ACG GTG TGC GCC AGG GCT CAG GCC        1824
Pro Tyr Leu Val Ala Tyr Gln Ala Thr Val Cys Ala Arg Ala Gln Ala
            595                 600                 605

CCA CCT CCA TCA TGG GAT CAA ATG TGG AAG TGT CTC ATA CGG CTG AAA        1872
Pro Pro Pro Ser Trp Asp Gln Met Trp Lys Cys Leu Ile Arg Leu Lys
            610                 615                 620

CCT ACG CTG CAC GGG CCA ACA CCC TTG CTG TAC AGG CTG GGA GCC GTC        1920
Pro Thr Leu His Gly Pro Thr Pro Leu Leu Tyr Arg Leu Gly Ala Val
625                 630                 635                 640

CAA AAT GAG GTC ACC CTC ACC CAC CCC ATA ACC AAA TAC ATC ATG GCA        1968
Gln Asn Glu Val Thr Leu Thr His Pro Ile Thr Lys Tyr Ile Met Ala
            645                 650                 655

TGC ATG TCG GCT GAC CTG GAG GTC GTC ACT                                 1998
Cys Met Ser Ala Asp Leu Glu Val Val Thr
            660                 665

(2) INFORMATION FOR SEQ ID NO:107:

(i) SEQUENCE CHARACTERISTICS:
        (A) LENGTH: 1998 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..1998

(xi) SEQUENCE DESCRIPTION: SEQ ID NO:107:

ATG GGC AGC AGC CAT CAT CAT CAT CAT CAC AGC AGC GGC CTG GTG CCG          48
Met Gly Ser Ser His His His His His His Ser Ser Gly Leu Val Pro
1               5                   10                  15

CGC GGC AGC CAT ATG GGT TCT GTT GTT ATT GTT GGT AGA ATT ATT TTA          96
Arg Gly Ser His Met Gly Ser Val Val Ile Val Gly Arg Ile Ile Leu
            20                  25                  30

TCT GGT AGT GGT AGT ATC ACG GCC TAC TCC CAA CAG ACG CGG GGC CTA         144
Ser Gly Ser Gly Ser Ile Thr Ala Tyr Ser Gln Gln Thr Arg Gly Leu
        35                  40                  45

CTT GGT TGC AAG ATC ACT AGC CTT ACA GGC CGG GAC AAG AAC CAG GTC         192
Leu Gly Cys Lys Ile Thr Ser Leu Thr Gly Arg Asp Lys Asn Gln Val
    50                  55                  60

GAG GGA GAG GTT CAG GTG GTT TCC ACC GCA ACA CAA TCC TTC CTG GCG         240
Glu Gly Glu Val Gln Val Val Ser Thr Ala Thr Gln Ser Phe Leu Ala
65                  70                  75                  80

ACC TGC GTC AAC GGC GTG TGT TGG ACC GTT TAC CAT GGT GCT GGC TCA         288
Thr Cys Val Asn Gly Val Cys Trp Thr Val Tyr His Gly Ala Gly Ser
                85                  90                  95

AAG ACC TTA GCC GGC CCA AAG GGG CCA ATC ACC CAG ATG TAC ACT AAT         336
Lys Thr Leu Ala Gly Pro Lys Gly Pro Ile Thr Gln Met Tyr Thr Asn
            100                 105                 110

GTG GAC CAG GAC CTC GTC GGC TGG CAG GCG CCC CCC GGG GCG CGT TCC         384
Val Asp Gln Asp Leu Val Gly Trp Gln Ala Pro Pro Gly Ala Arg Ser
        115                 120                 125

TTG ACA CCA TGC ACC TGT GGC AGC TCA GAC CTT TAC TTG GTC ACG AGA         432
Leu Thr Pro Cys Thr Cys Gly Ser Ser Asp Leu Tyr Leu Val Thr Arg
    130                 135                 140
```

```
CAT GCT GAC GTC ATT CCG GTG CGC CGG CGG GGC GAC AGT AGG GGG AGC      480
His Ala Asp Val Ile Pro Val Arg Arg Arg Gly Asp Ser Arg Gly Ser
145                 150                 155                 160

CTG CTC TCC CCC AGG CCT GTC TCC TAC TTG AAG GGC TCT GCT GGT GGT      528
Leu Leu Ser Pro Arg Pro Val Ser Tyr Leu Lys Gly Ser Ala Gly Gly
                165                 170                 175

CCA CTG CTC TGC CCT TCG GGG CAC GCT GTG GGC ATC TTC CGG GCT GCC      576
Pro Leu Leu Cys Pro Ser Gly His Ala Val Gly Ile Phe Arg Ala Ala
            180                 185                 190

GTA TGC ACC CGG GGG GTT GCG AAG GCG GTG GAC TTT GTG CCC GTA GAG      624
Val Cys Thr Arg Gly Val Ala Lys Ala Val Asp Phe Val Pro Val Glu
        195                 200                 205

TCC ATG GAA ACT ACT ATG CGG TCT CCG GTC TTC ACG GAC AAC TCA TCC      672
Ser Met Glu Thr Thr Met Arg Ser Pro Val Phe Thr Asp Asn Ser Ser
    210                 215                 220

CCC CCG GCC GTA CCG CAG TCA TTT CAA GTG GCC CAC CTA CAC GCT CCC      720
Pro Pro Ala Val Pro Gln Ser Phe Gln Val Ala His Leu His Ala Pro
225                 230                 235                 240

ACT GGC AGC GGC AAG AGT ACT AAA GTG CCG GCT GCA TAT GCA GCC CAA      768
Thr Gly Ser Gly Lys Ser Thr Lys Val Pro Ala Ala Tyr Ala Ala Gln
                245                 250                 255

GGG TAC AAG GTG CTC GTC CTC AAT CCG TCC GTT GCC GCT ACC TTA GGG      816
Gly Tyr Lys Val Leu Val Leu Asn Pro Ser Val Ala Ala Thr Leu Gly
            260                 265                 270

TTT GGG GCG TAT ATG TCT AAG GCA CAC GGT ATT GAC CCC AAC ATC AGA      864
Phe Gly Ala Tyr Met Ser Lys Ala His Gly Ile Asp Pro Asn Ile Arg
        275                 280                 285

ACT GGG GTA AGG ACC ATT ACC ACA GGC GCC CCC GTC ACA TAC TCT ACC      912
Thr Gly Val Arg Thr Ile Thr Thr Gly Ala Pro Val Thr Tyr Ser Thr
    290                 295                 300

TAT GGC AAG TTT CTT GCC GAT GGT GGT TGC TCT GGG GGC GCT TAT GAC      960
Tyr Gly Lys Phe Leu Ala Asp Gly Gly Cys Ser Gly Gly Ala Tyr Asp
305                 310                 315                 320

ATC ATA ATA TGT GAT GAG TGC CAT TCA ACT GAC TCG ACT ACA ATC TTG     1008
Ile Ile Ile Cys Asp Glu Cys His Ser Thr Asp Ser Thr Thr Ile Leu
                325                 330                 335

GGC ATC GGC ACA GTC CTG GAC CAA GCG GAG ACG GCT GGA GCG CGG CTT     1056
Gly Ile Gly Thr Val Leu Asp Gln Ala Glu Thr Ala Gly Ala Arg Leu
            340                 345                 350

GTC GTG CTC GCC ACC GCT ACG CCT CCG GGA TCG GTC ACC GTG CCA CAC     1104
Val Val Leu Ala Thr Ala Thr Pro Pro Gly Ser Val Thr Val Pro His
        355                 360                 365

CCA AAC ATC GAG GAG GTG GCC CTG TCT AAT ACT GGA GAG ATC CCC TTC     1152
Pro Asn Ile Glu Glu Val Ala Leu Ser Asn Thr Gly Glu Ile Pro Phe
    370                 375                 380

TAT GGC AAA GCC ATC CCC ATT GAA GCC ATC AGG GGG GGA AGG CAT CTC     1200
Tyr Gly Lys Ala Ile Pro Ile Glu Ala Ile Arg Gly Gly Arg His Leu
385                 390                 395                 400

ATT TTC TGT CAT TCC AAG AAG AAG TGC GAC GAG CTC GCC GCA AAG CTG     1248
Ile Phe Cys His Ser Lys Lys Lys Cys Asp Glu Leu Ala Ala Lys Leu
                405                 410                 415

TCA GGC CTC GGA ATC AAC GCT GTG GCG TAT TAC CGG GGG CTC GAT GTG     1296
Ser Gly Leu Gly Ile Asn Ala Val Ala Tyr Tyr Arg Gly Leu Asp Val
            420                 425                 430

TCC GTC ATA CCA ACT ATC GGA GAC GTC GTT GTC GTG GCA ACA GAC GCT     1344
Ser Val Ile Pro Thr Ile Gly Asp Val Val Val Val Ala Thr Asp Ala
        435                 440                 445

CTG ATG ACG GGC TAT ACG GGC GAC TTT GAC TCA GTG ATC GAC TGT AAC     1392
Leu Met Thr Gly Tyr Thr Gly Asp Phe Asp Ser Val Ile Asp Cys Asn
    450                 455                 460
```

```
ACA TGT GTC ACC CAG ACA GTC GAC TTC AGC TTG GAT CCC ACC TTC ACC    1440
Thr Cys Val Thr Gln Thr Val Asp Phe Ser Leu Asp Pro Thr Phe Thr
465             470                 475                 480

ATT GAG ACG ACG ACC GTG CCT CAA GAC GCA GTG TCG CGC TCG CAG CGG    1488
Ile Glu Thr Thr Thr Val Pro Gln Asp Ala Val Ser Arg Ser Gln Arg
        485                 490                 495

CGG GGT AGG ACT GGC AGG GGT AGG AGA GGC ATC TAC AGG TTT GTG ACT    1536
Arg Gly Arg Thr Gly Arg Gly Arg Arg Gly Ile Tyr Arg Phe Val Thr
            500                 505                 510

CCG GGA GAA CGG CCC TCG GGC ATG TTC GAT TCC TCG GTC CTG TGT GAG    1584
Pro Gly Glu Arg Pro Ser Gly Met Phe Asp Ser Ser Val Leu Cys Glu
                515                 520                 525

TGC TAT GAC GCG GGC TGT GCT TGG TAC GAG CTC ACC CCC GCC GAG ACC    1632
Cys Tyr Asp Ala Gly Cys Ala Trp Tyr Glu Leu Thr Pro Ala Glu Thr
        530                 535                 540

TCG GTT AGG TTG CGG GCC TAC CTG AAC ACA CCA GGG TTG CCC GTT TGC    1680
Ser Val Arg Leu Arg Ala Tyr Leu Asn Thr Pro Gly Leu Pro Val Cys
545             550                 555                 560

CAG GAC CAC CTG GAG TTC TGG GAG AGT GTC TTC ACA GGC CTC ACC CAT    1728
Gln Asp His Leu Glu Phe Trp Glu Ser Val Phe Thr Gly Leu Thr His
                565                 570                 575

ATA GAT GCA CAC TTC TTG TCC CAG ACC AAG CAG GCA GGA GAC AAC TTC    1776
Ile Asp Ala His Phe Leu Ser Gln Thr Lys Gln Ala Gly Asp Asn Phe
            580                 585                 590

CCC TAC CTG GTA GCA TAC CAA GCC ACG GTG TGC GCC AGG GCT CAG GCC    1824
Pro Tyr Leu Val Ala Tyr Gln Ala Thr Val Cys Ala Arg Ala Gln Ala
                595                 600                 605

CCA CCT CCA TCA TGG GAT CAA ATG TGG AAG TGT CTC ATA CGG CTG AAA    1872
Pro Pro Pro Ser Trp Asp Gln Met Trp Lys Cys Leu Ile Arg Leu Lys
610             615                 620

CCT ACG CTG CAC GGG CCA ACA CCC TTG CTG TAC AGG CTG GGA GCC GTC    1920
Pro Thr Leu His Gly Pro Thr Pro Leu Leu Tyr Arg Leu Gly Ala Val
625             630                 635                 640

CAA AAT GAG GTC ACC CTC ACC CAC CCC ATA ACC AAA TAC ATC ATG GCA    1968
Gln Asn Glu Val Thr Leu Thr His Pro Ile Thr Lys Tyr Ile Met Ala
                645                 650                 655

TGC ATG TCG GCT GAC CTG GAG GTC GTC ACT                            1998
Cys Met Ser Ala Asp Leu Glu Val Val Thr
                660                 665

(2) INFORMATION FOR SEQ ID NO:108:

(i) SEQUENCE CHARACTERISTICS:
        (A) LENGTH: 1998 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..1998

(xi) SEQUENCE DESCRIPTION: SEQ ID NO:108:

ATG GGC AGC AGC CAT CAT CAT CAT CAT CAC AGC AGC GGC CTG GTG CCG    48
Met Gly Ser Ser His His His His His His Ser Ser Gly Leu Val Pro
1               5                   10                  15

CGC GGC AGC CAT ATG GGT TCT GTT GTT ATT GTT GGT AGA ATT ATT TTA    96
Arg Gly Ser His Met Gly Ser Val Val Ile Val Gly Arg Ile Ile Leu
            20                  25                  30
```

```
                                                       -continued

TCT GGT AGT GGT AGT ATC ACG GCC TAC TCC CAA CAG ACG CGG GGC CTA      144
Ser Gly Ser Gly Ser Ile Thr Ala Tyr Ser Gln Gln Thr Arg Gly Leu
        35                  40                  45

CTT GGT TGC ATC AAG ACT AGC CTT ACA GGC CGG GAC AAG AAC CAG GTC      192
Leu Gly Cys Ile Lys Thr Ser Leu Thr Gly Arg Asp Lys Asn Gln Val
 50                  55                  60

GAG GGA GAG GTT CAG GTG GTT TCC ACC GCA ACA CAA TCC TTC CTG GCG      240
Glu Gly Glu Val Gln Val Val Ser Thr Ala Thr Gln Ser Phe Leu Ala
 65                  70                  75                  80

ACC TGC GTC AAC GGC GTG TGT TGG ACC GTT TAC CAT GGT GCT GGC TCA      288
Thr Cys Val Asn Gly Val Cys Trp Thr Val Tyr His Gly Ala Gly Ser
                 85                  90                  95

AAG ACC TTA GCC GGC CCA AAG GGG CCA ATC ACC CAG ATG TAC ACT AAT      336
Lys Thr Leu Ala Gly Pro Lys Gly Pro Ile Thr Gln Met Tyr Thr Asn
            100                 105                 110

GTG GAC CAG GAC CTC GTC GGC TGG CAG GCG CCC CCC GGG GCG CGT TCC      384
Val Asp Gln Asp Leu Val Gly Trp Gln Ala Pro Pro Gly Ala Arg Ser
            115                 120                 125

TTG ACA CCA TGC ACC TGT GGC AGC TCA GAC CTT TAC TTG GTC ACG AGA      432
Leu Thr Pro Cys Thr Cys Gly Ser Ser Asp Leu Tyr Leu Val Thr Arg
130                 135                 140

CAT GCT GAC GTC ATT CCG GTG CGC CGG CGG GGC GAC AGT AGG GGG AGC      480
His Ala Asp Val Ile Pro Val Arg Arg Arg Gly Asp Ser Arg Gly Ser
145                 150                 155                 160

CTG CTC TCC CCC AGG CCT GTC TCC TAC TTG AAG GGC TCT GCT GGT GGT      528
Leu Leu Ser Pro Arg Pro Val Ser Tyr Leu Lys Gly Ser Ala Gly Gly
                165                 170                 175

CCA CTG CTC TGC CCT TCG GGG CAC GCT GTG GGC ATC TTC CGG GCT GCC      576
Pro Leu Leu Cys Pro Ser Gly His Ala Val Gly Ile Phe Arg Ala Ala
            180                 185                 190

GTA TGC ACC CGG GGG GTT GCG AAG GCG GTG GAC TTT GTG CCC GTA GAG      624
Val Cys Thr Arg Gly Val Ala Lys Ala Val Asp Phe Val Pro Val Glu
            195                 200                 205

TCC ATG GAA ACT ACT ATG CGG TCT CCG GTC TTC ACG GAC AAC TCA TCC      672
Ser Met Glu Thr Thr Met Arg Ser Pro Val Phe Thr Asp Asn Ser Ser
210                 215                 220

CCC CCG GCC GTA CCG CAG TCA TTT CAA GTG GCC CAC CTA CAC GCT CCC      720
Pro Pro Ala Val Pro Gln Ser Phe Gln Val Ala His Leu His Ala Pro
225                 230                 235                 240

ACT GGC AGC GGC AAG AGT ACT AAA GTG CCG GCT GCA TAT GCA GCC CAA      768
Thr Gly Ser Gly Lys Ser Thr Lys Val Pro Ala Ala Tyr Ala Ala Gln
                245                 250                 255

GGG TAC AAG GTG CTC GTC CTC AAT CCG TCC GTT GCC GCT ACC TTA GGG      816
Gly Tyr Lys Val Leu Val Leu Asn Pro Ser Val Ala Ala Thr Leu Gly
            260                 265                 270

TTT GGG GCG TAT ATG TCT AAG GCA CAC GGT ATT GAC CCC AAC ATC AGA      864
Phe Gly Ala Tyr Met Ser Lys Ala His Gly Ile Asp Pro Asn Ile Arg
        275                 280                 285

ACT GGG GTA AGG ACC ATT ACC ACA GGC GCC CCC GTC ACA TAC TCT ACC      912
Thr Gly Val Arg Thr Ile Thr Thr Gly Ala Pro Val Thr Tyr Ser Thr
    290                 295                 300

TAT GGC AAG TTT CTT GCC GAT GGT GGT TGC TCT GGG GGC GCT TAT GAC      960
Tyr Gly Lys Phe Leu Ala Asp Gly Gly Cys Ser Gly Gly Ala Tyr Asp
305                 310                 315                 320

ATC ATA ATA TGT GAT GAG TGC CAT TCA ACT GAC TCG ACT ACA ATC TTG     1008
Ile Ile Ile Cys Asp Glu Cys His Ser Thr Asp Ser Thr Thr Ile Leu
                325                 330                 335

GGC ATC GGC ACA GTC CTG GAC CAA GCG GAG ACG GCT GGA GCG CGG CTT     1056
Gly Ile Gly Thr Val Leu Asp Gln Ala Glu Thr Ala Gly Ala Arg Leu
            340                 345                 350
```

```
GTC GTG CTC GCC ACC GCT ACG CCT CCG GGA TCG GTC ACC GTG CCA CAC        1104
Val Val Leu Ala Thr Ala Thr Pro Pro Gly Ser Val Thr Val Pro His
        355                 360                 365

CCA AAC ATC GAG GAG GTG GCC CTG TCT AAT ACT GGA GAG ATC CCC TTC        1152
Pro Asn Ile Glu Glu Val Ala Leu Ser Asn Thr Gly Glu Ile Pro Phe
        370                 375                 380

TAT GGC AAA GCC ATC CCC ATT GAA GCC ATC AGG GGG GGA AGG CAT CTC        1200
Tyr Gly Lys Ala Ile Pro Ile Glu Ala Ile Arg Gly Gly Arg His Leu
385                 390                 395                 400

ATT TTC TGT CAT TCC AAG AAG AAG TGC GAC GAG CTC GCC GCA AAG CTG        1248
Ile Phe Cys His Ser Lys Lys Lys Cys Asp Glu Leu Ala Ala Lys Leu
            405                 410                 415

TCA GGC CTC GGA ATC AAC GCT GTG GCG TAT TAC CGG GGG CTC GAT GTG        1296
Ser Gly Leu Gly Ile Asn Ala Val Ala Tyr Tyr Arg Gly Leu Asp Val
                420                 425                 430

TCC GTC ATA CCA ACT ATC GGA GAC GTC GTT GTC GTG GCA ACA GAC GCT        1344
Ser Val Ile Pro Thr Ile Gly Asp Val Val Val Val Ala Thr Asp Ala
            435                 440                 445

CTG ATG ACG GGC TAT ACG GGC GAC TTT GAC TCA GTG ATC GAC TGT AAC        1392
Leu Met Thr Gly Tyr Thr Gly Asp Phe Asp Ser Val Ile Asp Cys Asn
    450                 455                 460

ACA TGT GTC ACC CAG ACA GTC GAC TTC AGC TTG GAT CCC ACC TTC ACC        1440
Thr Cys Val Thr Gln Thr Val Asp Phe Ser Leu Asp Pro Thr Phe Thr
465                 470                 475                 480

ATT GAG ACG ACG ACC GTG CCT CAA GAC GCA GTG TCG CGC TCG CAG CGG        1488
Ile Glu Thr Thr Thr Val Pro Gln Asp Ala Val Ser Arg Ser Gln Arg
                485                 490                 495

CGG GGT AGG ACT GGC AGG GGT AGG AGA GGC ATC TAC AGG TTT GTG ACT        1536
Arg Gly Arg Thr Gly Arg Gly Arg Arg Gly Ile Tyr Arg Phe Val Thr
            500                 505                 510

CCG GGA GAA CGG CCC TCG GGC ATG TTC GAT TCC TCG GTC CTG TGT GAG        1584
Pro Gly Glu Arg Pro Ser Gly Met Phe Asp Ser Ser Val Leu Cys Glu
        515                 520                 525

TGC TAT GAC GCG GGC TGT GCT TGG TAC GAG CTC ACC CCC GCC GAG ACC        1632
Cys Tyr Asp Ala Gly Cys Ala Trp Tyr Glu Leu Thr Pro Ala Glu Thr
    530                 535                 540

TCG GTT AGG TTG CGG GCC TAC CTG AAC ACA CCA GGG TTG CCC GTT TGC        1680
Ser Val Arg Leu Arg Ala Tyr Leu Asn Thr Pro Gly Leu Pro Val Cys
545                 550                 555                 560

CAG GAC CAC CTG GAG TTC TGG GAG AGT GTC TTC ACA GGC CTC ACC CAT        1728
Gln Asp His Leu Glu Phe Trp Glu Ser Val Phe Thr Gly Leu Thr His
                565                 570                 575

ATA GAT GCA CAC TTC TTG TCC CAG ACC AAG CAG GCA GGA GAC AAC TTC        1776
Ile Asp Ala His Phe Leu Ser Gln Thr Lys Gln Ala Gly Asp Asn Phe
            580                 585                 590

CCC TAC CTG GTA GCA TAC CAA GCC ACG GTG TGC GCC AGG GCT CAG GCC        1824
Pro Tyr Leu Val Ala Tyr Gln Ala Thr Val Cys Ala Arg Ala Gln Ala
        595                 600                 605

CCA CCT CCA TCA TGG GAT CAA ATG TGG AAG TGT CTC ATA CGG CTG AAA        1872
Pro Pro Pro Ser Trp Asp Gln Met Trp Lys Cys Leu Ile Arg Leu Lys
    610                 615                 620

CCT ACG CTG CAC GGG CCA ACA CCC TTG CTG TAC AGG CTG GGA GCC GTC        1920
Pro Thr Leu His Gly Pro Thr Pro Leu Leu Tyr Arg Leu Gly Ala Val
625                 630                 635                 640

CAA AAT GAG GTC ACC CTC ACC CAC CCC ATA ACC AAA TAC ATC ATG GCA        1968
Gln Asn Glu Val Thr Leu Thr His Pro Ile Thr Lys Tyr Ile Met Ala
                645                 650                 655

TGC ATG TCG GCT GAC CTG GAG GTC GTC ACT                                1998
Cys Met Ser Ala Asp Leu Glu Val Val Thr
            660                 665
```

(2) INFORMATION FOR SEQ ID NO:109:

(i) SEQUENCE CHARACTERISTICS:
        (A) LENGTH: 1998 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..1998

(xi) SEQUENCE DESCRIPTION: SEQ ID NO:109:

```
ATG GGC AGC AGC CAT CAT CAT CAT CAT CAC AGC AGC GGC CTG GTG CCG        48
Met Gly Ser Ser His His His His His His Ser Ser Gly Leu Val Pro
 1               5                  10                  15

CGC GGC AGC CAT ATG GGT TCT GTT GTT ATT GTT GGT AGA ATT ATT TTA        96
Arg Gly Ser His Met Gly Ser Val Val Ile Val Gly Arg Ile Ile Leu
                20                  25                  30

TCT GGT AGT GGT AGT ATC ACG GCC TAC TCC CAA CAG ACG CGG GGC CTA       144
Ser Gly Ser Gly Ser Ile Thr Ala Tyr Ser Gln Gln Thr Arg Gly Leu
             35                  40                  45

CTT GGT TGC AAG AAG ACT AGC CTT ACA GGC CGG GAC AAG AAC CAG GTC       192
Leu Gly Cys Lys Lys Thr Ser Leu Thr Gly Arg Asp Lys Asn Gln Val
 50                  55                  60

GAG GGA GAG GTT CAG GTG GTT TCC ACC GCA ACA CAA TCC TTC CTG GCG       240
Glu Gly Glu Val Gln Val Val Ser Thr Ala Thr Gln Ser Phe Leu Ala
 65                  70                  75                  80

ACC TGC GTC AAC GGC GTG TGT TGG ACC GTT TAC CAT GGT GCT GGC TCA       288
Thr Cys Val Asn Gly Val Cys Trp Thr Val Tyr His Gly Ala Gly Ser
                 85                  90                  95

AAG ACC TTA GCC GGC CCA AAG GGG CCA ATC ACC CAG ATG TAC ACT AAT       336
Lys Thr Leu Ala Gly Pro Lys Gly Pro Ile Thr Gln Met Tyr Thr Asn
                100                 105                 110

GTG GAC CAG GAC CTC GTC GGC TGG CAG GCG CCC CCC GGG GCG CGT TCC       384
Val Asp Gln Asp Leu Val Gly Trp Gln Ala Pro Pro Gly Ala Arg Ser
            115                 120                 125

TTG ACA CCA TGC ACC TGT GGC AGC TCA GAC CTT TAC TTG GTC ACG AGA       432
Leu Thr Pro Cys Thr Cys Gly Ser Ser Asp Leu Tyr Leu Val Thr Arg
130                 135                 140

CAT GCT GAC GTC ATT CCG GTG CGC CGG CGG GGC GAC AGT AGG GGG AGC       480
His Ala Asp Val Ile Pro Val Arg Arg Arg Gly Asp Ser Arg Gly Ser
145                 150                 155                 160

CTG CTC TCC CCC AGG CCT GTC TCC TAC TTG AAG GGC TCT GCT GGT GGT       528
Leu Leu Ser Pro Arg Pro Val Ser Tyr Leu Lys Gly Ser Ala Gly Gly
                165                 170                 175

CCA CTG CTC TGC CCT TCG GGG CAC GCT GTG GGC ATC TTC CGG GCT GCC       576
Pro Leu Leu Cys Pro Ser Gly His Ala Val Gly Ile Phe Arg Ala Ala
            180                 185                 190

GTA TGC ACC CGG GGG GTT GCG AAG GCG GTG GAC TTT GTG CCC GTA GAG       624
Val Cys Thr Arg Gly Val Ala Lys Ala Val Asp Phe Val Pro Val Glu
        195                 200                 205

TCC ATG GAA ACT ACT ATG CGG TCT CCG GTC TTC ACG GAC AAC TCA TCC       672
Ser Met Glu Thr Thr Met Arg Ser Pro Val Phe Thr Asp Asn Ser Ser
210                 215                 220

CCC CCG GCC GTA CCG CAG TCA TTT CAA GTG GCC CAC CTA CAC GCT CCC       720
Pro Pro Ala Val Pro Gln Ser Phe Gln Val Ala His Leu His Ala Pro
225                 230                 235                 240

ACT GGC AGC GGC AAG AGT ACT AAA GTG CCG GCT GCA TAT GCA GCC CAA       768
Thr Gly Ser Gly Lys Ser Thr Lys Val Pro Ala Ala Tyr Ala Ala Gln
                245                 250                 255
```

-continued

| | |
|---|---|
| GGG TAC AAG GTG CTC GTC CTC AAT CCG TCC GTT GCC GCT ACC TTA GGG<br>Gly Tyr Lys Val Leu Val Leu Asn Pro Ser Val Ala Ala Thr Leu Gly<br>          260                    265                  270 | 816 |
| TTT GGG GCG TAT ATG TCT AAG GCA CAC GGT ATT GAC CCC AAC ATC AGA<br>Phe Gly Ala Tyr Met Ser Lys Ala His Gly Ile Asp Pro Asn Ile Arg<br>        275                  280                  285 | 864 |
| ACT GGG GTA AGG ACC ATT ACC ACA GGC GCC CCC GTC ACA TAC TCT ACC<br>Thr Gly Val Arg Thr Ile Thr Thr Gly Ala Pro Val Thr Tyr Ser Thr<br>290                    295                  300 | 912 |
| TAT GGC AAG TTT CTT GCC GAT GGT GGT TGC TCT GGG GGC GCT TAT GAC<br>Tyr Gly Lys Phe Leu Ala Asp Gly Gly Cys Ser Gly Gly Ala Tyr Asp<br>305                  310                  315                  320 | 960 |
| ATC ATA ATA TGT GAT GAG TGC CAT TCA ACT GAC TCG ACT ACA ATC TTG<br>Ile Ile Ile Cys Asp Glu Cys His Ser Thr Asp Ser Thr Thr Ile Leu<br>                    325                  330                  335 | 1008 |
| GGC ATC GGC ACA GTC CTG GAC CAA GCG GAG ACG GCT GGA GCG CGG CTT<br>Gly Ile Gly Thr Val Leu Asp Gln Ala Glu Thr Ala Gly Ala Arg Leu<br>            340                  345                  350 | 1056 |
| GTC GTC CTC GCC ACC GCT ACG CCT CCG GGA TCG GTC ACC GTG CCA CAC<br>Val Val Leu Ala Thr Ala Thr Pro Pro Gly Ser Val Thr Val Pro His<br>        355                  360                  365 | 1104 |
| CCA AAC ATC GAG GAG GTG GCC CTG TCT AAT ACT GGA GAG ATC CCC TTC<br>Pro Asn Ile Glu Glu Val Ala Leu Ser Asn Thr Gly Glu Ile Pro Phe<br>370                    375                  380 | 1152 |
| TAT GGC AAA GCC ATC CCC ATT GAA GCC ATC AGG GGG GGA AGG CAT CTC<br>Tyr Gly Lys Ala Ile Pro Ile Glu Ala Ile Arg Gly Gly Arg His Leu<br>385                    390                  395                  400 | 1200 |
| ATT TTC TGT CAT TCC AAG AAG AAG TGC GAC GAG CTC GCC GCA AAG CTG<br>Ile Phe Cys His Ser Lys Lys Lys Cys Asp Glu Leu Ala Ala Lys Leu<br>                    405                  410                  415 | 1248 |
| TCA GGC CTC GGA ATC AAC GCT GTG GCG TAT TAC CGG GGG CTC GAT GTG<br>Ser Gly Leu Gly Ile Asn Ala Val Ala Tyr Tyr Arg Gly Leu Asp Val<br>            420                  425                  430 | 1296 |
| TCC GTC ATA CCA ACT ATC GGA GAC GTC GTT GTC GTG GCA ACA GAC GCT<br>Ser Val Ile Pro Thr Ile Gly Asp Val Val Val Val Ala Thr Asp Ala<br>        435                  440                  445 | 1344 |
| CTG ATG ACG GGC TAT ACG GGC GAC TTT GAC TCA GTG ATC GAC TGT AAC<br>Leu Met Thr Gly Tyr Thr Gly Asp Phe Asp Ser Val Ile Asp Cys Asn<br>450                    455                  460 | 1392 |
| ACA TGT GTC ACC CAG ACA GTC GAC TTC AGC TTG GAT CCC ACC TTC ACC<br>Thr Cys Val Thr Gln Thr Val Asp Phe Ser Leu Asp Pro Thr Phe Thr<br>465                    470                  475                  480 | 1440 |
| ATT GAG ACG ACG ACC GTG CCT CAA GAC GCA GTG TCG CGC TCG CAG CGG<br>Ile Glu Thr Thr Thr Val Pro Gln Asp Ala Val Ser Arg Ser Gln Arg<br>                    485                  490                  495 | 1488 |
| CGG GGT AGG ACT GGC AGG GGT AGG AGA GGC ATC TAC AGG TTT GTG ACT<br>Arg Gly Arg Thr Gly Arg Gly Arg Arg Gly Ile Tyr Arg Phe Val Thr<br>            500                  505                  510 | 1536 |
| CCG GGA GAA CGG CCC TCG GGC ATG TTC GAT TCC TCG GTC CTG TGT GAG<br>Pro Gly Glu Arg Pro Ser Gly Met Phe Asp Ser Ser Val Leu Cys Glu<br>        515                  520                  525 | 1584 |
| TGC TAT GAC GCG GGC TGT GCT TGG TAC GAG CTC ACC CCC GCC GAG ACC<br>Cys Tyr Asp Ala Gly Cys Ala Trp Tyr Glu Leu Thr Pro Ala Glu Thr<br>530                    535                  540 | 1632 |
| TCG GTT AGG TTG CGG GCC TAC CTG AAC ACA CCA GGG TTG CCC GTT TGC<br>Ser Val Arg Leu Arg Ala Tyr Leu Asn Thr Pro Gly Leu Pro Val Cys<br>545                    550                  555                  560 | 1680 |
| CAG GAC CAC CTG GAG TTC TGG GAG AGT GTC TTC ACA GGC CTC ACC CAT<br>Gln Asp His Leu Glu Phe Trp Glu Ser Val Phe Thr Gly Leu Thr His<br>                    565                  570                  575 | 1728 |

```
ATA GAT GCA CAC TTC TTG TCC CAG ACC AAG CAG GCA GGA GAC AAC TTC      1776
Ile Asp Ala His Phe Leu Ser Gln Thr Lys Gln Ala Gly Asp Asn Phe
            580                 585                 590

CCC TAC CTG GTA GCA TAC CAA GCC ACG GTG TGC GCC AGG GCT CAG GCC      1824
Pro Tyr Leu Val Ala Tyr Gln Ala Thr Val Cys Ala Arg Ala Gln Ala
        595                 600                 605

CCA CCT CCA TCA TGG GAT CAA ATG TGG AAG TGT CTC ATA CGG CTG AAA      1872
Pro Pro Pro Ser Trp Asp Gln Met Trp Lys Cys Leu Ile Arg Leu Lys
610                 615                 620

CCT ACG CTG CAC GGG CCA ACA CCC TTG CTG TAC AGG CTG GGA GCC GTC      1920
Pro Thr Leu His Gly Pro Thr Pro Leu Leu Tyr Arg Leu Gly Ala Val
625                 630                 635                 640

CAA AAT GAG GTC ACC CTC ACC CAC CCC ATA ACC AAA TAC ATC ATG GCA      1968
Gln Asn Glu Val Thr Leu Thr His Pro Ile Thr Lys Tyr Ile Met Ala
            645                 650                 655

TGC ATG TCG GCT GAC CTG GAG GTC GTC ACT                              1998
Cys Met Ser Ala Asp Leu Glu Val Val Thr
            660                 665

(2) INFORMATION FOR SEQ ID NO:110:

(i) SEQUENCE CHARACTERISTICS:
        (A) LENGTH: 2016 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..2016

(xi) SEQUENCE DESCRIPTION: SEQ ID NO:110:

ATG GGC AGC AGC CAT CAT CAT CAT CAT CAC AGC AGC GGC CTG GTG CCG       48
Met Gly Ser Ser His His His His His His Ser Ser Gly Leu Val Pro
1                   5                  10                  15

CGC GGC AGC CAT ATG GCT TAC TCT CTG ACT ACG GGT TCT GTT GTT ATT       96
Arg Gly Ser His Met Ala Tyr Ser Leu Thr Thr Gly Ser Val Val Ile
                20                  25                  30

GTT GGT AGA ATT ATT TTA TCT GGT AGT GGT AGT ATC ACG GCC TAC TCC      144
Val Gly Arg Ile Ile Leu Ser Gly Ser Gly Ser Ile Thr Ala Tyr Ser
            35                  40                  45

CAA CAG ACG CGG GGC CTA CTT GGT TGC ATC ATC ACT AGC CTT ACA GGC      192
Gln Gln Thr Arg Gly Leu Leu Gly Cys Ile Ile Thr Ser Leu Thr Gly
    50                  55                  60

CGG GAC AAG AAC CAG GTC GAG GGA GAG GTT CAG GTG GTT TCC ACC GCA      240
Arg Asp Lys Asn Gln Val Glu Gly Glu Val Gln Val Val Ser Thr Ala
65                  70                  75                  80

ACA CAA TCC TTC CTG GCG ACC TGC GTC AAC GGC GTG TGT TGG ACC GTT      288
Thr Gln Ser Phe Leu Ala Thr Cys Val Asn Gly Val Cys Trp Thr Val
                85                  90                  95

TAC CAT GGT GCT GGC TCA AAG ACC TTA GCC GGC CCA AAG GGG CCA ATC      336
Tyr His Gly Ala Gly Ser Lys Thr Leu Ala Gly Pro Lys Gly Pro Ile
            100                 105                 110

ACC CAG ATG TAC ACT AAT GTG GAC CAG GAC CTC GTC GGC TGG CAG GCG      384
Thr Gln Met Tyr Thr Asn Val Asp Gln Asp Leu Val Gly Trp Gln Ala
        115                 120                 125

CCC CCC GGG GCG CGT TCC TTG ACA CCA TGC ACC TGT GGC AGC TCA GAC      432
Pro Pro Gly Ala Arg Ser Leu Thr Pro Cys Thr Cys Gly Ser Ser Asp
130                 135                 140
```

```
CTT TAC TTG GTC ACG AGA CAT GCT GAC GTC ATT CCG GTG CGC CGG CGG     480
Leu Tyr Leu Val Thr Arg His Ala Asp Val Ile Pro Val Arg Arg Arg
145                 150                 155                 160

GGC GAC AGT AGG GGG AGC CTG CTC TCC CCC AGG CCT GTC TCC TAC TTG     528
Gly Asp Ser Arg Gly Ser Leu Leu Ser Pro Arg Pro Val Ser Tyr Leu
                165                 170                 175

AAG GGC TCT TCG GGT GGT CCA CTG CTC TGC CCT TCG GGG CAC GCT GTG     576
Lys Gly Ser Ser Gly Gly Pro Leu Leu Cys Pro Ser Gly His Ala Val
            180                 185                 190

GGC ATC TTC CGG GCT GCC GTA TGC ACC CGG GGG GTT GCG AAG GCG GTG     624
Gly Ile Phe Arg Ala Ala Val Cys Thr Arg Gly Val Ala Lys Ala Val
        195                 200                 205

GAC TTT GTG CCC GTA GAG TCC ATG GAA ACT ACT ATG CGG TCT CCG GTC     672
Asp Phe Val Pro Val Glu Ser Met Glu Thr Thr Met Arg Ser Pro Val
210                 215                 220

TTC ACG GAC AAC TCA TCC CCC CCG GCC GTA CCG CAG TCA TTT CAA GTG     720
Phe Thr Asp Asn Ser Ser Pro Pro Ala Val Pro Gln Ser Phe Gln Val
225                 230                 235                 240

GCC CAC CTA CAC GCT CCC ACT GGC AGC GGC AAG AGT ACT AAA GTG CCG     768
Ala His Leu His Ala Pro Thr Gly Ser Gly Lys Ser Thr Lys Val Pro
                245                 250                 255

GCT GCA TAT GCA GCC CAA GGG TAC AAG GTG CTC GTC CTC AAT CCG TCC     816
Ala Ala Tyr Ala Ala Gln Gly Tyr Lys Val Leu Val Leu Asn Pro Ser
            260                 265                 270

GTT GCC GCT ACC TTA GGG TTT GGG GCG TAT ATG TCT AAG GCA CAC GGT     864
Val Ala Ala Thr Leu Gly Phe Gly Ala Tyr Met Ser Lys Ala His Gly
        275                 280                 285

ATT GAC CCC AAC ATC AGA ACT GGG GTA AGG ACC ATT ACC ACA GGC GCC     912
Ile Asp Pro Asn Ile Arg Thr Gly Val Arg Thr Ile Thr Thr Gly Ala
290                 295                 300

CCC GTC ACA TAC TCT ACC TAT GGC AAG TTT CTT GCC GAT GGT GGT TGC     960
Pro Val Thr Tyr Ser Thr Tyr Gly Lys Phe Leu Ala Asp Gly Gly Cys
305                 310                 315                 320

TCT GGG GGC GCT TAT GAC ATC ATA ATA TGT GAT GAG TGC CAT TCA ACT    1008
Ser Gly Gly Ala Tyr Asp Ile Ile Ile Cys Asp Glu Cys His Ser Thr
                325                 330                 335

GAC TCG ACT ACA ATC TTG GGC ATC GGC ACA GTC CTG GAC CAA GCG GAG    1056
Asp Ser Thr Thr Ile Leu Gly Ile Gly Thr Val Leu Asp Gln Ala Glu
            340                 345                 350

ACG GCT GGA GCG CGG CTT GTC GTG CTC GCC ACC GCT ACG CCT CCG GGA    1104
Thr Ala Gly Ala Arg Leu Val Val Leu Ala Thr Ala Thr Pro Pro Gly
        355                 360                 365

TCG GTC ACC GTG CCA CAC CCA AAC ATC GAG GAG GTG GCC CTG TCT AAT    1152
Ser Val Thr Val Pro His Pro Asn Ile Glu Glu Val Ala Leu Ser Asn
370                 375                 380

ACT GGA GAG ATC CCC TTC TAT GGC AAA GCC ATC CCC ATT GAA GCC ATC    1200
Thr Gly Glu Ile Pro Phe Tyr Gly Lys Ala Ile Pro Ile Glu Ala Ile
385                 390                 395                 400

AGG GGG GGA AGG CAT CTC ATT TTC TGT CAT TCC AAG AAG AAG TGC GAC    1248
Arg Gly Gly Arg His Leu Ile Phe Cys His Ser Lys Lys Lys Cys Asp
                405                 410                 415

GAG CTC GCC GCA AAG CTG TCA GGC CTC GGA ATC AAC GCT GTG GCG TAT    1296
Glu Leu Ala Ala Lys Leu Ser Gly Leu Gly Ile Asn Ala Val Ala Tyr
            420                 425                 430

TAC CGG GGG CTC GAT GTG TCC GTC ATA CCA ACT ATC GGA GAC GTC GTT    1344
Tyr Arg Gly Leu Asp Val Ser Val Ile Pro Thr Ile Gly Asp Val Val
        435                 440                 445

GTC GTG GCA ACA GAC GCT CTG ATG ACG GGC TAT ACG GGC GAC TTT GAC    1392
Val Val Ala Thr Asp Ala Leu Met Thr Gly Tyr Thr Gly Asp Phe Asp
450                 455                 460
```

-continued

```
TCA GTG ATC GAC TGT AAC ACA TGT GTC ACC CAG ACA GTC GAC TTC AGC      1440
Ser Val Ile Asp Cys Asn Thr Cys Val Thr Gln Thr Val Asp Phe Ser
465             470                 475                 480

TTG GAT CCC ACC TTC ACC ATT GAG ACG ACG ACC GTG CCT CAA GAC GCA      1488
Leu Asp Pro Thr Phe Thr Ile Glu Thr Thr Thr Val Pro Gln Asp Ala
                485                 490                 495

GTG TCG CGC TCG CAG CGG CGG GGT AGG ACT GGC AGG GGT AGG AGA GGC      1536
Val Ser Arg Ser Gln Arg Arg Gly Arg Thr Gly Arg Gly Arg Arg Gly
            500                 505                 510

ATC TAC AGG TTT GTG ACT CCG GGA GAA CGG CCC TCG GGC ATG TTC GAT      1584
Ile Tyr Arg Phe Val Thr Pro Gly Glu Arg Pro Ser Gly Met Phe Asp
        515                 520                 525

TCC TCG GTC CTG TGT GAG TGC TAT GAC GCG GGC TGT GCT TGG TAC GAG      1632
Ser Ser Val Leu Cys Glu Cys Tyr Asp Ala Gly Cys Ala Trp Tyr Glu
    530                 535                 540

CTC ACC CCC GCC GAG ACC TCG GTT AGG TTG CGG GCC TAC CTG AAC ACA      1680
Leu Thr Pro Ala Glu Thr Ser Val Arg Leu Arg Ala Tyr Leu Asn Thr
545                 550                 555                 560

CCA GGG TTG CCC GTT TGC CAG GAC CAC CTG GAG TTC TGG GAG AGT GTC      1728
Pro Gly Leu Pro Val Cys Gln Asp His Leu Glu Phe Trp Glu Ser Val
                565                 570                 575

TTC ACA GGC CTC ACC CAT ATA GAT GCA CAC TTC TTG TCC CAG ACC AAG      1776
Phe Thr Gly Leu Thr His Ile Asp Ala His Phe Leu Ser Gln Thr Lys
            580                 585                 590

CAG GCA GGA GAC AAC TTC CCC TAC CTG GTA GCA TAC CAA GCC ACG GTG      1824
Gln Ala Gly Asp Asn Phe Pro Tyr Leu Val Ala Tyr Gln Ala Thr Val
        595                 600                 605

TGC GCC AGG GCT CAG GCC CCA CCT CCA TCA TGG GAT CAA ATG TGG AAG      1872
Cys Ala Arg Ala Gln Ala Pro Pro Pro Ser Trp Asp Gln Met Trp Lys
    610                 615                 620

TGT CTC ATA CGG CTG AAA CCT ACG CTG CAC GGG CCA ACA CCC TTG CTG      1920
Cys Leu Ile Arg Leu Lys Pro Thr Leu His Gly Pro Thr Pro Leu Leu
625                 630                 635                 640

TAC AGG CTG GGA GCC GTC CAA AAT GAG GTC ACC CTC ACC CAC CCC ATA      1968
Tyr Arg Leu Gly Ala Val Gln Asn Glu Val Thr Leu Thr His Pro Ile
                645                 650                 655

ACC AAA TAC ATC ATG GCA TGC ATG TCG GCT GAC CTG GAG GTC GTC ACT      2016
Thr Lys Tyr Ile Met Ala Cys Met Ser Ala Asp Leu Glu Val Val Thr
            660                 665                 670

(2) INFORMATION FOR SEQ ID NO:111:

(i) SEQUENCE CHARACTERISTICS:
        (A) LENGTH: 2016 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..2016

(xi) SEQUENCE DESCRIPTION: SEQ ID NO:111:

ATG GGC AGC AGC CAT CAT CAT CAT CAT CAC AGC AGC GGC CTG GTG CCG       48
Met Gly Ser Ser His His His His His His Ser Ser Gly Leu Val Pro
1               5                   10                  15

CGC GGC AGC CAT ATG GCT TAC TCT CTG ACT ACG GGT TCT GTT GTT ATT       96
Arg Gly Ser His Met Ala Tyr Ser Leu Thr Thr Gly Ser Val Val Ile
            20                  25                  30
```

-continued

```
GTT GGT AGA ATT ATT TTA TCT GGT AGT GGT AGT ATC ACG GCC TAC TCC        144
Val Gly Arg Ile Ile Leu Ser Gly Ser Gly Ser Ile Thr Ala Tyr Ser
         35                  40                  45

CAA CAG ACG CGG GGC CTA CTT GGT TGC ATC ATC ACT AGC CTT ACA GGC        192
Gln Gln Thr Arg Gly Leu Leu Gly Cys Ile Ile Thr Ser Leu Thr Gly
 50                  55                  60

CGG GAC AAG AAC CAG GTC GAG GGA GAG GTT CAG GTG GTT TCC ACC GCA        240
Arg Asp Lys Asn Gln Val Glu Gly Glu Val Gln Val Val Ser Thr Ala
 65                  70                  75                  80

ACA CAA TCC TTC CTG GCG ACC TGC GTC AAC GGC GTG TGT TGG ACC GTT        288
Thr Gln Ser Phe Leu Ala Thr Cys Val Asn Gly Val Cys Trp Thr Val
                 85                  90                  95

TAC CAT GGT GCT GGC TCA AAG ACC TTA GCC GGC CCA AAG GGG CCA ATC        336
Tyr His Gly Ala Gly Ser Lys Thr Leu Ala Gly Pro Lys Gly Pro Ile
            100                 105                 110

ACC CAG ATG TAC ACT AAT GTG GAC CAG GAC CTC GTC GGC TGG CAG GCG        384
Thr Gln Met Tyr Thr Asn Val Asp Gln Asp Leu Val Gly Trp Gln Ala
            115                 120                 125

CCC CCC GGG GCG CGT TCC TTG ACA CCA TGC ACC TGT GGC AGC TCA GAC        432
Pro Pro Gly Ala Arg Ser Leu Thr Pro Cys Thr Cys Gly Ser Ser Asp
130                 135                 140

CTT TAC TTG GTC ACG AGA CAT GCT GAC GTC ATT CCG GTG CGC CGG CGG        480
Leu Tyr Leu Val Thr Arg His Ala Asp Val Ile Pro Val Arg Arg Arg
145                 150                 155                 160

GGC GAC AGT AGG GGG AGC CTG CTC TCC CCC AGG CCT GTC TCC TAC TTG        528
Gly Asp Ser Arg Gly Ser Leu Leu Ser Pro Arg Pro Val Ser Tyr Leu
                165                 170                 175

AAG GGC TCT GCT GGT GGT CCA CTG CTC TGC CCT TCG GGG CAC GCT GTG        576
Lys Gly Ser Ala Gly Gly Pro Leu Leu Cys Pro Ser Gly His Ala Val
            180                 185                 190

GGC ATC TTC CGG GCT GCC GTA TGC ACC CGG GGG GTT GCG AAG GCG GTG        624
Gly Ile Phe Arg Ala Ala Val Cys Thr Arg Gly Val Ala Lys Ala Val
            195                 200                 205

GAC TTT GTG CCC GTA GAG TCC ATG GAA ACT ACT ATG CGG TCT CCG GTC        672
Asp Phe Val Pro Val Glu Ser Met Glu Thr Thr Met Arg Ser Pro Val
210                 215                 220

TTC ACG GAC AAC TCA TCC CCC CCG GCC GTA CCG CAG TCA TTT CAA GTG        720
Phe Thr Asp Asn Ser Ser Pro Pro Ala Val Pro Gln Ser Phe Gln Val
225                 230                 235                 240

GCC CAC CTA CAC GCT CCC ACT GGC AGC GGC AAG AGT ACT AAA GTG CCG        768
Ala His Leu His Ala Pro Thr Gly Ser Gly Lys Ser Thr Lys Val Pro
                245                 250                 255

GCT GCA TAT GCA GCC CAA GGG TAC AAG GTG CTC GTC CTC AAT CCG TCC        816
Ala Ala Tyr Ala Ala Gln Gly Tyr Lys Val Leu Val Leu Asn Pro Ser
            260                 265                 270

GTT GCC GCT ACC TTA GGG TTT GGG GCG TAT ATG TCT AAG GCA CAC GGT        864
Val Ala Ala Thr Leu Gly Phe Gly Ala Tyr Met Ser Lys Ala His Gly
            275                 280                 285

ATT GAC CCC AAC ATC AGA ACT GGG GTA AGG ACC ATT ACC ACA GGC GCC        912
Ile Asp Pro Asn Ile Arg Thr Gly Val Arg Thr Ile Thr Thr Gly Ala
290                 295                 300

CCC GTC ACA TAC TCT ACC TAT GGC AAG TTT CTT GCC GAT GGT GGT TGC        960
Pro Val Thr Tyr Ser Thr Tyr Gly Lys Phe Leu Ala Asp Gly Gly Cys
305                 310                 315                 320

TCT GGG GGC GCT TAT GAC ATC ATA ATA TGT GAT GAG TGC CAT TCA ACT       1008
Ser Gly Gly Ala Tyr Asp Ile Ile Ile Cys Asp Glu Cys His Ser Thr
                325                 330                 335

GAC TCG ACT ACA ATC TTG GGC ATC GGC ACA GTC CTG GAC CAA GCG GAG       1056
Asp Ser Thr Thr Ile Leu Gly Ile Gly Thr Val Leu Asp Gln Ala Glu
            340                 345                 350
```

-continued

```
ACG GCT GGA GCG CGG CTT GTC GTG CTC GCC ACC GCT ACG CCT CCG GGA      1104
Thr Ala Gly Ala Arg Leu Val Val Leu Ala Thr Ala Thr Pro Pro Gly
            355                 360                 365

TCG GTC ACC GTG CCA CAC CCA AAC ATC GAG GAG GTG GCC CTG TCT AAT      1152
Ser Val Thr Val Pro His Pro Asn Ile Glu Glu Val Ala Leu Ser Asn
    370                 375                 380

ACT GGA GAG ATC CCC TTC TAT GGC AAA GCC ATC CCC ATT GAA GCC ATC      1200
Thr Gly Glu Ile Pro Phe Tyr Gly Lys Ala Ile Pro Ile Glu Ala Ile
385                 390                 395                 400

AGG GGG GGA AGG CAT CTC ATT TTC TGT CAT TCC AAG AAG AAG TGC GAC      1248
Arg Gly Gly Arg His Leu Ile Phe Cys His Ser Lys Lys Lys Cys Asp
                405                 410                 415

GAG CTC GCC GCA AAG CTG TCA GGC CTC GGA ATC AAC GCT GTG GCG TAT      1296
Glu Leu Ala Ala Lys Leu Ser Gly Leu Gly Ile Asn Ala Val Ala Tyr
            420                 425                 430

TAC CGG GGG CTC GAT GTG TCC GTC ATA CCA ACT ATC GGA GAC GTC GTT      1344
Tyr Arg Gly Leu Asp Val Ser Val Ile Pro Thr Ile Gly Asp Val Val
        435                 440                 445

GTC GTG GCA ACA GAC GCT CTG ATG ACG GGC TAT ACG GGC GAC TTT GAC      1392
Val Val Ala Thr Asp Ala Leu Met Thr Gly Tyr Thr Gly Asp Phe Asp
    450                 455                 460

TCA GTG ATC GAC TGT AAC ACA TGT GTC ACC CAG ACA GTC GAC TTC AGC      1440
Ser Val Ile Asp Cys Asn Thr Cys Val Thr Gln Thr Val Asp Phe Ser
465                 470                 475                 480

TTG GAT CCC ACC TTC ACC ATT GAG ACG ACG ACC GTG CCT CAA GAC GCA      1488
Leu Asp Pro Thr Phe Thr Ile Glu Thr Thr Thr Val Pro Gln Asp Ala
                485                 490                 495

GTG TCG CGC TCG CAG CGG CGG GGT AGG ACT GGC AGG GGT AGG AGA GGC      1536
Val Ser Arg Ser Gln Arg Arg Gly Arg Thr Gly Arg Gly Arg Arg Gly
            500                 505                 510

ATC TAC AGG TTT GTG ACT CCG GGA GAA CGG CCC TCG GGC ATG TTC GAT      1584
Ile Tyr Arg Phe Val Thr Pro Gly Glu Arg Pro Ser Gly Met Phe Asp
        515                 520                 525

TCC TCG GTC CTG TGT GAG TGC TAT GAC GCG GGC TGT GCT TGG TAC GAG      1632
Ser Ser Val Leu Cys Glu Cys Tyr Asp Ala Gly Cys Ala Trp Tyr Glu
    530                 535                 540

CTC ACC CCC GCC GAG ACC TCG GTT AGG TTG CGG GCC TAC CTG AAC ACA      1680
Leu Thr Pro Ala Glu Thr Ser Val Arg Leu Arg Ala Tyr Leu Asn Thr
545                 550                 555                 560

CCA GGG TTG CCC GTT TGC CAG GAC CAC CTG GAG TTC TGG GAG AGT GTC      1728
Pro Gly Leu Pro Val Cys Gln Asp His Leu Glu Phe Trp Glu Ser Val
                565                 570                 575

TTC ACA GGC CTC ACC CAT ATA GAT GCA CAC TTC TTG TCC CAG ACC AAG      1776
Phe Thr Gly Leu Thr His Ile Asp Ala His Phe Leu Ser Gln Thr Lys
            580                 585                 590

CAG GCA GGA GAC AAC TTC CCC TAC CTG GTA GCA TAC CAA GCC ACG GTG      1824
Gln Ala Gly Asp Asn Phe Pro Tyr Leu Val Ala Tyr Gln Ala Thr Val
        595                 600                 605

TGC GCC AGG GCT CAG GCC CCA CCT CCA TCA TGG GAT CAA ATG TGG AAG      1872
Cys Ala Arg Ala Gln Ala Pro Pro Pro Ser Trp Asp Gln Met Trp Lys
    610                 615                 620

TGT CTC ATA CGG CTG AAA CCT ACG CTG CAC GGG CCA ACA CCC TTG CTG      1920
Cys Leu Ile Arg Leu Lys Pro Thr Leu His Gly Pro Thr Pro Leu Leu
625                 630                 635                 640

TAC AGG CTG GGA GCC GTC CAA AAT GAG GTC ACC CTC ACC CAC CCC ATA      1968
Tyr Arg Leu Gly Ala Val Gln Asn Glu Val Thr Leu Thr His Pro Ile
                645                 650                 655

ACC AAA TAC ATC ATG GCA TGC ATG TCG GCT GAC CTG GAG GTC GTC ACT      2016
Thr Lys Tyr Ile Met Ala Cys Met Ser Ala Asp Leu Glu Val Val Thr
            660                 665                 670
```

(2) INFORMATION FOR SEQ ID NO:112:

(i) SEQUENCE CHARACTERISTICS:
        (A) LENGTH: 648 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..648

(xi) SEQUENCE DESCRIPTION: SEQ ID NO:112:

```
ATG GGC AGC AGC CAT CAT CAT CAT CAT CAC AGC AGC GGC CTG GTG CCG      48
Met Gly Ser Ser His His His His His His Ser Ser Gly Leu Val Pro
 1               5                  10                  15

CGC GGC AGC CAT ATG GGT TCT GTT GTT ATT GTT GGT AGA ATT ATT TTA      96
Arg Gly Ser His Met Gly Ser Val Val Ile Val Gly Arg Ile Ile Leu
             20                  25                  30

TCT CCT GCT GGT ATC ACG GCC TAC TCC CAA CAG ACG CGG GGC CTA CTT     144
Ser Pro Ala Gly Ile Thr Ala Tyr Ser Gln Gln Thr Arg Gly Leu Leu
         35                  40                  45

GGT TGC ATC ATC ACT AGC CTT ACA GGC CGG GAC AAG AAC CAG GTC GAG     192
Gly Cys Ile Ile Thr Ser Leu Thr Gly Arg Asp Lys Asn Gln Val Glu
 50                  55                  60

GGA GAG GTT CAG GTG GTT TCC ACC GCA ACA CAA TCC TTC CTG GCG ACC     240
Gly Glu Val Gln Val Val Ser Thr Ala Thr Gln Ser Phe Leu Ala Thr
 65                  70                  75                  80

TGC GTC AAC GGC GTG TGT TGG ACC GTT TAC CAT GGT GCT GGC TCA AAG     288
Cys Val Asn Gly Val Cys Trp Thr Val Tyr His Gly Ala Gly Ser Lys
                 85                  90                  95

ACC TTA GCC GGC CCA AAG GGG CCA ATC ACC CAG ATG TAC ACT AAT GTG     336
Thr Leu Ala Gly Pro Lys Gly Pro Ile Thr Gln Met Tyr Thr Asn Val
            100                 105                 110

GAC CAG GAC CTC GTC GGC TGG CAG GCG CCC CCC GGG GCG CGT TCC TTG     384
Asp Gln Asp Leu Val Gly Trp Gln Ala Pro Pro Gly Ala Arg Ser Leu
        115                 120                 125

ACA CCA TGC ACC TGT GGC AGC TCA GAC CTT TAC TTG GTC ACG AGA CAT     432
Thr Pro Cys Thr Cys Gly Ser Ser Asp Leu Tyr Leu Val Thr Arg His
    130                 135                 140

GCT GAC GTC ATT CCG GTG CGC CGG CGG GGC GAC AGT AGG GGG AGC CTG     480
Ala Asp Val Ile Pro Val Arg Arg Arg Gly Asp Ser Arg Gly Ser Leu
145                 150                 155                 160

CTC TCC CCC AGG CCT GTC TCC TAC TTG AAG GGC TCT TCG GGT GGT CCA     528
Leu Ser Pro Arg Pro Val Ser Tyr Leu Lys Gly Ser Ser Gly Gly Pro
                165                 170                 175

CTG CTC TGC CCT TCG GGG CAC GCT GTG GGC ATC TTC CGG GCT GCC GTA     576
Leu Leu Cys Pro Ser Gly His Ala Val Gly Ile Phe Arg Ala Ala Val
            180                 185                 190

TGC ACC CGG GGG GTT GCG AAG GCG GTG GAC TTT GTG CCC GTA GAG TCC     624
Cys Thr Arg Gly Val Ala Lys Ala Val Asp Phe Val Pro Val Glu Ser
        195                 200                 205

ATG GAA ACT ACT ATG CGG TCT TGA                                     648
Met Glu Thr Thr Met Arg Ser
    210                 215
```

(2) INFORMATION FOR SEQ ID NO:113:

(i) SEQUENCE CHARACTERISTICS:
        (A) LENGTH: 648 base pairs
        (B) TYPE: nucleic acid (C) STRANDEDNESS: single
        (D) TOPOLOGY: linear (ii) MOLECULE TYPE: cDNA (ix) FEATURE:
        (A) NAME/KEY: CDS
        (B) LOCATION: 1..648

(xi) SEQUENCE DESCRIPTION: SEQ ID NO:113:

| | | | | | | | | | | | | | | | | |
|---|---|---|---|---|---|---|---|---|---|---|---|---|---|---|---|---|
| ATG | GGC | AGC | AGC | CAT | CAT | CAT | CAT | CAT | CAC | AGC | AGC | GGC | CTG | GTG | CCG | 48 |
| Met | Gly | Ser | Ser | His | His | His | His | His | His | Ser | Ser | Gly | Leu | Val | Pro | |
| 1 | | | | 5 | | | | | 10 | | | | | 15 | | |

| CGC | GGC | AGC | CAT | ATG | GGT | TCT | GTT | GTT | ATT | GTT | GGT | AGA | ATT | ATT | TTA | 96 |
| Arg | Gly | Ser | His | Met | Gly | Ser | Val | Val | Ile | Val | Gly | Arg | Ile | Ile | Leu | |
| | | | 20 | | | | | 25 | | | | | 30 | | | |

| TCT | CCT | GCT | GGT | ATC | ACG | GCC | TAC | TCC | CAA | CAG | ACG | CGG | GGC | CTA | CTT | 144 |
| Ser | Pro | Ala | Gly | Ile | Thr | Ala | Tyr | Ser | Gln | Gln | Thr | Arg | Gly | Leu | Leu | |
| | | | 35 | | | | | 40 | | | | | 45 | | | |

| GGT | TGC | AAG | ATC | ACT | AGC | CTT | ACA | GGC | CGG | GAC | AAG | AAC | CAG | GTC | GAG | 192 |
| Gly | Cys | Lys | Ile | Thr | Ser | Leu | Thr | Gly | Arg | Asp | Lys | Asn | Gln | Val | Glu | |
| | 50 | | | | | 55 | | | | | 60 | | | | | |

| GGA | GAG | GTT | CAG | GTG | GTT | TCC | ACC | GCA | ACA | CAA | TCC | TTC | CTG | GCG | ACC | 240 |
| Gly | Glu | Val | Gln | Val | Val | Ser | Thr | Ala | Thr | Gln | Ser | Phe | Leu | Ala | Thr | |
| 65 | | | | | 70 | | | | | 75 | | | | | 80 | |

| TGC | GTC | AAC | GGC | GTG | TGT | TGG | ACC | GTT | TAC | CAT | GGT | GCT | GGC | TCA | AAG | 288 |
| Cys | Val | Asn | Gly | Val | Cys | Trp | Thr | Val | Tyr | His | Gly | Ala | Gly | Ser | Lys | |
| | | | | 85 | | | | | 90 | | | | | 95 | | |

| ACC | TTA | GCC | GGC | CCA | AAG | GGG | CCA | ATC | ACC | CAG | ATG | TAC | ACT | AAT | GTG | 336 |
| Thr | Leu | Ala | Gly | Pro | Lys | Gly | Pro | Ile | Thr | Gln | Met | Tyr | Thr | Asn | Val | |
| | | | 100 | | | | | 105 | | | | | 110 | | | |

| GAC | CAG | GAC | CTC | GTC | GGC | TGG | CAG | GCG | CCC | CCC | GGG | GCG | CGT | TCC | TTG | 384 |
| Asp | Gln | Asp | Leu | Val | Gly | Trp | Gln | Ala | Pro | Pro | Gly | Ala | Arg | Ser | Leu | |
| | | 115 | | | | | 120 | | | | | 125 | | | | |

| ACA | CCA | TGC | ACC | TGT | GGC | AGC | TCA | GAC | CTT | TAC | TTG | GTC | ACG | AGA | CAT | 432 |
| Thr | Pro | Cys | Thr | Cys | Gly | Ser | Ser | Asp | Leu | Tyr | Leu | Val | Thr | Arg | His | |
| | | 130 | | | | | 135 | | | | | 140 | | | | |

| GCT | GAC | GTC | ATT | CCG | GTG | CGC | CGG | CGG | GGC | GAC | AGT | AGG | GGG | AGC | CTG | 480 |
| Ala | Asp | Val | Ile | Pro | Val | Arg | Arg | Arg | Gly | Asp | Ser | Arg | Gly | Ser | Leu | |
| 145 | | | | | 150 | | | | | 155 | | | | | 160 | |

| CTC | TCC | CCC | AGG | CCT | GTC | TCC | TAC | TTG | AAG | GGC | TCT | TCG | GGT | GGT | CCA | 528 |
| Leu | Ser | Pro | Arg | Pro | Val | Ser | Tyr | Leu | Lys | Gly | Ser | Ser | Gly | Gly | Pro | |
| | | | 165 | | | | | 170 | | | | | 175 | | | |

| CTG | CTC | TGC | CCT | TCG | GGG | CAC | GCT | GTG | GGC | ATC | TTC | CGG | GCT | GCC | GTA | 576 |
| Leu | Leu | Cys | Pro | Ser | Gly | His | Ala | Val | Gly | Ile | Phe | Arg | Ala | Ala | Val | |
| | | | 180 | | | | | 185 | | | | | 190 | | | |

| TGC | ACC | CGG | GGG | GTT | GCG | AAG | GCG | GTG | GAC | TTT | GTG | CCC | GTA | GAG | TCC | 624 |
| Cys | Thr | Arg | Gly | Val | Ala | Lys | Ala | Val | Asp | Phe | Val | Pro | Val | Glu | Ser | |
| | | 195 | | | | | 200 | | | | | 205 | | | | |

| ATG | GAA | ACT | ACT | ATG | CGG | TCT | TGA | | | | | | | | | 648 |
| Met | Glu | Thr | Thr | Met | Arg | Ser | | | | | | | | | | |
| | 210 | | | | | 215 | | | | | | | | | | |

(2) INFORMATION FOR SEQ ID NO:114:

(i) SEQUENCE CHARACTERISTICS:
        (A) LENGTH: 648 base pairs
        (B) TYPE: nucleic acid
        (C) STRANDEDNESS: single
        (D) TOPOLOGY: linear (ii) MOLECULE TYPE: cDNA (ix) FEATURE:
    (A) NAME/KEY: CDS
    (B) LOCATION: 1..648

(xi) SEQUENCE DESCRIPTION: SEQ ID NO:114:

```
ATG GGC AGC AGC CAT CAT CAT CAT CAT CAC AGC AGC GGC CTG GTG CCG      48
Met Gly Ser Ser His His His His His His Ser Ser Gly Leu Val Pro
 1               5                  10                  15

CGC GGC AGC CAT ATG GGT TCT GTT GTT ATT GTT GGT AGA ATT ATT TTA      96
Arg Gly Ser His Met Gly Ser Val Val Ile Val Gly Arg Ile Ile Leu
                20                  25                  30

TCT GGT GGT TCT ATC ACG GCC TAC TCC CAA CAG ACG CGG GGC CTA CTT     144
Ser Gly Gly Ser Ile Thr Ala Tyr Ser Gln Gln Thr Arg Gly Leu Leu
            35                  40                  45

GGT TGC ATC ATC ACT AGC CTT ACA GGC CGG GAC AAG AAC CAG GTC GAG     192
Gly Cys Ile Ile Thr Ser Leu Thr Gly Arg Asp Lys Asn Gln Val Glu
        50                  55                  60

GGA GAG GTT CAG GTG GTT TCC ACC GCA ACA CAA TCC TTC CTG GCG ACC     240
Gly Glu Val Gln Val Val Ser Thr Ala Thr Gln Ser Phe Leu Ala Thr
 65                  70                  75                  80

TGC GTC AAC GGC GTG TGT TGG ACC GTT TAC CAT GGT GCT GGC TCA AAG     288
Cys Val Asn Gly Val Cys Trp Thr Val Tyr His Gly Ala Gly Ser Lys
                 85                  90                  95

ACC TTA GCC GGC CCA AAG GGG CCA ATC ACC CAG ATG TAC ACT AAT GTG     336
Thr Leu Ala Gly Pro Lys Gly Pro Ile Thr Gln Met Tyr Thr Asn Val
                100                 105                 110

GAC CAG GAC CTC GTC GGC TGG CAG GCG CCC CCC GGG GCG CGT TCC TTG     384
Asp Gln Asp Leu Val Gly Trp Gln Ala Pro Pro Gly Ala Arg Ser Leu
            115                 120                 125

ACA CCA TGC ACC TGT GGC AGC TCA GAC CTT TAC TTG GTC ACG AGA CAT     432
Thr Pro Cys Thr Cys Gly Ser Ser Asp Leu Tyr Leu Val Thr Arg His
        130                 135                 140

GCT GAC GTC ATT CCG GTG CGC CGG CGG GGC GAC AGT AGG GGG AGC CTG     480
Ala Asp Val Ile Pro Val Arg Arg Arg Gly Asp Ser Arg Gly Ser Leu
145                 150                 155                 160

CTC TCC CCC AGG CCT GTC TCC TAC TTG AAG GGC TCT TCG GGT GGT CCA     528
Leu Ser Pro Arg Pro Val Ser Tyr Leu Lys Gly Ser Ser Gly Gly Pro
                165                 170                 175

CTG CTC TGC CCT TCG GGG CAC GCT GTG GGC ATC TTC CGG GCT GCC GTA     576
Leu Leu Cys Pro Ser Gly His Ala Val Gly Ile Phe Arg Ala Ala Val
            180                 185                 190

TGC ACC CGG GGG GTT GCG AAG GCG GTG GAC TTT GTG CCC GTA GAG TCC     624
Cys Thr Arg Gly Val Ala Lys Ala Val Asp Phe Val Pro Val Glu Ser
        195                 200                 205

ATG GAA ACT ACT ATG CGG TCT TGA                                     648
Met Glu Thr Thr Met Arg Ser
210                 215
```

(2) INFORMATION FOR SEQ ID NO:115:

(i) SEQUENCE CHARACTERISTICS:
        (A) LENGTH: 648 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..648

(xi) SEQUENCE DESCRIPTION: SEQ ID NO:115:

```
ATG GGC AGC AGC CAT CAT CAT CAT CAT CAC AGC AGC GGC CTG GTG CCG        48
Met Gly Ser Ser His His His His His His Ser Ser Gly Leu Val Pro
  1               5                  10                  15

CGC GGC AGC CAT ATG GGT TCT GTT GTT ATT GTT GGT AGA ATT ATT TTA        96
Arg Gly Ser His Met Gly Ser Val Val Ile Val Gly Arg Ile Ile Leu
                 20                  25                  30

TCT GGT GGT TCT ATC ACG GCC TAC TCC CAA CAG ACG CGG GGC CTA CTT       144
Ser Gly Gly Ser Ile Thr Ala Tyr Ser Gln Gln Thr Arg Gly Leu Leu
             35                  40                  45

GGT TGC AAG ATC ACT AGC CTT ACA GGC CGG GAC AAG AAC CAG GTC GAG       192
Gly Cys Lys Ile Thr Ser Leu Thr Gly Arg Asp Lys Asn Gln Val Glu
         50                  55                  60

GGA GAG GTT CAG GTG GTT TCC ACC GCA ACA CAA TCC TTC CTG GCG ACC       240
Gly Glu Val Gln Val Val Ser Thr Ala Thr Gln Ser Phe Leu Ala Thr
 65                  70                  75                  80

TGC GTC AAC GGC GTG TGT TGG ACC GTT TAC CAT GGT GCT GGC TCA AAG       288
Cys Val Asn Gly Val Cys Trp Thr Val Tyr His Gly Ala Gly Ser Lys
                 85                  90                  95

ACC TTA GCC GGC CCA AAG GGG CCA ATC ACC CAG ATG TAC ACT AAT GTG       336
Thr Leu Ala Gly Pro Lys Gly Pro Ile Thr Gln Met Tyr Thr Asn Val
            100                 105                 110

GAC CAG GAC CTC GTC GGC TGG CAG GCG CCC CCC GGG GCG CGT TCC TTG       384
Asp Gln Asp Leu Val Gly Trp Gln Ala Pro Pro Gly Ala Arg Ser Leu
        115                 120                 125

ACA CCA TGC ACC TGT GGC AGC TCA GAC CTT TAC TTG GTC ACG AGA CAT       432
Thr Pro Cys Thr Cys Gly Ser Ser Asp Leu Tyr Leu Val Thr Arg His
    130                 135                 140

GCT GAC GTC ATT CCG GTG CGC CGG CGG GGC GAC AGT AGG GGG AGC CTG       480
Ala Asp Val Ile Pro Val Arg Arg Arg Gly Asp Ser Arg Gly Ser Leu
145                 150                 155                 160

CTC TCC CCC AGG CCT GTC TCC TAC TTG AAG GGC TCT TCG GGT GGT CCA       528
Leu Ser Pro Arg Pro Val Ser Tyr Leu Lys Gly Ser Ser Gly Gly Pro
                165                 170                 175

CTG CTC TGC CCT TCG GGG CAC GCT GTG GGC ATC TTC CGG GCT GCC GTA       576
Leu Leu Cys Pro Ser Gly His Ala Val Gly Ile Phe Arg Ala Ala Val
            180                 185                 190

TGC ACC CGG GGG GTT GCG AAG GCG GTG GAC TTT GTG CCC GTA GAG TCC       624
Cys Thr Arg Gly Val Ala Lys Ala Val Asp Phe Val Pro Val Glu Ser
        195                 200                 205

ATG GAA ACT ACT ATG CGG TCT TGA                                       648
Met Glu Thr Thr Met Arg Ser
    210                 215
```

(2) INFORMATION FOR SEQ ID NO:116:

(i) SEQUENCE CHARACTERISTICS:
        (A) LENGTH: 1941 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..1941

(xi) SEQUENCE DESCRIPTION: SEQ ID NO:116:

```
ATG CAT ATG CAT CAT CAT CAC CAT CAT CTG GTG CCG CGC GGC AGC GCG        48
Met His Met His His His His His His Leu Val Pro Arg Gly Ser Ala
  1               5                  10                  15
```

| | | |
|---|---|---|
| CCC ATC ACG GCC TAC TCC CAA CAG ACG CGG GGC CTA CTT GGT TGC AAG<br>Pro Ile Thr Ala Tyr Ser Gln Gln Thr Arg Gly Leu Leu Gly Cys Lys<br>              20                       25                30 | | 96 |
| ATC ACT AGC CTT ACA GGC CGG GAC AAG AAC CAG GTC GAG GGA GAG GTT<br>Ile Thr Ser Leu Thr Gly Arg Asp Lys Asn Gln Val Glu Gly Glu Val<br>       35                     40                     45 | | 144 |
| CAG GTG GTT TCC ACC GCA ACA CAA TCC TTC CTG GCG ACC TGC GTC AAC<br>Gln Val Val Ser Thr Ala Thr Gln Ser Phe Leu Ala Thr Cys Val Asn<br>50                       55                     60 | | 192 |
| GGC GTG TGT TGG ACC GTT TAC CAT GGT GCT GGC TCA AAG ACC TTA GCC<br>Gly Val Cys Trp Thr Val Tyr His Gly Ala Gly Ser Lys Thr Leu Ala<br>65                     70                     75                80 | | 240 |
| GGC CCA AAG GGG CCA ATC ACC CAG ATG TAC ACT AAT GTG GAC CAG GAC<br>Gly Pro Lys Gly Pro Ile Thr Gln Met Tyr Thr Asn Val Asp Gln Asp<br>                     85                     90                     95 | | 288 |
| CTC GTC GGC TGG CAG GCG CCC CCC GGG GCG CGT TCC TTG ACA CCA TGC<br>Leu Val Gly Trp Gln Ala Pro Pro Gly Ala Arg Ser Leu Thr Pro Cys<br>              100                       105                   110 | | 336 |
| ACC TGT GGC AGC TCA GAC CTT TAC TTG GTC ACG AGA CAT GCT GAC GTC<br>Thr Cys Gly Ser Ser Asp Leu Tyr Leu Val Thr Arg His Ala Asp Val<br>              115                       120                   125 | | 384 |
| ATT CCG GTG CGC CGG CGG GGC GAC AGT AGG GGG AGC CTG CTC TCC CCC<br>Ile Pro Val Arg Arg Arg Gly Asp Ser Arg Gly Ser Leu Leu Ser Pro<br>130                      135                     140 | | 432 |
| AGG CCT GTC TCC TAC TTG AAG GGC TCT TCG GGT GGT CCA CTG CTC TGC<br>Arg Pro Val Ser Tyr Leu Lys Gly Ser Ser Gly Gly Pro Leu Leu Cys<br>145                     150                     155                160 | | 480 |
| CCT TCG GGG CAC GCT GTG GGC ATC TTC CGG GCT GCC GTA TGC ACC CGG<br>Pro Ser Gly His Ala Val Gly Ile Phe Arg Ala Ala Val Cys Thr Arg<br>              165                       170                   175 | | 528 |
| GGG GTT GCG AAG GCG GTG GAC TTT GTG CCC GTA GAG TCC ATG GAA ACT<br>Gly Val Ala Lys Ala Val Asp Phe Val Pro Val Glu Ser Met Glu Thr<br>              180                       185                   190 | | 576 |
| ACT ATG CGG TCT CCG GTC TTC ACG GAC AAC TCA TCC CCC CCG GCC GTA<br>Thr Met Arg Ser Pro Val Phe Thr Asp Asn Ser Ser Pro Pro Ala Val<br>              195                       200                   205 | | 624 |
| CCG CAG TCA TTT CAA GTG GCC CAC CTA CAC GCT CCC ACT GGC AGC GGC<br>Pro Gln Ser Phe Gln Val Ala His Leu His Ala Pro Thr Gly Ser Gly<br>210                     215                     220 | | 672 |
| AAG AGT ACT AAA GTG CCG GCT GCA TAT GCA GCC CAA GGG TAC AAG GTG<br>Lys Ser Thr Lys Val Pro Ala Ala Tyr Ala Ala Gln Gly Tyr Lys Val<br>225                     230                     235                240 | | 720 |
| CTC GTC CTC AAT CCG TCC GTT GCC GCT ACC TTA GGG TTT GGG GCG TAT<br>Leu Val Leu Asn Pro Ser Val Ala Ala Thr Leu Gly Phe Gly Ala Tyr<br>              245                       250                   255 | | 768 |
| ATG TCT AAG GCA CAC GGT ATT GAC CCC AAC ATC AGA ACT GGG GTA AGG<br>Met Ser Lys Ala His Gly Ile Asp Pro Asn Ile Arg Thr Gly Val Arg<br>              260                       265                   270 | | 816 |
| ACC ATT ACC ACA GGC GCC CCC GTC ACA TAC TCT ACC TAT GGC AAG TTT<br>Thr Ile Thr Thr Gly Ala Pro Val Thr Tyr Ser Thr Tyr Gly Lys Phe<br>              275                       280                   285 | | 864 |
| CTT GCC GAT GGT GGT TGC TCT GGG GGC GCT TAT GAC ATC ATA ATA TGT<br>Leu Ala Asp Gly Gly Cys Ser Gly Gly Ala Tyr Asp Ile Ile Ile Cys<br>290                     295                     300 | | 912 |
| GAT GAG TGC CAT TCA ACT GAC TCG ACT ACA ATC TTG GGC ATC GGC ACA<br>Asp Glu Cys His Ser Thr Asp Ser Thr Thr Ile Leu Gly Ile Gly Thr<br>305                     310                     315                320 | | 960 |
| GTC CTG GAC CAA GCG GAG ACG GCT GGA GCG CGG CTT GTC GTG CTC GCC<br>Val Leu Asp Gln Ala Glu Thr Ala Gly Ala Arg Leu Val Val Leu Ala<br>              325                       330                   335 | | 1008 |

```
ACC GCT ACG CCT CCG GGA TCG GTC ACC GTG CCA CAC CCA AAC ATC GAG      1056
Thr Ala Thr Pro Pro Gly Ser Val Thr Val Pro His Pro Asn Ile Glu
        340                 345                 350

GAG GTG GCC CTG TCT AAT ACT GGA GAG ATC CCC TTC TAT GGC AAA GCC      1104
Glu Val Ala Leu Ser Asn Thr Gly Glu Ile Pro Phe Tyr Gly Lys Ala
        355                 360                 365

ATC CCC ATT GAA GCC ATC AGG GGG GGA AGG CAT CTC ATT TTC TGT CAT      1152
Ile Pro Ile Glu Ala Ile Arg Gly Gly Arg His Leu Ile Phe Cys His
    370                 375                 380

TCC AAG AAG AAG TGC GAC GAG CTC GCC GCA AAG CTG TCA GGC CTC GGA      1200
Ser Lys Lys Lys Cys Asp Glu Leu Ala Ala Lys Leu Ser Gly Leu Gly
385                 390                 395                 400

ATC AAC GCT GTG GCG TAT TAC CGG GGG CTC GAT GTG TCC GTC ATA CCA      1248
Ile Asn Ala Val Ala Tyr Tyr Arg Gly Leu Asp Val Ser Val Ile Pro
                405                 410                 415

ACT ATC GGA GAC GTC GTT GTC GTG GCA ACA GAC GCT CTG ATG ACG GGC      1296
Thr Ile Gly Asp Val Val Val Val Ala Thr Asp Ala Leu Met Thr Gly
            420                 425                 430

TAT ACG GGC GAC TTT GAC TCA GTG ATC GAC TGT AAC ACA TGT GTC ACC      1344
Tyr Thr Gly Asp Phe Asp Ser Val Ile Asp Cys Asn Thr Cys Val Thr
        435                 440                 445

CAG ACA GTC GAC TTC AGC TTG GAT CCC ACC TTC ACC ATT GAG ACG ACG      1392
Gln Thr Val Asp Phe Ser Leu Asp Pro Thr Phe Thr Ile Glu Thr Thr
    450                 455                 460

ACC GTG CCT CAA GAC GCA GTG TCG CGC TCG CAG CGG CGG GGT AGG ACT      1440
Thr Val Pro Gln Asp Ala Val Ser Arg Ser Gln Arg Arg Gly Arg Thr
465                 470                 475                 480

GGC AGG GGT AGG AGA GGC ATC TAC AGG TTT GTG ACT CCG GGA GAA CGG      1488
Gly Arg Gly Arg Arg Gly Ile Tyr Arg Phe Val Thr Pro Gly Glu Arg
                485                 490                 495

CCC TCG GGC ATG TTC GAT TCC TCG GTC CTG TGT GAG TGC TAT GAC GCG      1536
Pro Ser Gly Met Phe Asp Ser Ser Val Leu Cys Glu Cys Tyr Asp Ala
            500                 505                 510

GGC TGT GCT TGG TAC GAG CTC ACC CCC GCC GAG ACC TCG GTT AGG TTG      1584
Gly Cys Ala Trp Tyr Glu Leu Thr Pro Ala Glu Thr Ser Val Arg Leu
        515                 520                 525

CGG GCC TAC CTG AAC ACA CCA GGG TTG CCC GTT TGC CAG GAC CAC CTG      1632
Arg Ala Tyr Leu Asn Thr Pro Gly Leu Pro Val Cys Gln Asp His Leu
    530                 535                 540

GAG TTC TGG GAG AGT GTC TTC ACA GGC CTC ACC CAT ATA GAT GCA CAC      1680
Glu Phe Trp Glu Ser Val Phe Thr Gly Leu Thr His Ile Asp Ala His
545                 550                 555                 560

TTC TTG TCC CAG ACC AAG CAG GCA GGA GAC AAC TTC CCC TAC CTG GTA      1728
Phe Leu Ser Gln Thr Lys Gln Ala Gly Asp Asn Phe Pro Tyr Leu Val
                565                 570                 575

GCA TAC CAA GCC ACG GTG TGC GCC AGG GCT CAG GCC CCA CCT CCA TCA      1776
Ala Tyr Gln Ala Thr Val Cys Ala Arg Ala Gln Ala Pro Pro Pro Ser
            580                 585                 590

TGG GAT CAA ATG TGG AAG TGT CTC ATA CGG CTG AAA CCT ACG CTG CAC      1824
Trp Asp Gln Met Trp Lys Cys Leu Ile Arg Leu Lys Pro Thr Leu His
        595                 600                 605

GGG CCA ACA CCC TTG CTG TAC AGG CTG GGA GCC GTC CAA AAT GAG GTC      1872
Gly Pro Thr Pro Leu Leu Tyr Arg Leu Gly Ala Val Gln Asn Glu Val
    610                 615                 620

ACC CTC ACC CAC CCC ATA ACC AAA TAC ATC ATG GCA TGC ATG TCG GCC      1920
Thr Leu Thr His Pro Ile Thr Lys Tyr Ile Met Ala Cys Met Ser Ala
625                 630                 635                 640

GAC CTG GAG GTC GTT ACG TAG                                          1941
Asp Leu Glu Val Val Thr
            645
```

(2) INFORMATION FOR SEQ ID NO:117:

(i) SEQUENCE CHARACTERISTICS:
        (A) LENGTH: 1941 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..1941

(xi) SEQUENCE DESCRIPTION: SEQ ID NO:117:

```
ATG CAT ATG CAT CAT CAT CAC CAT CAT CTG GTG CCG CGC GGC AGC GCG      48
Met His Met His His His His His His Leu Val Pro Arg Gly Ser Ala
  1               5                  10                  15

CCC ATC ACG GCC TAC TCC CAA CAG ACG CGG GGC CTA CTT GGT TGC ATC      96
Pro Ile Thr Ala Tyr Ser Gln Gln Thr Arg Gly Leu Leu Gly Cys Ile
             20                  25                  30

AAG ACT AGC CTT ACA GGC CGG GAC AAG AAC CAG GTC GAG GGA GAG GTT     144
Lys Thr Ser Leu Thr Gly Arg Asp Lys Asn Gln Val Glu Gly Glu Val
         35                  40                  45

CAG GTG GTT TCC ACC GCA ACA CAA TCC TTC CTG GCG ACC TGC GTC AAC     192
Gln Val Val Ser Thr Ala Thr Gln Ser Phe Leu Ala Thr Cys Val Asn
     50                  55                  60

GGC GTG TGT TGG ACC GTT TAC CAT GGT GCT GGC TCA AAG ACC TTA GCC     240
Gly Val Cys Trp Thr Val Tyr His Gly Ala Gly Ser Lys Thr Leu Ala
 65                  70                  75                  80

GGC CCA AAG GGG CCA ATC ACC CAG ATG TAC ACT AAT GTG GAC CAG GAC     288
Gly Pro Lys Gly Pro Ile Thr Gln Met Tyr Thr Asn Val Asp Gln Asp
                 85                  90                  95

CTC GTC GGC TGG CAG GCG CCC CCC GGG GCG CGT TCC TTG ACA CCA TGC     336
Leu Val Gly Trp Gln Ala Pro Pro Gly Ala Arg Ser Leu Thr Pro Cys
            100                 105                 110

ACC TGT GGC AGC TCA GAC CTT TAC TTG GTC ACG AGA CAT GCT GAC GTC     384
Thr Cys Gly Ser Ser Asp Leu Tyr Leu Val Thr Arg His Ala Asp Val
        115                 120                 125

ATT CCG GTG CGC CGG CGG GGC GAC AGT AGG GGG AGC CTG CTC TCC CCC     432
Ile Pro Val Arg Arg Arg Gly Asp Ser Arg Gly Ser Leu Leu Ser Pro
    130                 135                 140

AGG CCT GTC TCC TAC TTG AAG GGC TCT TCG GGT GGT CCA CTG CTC TGC     480
Arg Pro Val Ser Tyr Leu Lys Gly Ser Ser Gly Gly Pro Leu Leu Cys
145                 150                 155                 160

CCT TCG GGG CAC GCT GTG GGC ATC TTC CGG GCT GCC GTA TGC ACC CGG     528
Pro Ser Gly His Ala Val Gly Ile Phe Arg Ala Ala Val Cys Thr Arg
                165                 170                 175

GGG GTT GCG AAG GCG GTG GAC TTT GTG CCC GTA GAG TCC ATG GAA ACT     576
Gly Val Ala Lys Ala Val Asp Phe Val Pro Val Glu Ser Met Glu Thr
            180                 185                 190

ACT ATG CGG TCT CCG GTC TTC ACG GAC AAC TCA TCC CCC CCG GCC GTA     624
Thr Met Arg Ser Pro Val Phe Thr Asp Asn Ser Ser Pro Pro Ala Val
        195                 200                 205

CCG CAG TCA TTT CAA GTG GCC CAC CTA CAC GCT CCC ACT GGC AGC GGC     672
Pro Gln Ser Phe Gln Val Ala His Leu His Ala Pro Thr Gly Ser Gly
    210                 215                 220

AAG AGT ACT AAA GTG CCG GCT GCA TAT GCA GCC CAA GGG TAC AAG GTG     720
Lys Ser Thr Lys Val Pro Ala Ala Tyr Ala Ala Gln Gly Tyr Lys Val
225                 230                 235                 240

CTC GTC CTC AAT CCG TCC GTT GCC GCT ACC TTA GGG TTT GGG GCG TAT     768
Leu Val Leu Asn Pro Ser Val Ala Ala Thr Leu Gly Phe Gly Ala Tyr
                245                 250                 255
```

```
ATG TCT AAG GCA CAC GGT ATT GAC CCC AAC ATC AGA ACT GGG GTA AGG         816
Met Ser Lys Ala His Gly Ile Asp Pro Asn Ile Arg Thr Gly Val Arg
        260                 265                 270

ACC ATT ACC ACA GGC GCC CCC GTC ACA TAC TCT ACC TAT GGC AAG TTT         864
Thr Ile Thr Thr Gly Ala Pro Val Thr Tyr Ser Thr Tyr Gly Lys Phe
            275                 280                 285

CTT GCC GAT GGT GGT TGC TCT GGG GGC GCT TAT GAC ATC ATA ATA TGT         912
Leu Ala Asp Gly Gly Cys Ser Gly Gly Ala Tyr Asp Ile Ile Ile Cys
        290                 295                 300

GAT GAG TGC CAT TCA ACT GAC TCG ACT ACA ATC TTG GGC ATC GGC ACA         960
Asp Glu Cys His Ser Thr Asp Ser Thr Thr Ile Leu Gly Ile Gly Thr
305                 310                 315                 320

GTC CTG GAC CAA GCG GAG ACG GCT GGA GCG CGG CTT GTC GTG CTC GCC        1008
Val Leu Asp Gln Ala Glu Thr Ala Gly Ala Arg Leu Val Val Leu Ala
                325                 330                 335

ACC GCT ACG CCT CCG GGA TCG GTC ACC GTG CCA CAC CCA AAC ATC GAG        1056
Thr Ala Thr Pro Pro Gly Ser Val Thr Val Pro His Pro Asn Ile Glu
            340                 345                 350

GAG GTG GCC CTG TCT AAT ACT GGA GAG ATC CCC TTC TAT GGC AAA GCC        1104
Glu Val Ala Leu Ser Asn Thr Gly Glu Ile Pro Phe Tyr Gly Lys Ala
        355                 360                 365

ATC CCC ATT GAA GCC ATC AGG GGG GGA AGG CAT CTC ATT TTC TGT CAT        1152
Ile Pro Ile Glu Ala Ile Arg Gly Gly Arg His Leu Ile Phe Cys His
370                 375                 380

TCC AAG AAG AAG TGC GAC GAG CTC GCC GCA AAG CTG TCA GGC CTC GGA        1200
Ser Lys Lys Lys Cys Asp Glu Leu Ala Ala Lys Leu Ser Gly Leu Gly
385                 390                 395                 400

ATC AAC GCT GTG GCG TAT TAC CGG GGG CTC GAT GTG TCC GTC ATA CCA        1248
Ile Asn Ala Val Ala Tyr Tyr Arg Gly Leu Asp Val Ser Val Ile Pro
                405                 410                 415

ACT ATC GGA GAC GTC GTT GTC GTG GCA ACA GAC GCT CTG ATG ACG GGC        1296
Thr Ile Gly Asp Val Val Val Val Ala Thr Asp Ala Leu Met Thr Gly
            420                 425                 430

TAT ACG GGC GAC TTT GAC TCA GTG ATC GAC TGT AAC ACA TGT GTC ACC        1344
Tyr Thr Gly Asp Phe Asp Ser Val Ile Asp Cys Asn Thr Cys Val Thr
        435                 440                 445

CAG ACA GTC GAC TTC AGC TTG GAT CCC ACC TTC ACC ATT GAG ACG ACG        1392
Gln Thr Val Asp Phe Ser Leu Asp Pro Thr Phe Thr Ile Glu Thr Thr
450                 455                 460

ACC GTG CCT CAA GAC GCA GTG TCG CGC TCG CAG CGG CGG GGT AGG ACT        1440
Thr Val Pro Gln Asp Ala Val Ser Arg Ser Gln Arg Arg Gly Arg Thr
465                 470                 475                 480

GGC AGG GGT AGG AGA GGC ATC TAC AGG TTT GTG ACT CCG GGA GAA CGG        1488
Gly Arg Gly Arg Arg Gly Ile Tyr Arg Phe Val Thr Pro Gly Glu Arg
                485                 490                 495

CCC TCG GGC ATG TTC GAT TCC TCG GTC CTG TGT GAG TGC TAT GAC GCG        1536
Pro Ser Gly Met Phe Asp Ser Ser Val Leu Cys Glu Cys Tyr Asp Ala
            500                 505                 510

GGC TGT GCT TGG TAC GAG CTC ACC CCC GCC GAG ACC TCG GTT AGG TTG        1584
Gly Cys Ala Trp Tyr Glu Leu Thr Pro Ala Glu Thr Ser Val Arg Leu
        515                 520                 525

CGG GCC TAC CTG AAC ACA CCA GGG TTG CCC GTT TGC CAG GAC CAC CTG        1632
Arg Ala Tyr Leu Asn Thr Pro Gly Leu Pro Val Cys Gln Asp His Leu
        530                 535                 540

GAG TTC TGG GAG AGT GTC TTC ACA GGC CTC ACC CAT ATA GAT GCA CAC        1680
Glu Phe Trp Glu Ser Val Phe Thr Gly Leu Thr His Ile Asp Ala His
545                 550                 555                 560

TTC TTG TCC CAG ACC AAG CAG GCA GGA GAC AAC TTC CCC TAC CTG GTA        1728
Phe Leu Ser Gln Thr Lys Gln Ala Gly Asp Asn Phe Pro Tyr Leu Val
                565                 570                 575
```

```
GCA TAC CAA GCC ACG GTG TGC GCC AGG GCT CAG GCC CCA CCT CCA TCA    1776
Ala Tyr Gln Ala Thr Val Cys Ala Arg Ala Gln Ala Pro Pro Pro Ser
            580                 585                 590

TGG GAT CAA ATG TGG AAG TGT CTC ATA CGG CTG AAA CCT ACG CTG CAC    1824
Trp Asp Gln Met Trp Lys Cys Leu Ile Arg Leu Lys Pro Thr Leu His
            595                 600                 605

GGG CCA ACA CCC TTG CTG TAC AGG CTG GGA GCC GTC CAA AAT GAG GTC    1872
Gly Pro Thr Pro Leu Leu Tyr Arg Leu Gly Ala Val Gln Asn Glu Val
    610                 615                 620

ACC CTC ACC CAC CCC ATA ACC AAA TAC ATC ATG GCA TGC ATG TCG GCC    1920
Thr Leu Thr His Pro Ile Thr Lys Tyr Ile Met Ala Cys Met Ser Ala
625                 630                 635                 640

GAC CTG GAG GTC GTT ACG TAG                                        1941
Asp Leu Glu Val Val Thr
                645
```

(2) INFORMATION FOR SEQ ID NO:118:

(i) SEQUENCE CHARACTERISTICS:
        (A) LENGTH: 1941 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..1941

(xi) SEQUENCE DESCRIPTION: SEQ ID NO:118:

```
ATG CAT ATG CAT CAT CAT CAC CAT CAT CTG GTG CCG CGC GGC AGC GCG     48
Met His Met His His His His His His Leu Val Pro Arg Gly Ser Ala
1               5                   10                  15

CCC ATC ACG GCC TAC TCC CAA CAG ACG CGG GGC CTA CTT GGT TGC ATC     96
Pro Ile Thr Ala Tyr Ser Gln Gln Thr Arg Gly Leu Leu Gly Cys Ile
                20                  25                  30

ATC ACT AGC CTT ACA GGC CGG GAC AAG AAC CAG GTC GAG GGA GAG GTT    144
Ile Thr Ser Leu Thr Gly Arg Asp Lys Asn Gln Val Glu Gly Glu Val
        35                  40                  45

CAG GTG GTT TCC ACC GCA ACA CAA TCC TTC CTG GCG ACC TGC GTC AAC    192
Gln Val Val Ser Thr Ala Thr Gln Ser Phe Leu Ala Thr Cys Val Asn
    50                  55                  60

GGC GTG TGT TGG ACC GTT TAC CAT GGT GCT GGC TCA AAG ACC TTA GCC    240
Gly Val Cys Trp Thr Val Tyr His Gly Ala Gly Ser Lys Thr Leu Ala
65                  70                  75                  80

GGC CCA AAG GGG CCA ATC ACC CAG ATG TAC ACT AAT GTG GAC CAG GAC    288
Gly Pro Lys Gly Pro Ile Thr Gln Met Tyr Thr Asn Val Asp Gln Asp
                85                  90                  95

CTC GTC GGC TGG CAG GCG CCC CCC GGG GCG CGT TCC TTG ACA CCA TGC    336
Leu Val Gly Trp Gln Ala Pro Pro Gly Ala Arg Ser Leu Thr Pro Cys
            100                 105                 110

ACC TGT GGC AGC TCA GAC CTT TAC TTG GTC ACG AGA CAT GCT GAC GTC    384
Thr Cys Gly Ser Ser Asp Leu Tyr Leu Val Thr Arg His Ala Asp Val
        115                 120                 125

ATT CCG GTG CGC CGG CGG GGC GAC AGT AGG GGG AGC CTG CTC TCC CCC    432
Ile Pro Val Arg Arg Arg Gly Asp Ser Arg Gly Ser Leu Leu Ser Pro
    130                 135                 140

AGG CCT GTC TCC TAC TTG AAG GGC TCT GCT GGT GGT CCA CTG CTC TGC    480
Arg Pro Val Ser Tyr Leu Lys Gly Ser Ala Gly Gly Pro Leu Leu Cys
145                 150                 155                 160
```

```
CCT TCG GGG CAC GCT GTG GGC ATC TTC CGG GCT GCC GTA TGC ACC CGG      528
Pro Ser Gly His Ala Val Gly Ile Phe Arg Ala Ala Val Cys Thr Arg
            165                 170                 175

GGG GTT GCG AAG GCG GTG GAC TTT GTG CCC GTA GAG TCC ATG GAA ACT      576
Gly Val Ala Lys Ala Val Asp Phe Val Pro Val Glu Ser Met Glu Thr
        180                 185                 190

ACT ATG CGG TCT CCG GTC TTC ACG GAC AAC TCA TCC CCC CCG GCC GTA      624
Thr Met Arg Ser Pro Val Phe Thr Asp Asn Ser Ser Pro Pro Ala Val
    195                 200                 205

CCG CAG TCA TTT CAA GTG GCC CAC CTA CAC GCT CCC ACT GGC AGC GGC      672
Pro Gln Ser Phe Gln Val Ala His Leu His Ala Pro Thr Gly Ser Gly
210                 215                 220

AAG AGT ACT AAA GTG CCG GCT GCA TAT GCA GCC CAA GGG TAC AAG GTG      720
Lys Ser Thr Lys Val Pro Ala Ala Tyr Ala Ala Gln Gly Tyr Lys Val
225                 230                 235                 240

CTC GTC CTC AAT CCG TCC GTT GCC GCT ACC TTA GGG TTT GGG GCG TAT      768
Leu Val Leu Asn Pro Ser Val Ala Ala Thr Leu Gly Phe Gly Ala Tyr
                245                 250                 255

ATG TCT AAG GCA CAC GGT ATT GAC CCC AAC ATC AGA ACT GGG GTA AGG      816
Met Ser Lys Ala His Gly Ile Asp Pro Asn Ile Arg Thr Gly Val Arg
            260                 265                 270

ACC ATT ACC ACA GGC GCC CCC GTC ACA TAC TCT ACC TAT GGC AAG TTT      864
Thr Ile Thr Thr Gly Ala Pro Val Thr Tyr Ser Thr Tyr Gly Lys Phe
        275                 280                 285

CTT GCC GAT GGT GGT TGC TCT GGG GGC GCT TAT GAC ATC ATA ATA TGT      912
Leu Ala Asp Gly Gly Cys Ser Gly Gly Ala Tyr Asp Ile Ile Ile Cys
    290                 295                 300

GAT GAG TGC CAT TCA ACT GAC TCG ACT ACA ATC TTG GGC ATC GGC ACA      960
Asp Glu Cys His Ser Thr Asp Ser Thr Thr Ile Leu Gly Ile Gly Thr
305                 310                 315                 320

GTC CTG GAC CAA GCG GAG ACG GCT GGA GCG CGG CTT GTC GTG CTC GCC     1008
Val Leu Asp Gln Ala Glu Thr Ala Gly Ala Arg Leu Val Val Leu Ala
                325                 330                 335

ACC GCT ACG CCT CCG GGA TCG GTC ACC GTG CCA CAC CCA AAC ATC GAG     1056
Thr Ala Thr Pro Pro Gly Ser Val Thr Val Pro His Pro Asn Ile Glu
            340                 345                 350

GAG GTG GCC CTG TCT AAT ACT GGA GAG ATC CCC TTC TAT GGC AAA GCC     1104
Glu Val Ala Leu Ser Asn Thr Gly Glu Ile Pro Phe Tyr Gly Lys Ala
        355                 360                 365

ATC CCC ATT GAA GCC ATC AGG GGG GGA AGG CAT CTC ATT TTC TGT CAT     1152
Ile Pro Ile Glu Ala Ile Arg Gly Gly Arg His Leu Ile Phe Cys His
    370                 375                 380

TCC AAG AAG AAG TGC GAC GAG CTC GCC GCA AAG CTG TCA GGC CTC GGA     1200
Ser Lys Lys Lys Cys Asp Glu Leu Ala Ala Lys Leu Ser Gly Leu Gly
385                 390                 395                 400

ATC AAC GCT GTG GCG TAT TAC CGG GGG CTC GAT GTG TCC GTC ATA CCA     1248
Ile Asn Ala Val Ala Tyr Tyr Arg Gly Leu Asp Val Ser Val Ile Pro
                405                 410                 415

ACT ATC GGA GAC GTC GTT GTC GTG GCA ACA GAC GCT CTG ATG ACG GGC     1296
Thr Ile Gly Asp Val Val Val Val Ala Thr Asp Ala Leu Met Thr Gly
            420                 425                 430

TAT ACG GGC GAC TTT GAC TCA GTG ATC GAC TGT AAC ACA TGT GTC ACC     1344
Tyr Thr Gly Asp Phe Asp Ser Val Ile Asp Cys Asn Thr Cys Val Thr
        435                 440                 445

CAG ACA GTC GAC TTC AGC TTG GAT CCC ACC TTC ACC ATT GAG ACG ACG     1392
Gln Thr Val Asp Phe Ser Leu Asp Pro Thr Phe Thr Ile Glu Thr Thr
    450                 455                 460

ACC GTG CCT CAA GAC GCA GTG TCG CGC TCG CAG CGG CGG GGT AGG ACT     1440
Thr Val Pro Gln Asp Ala Val Ser Arg Ser Gln Arg Arg Gly Arg Thr
465                 470                 475                 480
```

```
GGC AGG GGT AGG AGA GGC ATC TAC AGG TTT GTG ACT CCG GGA GAA CGG      1488
Gly Arg Gly Arg Arg Gly Ile Tyr Arg Phe Val Thr Pro Gly Glu Arg
            485                 490                 495

CCC TCG GGC ATG TTC GAT TCC TCG GTC CTG TGT GAG TGC TAT GAC GCG      1536
Pro Ser Gly Met Phe Asp Ser Ser Val Leu Cys Glu Cys Tyr Asp Ala
        500                 505                 510

GGC TGT GCT TGG TAC GAG CTC ACC CCC GCC GAG ACC TCG GTT AGG TTG      1584
Gly Cys Ala Trp Tyr Glu Leu Thr Pro Ala Glu Thr Ser Val Arg Leu
            515                 520                 525

CGG GCC TAC CTG AAC ACA CCA GGG TTG CCC GTT TGC CAG GAC CAC CTG      1632
Arg Ala Tyr Leu Asn Thr Pro Gly Leu Pro Val Cys Gln Asp His Leu
        530                 535                 540

GAG TTC TGG GAG AGT GTC TTC ACA GGC CTC ACC CAT ATA GAT GCA CAC      1680
Glu Phe Trp Glu Ser Val Phe Thr Gly Leu Thr His Ile Asp Ala His
545                 550                 555                 560

TTC TTG TCC CAG ACC AAG CAG GCA GGA GAC AAC TTC CCC TAC CTG GTA      1728
Phe Leu Ser Gln Thr Lys Gln Ala Gly Asp Asn Phe Pro Tyr Leu Val
            565                 570                 575

GCA TAC CAA GCC ACG GTG TGC GCC AGG GCT CAG GCC CCA CCT CCA TCA      1776
Ala Tyr Gln Ala Thr Val Cys Ala Arg Ala Gln Ala Pro Pro Pro Ser
        580                 585                 590

TGG GAT CAA ATG TGG AAG TGT CTC ATA CGG CTG AAA CCT ACG CTG CAC      1824
Trp Asp Gln Met Trp Lys Cys Leu Ile Arg Leu Lys Pro Thr Leu His
            595                 600                 605

GGG CCA ACA CCC TTG CTG TAC AGG CTG GGA GCC GTC CAA AAT GAG GTC      1872
Gly Pro Thr Pro Leu Leu Tyr Arg Leu Gly Ala Val Gln Asn Glu Val
        610                 615                 620

ACC CTC ACC CAC CCC ATA ACC AAA TAC ATC ATG GCA TGC ATG TCG GCC      1920
Thr Leu Thr His Pro Ile Thr Lys Tyr Ile Met Ala Cys Met Ser Ala
625                 630                 635                 640

GAC CTG GAG GTC GTT ACG TAG                                          1941
Asp Leu Glu Val Val Thr
            645

(2) INFORMATION FOR SEQ ID NO:119:

(i) SEQUENCE CHARACTERISTICS:
        (A) LENGTH: 1941 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..1941

(xi) SEQUENCE DESCRIPTION: SEQ ID NO:119:

ATG CAT ATG CAT CAT CAT CAC CAT CAT CTG GTG CCG CGC GGC AGC GCG       48
Met His Met His His His His His His Leu Val Pro Arg Gly Ser Ala
  1               5                  10                  15

CCC ATC ACG GCC TAC TCC CAA CAG ACG CGG GGC CTA CTT GGT TGC ATC       96
Pro Ile Thr Ala Tyr Ser Gln Gln Thr Arg Gly Leu Leu Gly Cys Ile
             20                  25                  30

ATC ACT AGC CTT ACA GGC CGG GAC AAG AAC CAG GTC GAG GGA GAG GTT      144
Ile Thr Ser Leu Thr Gly Arg Asp Lys Asn Gln Val Glu Gly Glu Val
         35                  40                  45

CAG GTG GTT TCC ACC GCA ACA CAA TCC TTC CTG GCG ACC TGC GTC AAC      192
Gln Val Val Ser Thr Ala Thr Gln Ser Phe Leu Ala Thr Cys Val Asn
     50                  55                  60
```

-continued

```
GGC GTG TGT TGG ACC GTT TAC CAT GGT GCT GGC TCA AAG ACC TTA GCC      240
Gly Val Cys Trp Thr Val Tyr His Gly Ala Gly Ser Lys Thr Leu Ala
 65              70                  75                  80

GGC CCA AAG GGG CCA ATC ACC CAG ATG TAC ACT AAT GTG GAC CAG GAC      288
Gly Pro Lys Gly Pro Ile Thr Gln Met Tyr Thr Asn Val Asp Gln Asp
                 85                  90                  95

CTC GTC GGC TGG CAG GCG CCC CCC GGG GCG CGT TCC TTG ACA CCA TGC      336
Leu Val Gly Trp Gln Ala Pro Pro Gly Ala Arg Ser Leu Thr Pro Cys
            100                 105                 110

ACC TGT GGC AGC TCA GAC CTT TAC TTG GTC ACG AGA CAT GCT GAC GTC      384
Thr Cys Gly Ser Ser Asp Leu Tyr Leu Val Thr Arg His Ala Asp Val
        115                 120                 125

ATT CCG GTG CGC CGG CGG GGC GAC AGT AGG GGG AGC CTG CTC TCC CCC      432
Ile Pro Val Arg Arg Arg Gly Asp Ser Arg Gly Ser Leu Leu Ser Pro
    130                 135                 140

AGG CCT GTC TCC TAC TTG AAG GGC TCT TCG GGT GGT CCA CTG CTC TGC      480
Arg Pro Val Ser Tyr Leu Lys Gly Ser Ser Gly Gly Pro Leu Leu Cys
145                 150                 155                 160

CCT TCG GGG CAC GCT GTG GGC ATC TTC CGG GCT GCC GTA TGC ACC CGG      528
Pro Ser Gly His Ala Val Gly Ile Phe Arg Ala Ala Val Cys Thr Arg
                165                 170                 175

GGG GTT GCG AAG GCG GTG GAC TTT GTG CCC GTA GAG TCC ATG GAA ACT      576
Gly Val Ala Lys Ala Val Asp Phe Val Pro Val Glu Ser Met Glu Thr
            180                 185                 190

ACT ATG CGG TCT CCG GTC TTC ACG GAC AAC TCA TCC CCC CCG GCC GTA      624
Thr Met Arg Ser Pro Val Phe Thr Asp Asn Ser Ser Pro Pro Ala Val
        195                 200                 205

CCG CAG TCA TTT CAA GTG GCC CAC CTA CAC GCT CCC ACT GGC AGC GGC      672
Pro Gln Ser Phe Gln Val Ala His Leu His Ala Pro Thr Gly Ser Gly
    210                 215                 220

AAG AGT ACT AAA GTG CCG GCT GCA TAT GCA GCC CAA GGG TAC AAG GTG      720
Lys Ser Thr Lys Val Pro Ala Ala Tyr Ala Ala Gln Gly Tyr Lys Val
225                 230                 235                 240

CTC GTC CTC AAT CCG TCC GTT GCC GCT ACC TTA GGG TTT GGG GCG TAT      768
Leu Val Leu Asn Pro Ser Val Ala Ala Thr Leu Gly Phe Gly Ala Tyr
                245                 250                 255

ATG TCT AAG GCA CAC GGT ATT GAC CCC AAC ATC AGA ACT GGG GTA AGG      816
Met Ser Lys Ala His Gly Ile Asp Pro Asn Ile Arg Thr Gly Val Arg
            260                 265                 270

ACC ATT ACC ACA GGC GCC CCC GTC ACA TAC TCT ACC TAT GGC AAG TTT      864
Thr Ile Thr Thr Gly Ala Pro Val Thr Tyr Ser Thr Tyr Gly Lys Phe
        275                 280                 285

CTT GCC GAT GGT GGT TGC TCT GGG GGC GCT TAT GAC ATC ATA ATA TGT      912
Leu Ala Asp Gly Gly Cys Ser Gly Gly Ala Tyr Asp Ile Ile Ile Cys
    290                 295                 300

GAT GAG TGC CAT TCA ACT GAC TCG ACT ACA ATC TTG GGC ATC GGC ACA      960
Asp Glu Cys His Ser Thr Asp Ser Thr Thr Ile Leu Gly Ile Gly Thr
305                 310                 315                 320

GTC CTG GAC CAA GCG GAG ACG GCT GGA GCG CGG CTT GTC GTG CTC GCC     1008
Val Leu Asp Gln Ala Glu Thr Ala Gly Ala Arg Leu Val Val Leu Ala
                325                 330                 335

ACC GCT ACG CCT CCG GGA TCG GTC ACC GTG CCA CAC CCA AAC ATC GAG     1056
Thr Ala Thr Pro Pro Gly Ser Val Thr Val Pro His Pro Asn Ile Glu
            340                 345                 350

GAG GTG GCC CTG TCT AAT ACT GGA GAG ATC CCC TTC TAT GGC AAA GCC     1104
Glu Val Ala Leu Ser Asn Thr Gly Glu Ile Pro Phe Tyr Gly Lys Ala
        355                 360                 365

ATC CCC ATT GAA GCC ATC AGG GGG GGA AGG CAT CTC ATT TTC TGT CAT     1152
Ile Pro Ile Glu Ala Ile Arg Gly Gly Arg His Leu Ile Phe Cys His
    370                 375                 380
```

```
TCC AAG AAG AAG TGC GAC GAG CTC GCC GCA AAG CTG TCA GGC CTC GGA      1200
Ser Lys Lys Lys Cys Asp Glu Leu Ala Ala Lys Leu Ser Gly Leu Gly
385                 390                 395                 400

ATC AAC GCT GTG GCG TAT TAC CGG GGG CTC GAT GTG TCC GTC ATA CCA      1248
Ile Asn Ala Val Ala Tyr Tyr Arg Gly Leu Asp Val Ser Val Ile Pro
                405                 410                 415

ACT TCC GGA GAC GTC GTT GTC GTG GCA ACA GAC GCT CTG ATG ACG GGC      1296
Thr Ser Gly Asp Val Val Val Val Ala Thr Asp Ala Leu Met Thr Gly
            420                 425                 430

TAT ACG GGC GAC TTT GAC TCA GTG ATC GAC TGT AAC ACA TGT GTC ACC      1344
Tyr Thr Gly Asp Phe Asp Ser Val Ile Asp Cys Asn Thr Cys Val Thr
        435                 440                 445

CAG ACA GTC GAC TTC AGC TTG GAT CCC ACC TTC ACC ATT GAG ACG ACG      1392
Gln Thr Val Asp Phe Ser Leu Asp Pro Thr Phe Thr Ile Glu Thr Thr
    450                 455                 460

ACC GTG CCT CAA GAC GCA GTG TCG CGC TCG CAG CGG CGG GGT AGG ACT      1440
Thr Val Pro Gln Asp Ala Val Ser Arg Ser Gln Arg Arg Gly Arg Thr
465                 470                 475                 480

GGC AGG GGT AGG AGA GGC ATC TAC AGG TTT GTG ACT CCG GGA GAA CGG      1488
Gly Arg Gly Arg Arg Gly Ile Tyr Arg Phe Val Thr Pro Gly Glu Arg
                485                 490                 495

CCC TCG GGC ATG TTC GAT TCC TCG GTC CTG TGT GAG TGC TAT GAC GCG      1536
Pro Ser Gly Met Phe Asp Ser Ser Val Leu Cys Glu Cys Tyr Asp Ala
            500                 505                 510

GGC TGT GCT TGG TAC GAG CTC ACC CCC GCC GAG ACC TCG GTT AGG TTG      1584
Gly Cys Ala Trp Tyr Glu Leu Thr Pro Ala Glu Thr Ser Val Arg Leu
        515                 520                 525

CGG GCC TAC CTG AAC ACA CCA GGG TTG CCC GTT TGC CAG GAC CAC CTG      1632
Arg Ala Tyr Leu Asn Thr Pro Gly Leu Pro Val Cys Gln Asp His Leu
    530                 535                 540

GAG TTC TGG GAG AGT GTC TTC ACA GGC CTC ACC CAT ATA GAT GCA CAC      1680
Glu Phe Trp Glu Ser Val Phe Thr Gly Leu Thr His Ile Asp Ala His
545                 550                 555                 560

TTC TTG TCC CAG ACC AAG CAG GCA GGA GAC AAC TTC CCC TAC CTG GTA      1728
Phe Leu Ser Gln Thr Lys Gln Ala Gly Asp Asn Phe Pro Tyr Leu Val
                565                 570                 575

GCA TAC CAA GCC ACG GTG TGC GCC AGG GCT CAG GCC CCA CCT CCA TCA      1776
Ala Tyr Gln Ala Thr Val Cys Ala Arg Ala Gln Ala Pro Pro Pro Ser
            580                 585                 590

TGG GAT CAA ATG TGG AAG TGT CTC ATA CGG CTG AAA CCT ACG CTG CAC      1824
Trp Asp Gln Met Trp Lys Cys Leu Ile Arg Leu Lys Pro Thr Leu His
        595                 600                 605

GGG CCA ACA CCC TTG CTG TAC AGG CTG GGA GCC GTC CAA AAT GAG GTC      1872
Gly Pro Thr Pro Leu Leu Tyr Arg Leu Gly Ala Val Gln Asn Glu Val
    610                 615                 620

ACC CTC ACC CAC CCC ATA ACC AAA TAC ATC ATG GCA TGC ATG TCG GCC      1920
Thr Leu Thr His Pro Ile Thr Lys Tyr Ile Met Ala Cys Met Ser Ala
625                 630                 635                 640

GAC CTG GAG GTC GTT ACG TAG                                          1941
Asp Leu Glu Val Val Thr
                645
```

(2) INFORMATION FOR SEQ ID NO:120:

(i) SEQUENCE CHARACTERISTICS:
        (A) LENGTH: 1941 base pairs
        (B) TYPE: nucleic acid
        (C) STRANDEDNESS: single
        (D) TOPOLOGY: linear (ii) MOLECULE TYPE: cDNA (ix) FEATURE:
    (A) NAME/KEY: CDS
    (B) LOCATION: 1..1941

(xi) SEQUENCE DESCRIPTION: SEQ ID NO:120:

```
ATG CAT ATG CAT CAT CAT CAC CAT CAT CTG GTG CCG CGC GGC AGC GCG      48
Met His Met His His His His His His Leu Val Pro Arg Gly Ser Ala
 1               5                  10                  15

CCC ATC ACG GCC TAC TCC CAA CAG ACG CGG GGC CTA CTT GGT TGC ATC      96
Pro Ile Thr Ala Tyr Ser Gln Gln Thr Arg Gly Leu Leu Gly Cys Ile
             20                  25                  30

ATC ACT AGC CTT ACA GGC CGG GAC AAG AAC CAG GTC GAG GGA GAG GTT     144
Ile Thr Ser Leu Thr Gly Arg Asp Lys Asn Gln Val Glu Gly Glu Val
         35                  40                  45

CAG GTG GTT TCC ACC GCA ACA CAA TCC TTC CTG GCG ACC TGC GTC AAC     192
Gln Val Val Ser Thr Ala Thr Gln Ser Phe Leu Ala Thr Cys Val Asn
     50                  55                  60

GGC GTG TGT TGG ACC GTT TAC CAT GGT GCT GGC TCA AAG ACC TTA GCC     240
Gly Val Cys Trp Thr Val Tyr His Gly Ala Gly Ser Lys Thr Leu Ala
 65              70                  75                  80

GGC CCA AAG GGG CCA ATC ACC CAG ATG TAC ACT AAT GTG GAC CAG GAC     288
Gly Pro Lys Gly Pro Ile Thr Gln Met Tyr Thr Asn Val Asp Gln Asp
             85                  90                  95

CTC GTC GGC TGG CAG GCG CCC CCC GGG GCG CGT TCC TTG ACA CCA TGC     336
Leu Val Gly Trp Gln Ala Pro Pro Gly Ala Arg Ser Leu Thr Pro Cys
         100                 105                 110

ACC TGT GGC AGC TCA GAC CTT TAC TTG GTC ACG AGA CAT GCT GAC GTC     384
Thr Cys Gly Ser Ser Asp Leu Tyr Leu Val Thr Arg His Ala Asp Val
     115                 120                 125

ATT CCG GTG CGC CGG CGG GGC GAC AGT AGG GGG AGC CTG CTC TCC CCC     432
Ile Pro Val Arg Arg Arg Gly Asp Ser Arg Gly Ser Leu Leu Ser Pro
130                 135                 140

AGG CCT GTC TCC TAC TTG AAG GGC TCT TCG GGT GGT CCA CTG CTC TGC     480
Arg Pro Val Ser Tyr Leu Lys Gly Ser Ser Gly Gly Pro Leu Leu Cys
145                 150                 155                 160

CCT TCG GGG CAC GCT GTG GGC ATC TTC CGG GCT GCC GTA TGC ACC CGG     528
Pro Ser Gly His Ala Val Gly Ile Phe Arg Ala Ala Val Cys Thr Arg
                165                 170                 175

GGG GTT GCG AAG GCG GTG GAC TTT GTG CCC GTA GAG TCC ATG GAA ACT     576
Gly Val Ala Lys Ala Val Asp Phe Val Pro Val Glu Ser Met Glu Thr
            180                 185                 190

ACT ATG CGG TCT CCG GTC TTC ACG GAC AAC TCA TCC CCC CCG GCC GTA     624
Thr Met Arg Ser Pro Val Phe Thr Asp Asn Ser Ser Pro Pro Ala Val
        195                 200                 205

CCG CAG TCA TTT CAA GTG GCC CAC CTA CAC GCT CCC ACT GGC AGC GGC     672
Pro Gln Ser Phe Gln Val Ala His Leu His Ala Pro Thr Gly Ser Gly
    210                 215                 220

AAG AGT ACT AAA GTG CCG GCT GCC TAC GCA GCC CAA GGG TAC AAG GTG     720
Lys Ser Thr Lys Val Pro Ala Ala Tyr Ala Ala Gln Gly Tyr Lys Val
225                 230                 235                 240

CTC GTC CTC AAT CCG TCC GTT GCC GCT ACC TTA GGG TTT GGG GCG TAT     768
Leu Val Leu Asn Pro Ser Val Ala Ala Thr Leu Gly Phe Gly Ala Tyr
                245                 250                 255

ATG TCT AAG GCA CAC GGT ATT GAC CCC AAC ATC AGA ACT GGG GTA AGG     816
Met Ser Lys Ala His Gly Ile Asp Pro Asn Ile Arg Thr Gly Val Arg
            260                 265                 270

ACC ATT ACC ACA GGC GCC CCC GTC ACA TAC TCT ACC TAT GGC AAG TTT     864
Thr Ile Thr Thr Gly Ala Pro Val Thr Tyr Ser Thr Tyr Gly Lys Phe
        275                 280                 285
```

```
CTT GCC GAT GGT GGT TGC TCT GGG GGC GCT TAT GAC ATC ATA ATA TGT      912
Leu Ala Asp Gly Gly Cys Ser Gly Gly Ala Tyr Asp Ile Ile Ile Cys
    290                 295                 300

GAT GAG TGC CAT TCA ACT GAC TCG ACT ACA ATC TTG GGC ATC GGC ACA      960
Asp Glu Cys His Ser Thr Asp Ser Thr Thr Ile Leu Gly Ile Gly Thr
305                 310                 315                 320

GTC CTG GAC CAA GCG GAG ACG GCT GGA GCG CGG CTT GTC GTG CTC GCC     1008
Val Leu Asp Gln Ala Glu Thr Ala Gly Ala Arg Leu Val Val Leu Ala
                325                 330                 335

ACC GCT ACG CCT CCG GGA TCG GTC ACC GTG CCA CAC CCA AAC ATC GAG     1056
Thr Ala Thr Pro Pro Gly Ser Val Thr Val Pro His Pro Asn Ile Glu
            340                 345                 350

GAG GTG GCC CTG TCT AAT ACT GGA GAG ATC CCC TTC TAT GGC AAA GCC     1104
Glu Val Ala Leu Ser Asn Thr Gly Glu Ile Pro Phe Tyr Gly Lys Ala
        355                 360                 365

ATC CCC ATT GAA GCC ATC AGG GGG GGA AGG CAT CTC ATT TTC TGT CAT     1152
Ile Pro Ile Glu Ala Ile Arg Gly Gly Arg His Leu Ile Phe Cys His
    370                 375                 380

TCC AAG AAG AAG TGC GAC GAG CTC GCC GCA AAG CTG TCA GGC CTC GGA     1200
Ser Lys Lys Lys Cys Asp Glu Leu Ala Ala Lys Leu Ser Gly Leu Gly
385                 390                 395                 400

ATC AAC GCT GTG GCG TAT TAC CGG GGG CTC GAT GTG TCC GTC ATA CCA     1248
Ile Asn Ala Val Ala Tyr Tyr Arg Gly Leu Asp Val Ser Val Ile Pro
                405                 410                 415

ACT ATC GGA GAC GTC GTT GTC GTG GCA ACA GAC GCT CTG ATG ACG GGC     1296
Thr Ile Gly Asp Val Val Val Val Ala Thr Asp Ala Leu Met Thr Gly
            420                 425                 430

TAT ACG GGC GAC TTT GAC TCA GTG ATC GAC TGT AAC ACA TGT GTC ACC     1344
Tyr Thr Gly Asp Phe Asp Ser Val Ile Asp Cys Asn Thr Cys Val Thr
        435                 440                 445

CAG ACA GTC GAC TTC AGC TTG GAT CCC ACC TTC ACC ATT GAG ACG ACG     1392
Gln Thr Val Asp Phe Ser Leu Asp Pro Thr Phe Thr Ile Glu Thr Thr
    450                 455                 460

ACC GTG CCT CAA GAC GCA GTG TCG CGC TCG CAG CGG CGG GGT AGG ACT     1440
Thr Val Pro Gln Asp Ala Val Ser Arg Ser Gln Arg Arg Gly Arg Thr
465                 470                 475                 480

GGC AGG GGT AGG AGA GGC ATC TAC AGG TTT GTG ACT CCG GGA GAA CGG     1488
Gly Arg Gly Arg Arg Gly Ile Tyr Arg Phe Val Thr Pro Gly Glu Arg
                485                 490                 495

CCC TCG GGC ATG TTC GAT TCC TCG GTC CTG TGT GAG TGC TAT GAC GCG     1536
Pro Ser Gly Met Phe Asp Ser Ser Val Leu Cys Glu Cys Tyr Asp Ala
            500                 505                 510

GGC TGT GCT TGG TAC GAG CTC ACC CCC GCC GAG ACC TCG GTT AGG TTG     1584
Gly Cys Ala Trp Tyr Glu Leu Thr Pro Ala Glu Thr Ser Val Arg Leu
        515                 520                 525

CGG GCC TAC CTG AAC ACA CCA GGG TTG CCC GTT TGC CAG GAC CAC CTG     1632
Arg Ala Tyr Leu Asn Thr Pro Gly Leu Pro Val Cys Gln Asp His Leu
    530                 535                 540

GAG TTC TGG GAG AGT GTC TTC ACA GGC CTC ACC CAT ATA GAT GCA CAC     1680
Glu Phe Trp Glu Ser Val Phe Thr Gly Leu Thr His Ile Asp Ala His
545                 550                 555                 560

TTC TTG TCC CAG ACC AAG CAG GCA GGA GAC AAC TTC CCC TAC CTG GTA     1728
Phe Leu Ser Gln Thr Lys Gln Ala Gly Asp Asn Phe Pro Tyr Leu Val
                565                 570                 575

GCA TAC CAA GCC ACG GTG TGC GCC AGG GCT CAG GCC CCA CCT CCA TCA     1776
Ala Tyr Gln Ala Thr Val Cys Ala Arg Ala Gln Ala Pro Pro Pro Ser
            580                 585                 590

TGG GAT CAA ATG TGG AAG TGT CTC ATA CGG CTG AAA CCT ACG CTG CAC     1824
Trp Asp Gln Met Trp Lys Cys Leu Ile Arg Leu Lys Pro Thr Leu His
        595                 600                 605
```

```
GGG CCA ACA CCC TTG CTG TAC AGG CTG GGA GCC GTC CAA AAT GAG GTC         1872
Gly Pro Thr Pro Leu Leu Tyr Arg Leu Gly Ala Val Gln Asn Glu Val
    610                 615                 620

ACC CTC ACC CAC CCC ATA ACC AAA TAC ATC ATG GCA TGC ATG TCG GCC         1920
Thr Leu Thr His Pro Ile Thr Lys Tyr Ile Met Ala Cys Met Ser Ala
625                 630                 635                 640

GAC CTG GAG GTC GTT ACG TAG                                             1941
Asp Leu Glu Val Val Thr
                645
```

(2) INFORMATION FOR SEQ ID NO:121:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: RNA (genomic)

(xi) SEQUENCE DESCRIPTION: SEQ ID NO:121:

```
GCUCGCCCGG GGAUCCUCUA GGAAUACACG UUCGAU                                 36
```

(2) INFORMATION FOR SEQ ID NO:122:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: RNA (genomic)

(xi) SEQUENCE DESCRIPTION: SEQ ID NO:122:

```
CUAGAGGAUC CCCGGGCGAG CCCUAUAGUG AGUCGU                                 36
```

(2) INFORMATION FOR SEQ ID NO:123:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:123:

```
GCTCGCCCGG GGATCCTCTA G                                                 21
```